United States Patent
Canner et al.

(10) Patent No.: US 12,239,509 B2
(45) Date of Patent: Mar. 4, 2025

(54) NEGATIVE PRESSURE WOUND CLOSURE DEVICE

(71) Applicants: Smith & Nephew, Inc., Memphis, TN (US); University of Massachusetts, Boston, MA (US)

(72) Inventors: Philip David Canner, Cambridge (GB); Raymond M. Dunn, Shrewsbury, MA (US); John Alan Greenwood, West Yorkshire (GB); Victoria Jody Hammond, Hull (GB); Edward Yerbury Hartwell, Hull (GB); John Kenneth Hicks, Pocklington (GB); Elizabeth Mary Huddleston, Copmanthorpe (GB); Andrew Kelly, Hitchin (GB); Andrew Linton, Woodthorpe (GB); Marcus Damian Phillips, Grimsby (GB); Mark Richardson, Grimsby (GB); Carl Saxby, Brough (GB); Tim Stern, Belper (GB)

(73) Assignees: Smith & Nephew, Inc., Memphis, TN (US); University of Massachusetts, Boston, MA (US)

(*) Notice: Subject to any disclaimer, the term of this patent is extended or adjusted under 35 U.S.C. 154(b) by 0 days.

(21) Appl. No.: 18/130,317

(22) Filed: Apr. 3, 2023

(65) Prior Publication Data

US 2023/0301838 A1  Sep. 28, 2023

Related U.S. Application Data

(63) Continuation of application No. 16/868,379, filed on May 6, 2020, which is a continuation of application
(Continued)

(51) Int. Cl.
*A61M 1/00* (2006.01)
*A61F 13/00* (2006.01)
*A61F 13/05* (2024.01)

(52) U.S. Cl.
CPC ........ *A61F 13/05* (2024.01); *A61F 13/00995* (2013.01); *A61M 1/915* (2021.05);
(Continued)

(58) Field of Classification Search
CPC ................ A61F 13/05; A61F 13/00995; A61F 2013/00357; A61F 2013/00536;
(Continued)

(56) References Cited

U.S. PATENT DOCUMENTS

| 1,006,716 A | 10/1911 | Bloomer |
| 3,014,483 A | 12/1961 | Frank et al. |

(Continued)

FOREIGN PATENT DOCUMENTS

| AU | 2012261793 B2 | 11/2014 |
| AU | 2013206230 B2 | 5/2016 |

(Continued)

OTHER PUBLICATIONS

"Definition of 3D Printer," American Heritage Dictionary of the English Language, Fifth Edition, accessed on Feb. 22, 2018 from URL: https://www.thefreedictionary.com, 2016, 1 page.
(Continued)

*Primary Examiner* — Philip R Wiest
*Assistant Examiner* — Brandon W. Levy
(74) *Attorney, Agent, or Firm* — Knobbe, Martens, Olson & Bear, LLP

(57) ABSTRACT

Examples of a negative pressure wound closure system and methods for using such a system are presented. Certain embodiments facilitate closure of the wound by preferentially contracting to provide for movement of the tissue.
(Continued)

Certain embodiments can utilize tissue securing portions that aid in securing the system within a wound.

20 Claims, 138 Drawing Sheets

Related U.S. Application Data

No. 15/030,841, filed as application No. PCT/US2014/061627 on Oct. 21, 2014, now Pat. No. 10,660,992.

(60) Provisional application No. 62/051,834, filed on Sep. 17, 2014, provisional application No. 61/930,913, filed on Jan. 23, 2014, provisional application No. 61/930,436, filed on Jan. 22, 2014, provisional application No. 61/930,427, filed on Jan. 22, 2014, provisional application No. 61/930,426, filed on Jan. 22, 2014, provisional application No. 61/930,414, filed on Jan. 22, 2014, provisional application No. 61/930,423, filed on Jan. 22, 2014, provisional application No. 61/913,210, filed on Dec. 6, 2013, provisional application No. 61/893,821, filed on Oct. 21, 2013.

(52) U.S. Cl.
CPC ... *A61M 1/916* (2021.05); *A61F 2013/00357* (2013.01); *A61M 1/913* (2021.05); *A61M 1/96* (2021.05); *A61M 1/985* (2021.05)

(58) Field of Classification Search
CPC ............ A61F 13/01038; A61F 13/023; A61F 13/0209; A61F 15/008; A61F 13/0226; A61F 13/00; A61F 13/0289; A61F 13/00059; A61F 2013/0054; A61F 13/0203; A61F 15/02; A61F 2013/00174; A61F 2013/0074; A61F 2013/00863; A61F 2013/00255; A61F 2013/00544; A61F 2013/00548; A61M 1/915; A61M 1/916; A61M 1/913; A61M 1/96; A61M 1/985; A61M 1/74; A61M 2210/1021; A61M 1/90; A61M 27/00; Y10T 29/49; Y10T 156/1052; A61B 46/00; A61L 15/425; A61L 27/56; A61P 17/02
See application file for complete search history.

(56) References Cited

U.S. PATENT DOCUMENTS

| | | | |
|---|---|---|---|
| 3,194,239 | A | 7/1965 | Sullivan et al. |
| 3,578,003 | A | 5/1971 | Everett |
| 3,648,692 | A | 3/1972 | Wheeler |
| 3,665,918 | A | 5/1972 | Lindquist et al. |
| 3,789,851 | A | 2/1974 | LeVeen |
| 3,812,616 | A | 5/1974 | Koziol |
| 3,952,633 | A | 4/1976 | Nakai |
| 3,975,567 | A | 8/1976 | Lock |
| 3,978,266 | A | 8/1976 | Lock |
| 3,978,855 | A | 9/1976 | McRae et al. |
| 4,000,845 | A | 1/1977 | Zeller |
| 4,040,884 | A | 8/1977 | Roth |
| 4,233,969 | A | 11/1980 | Lock et al. |
| 4,373,519 | A | 2/1983 | Errede et al. |
| 4,467,805 | A | 8/1984 | Fukuda |
| 4,525,166 | A | 6/1985 | Leclerc |
| 4,608,041 | A | 8/1986 | Nielsen |
| 4,637,819 | A | 1/1987 | Ouellette et al. |
| 4,664,662 | A | 5/1987 | Webster |
| 4,699,134 | A * | 10/1987 | Samuelsen .......... A61F 13/0253 602/56 |
| 4,771,482 | A | 9/1988 | Shlenker |
| 4,815,468 | A | 3/1989 | Annand |
| 4,969,880 | A | 11/1990 | Zamierowski |
| 5,176,663 | A | 1/1993 | Svedman et al. |
| 5,264,218 | A * | 11/1993 | Rogozinski ............ A61L 15/42 424/443 |
| 5,298,015 | A | 3/1994 | Komatsuzaki et al. |
| 5,332,149 | A | 7/1994 | Gepfer |
| 5,368,910 | A | 11/1994 | Langdon |
| 5,368,930 | A | 11/1994 | Samples |
| 5,376,067 | A | 12/1994 | Daneshvar |
| 5,409,472 | A | 4/1995 | Rawlings et al. |
| 5,415,715 | A | 5/1995 | Delage et al. |
| 5,423,857 | A | 6/1995 | Rosenman et al. |
| 5,512,041 | A | 4/1996 | Bogart |
| 5,514,105 | A | 5/1996 | Goodman, Jr. et al. |
| 5,562,107 | A | 10/1996 | Lavender et al. |
| 5,584,859 | A | 12/1996 | Brotz |
| 5,636,643 | A | 6/1997 | Argenta et al. |
| 5,695,777 | A | 12/1997 | Donovan et al. |
| 5,782,787 | A | 7/1998 | Webster |
| 5,853,863 | A | 12/1998 | Kim |
| 5,928,210 | A | 7/1999 | Ouellette et al. |
| 5,960,497 | A | 10/1999 | Castellino et al. |
| 6,000,403 | A | 12/1999 | Cantwell |
| 6,080,168 | A | 6/2000 | Levin et al. |
| 6,086,591 | A | 7/2000 | Bojarski |
| 6,142,982 | A | 11/2000 | Hunt et al. |
| 6,176,868 | B1 | 1/2001 | Detour |
| 6,291,050 | B1 | 9/2001 | Cree et al. |
| 6,398,767 | B1 | 6/2002 | Fleischmann |
| 6,471,715 | B1 | 10/2002 | Weiss |
| 6,500,112 | B1 | 12/2002 | Khouri |
| 6,503,208 | B1 | 1/2003 | Skovlund |
| 6,530,941 | B1 | 3/2003 | Muller et al. |
| 6,548,727 | B1 | 4/2003 | Swenson |
| 6,553,998 | B2 | 4/2003 | Heaton et al. |
| 6,566,575 | B1 | 5/2003 | Stickels et al. |
| 6,641,575 | B1 | 11/2003 | Lonky |
| 6,685,681 | B2 | 2/2004 | Lockwood et al. |
| 6,695,823 | B1 | 2/2004 | Lina et al. |
| 6,712,830 | B2 | 3/2004 | Esplin |
| 6,712,839 | B1 | 3/2004 | Lonne |
| 6,767,334 | B1 | 7/2004 | Randolph |
| 6,770,794 | B2 | 8/2004 | Fleischmann |
| 6,776,769 | B2 | 8/2004 | Smith |
| 6,787,682 | B2 | 9/2004 | Gilman |
| 6,814,079 | B2 | 11/2004 | Heaton et al. |
| 6,883,531 | B1 | 4/2005 | Perttu |
| 6,893,452 | B2 | 5/2005 | Jacobs |
| 6,936,037 | B2 | 8/2005 | Bubb et al. |
| 6,951,553 | B2 | 10/2005 | Bubb et al. |
| 6,977,323 | B1 | 12/2005 | Swenson |
| 6,994,702 | B1 | 2/2006 | Johnson |
| 7,004,915 | B2 | 2/2006 | Boynton et al. |
| 7,025,755 | B2 | 4/2006 | Epstein et al. |
| 7,070,584 | B2 | 7/2006 | Johnson et al. |
| 7,117,869 | B2 | 10/2006 | Heaton et al. |
| 7,128,735 | B2 | 10/2006 | Weston |
| 7,144,390 | B1 | 12/2006 | Hannigan et al. |
| 7,153,312 | B1 | 12/2006 | Torrie et al. |
| 7,156,862 | B2 | 1/2007 | Jacobs et al. |
| 7,172,615 | B2 | 2/2007 | Morriss et al. |
| 7,189,238 | B2 | 3/2007 | Lombardo et al. |
| 7,196,054 | B1 | 3/2007 | Drohan et al. |
| 7,198,046 | B1 | 4/2007 | Argenta et al. |
| 7,216,651 | B2 | 5/2007 | Argenta et al. |
| D544,092 | S | 6/2007 | Lewis |
| 7,262,174 | B2 | 8/2007 | Jiang et al. |
| 7,279,612 | B1 | 10/2007 | Heaton et al. |
| 7,315,183 | B2 | 1/2008 | Hinterscher |
| 7,351,250 | B2 | 4/2008 | Zamierowski |
| 7,361,184 | B2 | 4/2008 | Joshi |
| 7,367,342 | B2 | 5/2008 | Butler |
| 7,381,211 | B2 | 6/2008 | Zamierowski |
| 7,381,859 | B2 | 6/2008 | Hunt et al. |
| 7,413,571 | B2 | 8/2008 | Zamierowski |

(56) References Cited

U.S. PATENT DOCUMENTS

| | | |
|---|---|---|
| 7,438,705 B2 | 10/2008 | Karpowicz et al. |
| 7,494,482 B2 | 2/2009 | Orgill et al. |
| 7,534,240 B1 | 5/2009 | Johnson |
| 7,540,848 B2 | 6/2009 | Hannigan et al. |
| 7,553,306 B1 | 6/2009 | Hunt et al. |
| 7,553,923 B2 | 6/2009 | Williams et al. |
| 7,569,742 B2 | 8/2009 | Haggstrom et al. |
| 7,578,532 B2 | 8/2009 | Schiebler |
| D602,583 S | 10/2009 | Pidgeon et al. |
| 7,611,500 B1 | 11/2009 | Lina et al. |
| 7,612,248 B2 | 11/2009 | Burton et al. |
| 7,615,036 B2 | 11/2009 | Joshi et al. |
| 7,617,762 B1 | 11/2009 | Ragner |
| 7,618,382 B2 | 11/2009 | Vogel et al. |
| 7,622,629 B2 | 11/2009 | Aali |
| 7,625,362 B2 | 12/2009 | Boehringer et al. |
| 7,645,269 B2 | 1/2010 | Zamierowski |
| 7,651,484 B2 | 1/2010 | Heaton et al. |
| 7,670,323 B2 | 3/2010 | Hunt et al. |
| 7,678,102 B1 | 3/2010 | Heaton |
| 7,683,667 B2 | 3/2010 | Kim |
| 7,699,823 B2 | 4/2010 | Haggstrom et al. |
| 7,699,830 B2 | 4/2010 | Martin |
| 7,699,831 B2 | 4/2010 | Bengtson et al. |
| 7,700,819 B2 | 4/2010 | Ambrosio et al. |
| 7,708,724 B2 | 5/2010 | Weston |
| 7,713,743 B2 | 5/2010 | Villanueva et al. |
| 7,722,528 B2 | 5/2010 | Arnal et al. |
| 7,723,560 B2 | 5/2010 | Lockwood et al. |
| 7,754,937 B2 | 7/2010 | Boehringer et al. |
| 7,776,028 B2 | 8/2010 | Miller et al. |
| 7,777,522 B2 | 8/2010 | Yang et al. |
| 7,779,625 B2 | 8/2010 | Joshi et al. |
| D625,801 S | 10/2010 | Pidgeon et al. |
| 7,815,616 B2 | 10/2010 | Boehringer et al. |
| 7,820,453 B2 | 10/2010 | Heylen et al. |
| 7,846,141 B2 | 12/2010 | Weston |
| 7,851,484 B2 | 12/2010 | Morgan et al. |
| 7,857,806 B2 | 12/2010 | Karpowicz et al. |
| 7,863,495 B2 | 1/2011 | Aali |
| 7,892,181 B2 | 2/2011 | Christensen et al. |
| 7,896,856 B2 | 3/2011 | Petrosenko et al. |
| 7,909,805 B2 | 3/2011 | Weston |
| 7,910,789 B2 | 3/2011 | Sinyagin |
| 7,931,774 B2 | 4/2011 | Hall et al. |
| 7,942,866 B2 | 5/2011 | Radl et al. |
| 7,951,124 B2 | 5/2011 | Boehringer et al. |
| 7,964,766 B2 | 6/2011 | Blott et al. |
| 7,976,519 B2 | 7/2011 | Bubb et al. |
| 7,976,524 B2 | 7/2011 | Kudo et al. |
| 7,981,098 B2 | 7/2011 | Boehringer et al. |
| 8,030,534 B2 | 10/2011 | Radl et al. |
| 8,057,447 B2 | 11/2011 | Olson et al. |
| 8,062,272 B2 | 11/2011 | Weston |
| 8,062,295 B2 | 11/2011 | McDevitt et al. |
| 8,062,331 B2 | 11/2011 | Zamierowski |
| 8,067,662 B2 | 11/2011 | Aali et al. |
| 8,070,773 B2 | 12/2011 | Zamierowski |
| 8,080,702 B2 | 12/2011 | Blott et al. |
| 8,100,887 B2 | 1/2012 | Weston et al. |
| 8,114,126 B2 | 2/2012 | Heaton et al. |
| 8,123,781 B2 | 2/2012 | Zamierowski |
| 8,128,615 B2 | 3/2012 | Blott et al. |
| 8,129,580 B2 | 3/2012 | Wilkes et al. |
| 8,142,419 B2 | 3/2012 | Heaton et al. |
| 8,162,909 B2 | 4/2012 | Blott et al. |
| 8,172,816 B2 | 5/2012 | Kazala, Jr. et al. |
| 8,182,413 B2 | 5/2012 | Browning |
| 8,187,237 B2 | 5/2012 | Seegert |
| 8,188,331 B2 | 5/2012 | Barta et al. |
| 8,192,409 B2 | 6/2012 | Hardman et al. |
| 8,197,467 B2 | 6/2012 | Heaton et al. |
| 8,207,392 B2 | 6/2012 | Haggstrom et al. |
| 8,215,929 B2 | 7/2012 | Shen et al. |
| 8,235,955 B2 | 8/2012 | Blott et al. |
| 8,235,972 B2 | 8/2012 | Adahan |
| 8,246,590 B2 | 8/2012 | Hu et al. |
| 8,246,606 B2 | 8/2012 | Stevenson et al. |
| 8,246,607 B2 | 8/2012 | Karpowicz et al. |
| 8,257,328 B2 | 9/2012 | Augustine et al. |
| 8,273,105 B2 | 9/2012 | Cohen et al. |
| 8,328,776 B2 | 12/2012 | Kelch et al. |
| 8,337,411 B2 | 12/2012 | Nishtala et al. |
| 8,353,931 B2 | 1/2013 | Stopek et al. |
| 8,357,131 B2 | 1/2013 | Olson |
| 8,376,972 B2 | 2/2013 | Fleischmann |
| 8,399,730 B2 | 3/2013 | Kazala, Jr. et al. |
| 8,430,867 B2 | 4/2013 | Robinson et al. |
| 8,439,882 B2 | 5/2013 | Kelch |
| 8,444,392 B2 | 5/2013 | Turner et al. |
| 8,447,375 B2 | 5/2013 | Shuler |
| 8,454,990 B2 | 6/2013 | Canada et al. |
| 8,460,255 B2 | 6/2013 | Joshi et al. |
| 8,460,257 B2 | 6/2013 | Locke et al. |
| 8,481,804 B2 | 7/2013 | Timothy |
| 8,486,032 B2 | 7/2013 | Seegert et al. |
| 8,500,704 B2 | 8/2013 | Boehringer et al. |
| 8,500,776 B2 | 8/2013 | Ebner |
| 8,523,832 B2 | 9/2013 | Seegert |
| 8,535,296 B2 | 9/2013 | Blott et al. |
| 8,608,776 B2 | 12/2013 | Coward et al. |
| 8,622,981 B2 | 1/2014 | Hartwell et al. |
| 8,632,523 B2 | 1/2014 | Eriksson et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,708,984 B2 | 4/2014 | Robinson et al. |
| 8,715,256 B2 | 5/2014 | Greener |
| 8,721,629 B2 | 5/2014 | Hardman et al. |
| 8,746,662 B2 | 6/2014 | Poppe |
| 8,747,375 B2 | 6/2014 | Barta et al. |
| 8,764,732 B2 | 7/2014 | Hartwell |
| 8,784,392 B2 | 7/2014 | Vess et al. |
| 8,791,315 B2 | 7/2014 | Lattimore et al. |
| 8,791,316 B2 | 7/2014 | Greener |
| 8,801,685 B2 | 8/2014 | Armstrong et al. |
| 8,802,916 B2 | 8/2014 | Griffey et al. |
| 8,814,842 B2 | 8/2014 | Coulthard et al. |
| 8,821,535 B2 | 9/2014 | Greener |
| 8,843,327 B2 | 9/2014 | Vernon-Harcourt et al. |
| 8,853,486 B2 | 10/2014 | Wild et al. |
| 8,936,618 B2 | 1/2015 | Sealy et al. |
| 8,945,030 B2 | 2/2015 | Weston |
| 8,951,235 B2 | 2/2015 | Allen et al. |
| 8,956,336 B2 | 2/2015 | Haggstrom et al. |
| 9,017,302 B2 | 4/2015 | Vitaris et al. |
| 9,044,579 B2 | 6/2015 | Blott et al. |
| 9,050,398 B2 | 6/2015 | Armstrong et al. |
| 9,061,095 B2 | 6/2015 | Adie et al. |
| 9,180,132 B2 | 11/2015 | Fein et al. |
| 9,180,231 B2 | 11/2015 | Greener |
| 9,204,801 B2 | 12/2015 | Locke et al. |
| 9,220,822 B2 | 12/2015 | Hartwell |
| 9,226,737 B2 | 1/2016 | Dunn |
| 9,339,248 B2 | 5/2016 | Tout et al. |
| 9,408,755 B2 | 8/2016 | Larsson |
| 9,655,807 B2 | 5/2017 | Locke et al. |
| 9,737,649 B2 | 8/2017 | Begin et al. |
| 9,757,500 B2 | 9/2017 | Locke et al. |
| 9,820,888 B2 | 11/2017 | Greener et al. |
| 9,844,472 B2 | 12/2017 | Hammond et al. |
| 9,849,023 B2 | 12/2017 | Hall et al. |
| 9,895,270 B2 | 2/2018 | Coward et al. |
| 10,130,520 B2 | 11/2018 | Dunn et al. |
| 10,143,485 B2 | 12/2018 | Locke et al. |
| 10,485,707 B2 | 11/2019 | Sexton |
| 10,537,657 B2 | 1/2020 | Phillips et al. |
| 2001/0034499 A1 | 10/2001 | Sessions et al. |
| 2002/0022861 A1 | 2/2002 | Jacobs et al. |
| 2002/0077661 A1 | 6/2002 | Saadat |
| 2002/0161346 A1 | 10/2002 | Lockwood et al. |
| 2003/0114816 A1 | 6/2003 | Underhill et al. |
| 2003/0114818 A1 | 6/2003 | Benecke et al. |

(56) References Cited

U.S. PATENT DOCUMENTS

| | | |
|---|---|---|
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0178274 A1 | 9/2003 | Chi |
| 2003/0220660 A1 | 11/2003 | Kortenbach et al. |
| 2004/0006319 A1 | 1/2004 | Lina et al. |
| 2004/0010275 A1 | 1/2004 | Jacobs et al. |
| 2004/0054346 A1 | 3/2004 | Zhu et al. |
| 2004/0162512 A1 | 8/2004 | Liedtke et al. |
| 2004/0267312 A1 | 12/2004 | Kanner et al. |
| 2005/0107731 A1 | 5/2005 | Sessions |
| 2005/0119694 A1 | 6/2005 | Jacobs et al. |
| 2005/0131414 A1 | 6/2005 | Chana |
| 2005/0142331 A1 | 6/2005 | Anderson et al. |
| 2005/0222613 A1 | 10/2005 | Ryan |
| 2005/0258887 A1 | 11/2005 | Ito et al. |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0064124 A1 | 3/2006 | Zhu et al. |
| 2006/0069357 A1 | 3/2006 | Marasco |
| 2006/0079599 A1 | 4/2006 | Arthur |
| 2006/0135921 A1 | 6/2006 | Wiercinski et al. |
| 2006/0213527 A1 | 9/2006 | Argenta et al. |
| 2006/0217795 A1 | 9/2006 | Besselink et al. |
| 2006/0257457 A1 | 11/2006 | Gorman et al. |
| 2006/0259074 A1 | 11/2006 | Kelleher et al. |
| 2006/0271018 A1 | 11/2006 | Korf |
| 2007/0014837 A1 | 1/2007 | Johnson et al. |
| 2007/0027414 A1 | 2/2007 | Hoffman et al. |
| 2007/0027475 A1 | 2/2007 | Pagedas |
| 2007/0032755 A1 | 2/2007 | Walsh |
| 2007/0032763 A1 | 2/2007 | Vogel |
| 2007/0052144 A1 | 3/2007 | Knirck et al. |
| 2007/0055209 A1 | 3/2007 | Patel et al. |
| 2007/0104941 A1 | 5/2007 | Kameda et al. |
| 2007/0118096 A1 | 5/2007 | Smith et al. |
| 2007/0123816 A1 | 5/2007 | Zhu et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0179421 A1 | 8/2007 | Farrow |
| 2007/0185463 A1 | 8/2007 | Mulligan |
| 2007/0213597 A1 | 9/2007 | Wooster |
| 2007/0219513 A1 | 9/2007 | Lina et al. |
| 2007/0282309 A1 | 12/2007 | Bengtson et al. |
| 2007/0282374 A1 | 12/2007 | Sogard et al. |
| 2007/0299541 A1 | 12/2007 | Chernomorsky et al. |
| 2008/0041401 A1 | 2/2008 | Casola et al. |
| 2008/0103462 A1 | 5/2008 | Wenzel et al. |
| 2008/0108977 A1 | 5/2008 | Heaton et al. |
| 2008/0132821 A1 | 6/2008 | Propp et al. |
| 2008/0243096 A1 | 10/2008 | Svedman |
| 2008/0275409 A1 | 11/2008 | Kane et al. |
| 2008/0287973 A1 | 11/2008 | Aster et al. |
| 2008/0306456 A1 | 12/2008 | Riesinger |
| 2009/0005716 A1 | 1/2009 | Abuzaina et al. |
| 2009/0018578 A1 | 1/2009 | Wilke et al. |
| 2009/0018579 A1 | 1/2009 | Wilke et al. |
| 2009/0043268 A1 | 2/2009 | Eddy et al. |
| 2009/0054856 A1 | 2/2009 | Mormino et al. |
| 2009/0069760 A1 | 3/2009 | Finklestein |
| 2009/0069904 A1 | 3/2009 | Picha |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0131888 A1 | 5/2009 | Joshi |
| 2009/0137973 A1 | 5/2009 | Karpowicz et al. |
| 2009/0204423 A1 | 8/2009 | DeGheest et al. |
| 2009/0227938 A1 | 9/2009 | Fasching et al. |
| 2009/0227969 A1 | 9/2009 | Jaeb et al. |
| 2009/0246238 A1 | 10/2009 | Gorman et al. |
| 2009/0293887 A1 | 12/2009 | Wilkes et al. |
| 2009/0299307 A1 | 12/2009 | Barta et al. |
| 2009/0299341 A1 | 12/2009 | Kazala, Jr. et al. |
| 2009/0299342 A1 | 12/2009 | Cavanaugh, II et al. |
| 2009/0312685 A1 | 12/2009 | Olsen et al. |
| 2010/0022972 A1 | 1/2010 | Lina et al. |
| 2010/0022990 A1 | 1/2010 | Karpowicz et al. |
| 2010/0028407 A1 | 2/2010 | Del Priore et al. |
| 2010/0030132 A1 | 2/2010 | Niezgoda et al. |
| 2010/0036333 A1 | 2/2010 | Schenk, III et al. |
| 2010/0047324 A1 | 2/2010 | Fritz et al. |
| 2010/0081983 A1 | 4/2010 | Zocher et al. |
| 2010/0087854 A1 | 4/2010 | Stopek et al. |
| 2010/0106184 A1* | 4/2010 | Coward ............ A61F 13/01034 606/213 |
| 2010/0121287 A1 | 5/2010 | Smith et al. |
| 2010/0137775 A1 | 6/2010 | Hu et al. |
| 2010/0137890 A1 | 6/2010 | Martinez et al. |
| 2010/0150991 A1 | 6/2010 | Bernstein |
| 2010/0160874 A1 | 6/2010 | Robinson et al. |
| 2010/0160901 A1 | 6/2010 | Hu et al. |
| 2010/0179493 A1 | 7/2010 | Heagle et al. |
| 2010/0179515 A1 | 7/2010 | Swain et al. |
| 2010/0198128 A1 | 8/2010 | Turnlund et al. |
| 2010/0211030 A1 | 8/2010 | Turner et al. |
| 2010/0256672 A1 | 10/2010 | Weinberg et al. |
| 2010/0262092 A1 | 10/2010 | Hartwell |
| 2010/0262126 A1 | 10/2010 | Hu et al. |
| 2010/0280468 A1 | 11/2010 | Haggstrom et al. |
| 2010/0292717 A1 | 11/2010 | Petter-Puchner et al. |
| 2010/0298866 A1 | 11/2010 | Fischvogt |
| 2010/0305490 A1 | 12/2010 | Coulthard et al. |
| 2010/0312159 A1 | 12/2010 | Aali et al. |
| 2010/0318052 A1 | 12/2010 | Ha et al. |
| 2011/0004173 A1 | 1/2011 | Hu et al. |
| 2011/0015594 A1 | 1/2011 | Hu et al. |
| 2011/0015595 A1 | 1/2011 | Robinson et al. |
| 2011/0021965 A1 | 1/2011 | Karp et al. |
| 2011/0022082 A1 | 1/2011 | Burke et al. |
| 2011/0059291 A1 | 3/2011 | Boyce et al. |
| 2011/0066096 A1 | 3/2011 | Svedman |
| 2011/0077605 A1 | 3/2011 | Karpowicz et al. |
| 2011/0082480 A1 | 4/2011 | Viola |
| 2011/0105963 A1 | 5/2011 | Hu et al. |
| 2011/0106026 A1 | 5/2011 | Wu et al. |
| 2011/0110996 A1 | 5/2011 | Schoenberger et al. |
| 2011/0112458 A1 | 5/2011 | Holm et al. |
| 2011/0113559 A1 | 5/2011 | Dodd |
| 2011/0130774 A1 | 6/2011 | Criscuolo et al. |
| 2011/0152800 A1 | 6/2011 | Eckstein et al. |
| 2011/0172760 A1 | 7/2011 | Anderson |
| 2011/0178451 A1 | 7/2011 | Robinson et al. |
| 2011/0213287 A1* | 9/2011 | Lattimore ............. A61M 1/915 604/319 |
| 2011/0213319 A1 | 9/2011 | Blott et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0236460 A1 | 9/2011 | Stopek et al. |
| 2011/0238026 A1 | 9/2011 | Zhang et al. |
| 2011/0238095 A1 | 9/2011 | Browning |
| 2011/0238110 A1 | 9/2011 | Wilke et al. |
| 2011/0245682 A1 | 10/2011 | Robinson et al. |
| 2011/0245788 A1 | 10/2011 | Marquez Canada |
| 2011/0264138 A1 | 10/2011 | Avelar et al. |
| 2011/0282136 A1 | 11/2011 | Browning |
| 2011/0282310 A1 | 11/2011 | Boehringer et al. |
| 2011/0305736 A1 | 12/2011 | Wieland et al. |
| 2012/0004631 A9 | 1/2012 | Hartwell |
| 2012/0010637 A1 | 1/2012 | Stopek et al. |
| 2012/0016321 A1 | 1/2012 | Wu et al. |
| 2012/0016322 A1 | 1/2012 | Coulthard et al. |
| 2012/0029449 A1 | 2/2012 | Khosrowshahi |
| 2012/0029455 A1 | 2/2012 | Perez-Foullerat et al. |
| 2012/0035560 A1 | 2/2012 | Eddy et al. |
| 2012/0041402 A1 | 2/2012 | Greener |
| 2012/0059399 A1 | 3/2012 | Hoke et al. |
| 2012/0059412 A1 | 3/2012 | Fleischmann |
| 2012/0065664 A1 | 3/2012 | Avitable et al. |
| 2012/0071841 A1 | 3/2012 | Bengtson |
| 2012/0073736 A1 | 3/2012 | O'Connor et al. |
| 2012/0083755 A1 | 4/2012 | Lina et al. |

(56) References Cited

U.S. PATENT DOCUMENTS

| | | |
|---|---|---|
| 2012/0095426 A1 | 4/2012 | Visscher et al. |
| 2012/0109188 A1 | 5/2012 | Viola |
| 2012/0121556 A1 | 5/2012 | Fraser et al. |
| 2012/0123358 A1 | 5/2012 | Hall et al. |
| 2012/0130327 A1 | 5/2012 | Marquez Canada |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0143158 A1 | 6/2012 | Yang et al. |
| 2012/0144989 A1 | 6/2012 | Du Plessis et al. |
| 2012/0150078 A1 | 6/2012 | Chen et al. |
| 2012/0150133 A1 | 6/2012 | Heaton et al. |
| 2012/0172778 A1 | 7/2012 | Rastegar et al. |
| 2012/0172926 A1 | 7/2012 | Hotter |
| 2012/0191054 A1 | 7/2012 | Kazala, Jr. et al. |
| 2012/0191132 A1 | 7/2012 | Sargeant |
| 2012/0197415 A1 | 8/2012 | Montanari et al. |
| 2012/0209226 A1 | 8/2012 | Simmons et al. |
| 2012/0209227 A1* | 8/2012 | Dunn ............... A61M 1/84 604/319 |
| 2012/0220968 A1 | 8/2012 | Confalone et al. |
| 2012/0222687 A1 | 9/2012 | Czajka, Jr. et al. |
| 2012/0238931 A1 | 9/2012 | Rastegar et al. |
| 2012/0253302 A1 | 10/2012 | Corley |
| 2012/0277773 A1 | 11/2012 | Sargeant et al. |
| 2012/0302440 A1 | 11/2012 | Theliander et al. |
| 2012/0302979 A1 | 11/2012 | Locke et al. |
| 2013/0012891 A1 | 1/2013 | Gross et al. |
| 2013/0066365 A1 | 3/2013 | Belson et al. |
| 2013/0096518 A1 | 4/2013 | Hall et al. |
| 2013/0110058 A1 | 5/2013 | Adie et al. |
| 2013/0110066 A1 | 5/2013 | Sharma et al. |
| 2013/0150813 A1 | 6/2013 | Gordon et al. |
| 2013/0150814 A1 | 6/2013 | Buan |
| 2013/0190705 A1 | 7/2013 | Vess et al. |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0253401 A1 | 9/2013 | Locke et al. |
| 2013/0325142 A1 | 12/2013 | Hunter et al. |
| 2013/0331757 A1 | 12/2013 | Belson |
| 2014/0024989 A1 | 1/2014 | Ueda |
| 2014/0066868 A1 | 3/2014 | Freedman et al. |
| 2014/0109560 A1 | 4/2014 | Ilievski et al. |
| 2014/0163415 A1 | 6/2014 | Zaiken et al. |
| 2014/0180225 A1 | 6/2014 | Dunn |
| 2014/0180229 A1 | 6/2014 | Fuller et al. |
| 2014/0195004 A9 | 7/2014 | Engqvist et al. |
| 2014/0249495 A1 | 9/2014 | Mumby et al. |
| 2014/0316359 A1 | 10/2014 | Collinson et al. |
| 2014/0343517 A1 | 11/2014 | Jameson |
| 2014/0343518 A1 | 11/2014 | Riesinger |
| 2015/0000018 A1 | 1/2015 | Brandt |
| 2015/0025484 A1 | 1/2015 | Simmons et al. |
| 2015/0030806 A1 | 1/2015 | Fink |
| 2015/0057762 A1 | 2/2015 | Harms et al. |
| 2015/0065805 A1 | 3/2015 | Edmondson et al. |
| 2015/0065968 A1 | 3/2015 | Sealy et al. |
| 2015/0075697 A1 | 3/2015 | Gildersleeve |
| 2015/0100008 A1 | 4/2015 | Chatterjee |
| 2015/0119837 A1 | 4/2015 | Thompson, Jr. et al. |
| 2015/0157758 A1 | 6/2015 | Blucher et al. |
| 2015/0159066 A1 | 6/2015 | Hartwell et al. |
| 2015/0164174 A1 | 6/2015 | West |
| 2015/0174304 A1 | 6/2015 | Askem et al. |
| 2015/0320434 A1 | 11/2015 | Ingram et al. |
| 2015/0320602 A1 | 11/2015 | Locke et al. |
| 2015/0374561 A1 | 12/2015 | Hubbard, Jr. et al. |
| 2016/0067939 A1 | 3/2016 | Liebe et al. |
| 2016/0144085 A1 | 5/2016 | Melin et al. |
| 2016/0184496 A1 | 6/2016 | Jaecklein et al. |
| 2017/0065751 A1 | 3/2017 | Toth |
| 2017/0156611 A1 | 6/2017 | Burnett et al. |
| 2018/0221211 A1 | 8/2018 | Luckemeyer et al. |

FOREIGN PATENT DOCUMENTS

| | | |
|---|---|---|
| CN | 1438904 A | 8/2003 |
| CN | 101112326 A | 1/2008 |
| CN | 101123930 A | 2/2008 |
| CN | 101588836 A | 11/2009 |
| CN | 101744688 A | 6/2010 |
| CN | 201519362 U | 7/2010 |
| CN | 101065158 B | 9/2010 |
| CN | 102038575 A | 5/2011 |
| CN | 102046117 A | 5/2011 |
| CN | 102196830 A | 9/2011 |
| CN | 102781380 A | 11/2012 |
| CN | 202568632 U | 12/2012 |
| CN | 103071197 A | 5/2013 |
| CN | 103405846 A | 11/2013 |
| CN | 203408163 U | 1/2014 |
| DE | 2949920 A1 | 3/1981 |
| DE | 3443101 A1 | 5/1986 |
| DE | 102005007016 A1 | 8/2006 |
| DE | 102012001752 A1 | 8/2013 |
| EP | 0100148 A1 | 2/1984 |
| EP | 0392640 A2 | 10/1990 |
| EP | 0630629 A1 | 12/1994 |
| EP | 1320342 A1 | 6/2003 |
| EP | 2279016 A1 | 2/2011 |
| EP | 2366721 A1 | 9/2011 |
| EP | 2368523 A1 | 9/2011 |
| EP | 2404626 A2 | 1/2012 |
| EP | 2341955 B1 | 12/2012 |
| EP | 2529767 A2 | 12/2012 |
| EP | 2567682 A1 | 3/2013 |
| EP | 2567717 A1 | 3/2013 |
| EP | 2594299 A2 | 5/2013 |
| EP | 2601984 A2 | 6/2013 |
| EP | 2623137 A2 | 8/2013 |
| EP | 2367517 A4 | 9/2013 |
| EP | 3225261 A1 | 10/2017 |
| GB | 2195255 A | 4/1988 |
| GB | 2378392 A | 2/2003 |
| GB | 2389794 A | 12/2003 |
| GB | 2423019 A | 8/2006 |
| GB | 2489947 A | 10/2012 |
| GB | 2496310 A | 5/2013 |
| GB | 2524510 B | 2/2020 |
| IE | 20140129 A1 | 3/2016 |
| JP | S6257560 A | 3/1987 |
| JP | H09503923 A | 4/1997 |
| JP | 2006528038 A | 12/2006 |
| JP | 2007505678 A | 3/2007 |
| JP | 2008529618 A | 8/2008 |
| JP | 2009525087 A | 7/2009 |
| JP | 2009536851 A | 10/2009 |
| JP | 2011500170 A | 1/2011 |
| JP | 2011511128 A | 4/2011 |
| JP | 2011521740 A | 7/2011 |
| JP | 2011523575 A | 8/2011 |
| JP | 2011526798 A | 10/2011 |
| JP | 2012029791 A | 2/2012 |
| JP | 2012105840 A | 6/2012 |
| JP | 2012105841 A | 6/2012 |
| JP | 2014168573 A | 9/2014 |
| KR | 101333344 B1 | 11/2013 |
| RU | 1818103 A1 | 5/1993 |
| RU | 62504 U1 | 4/2007 |
| WO | WO-0185248 A1 | 11/2001 |
| WO | WO-0189392 A2 | 11/2001 |
| WO | WO-0205737 A1 | 1/2002 |
| WO | WO-03003948 A1 | 1/2003 |
| WO | WO-03049598 A2 | 6/2003 |
| WO | WO-2004018020 A1 | 3/2004 |
| WO | WO-2004037334 A1 | 5/2004 |
| WO | WO-2005046761 A1 | 5/2005 |
| WO | WO-2005105174 A1 | 11/2005 |
| WO | WO-2006041496 A1 | 4/2006 |
| WO | WO-2006046060 A2 | 5/2006 |
| WO | WO-2006100053 A2 | 9/2006 |
| WO | WO-2007030601 A2 | 3/2007 |
| WO | WO-2007120138 A2 | 10/2007 |

(56) References Cited

FOREIGN PATENT DOCUMENTS

| | | |
|---|---|---|
| WO | WO-2007133618 A2 | 11/2007 |
| WO | WO-2008027449 A2 | 3/2008 |
| WO | WO-2008039223 A1 | 4/2008 |
| WO | WO-2008039839 A2 | 4/2008 |
| WO | WO-2008064502 A1 | 6/2008 |
| WO | WO-2008091521 A2 | 7/2008 |
| WO | WO-2008104609 A1 | 9/2008 |
| WO | WO-2009019495 A1 | 2/2009 |
| WO | WO-2009071926 A1 | 6/2009 |
| WO | WO-2009071933 A2 | 6/2009 |
| WO | WO-2009093116 A1 | 7/2009 |
| WO | WO-2009112062 A1 | 9/2009 |
| WO | WO-2009112848 A1 | 9/2009 |
| WO | WO-2009114624 A2 | 9/2009 |
| WO | WO-2009156709 A1 | 12/2009 |
| WO | WO-2009158125 A1 | 12/2009 |
| WO | WO-2009158126 A1 | 12/2009 |
| WO | WO-2009158132 A1 | 12/2009 |
| WO | WO-2010033725 A2 | 3/2010 |
| WO | WO-2010051073 A1 | 5/2010 |
| WO | WO-2010059612 A2 | 5/2010 |
| WO | WO-2010075180 A2 | 7/2010 |
| WO | WO-2010092334 A1 | 8/2010 |
| WO | WO-2010097570 A1 | 9/2010 |
| WO | WO-2011023384 A1 | 3/2011 |
| WO | WO-2011087871 A2 | 7/2011 |
| WO | WO-2011091169 A1 | 7/2011 |
| WO | WO-2011106722 A1 | 9/2011 |
| WO | WO-2011116691 A1 | 9/2011 |
| WO | WO-2011135284 A1 | 11/2011 |
| WO | WO-2011135286 A1 | 11/2011 |
| WO | WO-2011135287 A1 | 11/2011 |
| WO | WO-2011137230 A1 | 11/2011 |
| WO | WO-2011144888 A1 | 11/2011 |
| WO | WO-2012021553 A1 | 2/2012 |
| WO | WO-2012038727 A2 | 3/2012 |
| WO | WO-2012057882 A1 | 5/2012 |
| WO | WO-2012069793 A1 | 5/2012 |
| WO | WO-2012069794 A1 | 5/2012 |
| WO | WO-2012082716 A2 | 6/2012 |
| WO | WO-2012082876 A1 | 6/2012 |
| WO | WO-2012106590 A2 | 8/2012 |
| WO | WO-2012112204 A1 | 8/2012 |
| WO | WO-2012136707 A1 | 10/2012 |
| WO | WO-2012142471 A1 | 10/2012 |
| WO | WO-2012156655 A1 | 11/2012 |
| WO | WO-2012168678 A1 | 12/2012 |
| WO | WO-2013007973 A2 | 1/2013 |
| WO | WO-2013012381 A1 | 1/2013 |
| WO | WO-2013043258 A1 | 3/2013 |
| WO | WO-2013071243 A2 | 5/2013 |
| WO | WO-2013076450 A1 | 5/2013 |
| WO | WO-2013079447 A1 | 6/2013 |
| WO | WO-2013079947 A1 | 6/2013 |
| WO | WO-2013090810 A1 | 6/2013 |
| WO | WO-2013175309 A1 | 11/2013 |
| WO | WO-2013175310 A2 | 11/2013 |
| WO | WO-2014013348 A2 | 1/2014 |
| WO | WO-2014014842 A1 | 1/2014 |
| WO | WO-2014014871 A1 | 1/2014 |
| WO | WO-2014014922 A1 | 1/2014 |
| WO | WO-2014020440 A1 | 2/2014 |
| WO | WO-2014024048 A1 | 2/2014 |
| WO | WO-2014140578 A1 | 9/2014 |
| WO | WO-2014158526 A1 | 10/2014 |
| WO | WO-2014165275 A1 | 10/2014 |
| WO | WO-2014178945 A1 | 11/2014 |
| WO | WO-2014194786 A1 | 12/2014 |
| WO | WO-2015008054 A1 | 1/2015 |
| WO | WO-2015061352 A2 | 4/2015 |
| WO | WO-2015109359 A1 | 7/2015 |
| WO | WO-2015110409 A1 | 7/2015 |
| WO | WO-2015110410 A1 | 7/2015 |
| WO | WO-2015169637 A1 | 11/2015 |
| WO | WO-2015172108 A1 | 11/2015 |
| WO | WO-2015193257 A1 | 12/2015 |
| WO | WO-2016018448 A1 | 2/2016 |

OTHER PUBLICATIONS

"Definition of Adhere," The Free Dictionary, accessed on Mar. 23, 2017 from http://www.thefreedictionary.com/adhere, 6 pages.
"Definition of Oculiform," Webster's Revised Unabridged Dictionary, accessed from The Free Dictionary on May 30, 2018 from URL: https://www.thefreedictionary.com/Oculiform, 1913, 1 page.
"Definition of Throughout," Merriam-Webster Dictionary, accessed on Aug. 29, 2017 from https://www.merriam-webster.com/dictionary/throughout, 11 pages.
Hougaard, et al., "The Open Abdomen: Temporary Closure with a Modified Negative Pressure Therapy Technique," International Wound Journal, ISSN 1742-4801, 2014, pp. 13-16.
International Preliminary Report on Patentability for Application No. PCT/US2014/061627, mailed on Apr. 26, 2016, 14 pages.
International Search Report and Written Opinion for Application No. PCT/GB2014/050786, mailed on Jun. 12, 2014, 14 pages.
International Search Report and Written Opinion for Application No. PCT/US2014/061627, mailed on Aug. 13, 2015, 22 pages.
Kapischke M., et al., "Self-Fixating Mesh for the Lichtenstein Procedure—a Prestudy," Langenbeck's Arch Surg, 2010, vol. 395, pp. 317-322.
Argenta L C., et al., "Vacuum-Assisted Closure: A New Method for Wound Control and Treatment: Clinical Experience," Annals of Plastic Surgery, vol. 38 (6), Jun. 1997, pp. 563-577.
Armstrong D.G., et al., "Negative Pressure Wound Therapy After Partial Diabetic Foot Amputation: A Multicentre, Randomised Controlled Trial," Lancet, Nov. 12, 2005, vol. 366 (9498), pp. 1704-1710.
Atkins B.Z., et al., "Does Negative Pressure Wound Therapy Have a Role in Preventing Poststernotomy Wound Complications?," Surgical Innovation, vol. 16 (2), Jun. 2009, pp. 140-146.
Bengezi O., et al., "Elevation as a Treatment for Fasciotomy Wound Closure," Canadian Society of Plastic Surgeons, 2013, vol. 21 (3), pp. 192-194.
Blume P.A., et al., "Comparison of Negative Pressure Wound Therapy Using Vacuum-Assisted Closure With Advanced Moist Wound Therapy In the Treatment of Diabetic Foot Ulcers: A Multicenter Randomized Controlled Trial," Diabetes Care, Apr. 2008, vol. 31 (4), pp. 631-636.
Easterlin B., et al., "A Novel Technique of Vacuum-Assisted Wound Closure That Functions as a Delayed Primary Closure," Wounds, Dec. 2007, vol. 19 (12), pp. 331-333.
Gomoll A.H., et al., "Incisional Vacuum-Assisted Closure Therapy," Journal of Orthopedic Trauma, Nov.-Dec. 2006, vol. 20 (10), pp. 705-709.
Grauhan O., et al., "Prevention of Poststernotomy Wound Infections In Obese Patients By Negative Pressure Wound Therapy," The Journal of Thoracic and Cardiovascular Surgery, May 2013, vol. 145 (5), pp. 1387-1392.
Kaplan M., et al., "Early Intervention of Negative Pressure Wound Therapy Using Vacuum-Assisted Closure In Trauma Patients: Impact on Hospital Length of Stay And Cost," Advances in Skin & Wound Care, Mar. 2009, vol. 22 (3), pp. 128-132.
Masden D., et al., "Negative Pressure Wound Therapy for At-Risk Surgical Closures In Patients With Multiple Comorbidities: A Prospective Randomized Controlled Study," Annals of Surgery, Jun. 2012, vol. 255 (6), pp. 1043-1047.
Pachowsky M., et al., "Negative Pressure Wound Therapy to Prevent Seromas and Treat Surgical Incisions After Total Hip Arthroplasty," International Orthopaedics, Apr. 2012, vol. 36 (4), pp. 719-722.
Pollock T.A., et al., "Progressive Tension Sutures in Abdominoplasty: A Review of 597 Consecutive Cases," Aesthetic Surgery Journal, Aug. 2012, vol. 32 (6), pp. 729-742.
Reddix R.N., Jr., et al., "Incisional Vacuum-Assisted Wound Closure in Morbidly Obese Patients Undergoing Acetabular Fracture Surgery," The American Journal of Orthopedics, Sep. 2009, pp. 446-449.

(56) References Cited

OTHER PUBLICATIONS

Reddix R.N., Jr., et al., "The Effect of Incisional Negative Pressure Therapy on Wound Complications After Acetabular Fracture Surgery," Journal of Surgical Orthopaedic Advances, vol. 19, No. 2, 2010, pp. 91-97.

Stannard J.P., et al., "Incisional Negative Pressure Wound Therapy After High-Risk Lower Extremity Fractures," J Orthop Trauma, vol. 26, No. 1, Jan. 2012, pp. 37-42.

Stannard J.P., et al., "Negative Pressure Wound Therapy to Treat Hematomas and Surgical Incisions Following High-Energy Trauma," The Journal of Trauma, Injury, Infection, and Critical Care, vol. 60, No. 6, Jun. 2006, pp. 1301-1306.

\* cited by examiner

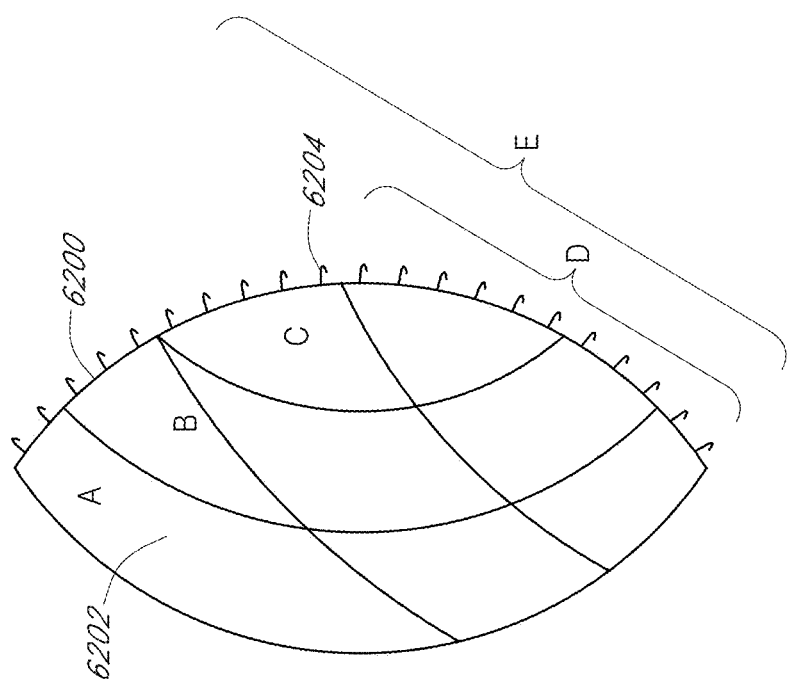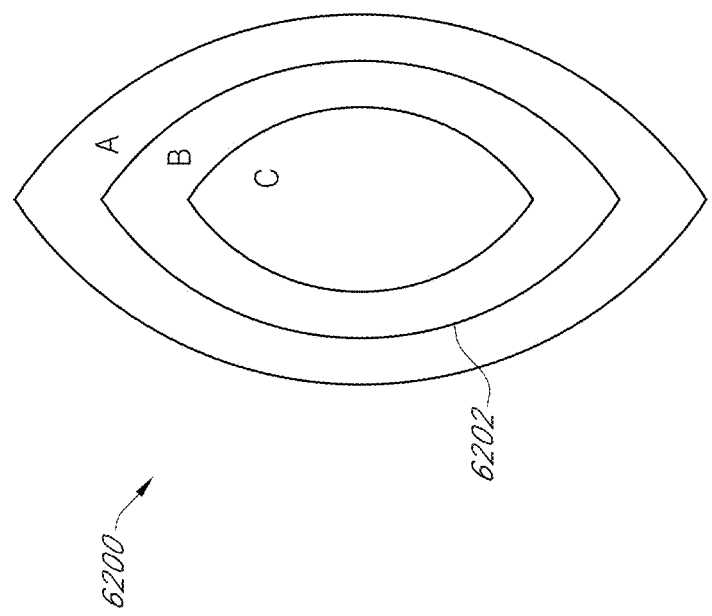
FIG. 19B

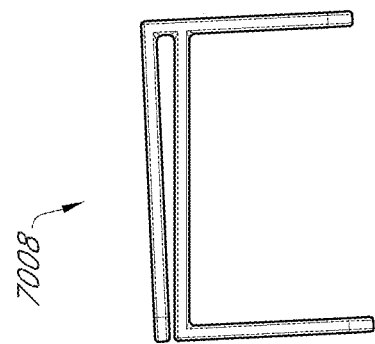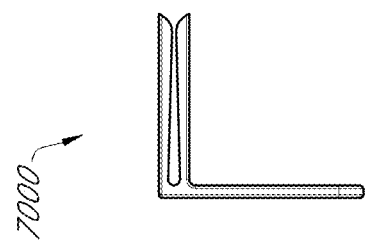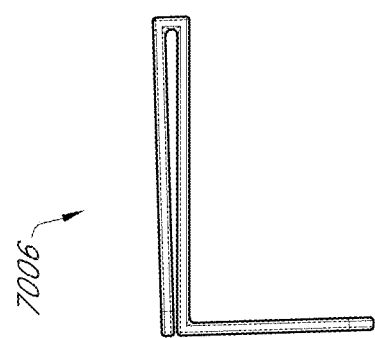
FIG. 52E

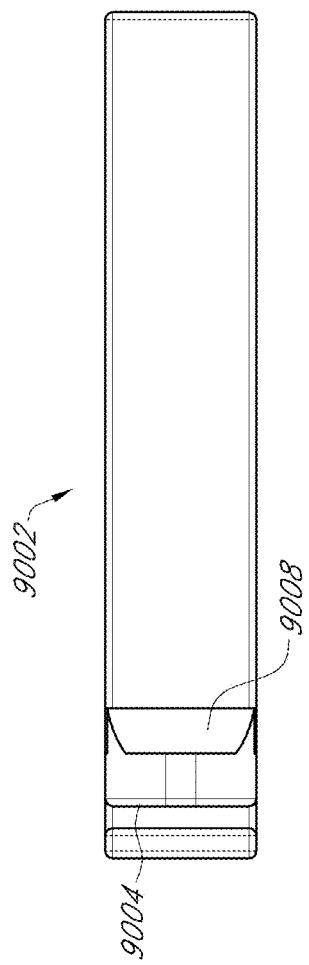

NEGATIVE PRESSURE WOUND CLOSURE DEVICE

CROSS-REFERENCE TO RELATED APPLICATIONS

This application is a continuation of U.S. patent application Ser. No. 16/868,379, filed May 6, 2020, which is a continuation of U.S. patent application Ser. No. 15/030,841, filed Apr. 20, 2016 and now U.S. Pat. No. 10,660,992, which is a U.S. National Phase of the PCT International Application No. PCT/US2014/061627, filed Oct. 21, 2014, entitled NEGATIVE PRESSURE WOUND CLOSURE DEVICE, which claims the benefit of U.S. Provisional Application No. 61/893,821, filed Oct. 21, 2013, entitled TISSUE ANCHORING DEVICE, U.S. Provisional Application No. 61/913,210, filed Dec. 6, 2013, entitled TEARABLE WOUND TREATMENT AND CLOSURE DEVICES, U.S. Provisional Application No. 61/930,414, filed Jan. 22, 2014, entitled NEGATIVE PRESSURE WOUND CLOSURE DEVICE, U.S. Provisional Application No. 61/930,436, filed Jan. 22, 2014, entitled NEGATIVE PRESSURE WOUND CLOSURE DEVICE, U.S. Provisional Application No. 61/930,426, filed Jan. 22, 2014, entitled NEGATIVE PRESSURE WOUND CLOSURE DEVICE, U.S. Provisional Application No. 61/930,427, filed Jan. 22, 2014, entitled NEGATIVE PRESSURE WOUND CLOSURE DEVICE, U.S. Provisional Application No. 61/930,423, filed Jan. 22, 2014, entitled NEGATIVE PRESSURE WOUND CLOSURE DEVICE, U.S. Provisional Application No. 61/930,913, filed Jan. 23, 2014, entitled NEGATIVE PRESSURE WOUND CLOSURE DEVICE, and U.S. Provisional Application No. 62/051,834, filed Sep. 17, 2014, entitled NEGATIVE PRESSURE WOUND CLOSURE DEVICE. The contents of the aforementioned applications are hereby incorporated by reference in their entireties as if fully set forth herein. The benefit of priority to the foregoing applications is claimed under the appropriate legal basis, including, without limitation, under 35 U.S.C. § 119 (e).

BACKGROUND OF THE INVENTION

Field of the Invention

This application describes embodiments of apparatuses, methods, and systems for the treatment of wounds, specifically to aid in the closure of large wounds, in conjunction with the administration of negative pressure.

Description of the Related Art

Negative pressure wound therapy has been used in the treatment of wounds, and in many cases can improve the rate of healing while also removing exudates and other deleterious substances from the wound site.

Abdominal compartment syndrome is caused by fluid accumulation in the peritoneal space due to edema and other such causes, and results in greatly increased intra-abdominal pressure that may cause organ failure eventually resulting in death. Causes may include sepsis or severe trauma. Treatment of abdominal compartment syndrome may require an abdominal incision to permit decompression of the abdominal space, and as such, a large wound may be created onto the patient. Closure of this wound, while minimizing the risk of secondary infections and other complications, and after the underlying edema has subsided, then becomes a priority. However, acute open abdominal conditions may be caused by other reasons in addition to compartment syndrome, as described further below.

Other large or incisional wounds, either as a result of surgery, trauma, or other conditions, may also require closure. For example, wound resulting from sterniotomies, fasciotomies, and other abdominal wounds may require closure. Wound dehiscence of existing wounds is another complication that may arise, possibly due to incomplete underlying fascial closure, or secondary factors such as infection.

Existing negative pressure treatment systems, while permitting eventual wound closure, still require lengthy closure times. Although these may be combined with other tissue securement means, such as sutures, there is also a risk that underlying muscular and fascial tissue is not appropriately reapproximated so as to permit complete wound closure. Further, when foam or other wound fillers are inserted into the wound, the application of negative pressure to the wound and the foam may cause atmospheric pressure to bear down onto the wound, compressing the foam downward and outward against the margins of the wound. This downward compression of the wound filler slows the healing process and slows or prevents the joining of wound margins. Additionally, inflammation of the fascia in the form of certain types of fasciitis can lead to rapid and excessive tissue loss, potentially meriting the need for more advanced negative pressure treatment systems. Accordingly, there is a need to provide for an improved apparatus, method, and system for the treatment and closure of wounds.

SUMMARY OF THE INVENTION

Embodiments of the present invention relate to negative pressure wound closure devices, methods, and systems that facilitate closure of a wound. It will be understood by one of skill in the art that the wounds described herein this specification may encompass any wound, and are not limited to a particular location or type of wound. The devices, methods, and systems may operate to reduce the need for repetitive replacement of wound filler material currently employed and can advance the rate of healing. The devices, methods, and systems may be simultaneously used with negative pressure to remove wound fluids.

In one embodiment, an apparatus for treating a wound with negative pressure wound therapy may comprise:
  a stabilizing structure for insertion into or over a wound, the stabilizing structure configured to collapse under negative pressure, the stabilizing structure having a length extending along a central longitudinal axis of the stabilizing structure, a width transverse to the length extending along a central transverse axis of the stabilizing structure, and a thickness transverse to the length and the width, wherein the length and width are greater than the thickness, and wherein the stabilizing structure comprises:
    a first side and a second side extending the length of the stabilizing structure, and a third side and a fourth side extending the width of the stabilizing structure, wherein the first side is opposite the second side and the third side is opposite the fourth side, and wherein the first side and the second side are curved or bent outwardly relative to the central longitudinal axis to provide an outer perimeter of the stabilizing structure with an at least partially elliptical shape;
    a plurality of elongate strips extending the length of the stabilizing structure from the third side to the fourth side, wherein the plurality of elongate strips comprise outermost elongate strips defining the first and second sides of the stabilizing structure and a plurality of inner elongate strips positioned between the outermost elongate strips;

a plurality of intervening members connecting the elongate strips, wherein the plurality of intervening members are configured to pivot relative to the strips to allow the plurality of elongate strips to collapse relative to one another; and a plurality of cells provided side-by-side in a horizontal plane parallel to the length and width of the stabilizing structure, each cell defined by a plurality of walls extending in a vertical direction perpendicular to the horizontal plane and formed by either the elongate strips or the intervening members, each cell having a top end and a bottom end with an opening extending through the top and bottom ends;

wherein the stabilizing structure is configured to collapse more in the horizontal plane than in the vertical direction by collapsing the plurality of cells.

In some embodiments, the length of the stabilizing structure is greater than the width of the stabilizing structure. The third and fourth sides may form a zig-zag shape defined by intervening members between adjacent elongate strips. The stabilizing structure may be symmetrical about the central longitudinal axis. The stabilizing structure may be symmetrical about the central transverse axis. Some embodiments may call for a straight, central inner elongate strip provided along the central longitudinal axis of the stabilizing structure. In certain embodiments, the apparatus may comprise a plurality of straight inner elongate strips. The apparatus may comprise inner elongate strips provided on opposite sides of the longitudinal axis that are curved or bent outwardly relative to the longitudinal axis. In certain embodiments, each of the elongate strips may be arranged in semi-parallel. In some embodiments, some of the cells are diamond-shaped. Some of the diamond-shaped cells may be subdivided from larger diamond-shaped cells. In some embodiments, some of the cells are parallelpiped-shaped. In certain embodiments, the stabilizing structure may comprise a plurality of cells having four sides, wherein the dimensions of each of the cells having four sides is defined by the formula a+b=c+d, wherein a, b, c and d are the lengths of individual sides of the cell, and wherein lengths a and c are provided on adjacent elongate strips defining the cell and lengths b and d are provided on adjacent intervening members defining the cell. In some embodiments, the lengths of the cells along an elongate strip are progressively longer toward the central transverse axis. In certain embodiments, a lower portion of the stabilizing structure is concave. In some embodiments, an upper portion of the stabilizing structure is convex. In some embodiments, the stabilizing structure may be is tearable. The stabilizing structure may further comprise weakened sections, the weakened sections configured to be torn.

In another embodiment, an apparatus for treating a wound with negative pressure wound therapy comprises:

a stabilizing structure for insertion into or over a wound, the stabilizing structure configured to collapse under negative pressure;

wherein the stabilizing structure has a concave surface along at least a lower portion of the stabilizing structure.

The stabilizing structure may further comprise:

a plurality of cells provided side-by-side, each cell defined by one or more walls, each cell having a top end and a bottom end with an opening extending through the top and bottom ends;

wherein the stabilizing structure is configured to collapse by collapsing one or more cells.

In some embodiments, the stabilizing structure may have an outer perimeter that defines an at least partially elliptical shape.

In another embodiment, an apparatus for treating a wound with negative pressure wound therapy comprises:

a stabilizing structure for insertion into or over a wound, the stabilizing structure configured to collapse under negative pressure, wherein the stabilizing structure comprises:

a plurality of cells provided side-by-side, each cell defined by one or more walls, each cell having a top end and a bottom end with an opening extending through the top and bottom ends;

wherein the stabilizing structure is configured to collapse by collapsing one or more cells;

wherein the stabilizing structure has an outer perimeter defining an at least partially elliptical shape.

In certain embodiments, the stabilizing structure comprises:

a plurality of elongate strips; and a plurality of intervening members connecting the elongate strips, wherein the plurality of intervening members are configured to pivot relative to the strips to allow the plurality of elongate strips to collapse relative to one another.

The stabilizing structure may comprise one or more rows of cells between adjacent strips configured to collapse in a first direction, and one or more rows of cells between adjacent strips configured to collapse in a second direction opposite the first direction. The elongate strips can be parallel to each other and/or they may be curved along their lengths. In certain embodiments, at least some of the elongate strips may be curved along their lengths outward away from a center of the stabilizing structure. Some of the elongate strips may be connected at their ends. Some of the elongate strips may have regions of increased flexibility to allow for lengthening or shortening of the elongate strips. In certain embodiments, a lower portion of the stabilizing structure may be concave in a first horizontal direction and a second horizontal direction perpendicular to the first horizontal direction. In some embodiments, an upper portion of the stabilizing structure is convex along at least an upper portion of the stabilizing structure. An upper portion of the stabilizing structure may be convex in a first horizontal direction and a second horizontal direction perpendicular to the first horizontal direction. In certain embodiments, the stabilizing structure may be pre-formed to have either or both of a concave lower surface and a convex upper surface. The stabilizing structure can have an outer perimeter defining a bi-elliptical shape. In some embodiments, the stabilizing structure is configured to be placed into an abdominal wound and conform to the shape of internal organs. In some embodiments, the apparatus may comprise one or more wound covers configured to be placed over the stabilizing structure to maintain negative pressure over the wound. The apparatus may further comprise a negative pressure port configured to deliver negative pressure to the stabilizing structure to cause the stabilizing structure to collapse. In certain embodiments, the apparatus can comprise a negative pressure source configured to deliver negative pressure to the stabilizing structure to cause the stabilizing structure to collapse.

In another embodiment, an apparatus for treating a wound comprises:
- a wound filler comprising an initial elliptical shape having a first curved side and a second curved side opposite the first curved side; and
- a first plurality of designated pre-cut lines formed in the wound filler, wherein each of said pre-cut lines intersects the second curved side of the wound filler and has a curvature following that of the first curved side such that removal of a portion of the wound filler along one of the designated pre-cut lines provides a remaining wound filler having a smaller elliptical shape than the initial elliptical shape.

The wound filler may comprise a porous material. In some embodiments, the wound filler can comprise a stabilizing structure. Some embodiments may call for the apparatus to further comprise a second plurality of designated pre-cut lines that intersect with the first plurality of designated pre-cut lines, the first curved side and the second curved side. In certain embodiments, the apparatus may further comprise anchors provided on the second curved side.

In another embodiment, a wound closure device may comprise:
- a stabilizing structure for insertion into a wound, the stabilizing structure having a length, a width transverse to the length and a thickness transverse to the length and the width, wherein the length and width are greater than the thickness, and wherein the stabilizing structure comprises an outer perimeter comprising at least one outer wall, and wherein the stabilizing structure is configured to collapse more in a horizontal plane parallel to the length and width of the stabilizing structure than in a vertical plane perpendicular to the horizontal plane; and
- at least one stabilizing clip attachable to the outer wall of the stabilizing structure, the stabilizing clip configured to extend outward into the surrounding tissue and prevent the stabilizing structure from lifting upwards in a direction out of the wound.

In some embodiments, the stabilizing structure may comprise a plurality of cells provided side-by-side, each cell defined by one or more walls, each cell having a top end and a bottom end with an opening extending through the top and bottom ends, and wherein the stabilizing structure is configured to collapse by collapsing one or more cells. The junctions between the walls of the stabilizing structure can be thinned and configured to rotate.

In some embodiments, the stabilizing structure may comprise:
- a plurality of elongate strips; and
- a plurality of intervening members connecting the elongate strips, wherein the plurality of intervening members are configured to pivot relative to the strips to allow the plurality of elongate strips to collapse relative to one another.

The stabilizing structure may have a first side and a second side extending along the length of the stabilizing structure, and a third side and a fourth side extending along the width of the stabilizing structure, wherein the first side is opposite the second side and the third side is opposite the fourth side. In some embodiments, the first and second sides define flat surfaces that are parallel to each other. The first and second sides may define a curved shape. The third and fourth sides may comprise a zig-zag shape. In some embodiments the stabilizing clip is rigid. In certain embodiments there may be more than one stabilizing clip. The stabilizing clip may comprise an attachment portion configured to clip to a wall of the stabilizing structure and a securing portion that extends outward from the attachment portion in a horizontal direction. The securing portion may extend from a lower end of the attachment portion. The securing portion may extend from an upper end of the attachment portion. In some embodiments, the stabilizing clip comprises a first securing portion extending outward from an upper end of the attachment portion and a second securing portion extending outward from a lower end of the attachment portion. The stabilizing clip may be attached to the outer wall of the stabilizing structure. The stabilizing clip can comprise a recess where the securing portion extends from the attachment portion. In some embodiments, the attachment portion is configured to loop over the outer wall of the stabilizing structure, and the attachment portion comprises a foot at an end of the loop of the attachment portion. The securing portion can comprise grippers configured to extend into the surrounding tissue.

In another embodiment, a method of treating a wound comprises:
- providing a stabilizing structure, the stabilizing structure defining an initial outer perimeter;
- sizing the stabilizing structure to a desired dimension, wherein after sizing the stabilizing structure has a final outer perimeter;
- attaching a stabilizing clip to the outside of the stabilizing structure, the stabilizing clip comprising a securing portion extending horizontally outward from the stabilizing structure; and
- inserting the stabilizing structure into the wound, wherein after insertion the securing portion of the stabilizing clip engages tissue to prevent the stabilizing structure from lifting upwards in a direction out of the wound.

In some embodiments, the method may further comprise:
- covering the stabilizing structure with at least one drape sealed to skin surrounding the wound; and
- applying negative pressure through the at least one drape to the wound via a source of negative pressure, wherein the application of negative pressure causes the stabilizing structure to horizontally collapse.

The method may comprise inserting a tissue protection layer over the wound before inserting the stabilizing structure. In some embodiments, the securing portion of the stabilizing clip extends below tissue surrounding the stabilizing structure. The securing portion of the stabilizing clip may comprise at least one gripper configured to extend into tissue surrounding the stabilizing structure. The stabilizing clip may be attached to the stabilizing structure with an attachment portion that loops over the outside of the stabilizing structure, the attachment portion comprising a foot at an end of the loop of the attachment portion. The stabilizing clip can comprise a recess where the securing portion extends horizontally from the stabilizing clip. In certain embodiments a plurality of stabilizing clips may be attached to the outside of the stabilizing structure.

In another embodiment, a wound closure device comprises:
- a stabilizing structure;
- a porous layer configured to at least partially surround a perimeter of the stabilizing structure; and
- an anchoring layer comprising anchors configured to at least partially surround the layer of porous material when the layer of porous material at least partially surrounds the stabilizing structure, wherein the anchors are configured to attach to tissues within the wound.

In some embodiments, the anchors may comprise any type of anchor substantially described herein this application. In certain embodiments, the wound closure device can comprise layers of foam above and below the stabilizing structure. The anchors can comprise at least two different types of anchors as described herein this application. In certain embodiments, the anchoring layer comprises a plurality of bands comprising different types of anchors as described herein this application.

In some embodiments, the anchoring layer may comprise a first band of a first type of anchors configured to be positioned above a second band of a second type of anchors. In some embodiments, each band comprises between 1 and 30 individual rows of anchors. The anchoring layer can comprise a plurality of alternating bands of different types of anchors as substantially described herein this specification. In some embodiments, the anchors are biodegradable. The anchors can comprise any of the biodegradable materials substantially described herein this specification. In further embodiments, the anchors may be configured to penetrate any of the tissue types as substantially described herein this specification.

In another embodiment, a method of closing a wound comprises: shaping a first layer of foam into the shape of the wound;
  placing the first layer of foam in the wound;
  shaping a stabilizing structure into the shape of the wound;
  attaching a ribbon of foam to the perimeter of the stabilizing structure to at least partially surround the perimeter of the stabilizing structure;
  attaching an anchoring layer comprising anchors to the foam ribbon;
  placing the stabilizing structure with the ribbon of foam and the anchoring layer into the wound, wherein placing the stabilizing structure comprises first horizontally compressing the stabilizing structure and allowing the stabilizing structure to expand once within the wound to cause the anchors to engage tissue;
  covering the stabilizing structure with a second layer of foam;
  covering the stabilizing structure with at least one drape sealed to skin surrounding the wound; and
  applying negative pressure through the at least one drape to the wound via a source of negative pressure, wherein the application of negative pressure causes the stabilizing structure to horizontally collapse with the anchors engaging tissue.

In another embodiment, a wound closure device comprises:
  a stabilizing structure for insertion into a wound, the stabilizing structure having a length, a width transverse to the length and a thickness transverse to the length and the width, wherein the length and width are greater than the thickness, and wherein the stabilizing structure comprises an outer perimeter comprising at least one outer wall;
  a first porous layer pre-attached to only part of the outer perimeter of the stabilizing structure; and
  a second porous layer separate from the first porous layer configured to be attached to a remaining outer perimeter of the stabilizing structure after the stabilizing structure has been appropriately sized.

In certain embodiments, the stabilizing structure may have a first side and a second side extending along the length of the stabilizing structure, and a third side and a fourth side extending along the width of the stabilizing structure, wherein the first side is opposite the second side and the third side is opposite the fourth side. In some embodiments, the first porous layer is pre-attached only to the first side and the third side. In particular embodiments, the wound closure device may further comprise a plurality of anchors attached to at least a portion of the porous layer pre-attached to only part of the outer perimeter of the stabilizing structure. The device may further comprise a plurality of anchors attached only to a portion of the first porous layer pre-attached to the first side. In some embodiments, the device may further comprise a plurality of anchors attached to at least a portion of the second porous layer. The stabilizing structure can comprise opposing sides that define flat surfaces that are parallel to each other, wherein the first porous layer is pre-attached to one of the parallel opposing sides. The stabilizing structure can comprise opposing sides having a straight, curved or zig-zag shape, wherein the first porous layer is pre-attached to one of the opposing sides having the straight, curved or zig-zag shape. In some embodiments, the stabilizing structure may have a constant thickness defined between upper and lower surfaces of the stabilizing structure.

In certain embodiments, the stabilizing structure may comprise:
  a plurality of cells provided side-by-side, each cell defined by one or more walls, each cell having a top end and a bottom end with an opening extending through the top and bottom ends;
  wherein the stabilizing structure is configured to collapse by collapsing one or more cells.

In particular embodiments, the stabilizing structure comprises:
  a plurality of elongate strips; and
  a plurality of intervening members connecting the elongate strips, wherein the plurality of intervening members are configured to pivot relative to the strips to allow the plurality of elongate strips to collapse relative to one another.

In further embodiments, the stabilizing structure may comprise one or more rows of cells between adjacent strips configured to collapse in a first direction, and one or more rows of cells between adjacent strips configured to collapse in a second direction opposite the first direction. The wound closure device may further comprise a porous layer attached to a lower surface of the stabilizing structure. In certain embodiments, the wound closure device may further comprise a porous layer attached to an upper surface of the stabilizing structure. In certain embodiments, the porous layer(s) attached to the lower and/or upper surface of the stabilizing structure comprises protrusions configured to extend into openings in the stabilizing structure. The length of the wound closure device may be greater than the width.

In another embodiment, a method of treating a wound, comprises:
  providing a stabilizing structure, the stabilizing structure defining an initial outer perimeter and having a first porous layer attached to only a portion of the initial outer perimeter;
  sizing the stabilizing structure to a desired dimension, wherein after sizing the stabilizing structure has a final outer perimeter that includes the portion of the initial outer perimeter having the first porous layer attached thereto, and an exposed portion where the first porous layer is not attached; and attaching a second porous layer to the exposed portion of the final outer perimeter;

inserting the stabilizing structure into the wound.

The first porous layer may comprise a plurality of anchors. In some embodiments, the second porous layer can comprise a plurality of anchors.

In some embodiments, the method can further comprise:

covering the stabilizing structure with at least one drape sealed to skin surrounding the wound; and applying negative pressure through the at least one drape to the wound via a source of negative pressure, wherein the application of negative pressure causes the stabilizing structure to horizontally collapse.

In certain embodiments, the stabilizing structure may have a porous layer attached to one or both of an upper and lower surface thereof. The method may further comprise inserting a tissue protection layer over the wound before inserting the stabilizing structure.

In another embodiment, a wound closure device comprises:

a stabilizing structure for insertion into a wound; and a porous layer configured to be attached to at least a portion of an outer perimeter of the stabilizing structure, wherein the porous layer comprises a lower lip portion configured to extend outwardly from the stabilizing structure beneath tissue surrounding the wound and an upper lip portion configured to extend outwardly from the stabilizing structure over tissue surrounding the wound.

The lower lip portion and the upper lip portion can comprise adhesive. The porous layer can comprises a plurality of anchors configured to engage tissue surrounding the wound. Some of the plurality of anchors may be provided on the lower lip portion and the upper lip portion. The lower lip may be configured to extend beneath the fascia. In certain embodiments, the upper lip is configured to extend over the dermis.

In another embodiment, a method of treating a wound comprises:

positioning a stabilizing structure as described herein this specification into a wound with the lower lip extending outwardly from the stabilizing structure beneath tissue surrounding the wound and the upper lip extending outwardly from the stabilizing structure over tissue surrounding the wound.

In particular embodiments, the method may further comprise:

covering the stabilizing structure with at least one drape sealed to skin surrounding the wound; and applying negative pressure through the at least one drape to the wound via a source of negative pressure, wherein the application of negative pressure causes the stabilizing structure to horizontally collapse.

The stabilizing structure can have a porous layer attached to one or both of an upper and lower surface thereof. In some embodiments, the method further comprises inserting a tissue protection layer over the wound before inserting the stabilizing structure.

In another embodiment, a wound closure device for negative pressure wound therapy comprises:

a stabilizing structure configured to collapse under negative pressure; and a mechanism configured to maintain the stabilizing structure in a collapsed configuration after negative pressure has been removed.

In certain embodiments, the stabilizing structure comprises:

a plurality of cells provided side-by-side, each cell defined by one or more walls, each cell having a top end and a bottom end with an opening extending through the top and bottom ends; and wherein the stabilizing structure is configured to collapse by collapsing one or more cells.

The stabilizing structure may comprise:

a plurality of elongate strips; and a plurality of intervening members connecting the elongate strips, wherein the plurality of intervening members are configured to pivot relative to the strips to allow the plurality of elongate strips to collapse relative to one another.

In certain embodiments, the mechanism comprises one or more latching members attached to one or more of the strips of the stabilizing structure, the latching members configured to latch onto an adjacent strip when the stabilizing structure moves to a collapsed position. The one or more latching members may comprise a latching element that latches to said adjacent strip. In certain embodiments, the latching element comprises multiple teeth, each of the teeth configured to latch onto said adjacent strip when the stabilizing structure is in a different collapsed or compressed position. The latching element may be disposed at an intermediate position along an elongate member of the latching member, the latching element configured to pass through an opening in said adjacent strip to latch the latching member to said adjacent strip. The device may further comprise a release mechanism comprising an arch portion interconnecting adjacent latching members, the arch portion configured to receive a force thereon to lift the latching members from engagement with said adjacent strip of the stabilizing structure. The mechanism can comprise one or more first latching members attached to one or more of the strips of the stabilizing structure and one or more second latching members attached to one or more of the intervening members of the stabilizing structure, the first latching members configured to contact the second latching members when the stabilizing structure moves to the collapsed configuration. The first latching members may extend at a non-perpendicular angle relative to their corresponding strips and wherein the second latching members extend at a non-perpendicular angle relative to their corresponding intervening members.

In another embodiment, a wound closure device for negative pressure wound therapy comprises:

a stabilizing structure configured to collapse under negative pressure, the stabilizing structure comprising:

a plurality of elongate strips; and a plurality of intervening members connecting the elongate strips, wherein the plurality of intervening members are configured to pivot relative to the strips to allow the plurality of elongate strips to collapse relative to one another; and a mechanism configured to maintain the stabilizing structure in a collapsed configuration after negative pressure has been removed, the mechanism comprising one or more latching members attached to one or more of the strips of the stabilizing structure, the latching members configured to latch onto an adjacent strip when the stabilizing structure moves to a collapsed configuration.

In certain embodiments, the one or more latching members comprise a latching element that latches to said adjacent strip. The latching element can comprise multiple teeth, each of the teeth configured to latch onto said adjacent strip when the stabilizing structure is in a different collapsed or compressed position. The latching element may be disposed at an intermediate position along an elongate member of the latching member, the latching element configured to pass through an opening in said adjacent strip to latch the latching member to said adjacent strip. In certain embodiments, the device may comprise a release mechanism comprising an arch portion interconnecting adjacent latching members, the arch portion configured to receive a force thereon to lift the latching members from engagement with said adjacent strip of the stabilizing structure.

In another embodiment, a wound closure device for negative pressure wound therapy comprises:
 a stabilizing structure configured to collapse under negative pressure, the stabilizing structure comprising:
  a plurality of elongate strips; and
  a plurality of intervening members connecting the elongate strips, wherein the plurality of intervening members are configured to pivot relative to the strips to allow the plurality of elongate strips to collapse relative to one another; and
 a mechanism configured to maintain the stabilizing structure in a collapsed configuration after negative pressure has been removed, the mechanism comprising one or more first latching members attached to one or more of the strips of the stabilizing structure and one or more second latching members attached to one or more of the intervening members of the stabilizing structure, the first latching members configured to contact the second latching members when the stabilizing structure moves to the collapsed configuration.

In some embodiments, the first latching members may extend at a non-perpendicular angle relative to their corresponding strips and the second latching members can extend at a non-perpendicular angle relative to their corresponding intervening members.

In another embodiment, a wound closure device for negative pressure wound therapy comprises:
 a stabilizing structure configured to collapse under negative pressure; and
 a support structure attached to the stabilizing structure, the support structure configured to at least partially prevent the collapse of the stabilizing structure.

In certain embodiments, the support structure is sized to prevent the collapse of the entire stabilizing structure. The support structure may be sized to prevent the collapse of a portion of the stabilizing structure, while another portion of the stabilizing structure collapses when under negative pressure.

In some embodiments, the support structure comprises:
 a plurality of support elements attachable to each other and configured to extend along a plane adjacent a top or bottom end of the stabilizing structure when attached thereto; and
 a plurality of inserts configured to extend into the stabilizing structure and bear against one or more surfaces of the stabilizing structure to at least partially prevent the collapse of the stabilizing structure.

Each of the support elements may comprise one or more frangible joint portions configured to allow a size of the support element to the adjusted. In certain embodiments, the support structure may comprise:
 a plurality of support elements configured to extend along a plane adjacent a top or bottom end of the stabilizing structure when attached thereto, each of the support elements having a plurality of inserts configured to extend into the stabilizing structure and bear against one or more surfaces of the stabilizing structure to at least partially prevent the collapse of the stabilizing structure,
 wherein the plurality of inserts are expandable via introduction of a fluid into the support structure.

Each of the support elements can comprise one or more seals configured to fluidly isolate a portion of the support structure from another portion of the support structure to allow adjustment in a size of the support structure.

In another embodiment, a wound closure device for negative pressure wound therapy comprises:
 a stabilizing structure configured to collapse under negative pressure; and
 a support structure attached to the stabilizing structure, the support structure comprising:
  a plurality of substantially rigid support elements attachable to each other and configured to extend along a plane adjacent a top or bottom end of the stabilizing structure when attached thereto, and
  a plurality of inserts configured to extend into the stabilizing structure
  and bear against one or more surfaces of the stabilizing structure, wherein the support structure is configured to at least partially prevent the collapse of the stabilizing structure.

In certain embodiments, each of the support elements comprises one or more frangible joint portions configured to allow a size of the support element to the adjusted.

In another embodiment, a wound closure device for negative pressure wound therapy comprises:
 a stabilizing structure configured to collapse under negative pressure; and
 a support structure attached to the stabilizing structure, the support structure comprising:
  a plurality of support elements configured to extend along a plane adjacent a top or bottom end of the stabilizing structure when attached thereto, each of the support elements having a plurality of inserts configured to extend into the stabilizing structure and bear against one or more surfaces of the stabilizing structure, the plurality of inserts being expandable via introduction of a fluid into the support structure,
  wherein the support structure is configured to at least partially prevent the collapse of the stabilizing structure.

In some embodiments, each of the support elements may comprise one or more seals configured to fluidly isolate a portion of the support structure from another portion of the support structure to allow adjustment in a size of the support structure.

In another embodiment, a wound closure device for negative pressure wound therapy comprises:
 a stabilizing structure configured to collapse under negative pressure, wherein the stabilizing structure comprises a plurality of cells defining a plurality of internal surfaces; and
 a porous layer, channels or grooves attached to at least some of the internal surfaces, such that removal of a portion of the stabilizing structure to size it for placement into a wound results in the structure having an outer perimeter including at least a portion thereof covered with the porous layer, channels or grooves.

The stabilizing structure may comprise a plurality of cells provided side-by-side, each cell defined by one or more vertical walls, each cell having a top end and a bottom end with an opening extending through the top and bottom ends, and wherein the porous layer, channels or grooves are attached to at least one or more of the vertical walls. A foam layer may be attached to at least some of the internal surfaces. An elastomer layer may be attached to at least some of the internal surfaces. The wound therapy device may further comprise a porous layer, channels or grooves attached to at least a portion of an outer perimeter of the stabilizing structure.

In another embodiment, a method of treating a wound comprises:
   providing a stabilizing structure, the stabilizing structure defining an initial outer perimeter and having internal surfaces at least partially covered by a porous layer, channels or grooves; and
   sizing the stabilizing structure to a desired dimension, wherein after sizing the stabilizing structure has a final outer perimeter that includes the internal surfaces covered by the porous layer, channels or grooves.

In another embodiment, a wound closure device for negative pressure wound therapy comprises:
   a stabilizing structure configured to collapse under negative pressure, wherein the stabilizing structure comprises a plurality of cells defining a plurality of internal surfaces; and
   a porous layer, channels or grooves attached to or within at least a portion of some of the internal surfaces, such that removal of a portion of the stabilizing structure to size it for placement into a wound results in the structure having either:
      an outer perimeter including at least a portion thereof covered with the porous layer, channels or grooves;
      one or more internal surfaces of the cells including at least a portion thereof covered with the porous layer, channels or grooves; or
      both the one or more internal surfaces of the cells and outer perimeter including at least a portion thereof covered with the porous layer, channels or grooves.

The stabilizing structure may comprise a plurality of cells provided side-by-side, each cell defined by one or more vertical walls, each cell having a top end and a bottom end with an opening extending through the top and bottom ends, and wherein the porous layer, channels or grooves are attached to at least one or more of the vertical walls. A foam layer may be attached to at least some of the internal surfaces. In some embodiments, a wicking or acquisition distribution layer (ADL) can be attached to at least some of the internal surfaces. An elastomer layer may be attached to at least some of the internal surfaces. In certain embodiments, the device may further comprise a porous layer, channels or grooves attached to at least a portion of an outer perimeter of the stabilizing structure. In one embodiment, the porous layer, channels or grooves extend generally vertically between a bottom end of the cell and a top end of the cell. The porous layer, channel or grooves are configured to guide fluid therethrough (e.g., act as a conduit for fluid, such as wound exudate).

In one embodiment, the porous layer, channels or grooves can be disposed on at least a portion of one internal surface of the one or more cells of the stabilizing structure. For example, in an embodiment of a stabilizing structure that comprises cells that can be considered to include four quadrants, the porous layer, channels or grooves are disposed on or in one quadrant of the cell. In one embodiment, the porous layer, channels or grooves are disposed so as to not restrict movement of the one or more walls of the cell as the cell collapses when the stabilizing structure moves to a collapsed position, such as during the application of negative pressure thereto. For example, where the cell is defined by two strips and two intervening members, the porous layer, channels or grooves can be disposed on a surface of an intervening member or a strip that defines an obtuse angle as the cell collapses, thereby avoiding restricting the collapsing movement of the cell.

In one embodiment, the porous layer, channels or grooves can be disposed on medially-facing surfaces of the one or more cells of the stabilizing structure, such that when the size of the stabilizing structure is adjusted (e.g., by cutting one or more strips and/or intervening members) to better fit the wound site, the laterally-facing surfaces of the one or more cells of the stabilizing structure can have a substantially flat or planar, and in some embodiments smooth, surface. In one embodiment, anchoring members (e.g., an anchoring layer) can be attached to said laterally-facing surfaces after the size of the stabilizing structure has been adjusted.

In another embodiment, a wound closure device for negative pressure wound therapy comprises:
   a stabilizing structure configured to collapse under negative pressure, wherein the stabilizing structure comprises a plurality of cells, each of the cells defined by one or more vertical walls with a medial surface and a lateral surface; and
   a porous layer, channels or grooves disposed on at least a portion of the medial surface, such that removal of a portion of the stabilizing structure to size it for placement into a wound results in the structure still retaining one or more medial surfaces with said porous layer, channels or grooves in the resized stabilizing structure.

In some embodiments, the porous layer, channels or grooves may be disposed on at least a portion of the medial surface such that the porous layer, channels or grooves do not restrict movement of the cells toward a collapsed position when the stabilizing structure collapses under negative pressure. The one or more vertical walls may comprise a hydrophilic material. In certain embodiments, the device can further comprise one or more anchors disposed on at least a portion of the lateral surface, such that removal of the portion of the stabilizing structure to size it for placement into a wound results in the structure still retaining one or more lateral surfaces with said one or more anchors in the resized stabilizing structure.

In another embodiment, a method of treating a wound comprises:
   providing a stabilizing structure, the stabilizing structure defining an initial outer perimeter and comprising a plurality of cells having medial and lateral internal surfaces, wherein at least some of the internal surfaces are at least partially covered by a porous layer, channels or grooves; and
   sizing the stabilizing structure to a desired dimension, wherein after sizing the stabilizing structure includes cells having internal surfaces covered by the porous layer, channels or grooves.

In another embodiment, a porous pad for the treatment of wounds using negative pressure comprises:
   a porous material suitable for channeling wound exudate from a wound site and negative pressure to the wound site;
   a plurality of stabilizing structures at least partially embedded within the porous material comprising a plurality of cells provided side-by-side in a plane, wherein the stabilizing structures are configured to collapse more within the plane than along the direction perpendicular to the plane; and wherein the pad is dimensioned to have a generally planar shape with a thickness less than the width and length, wherein the pad comprises at least one cut or perforation extending through at least a portion of the thickness of the pad dividing the pad into a plurality of regions at least of two of which contain a stabilizing structure, wherein at least one of the regions is detachable, the cut or perforation defining a pad section detachable from the pad to modify the size of the pad.

In some embodiments, the pad may comprise an open-celled foam. The pad can comprise a polyurethane foam. In some embodiments, the foam may be hydrophobic, hydrophilic, open-celled, close-celled, mixed open and close-celled, and/or reticulated. Certain embodiments may call for the foam to comprise polyvinyl alcohol, polyurethane, polyester, silicone, and/or other suitable materials. The pad may comprise at least two arcuate cuts or perforations extending along the pad length, and at least two arcuate cuts or perforations extending along the pad width. In some embodiments, the pad can comprise a plurality of outer cuts or perforations having an elliptical shape and a plurality of inner cuts or perforations having a similar elliptical shape. In certain embodiments, the porous pad further comprises a plurality of intermediate cuts or perforations between the outer cuts and the inner cuts or perforations, at least some of the intermediate cuts or perforations extending generally lengthwise across the pad and at least some of the intermediate cuts or perforations extending generally widthwise across the pad. The pad may comprise a plurality of concentric cuts or perforations.

In certain embodiments, the pad may comprise a three-dimensional structure having a plurality of cuts or perforations in the x, y and z dimensions. In certain embodiments, the pad may comprise at least two stabilizing structures spaced along the height of the pad. In some embodiments, the stabilizing structures can be constructed from a material selected from the group consisting of silicone, polyurethanes, flexible plastics, rigid plastics, and foam. In some embodiments, the cells of the one or more stabilizing structures may comprise a plurality of sizes. Alternatively, all of the cells of the stabilizing structures are identical. In some cases, one or more of the cells may be differently shaped from other cells. In certain embodiments, the shape of each cell may be selected from the group consisting of square, diamond, oblong, oval, and parallelepiped.

In some embodiments, the one or more stabilizing structures are configured to collapse in a plurality of directions. The porous pad may comprise at least one stabilizing structure comprising a plurality of planar support structures connected by spring elements. The porous pad can comprise at least one stabilizing structure having cells defined by one or more walls, each cell having a top end and a bottom end with an opening extending through the top and bottom ends in the direction perpendicular to the plane. The porous pad may comprise at least one stabilizing structure comprising a plurality of elongate strips extending in a first direction. The porous pad can further comprise a plurality of intersecting strips extending in a second direction perpendicular to the first direction, wherein the structure is collapsible in the first and second directions. The porous pad may further comprise a plurality of intervening members connecting the elongate strips, wherein the plurality of intervening members are configured to pivot relative to the strips to allow the plurality of elongate strips to collapse relative to one another. In certain embodiments, the stabilizing structures are completely encased by the porous material. In some embodiments, the pad is surrounded by a flexible anchoring layer.

The plurality of stabilizing structures may be completely separated from each other. In certain embodiments, at least some of the stabilizing structures are connected to each other across at least two regions of the pad, wherein the stabilizing structures are separable from each other.

In another embodiment, a negative pressure wound treatment system, comprises:
   a porous pad as described herein this section or elsewhere in the specification;
   a drape sized and configured to be placed over the porous pad and to form a substantially fluid-tight seal against a region of skin surrounding the wound; and
   a port configured to connect the drape to a source of negative pressure.

Some embodiments of the system may call for the addition of a source of negative pressure configured to be in fluid communication with the wound.

In another embodiment, a method of treating a wound comprises;
   providing a porous pad as described herein this section or elsewhere in the specification;
   removing portions of the porous pad to shape the pad into a desired shape;
   placing the porous pad into a wound;
   covering the porous pad with a wound cover or drape; and
   applying negative pressure to the wound via a source of negative pressure.

In another embodiment, a method of manufacture of a porous pad comprises the steps of:
   providing a body of a porous material comprising a stabilizing structure configured to collapse substantially more in a first direction than a second direction; and,
   forming at least one partial pre-cut in a first orientation in said body, said at least one partial pre-cut severing regions of the body to leave detachable regions of the body, the frangible regions allowing the portions to be selectively removed from the body.

The partial pre-cuts may be formed by die cutting. The die cutting may involve providing a plurality of blades in a suitable arrangement to provide the desired partial pre-cuts and tearable regions.

BRIEF DESCRIPTION OF THE DRAWINGS

Other features and advantages of the present invention will be apparent from the following detailed description of the invention, taken in conjunction with the accompanying drawings of which:

FIG. 2A illustrates a perspective view of an embodiment of a stabilizing structure. FIG. 2B illustrates a top view of an embodiment of a stabilizing structure. FIG. 2C illustrates an embodiment of a supporting segment. FIG. 2D illustrates an embodiment of a supporting segment. FIG. 2E illustrates an embodiment of an insert. FIG. 2F illustrates a side view of an embodiment of an insert.

FIG. 2G illustrates an embodiment of a stabilizing structure. FIG. 2H illustrates a side view of an embodiment of a stabilizing structure. FIG. 2I illustrates a side view of an embodiment of a stabilizing structure.

FIG. 5A illustrates a side view of an embodiment of a stabilizing structure with surrounding anchoring and foam layers. FIG. 5B illustrates a view of an embodiment of a stabilizing structure anchoring layer. FIG. 5C illustrates a view of an embodiment of a stabilizing structure anchoring layer. FIG. 5D illustrates a top view of an embodiment of a stabilizing structure anchoring layer.

FIG. 9A illustrates an embodiment of a step of a method of treating a wound. FIG. 9B illustrates an embodiment of a step of a method of treating a wound. FIG. 9C illustrates an embodiment of a step of a method of treating a wound.

FIG. 10A illustrates an embodiment of steps of a method of treating a wound. FIG. 9B illustrates an embodiment of steps of a method of treating a wound. FIG. 9C illustrates an embodiment of steps of a method of treating a wound.

FIG. 12A illustrates an embodiment of a step of a method of treating a wound. FIG. 12B illustrates an embodiment of a step of a method of treating a wound. FIG. 12C illustrates an embodiment of a step of a method of treating a wound. FIG. 12D illustrates an embodiment of a step of a method of treating a wound. FIG. 12E illustrates an embodiment of a step of a method of treating a wound. FIG. 12F illustrates an embodiment of a step of a method of treating a wound. FIG. 12G illustrates an embodiment of a step of a method of treating a wound.

FIG. 13A illustrates an embodiment of a stabilizing structures with rounded out walls. FIG. 13B illustrates a top view of an embodiment of a stabilizing structures with rounded out walls. FIG. 13C illustrates an embodiment of a stabilizing structures with rounded out walls. FIG. 13D illustrates an embodiment of a stabilizing structures with rounded out walls.

FIG. 14A illustrates an embodiment of a stabilizing structure optimized for collapse within a wound. FIG. 14B illustrates an embodiment of a stabilizing structure optimized for collapse within a wound. FIG. 14C illustrates an embodiment of a stabilizing structure optimized for collapse within a wound.

FIG. 15A illustrates an embodiment of a method for optimizing the design of a stabilizing structure. FIG. 15B illustrates an embodiment of a method for optimizing the design of a stabilizing structure. FIG. 15C illustrates an embodiment of a method for optimizing the design of a stabilizing structure. FIG. 15D illustrates an embodiment of a method for optimizing the design of a stabilizing structure. FIG. 15E illustrates an embodiment of a method for optimizing the design of a stabilizing structure.

FIG. 18A illustrates a side view of an embodiments of a stabilizing structure. FIG. 18B illustrates a side view of an embodiments of a stabilizing structure. FIG. 18C illustrates a side view of an embodiments of a stabilizing structure.

FIG. 19A-B illustrates embodiments of methods for the preparation of different wound filler shapes. FIG. 19A illustrates an embodiment of a method for the preparation of different wound filler shapes. FIG. 19B illustrates an embodiment of a method for the preparation of different wound filler shapes.

FIG. 20A illustrates an embodiment of a stabilizing structure with attachable porous and anchoring layers. FIG. 20B illustrates an embodiment of a stabilizing structure with attachable porous and anchoring layers. FIG. 20C shows an image of an embodiment of a stabilizing structure with an attachable anchoring layer.

FIG. 22A shows an image of an embodiment of a stabilizing structure with anchoring and porous layers. FIG. 22B shows an image of an embodiment of a stabilizing structure with anchoring and porous layers. FIG. 22C shows an image of an embodiment of a stabilizing structure with anchoring and porous layers. FIG. 22D illustrates an embodiment of a stabilizing structure with anchoring and porous layers.

FIG. 27A illustrates an embodiment of a stabilizing structure within a porous material.

FIG. 27B illustrates an embodiment of a stabilizing structure within a porous material.

FIGS. 52A-F illustrate embodiments of stabilizing clips for attachment to a stabilizing structures. FIG. 52A illustrates an embodiment of a stabilizing clip for attachment to a stabilizing structure. FIG. 52B illustrates an embodiment of a stabilizing clip for attachment to a stabilizing structure. FIG. 52C illustrates an embodiment of a stabilizing clip for attachment to a stabilizing structure. FIG. 52D illustrates an embodiment of a stabilizing clip for attachment to a stabilizing structure. FIG. 52E illustrates an embodiment of a stabilizing clip for attachment to a stabilizing structure. FIG. 52F illustrates an embodiment of a stabilizing clip for attachment to a stabilizing structure.

FIG. 53A illustrates an embodiment of a stabilizing structure with an attached stabilizing clip. FIG. 53B illustrates an embodiment of a stabilizing structure with an attached stabilizing clip. FIG. 53C illustrates an embodiment of a stabilizing structure with an attached stabilizing clip.

FIG. 54A illustrates an embodiment of an elliptical stabilizing structure with attached stabilizing clips. FIG. 54B illustrates an embodiment of an elliptical stabilizing structure with attached stabilizing clips. FIG. 54C illustrates an embodiment of an elliptical stabilizing structure with attached stabilizing clips. FIG. 54D illustrates an embodiment of an elliptical stabilizing structure with attached stabilizing clips. FIG. 54E illustrates an embodiment of an elliptical stabilizing structure with attached stabilizing clips. FIG. 54F illustrates an embodiment of an elliptical stabilizing structure with attached stabilizing clips. FIG. 54G illustrates an embodiment of an elliptical stabilizing structure with attached stabilizing clips.

FIGS. 55A-G illustrate embodiments of stabilizing clips with grippers. FIG. 55A illustrates an embodiment of a stabilizing clip with grippers. FIG. 55B illustrates an embodiment of a stabilizing clip with grippers. FIG. 55C illustrates an embodiment of a stabilizing clip with grippers. FIG. 55D illustrates an embodiment of a stabilizing clip with grippers. FIG. 55E illustrates an embodiment of a stabilizing clip with grippers. FIG. 55F illustrates an embodiment of a stabilizing clip with grippers. FIG. 55G illustrates an embodiment of a stabilizing clip with grippers FIG. 56A illustrates an embodiment of a stabilizing clip for attachment to a stabilizing structure with a step or recess at the intersection of the securing portion and the attachment portion. FIG. 56B illustrates an embodiment of a stabilizing clip for attachment to a stabilizing structure with a step or recess at the intersection of the securing portion and the attachment portion. FIG. 56C illustrates an embodiment of a stabilizing clip for attachment to a stabilizing structure with a step or recess at the intersection of the securing portion and the attachment portion. FIG. 56D illustrates an embodiment of a stabilizing clip for attachment to a stabilizing structure with a step or recess at the intersection of the securing portion and the attachment portion. FIG. 56E illustrates an embodiment of a stabilizing clip for attachment to a stabilizing structure with a step or recess at the intersection of the securing portion and the attachment portion. FIG. 56F illustrates an embodiment of a stabilizing clip for attachment to a stabilizing structure with a step or recess at the intersection of the securing portion and the attachment portion. FIG. 56G illustrates an embodiment of a stabilizing clip for attachment to a stabilizing structure with a step or recess at the intersection of the securing portion and the attachment portion. FIG. 56H illustrates an embodiment stabilizing structure with a stabilizing clip. FIG. 56I illustrates an embodiment stabilizing structure with a stabilizing clip. FIG. 56J illustrates an embodiment stabilizing structure with a stabilizing clip.

FIG. 57A illustrates an embodiment of a stabilizing clip with a foot for attachment to a stabilizing structure. FIG. 57B illustrates an embodiment of a stabilizing clip with a foot for attachment to a stabilizing structure. FIG. 57C illustrates an embodiment of a stabilizing clip with a foot for attachment to a stabilizing structure. FIG. 57D illustrates an embodiment of a stabilizing clip with a foot for attachment to a stabilizing structure. FIG. 57E illustrates an embodiment of a stabilizing clip with a foot for attachment to a stabilizing structure. FIG. 57F illustrates an embodiment of a stabilizing clip with a foot for attachment to a stabilizing structure. FIG. 57G illustrates an embodiment of a stabilizing clip with a foot for attachment to a stabilizing structure. FIG. 57H illustrates an embodiment of a stabilizing structure with a clip with a foot for attachment to the stabilizing structure. FIG. 57I illustrates an embodiment of a stabilizing structure with a clip with a foot for attachment to the stabilizing structure. FIG. 57J illustrates an embodiment of a stabilizing structure with a clip with a foot for attachment to the stabilizing structure.

FIG. 58A illustrates an embodiment of a stabilizing device for attachment to a stabilizing structure. FIG. 58B illustrates an embodiment of a stabilizing device for attachment to a stabilizing structure.

DETAILED DESCRIPTION OF THE PREFERRED EMBODIMENTS

Figure 1:
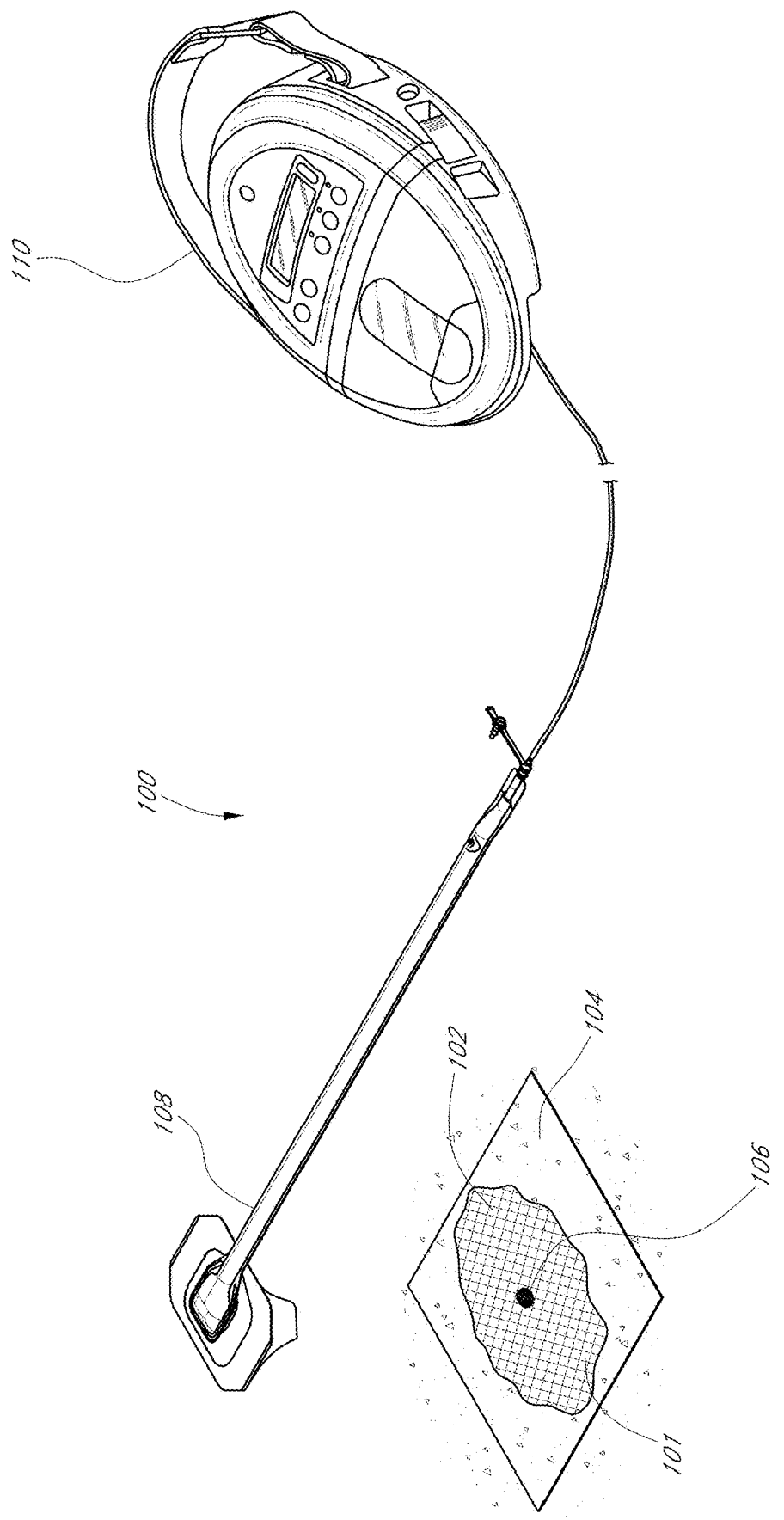
FIG. 1 illustrates an embodiment of a negative pressure treatment system.

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, electrical burns, diabetic ulcers, pressure ulcers, stoma, surgical wounds, trauma and venous ulcers or the like.

As is used in this section or elsewhere in this specification, reduced or negative pressure levels, such as –X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of –X mmHg reflects absolute pressure that is X mmHg below 760 mmHg or, in other words, an absolute pressure of (760-X) mmHg. In addition, negative pressure that is "less" or "smaller" than –X mmHg corresponds to pressure that is closer to atmospheric pressure (e.g., –40 mmHg is less than –60 mmHg). Negative pressure that is "more" or "greater" than –X mmHg corresponds to pressure that is further from atmospheric pressure (e.g., –80 mmHg is more than –60 mmHg).

The negative pressure range for some embodiments of the present disclosure can be approximately –80 mmHg, or between about –10 mmHg and –200 mmHg. Note that these pressures are relative to normal ambient atmospheric pressure. Thus, –200 mmHg would be about 560 mmHg in practical terms. In some embodiments, the pressure range can be between about –40 mmHg and –150 mmHg. Alternatively, a pressure range of up to –75 mmHg, up to –80 mmHg or over –80 mmHg can be used. Also in other embodiments a pressure range of below –75 mmHg can be used. Alternatively, a pressure range of over approximately –100 mmHg, or even –150 mmHg, can be supplied by the negative pressure apparatus. In some embodiments, the negative pressure range can be as small as about –20 mmHg or about –25 mmHg, which may be useful to reduce fistulas. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat).

Examples of such applications where additional disclosure relating to the preceding descriptions may be found include application Ser. No. 11/919,355, titled "Wound treatment apparatus and method," filed Oct. 26, 2007, published as US 2009/0306609; and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described in this section or elsewhere in this specification may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227, the entireties of each of which are hereby incorporated by reference. Still more applications that may contain teachings relevant for use with the embodiments described in this specification are application Ser. No. 13/942,493, titled "Negative Pressure Wound Closure Device," filed Jul. 15, 2013, published as US 2014/0180225; PCT App. No. PCT/US2013/050619, filed Jul. 16, 2013 titled "Negative Pressure Wound Closure Device," published as WO 2014/014871 A1; PCT App. No. PCT/US2013/050698, filed Jul. 16, 2013 titled "Negative Pressure Wound Closure Device," published as WO 2014/014922 A1; PCT App. No. PCT/IB2013/01555, titled "Devices and Methods for Treating and Closing Wounds with Negative Pressure," filed May 5, 2013, published as WO 2013/175309 A1; PCT App. No. PCT/US2014/025059, titled "Negative Pressure Wound Closure Device and Systems and Methods of Use in Treating Wounds with Negative Pressure," filed Mar. 12, 2014, published as WO 2014/165275 A1; and PCT App. No. PCT/GB2014/050746, "Compressible Wound Fillers and Systems and Methods of Use In Treating Wounds With Negative Pressure," filed Mar. 13, 2014, published as WO 2014/140578 A1, the entireties of each of which are hereby incorporated by reference.

It will be understood that throughout this specification in some embodiments reference is made to an elongate, elongated or longitudinal strip or strips. It is to be understood that these terms are to be broadly construed and refer in some embodiments to an elongate material having two parallel or substantially parallel faces, where in cross-section a thickness of the material as measured perpendicular to the faces is relatively smaller than a height of the material measured parallel to the faces. While in some embodiments the strips may be constructed from discrete lengths of material, in other embodiments the strips may simply refer to elongate portions of an overall structure having two parallel or substantially parallel faces. The strips in some embodiments have a rectangular or generally rectangular-shaped faces, wherein a length of the face is longer than the height of the face. In some embodiments, the length of the face may be more than 2 times, 4 times, 6 times, 8 times or 10 times greater than the height of the face.

As used in this section or elsewhere in this specification, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal," and "lateral" may also be used to describe the stabilizing structures and wound closure devices described throughout this specification. When describing these structures or devices, these terms should not be construed to require that the structures or devices necessarily be placed into a wound in a certain orientation, though in certain embodiments, it may be preferable to do so.

FIG. 1 illustrates an embodiment of a negative pressure treatment system 100 that comprises a wound packer 102 inserted into a wound 101. The wound packer 102 may comprise porous materials such as foam, and in some embodiments may comprise one or more embodiments of wound closure devices described in further detail in this section or elsewhere in this specification. In some embodiments, the perimeter or top of any wound closure device inserted into the wound 101 may also be covered with foam or other porous materials. A single drape 104 or multiple drapes may be placed over the wound 101, and is preferably adhered or sealed to the skin on the periphery of the wound 101 so as to create a fluid-tight seal. An aperture 106 may be made through the drape 104 which can be manually made or preformed into the drape 104 so as to provide a fluidic connection from the wound 101 to a source of negative pressure such as a pump 110. Preferably, the fluidic connection between the aperture 106 and the pump 110 is made via a conduit 108. In some embodiments, the conduit 108 may comprise a RENASYS® Soft Port™, manufactured by Smith & Nephew. Of course, in some embodiments, the drape 104 may not necessarily comprise an aperture 106, and the fluidic connection to the pump 110 may be made by placing the conduit 108 below the drape. In some wounds, particularly larger wounds, multiple conduits 108 may be used, fluidically connected via one or more apertures 106.

In some embodiments, the drape 104 may be provided with one or more corrugations or folds. Preferably, the corrugations are aligned along the longitudinal axis of the wound, and as such may support closure of the wound by preferentially collapsing in a direction perpendicular to the longitudinal axis of the wound. Such corrugations may aid in the application of contractile forces parallel to the wound surface and in the direction of wound closure. Examples of such drapes may be found in application Ser. No. 12/922, 118, titled "Vacuum Closure Device," filed Nov. 17, 2010 (published as US 2011/0054365), which is hereby incorporated by reference in its entirety.

In use, the wound 101 is prepared and cleaned. In some cases, such as abdominal wounds, a non- or minimally-adherent organ protection layer (not illustrated) may be applied over any exposed viscera. The wound packer 102 is then inserted into the wound, and is covered with the drape 104 so as to form a fluid-tight seal. A first end of the conduit 108 is then placed in fluidic communication with the wound, for example via the aperture 106. The second end of the conduit 108 is connected to the pump 110. The pump 110 may then be activated so as to supply negative pressure to the wound 101 and evacuate wound exudate from the wound 101. As will be described in additional detail below and in relation to the embodiments of the foregoing wound closure devices, negative pressure may also aid in promoting closure of the wound 101, for example by approximating opposing wound margins.

Stabilizing Structures and Wound Closure Devices of FIGS. 2A-5D

FIGS. 2A-F illustrate embodiments of a stabilizing structure 4200. The stabilizing structure may comprise a plurality of elongate strips 4202 arranged in parallel, whose longitudinal length can be aligned with the longitudinal axis when placed in a wound. The stabilizing structure can further comprise a plurality of intervening members 4204 connected to the elongate strips 4202 via joints 4206. In certain embodiments, the stabilizing structure 4200 can collapse in any manner described in this section or elsewhere in this specification with or without the application of negative pressure. For example, the stabilizing structure may collapse significantly more in one plane than in another plane. In some embodiments, the stabilizing structure is configured to collapse more in a horizontal plane parallel to the length and width of the stabilizing structure than in a vertical plane perpendicular to the horizontal plane. In some embodiments, the stabilizing structure can be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam.

The stabilizing structure 4200 and all stabilizing structures and wound closure devices described in this section or elsewhere in this specification can collapse on a variety of timescales in a dynamic fashion. In certain embodiments, the majority of the collapse may occur within the first few minutes upon application of negative pressure. However, after the initial collapse, the stabilizing structure or wound closure device may continue to collapse at a much slower rate, thereby applying increasing longitudinal tension over a long period of time and drawing the edges of the wound closer together. By slowly drawing the wound edges closer together over time, the stabilizing structure or wound closure device allows the surrounding healing tissue to remodel synergistically with the closure of the device or stabilizing structure. Slow, dynamic wound closure may allow the surrounding tissue to heal at an accelerated rate, because the collapsing structure or device slowly brings the edges of the wound closer together without stressing the newly formed or weakened tissue too quickly.

In some embodiments, the stabilizing structures described in this section or elsewhere in this specification can placed into a wound for a period of time and then removed or replaced with another stabilizing structure. For example, a stabilizing structure could be inserted into a wound for a period of time, promoting closure of the wound by drawing the edges closer together. After a period of time has passed, the stabilizing structure can be replaced by a stabilizing structure of a different size or collapsibility, for example a stabilizing structure of a smaller size or decreased density. This process could be repeated over and over, thereby continuously drawing the edges of the wound together over time and allowing for continuing repair and remodeling of the surrounding tissue. In certain embodiments, the stabilizing structure is configured to remain in the wound for at least about less than 1 hour, at least about 1 hour, at least about 2 hours, at least about 4 hours, at least about 6 hours, at least about 8 hours, at least about 12 hours, at least about 24 hours, at least about 2 days, at least about 4 days, at least about 6 days, at least about 1 week, at least about 2 weeks, at least about 3 weeks, or more than 3 weeks.

In certain embodiments, up to 90% of the collapse of the stabilizing structure or wound closure device may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In other embodiments, the stabilizing structure can collapse at a variable rate. In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and irrigant fluid.

Figure 2A:
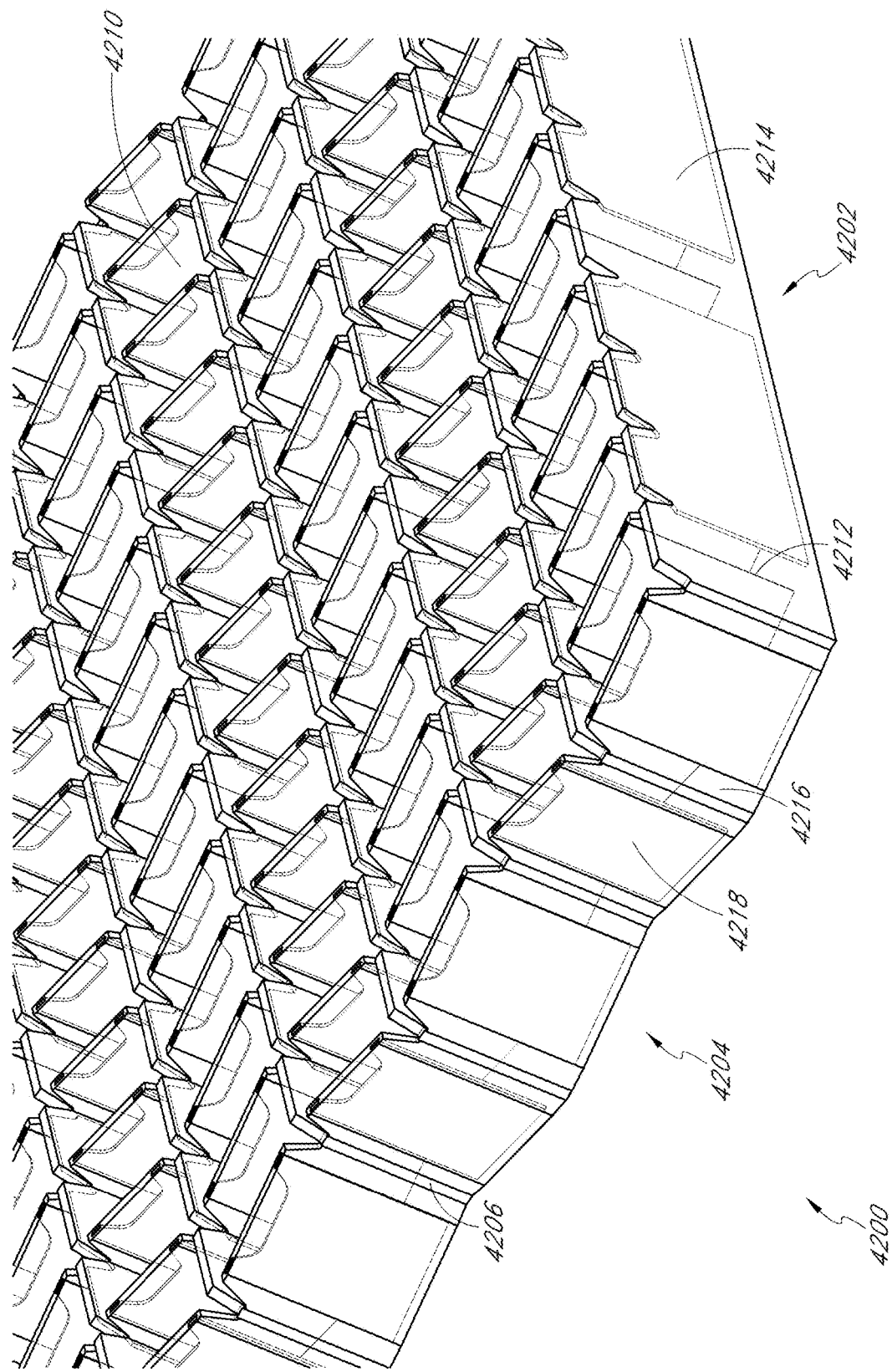
FIGS. 2A-F illustrate multiple views of an embodiment of a stabilizing structure.
Figure 2B:
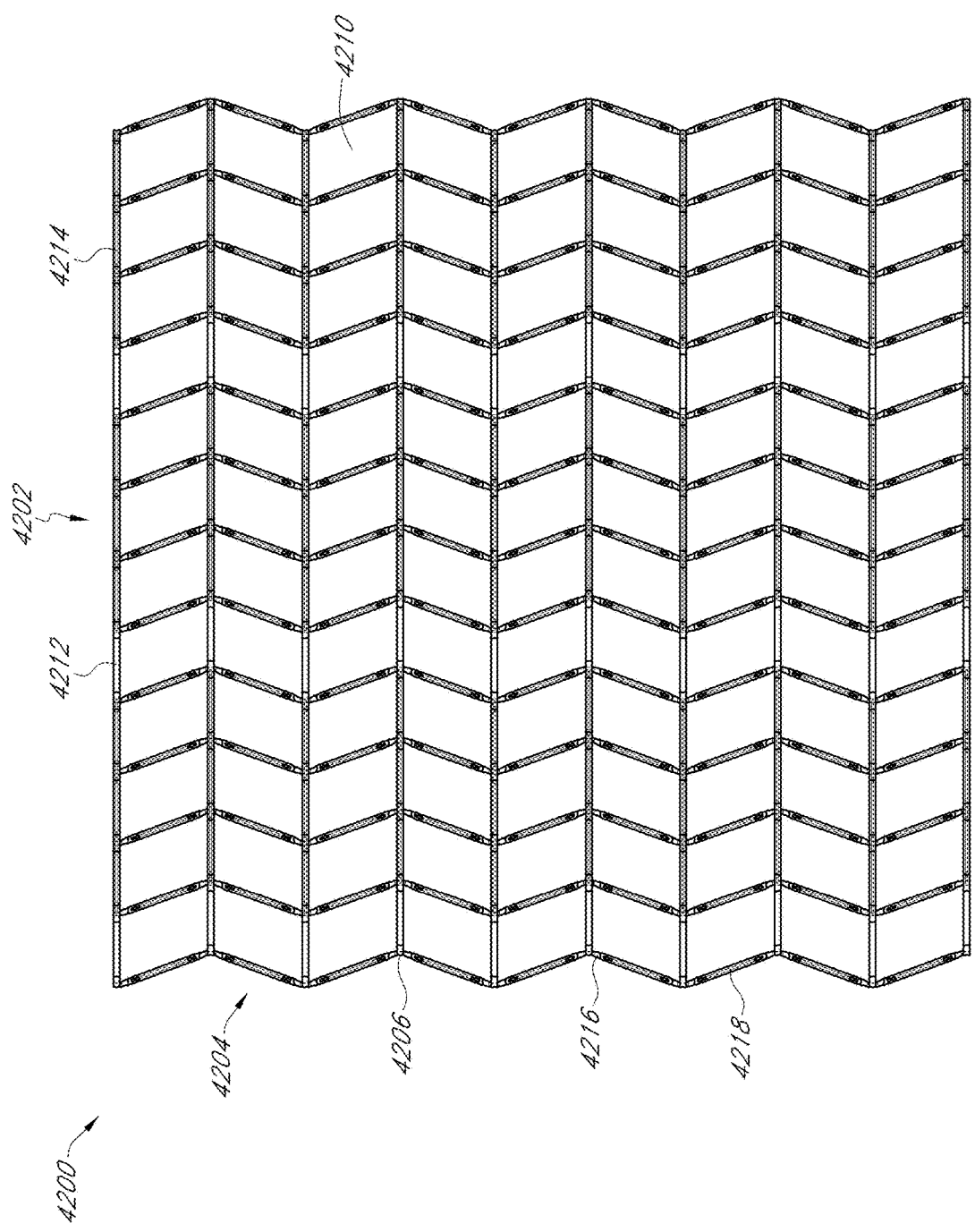

As illustrated in the perspective view of FIG. 2A and the top view of FIG. 2B, the intersection of the intervening members 4204 and the elongate strips 4202 may define a plurality of cells 4210. In certain embodiments, the cells 4210 may be of any of the shapes and sizes described in this section or elsewhere in this specification. For instance, a cell may be in the shape of a square, a diamond, an oblong, an oval, and/or a parallelepiped. The joints 4206 are configured to allow the intervening members 4204 to collapse. The joints 4206 can be configured to allow the intervening members to collapse in any manner as described in this section or elsewhere in this specification in relation to other embodiments. For example, the joints 4206 may be configured to allow or preferentially cause a first row of intervening members 4204 to collapse in one direction, while allowing or preferentially causing an adjacent row to collapse in another direction. The elongate strips 4202 may comprise alternating flexing segments 4212 and supporting segments 4214. In a preferred embodiment, the flexing segments 4212 may be constructed from a flexible or semi-flexible material such as silicone and/or polyurethane. However, any flexible or semi-flexible material may be suitable. The flexing segments 4212 can flex in any direction, allowing the stabilizing structure to collapse more readily in any direction, but particularly in the horizontal plane. In a preferred embodiment, the supporting segments 4214 can be constructed from a rigid or semi-rigid material such as polyvinyl chloride (PVC). However, any rigid or semi-rigid material may be suitable. In the embodiment illustrated, the elongate strips 4202 comprise elongate strips of a first material such as silicone and/or polyurethane, with a plurality of elongate inserts of a second, more rigid material 4214 embedded into the first material. Thus, the flexing segments 4212 are the areas in the elongate strips 4202 where the more rigid inserts are not located.

As illustrated in FIGS. 2A-D, the supporting segments 4214 may be larger than the flexing segments 4212. In one embodiment, the supporting segments 4214 can be approximately three times as large as the flexing segments 4212 (such as by spanning three cells 4210). In other embodiments, the supporting segments 4214 may be the same size as the flexing segments 4212. In further embodiments, the flexing segments 4212 can be larger than the supporting segments 4214. Alternatively, the lengths and widths of the individual segments of the elongate strips 4202 can be variable. For example, the height of the supporting segments 4214 can be reduced, such that they do not extend from approximately the top to approximately the bottom of the stabilizing structure 4200. In some embodiments a smaller supporting segment could encompass approximately half the height of the elongate strip 4202. In certain embodiments, the supporting segment 4214 could be located in the upper or in the lower portion of the elongate strip. Such embodiments may be accomplished by utilizing an insert of a second material that has a smaller height than the height of the first material forming the elongate strip 4202.

In some embodiments, the supporting segment does not alternate with the flexing segment 4212 and instead, the elongate strips 4202 are comprised entirely of supporting segments 4214 (e.g., a silicone strip or other material with an embedded more rigid insert extending the entire length thereof, or simply a more rigid material by itself). Alternatively, the entirety of the elongate strip 4202 can be comprised only of flexing segments 4212 (e.g., a strip made only of silicone or other more flexible material). The elongate strips 4202 may be manufactured from a female mold that may further encompass the entire stabilizing structure 4200. The supporting segments 4214 can be inserted into the female mold, followed by an injection of a flexible polymer such as silicone and/or polyurethane to encase the supporting segments 4214 within the flexible polymer frame. The supporting segments 4214 can be inserted into the mold in any desired manner or quantity, allowing for many potential variations of the stabilizing device.

In further embodiments, the supporting segments 4214 are insertable and/or removable from the elongate strips 4202, and may be inserted and/or removed to alter the collapsibility of the stabilizing structure 4200. Supporting segments 4214 can be inserted and/or removed from the stabilizing structure 4200 after it has been placed in a wound to variably control the collapse of the stabilizing structure 4200. In such embodiments, the elongate strips 4202 may form pockets that are open from one side (e.g., from the top) to allow insertion and removal of the supporting segments 4214.

Figure 2C:
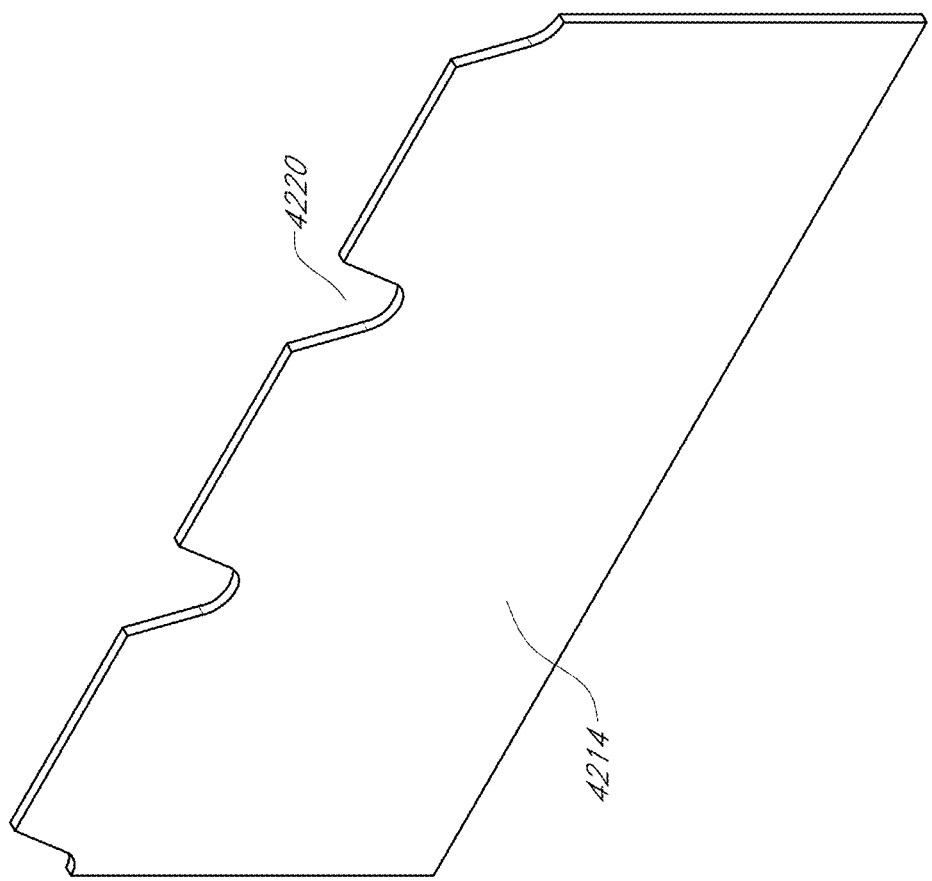
Figure 2D:
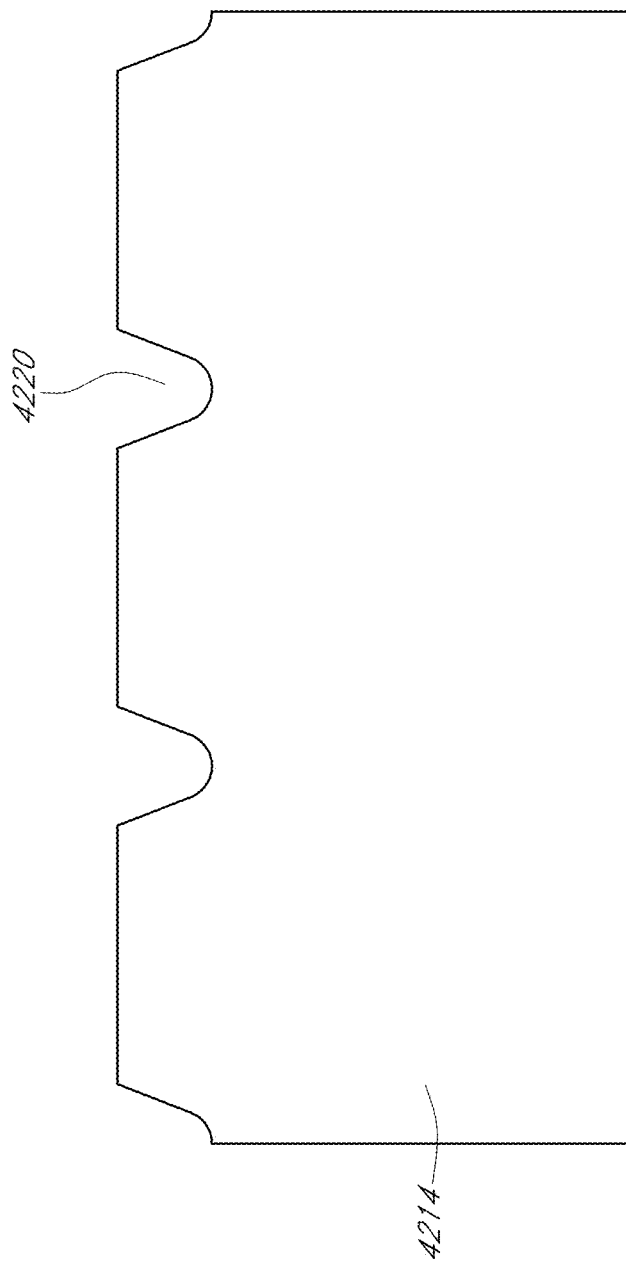

FIGS. 2C-D illustrate in greater detail an embodiment of an individual supporting segment 4214. The supporting member 4214 may be a flat, plate-like structure having a rectangular shape, with a length greater than its height, and two parallel surfaces. The supporting segment can comprise at least one notch 4220, preferably located on the upper edge of the supporting segment. In other embodiments, the notch or notches can be located on the bottom or the sides of the supporting segment. In further embodiments, the top notch could have a corresponding bottom notch, or the notches could be located semi-randomly on the top and bottom of the stabilizing structure. In certain embodiments, the notch could be configured so as to allow tearing of the supporting segment in a transecting line across the supporting segment. The notch or notches 4220 may advantageously provide flexibility to the structure. The notches 4220 may allow the stabilizing structure to flex more easily in the horizontal plane or in the vertical plane. The notches 4220 may further allow the stabilizing structure to twist in multiple planes. The notches 4220 may also improve fluid flow within the stabilizing structure 4200. In some embodiments, the supporting segment does not contain a notch and the uppermost edge is flat. The notch 4220 can be located at other locations on the supporting segment, for example the bottom edge or the sides. The shape of the notch can be a rounded triangle as in FIGS. 2C-D or any other similar shape.

Figure 2E:
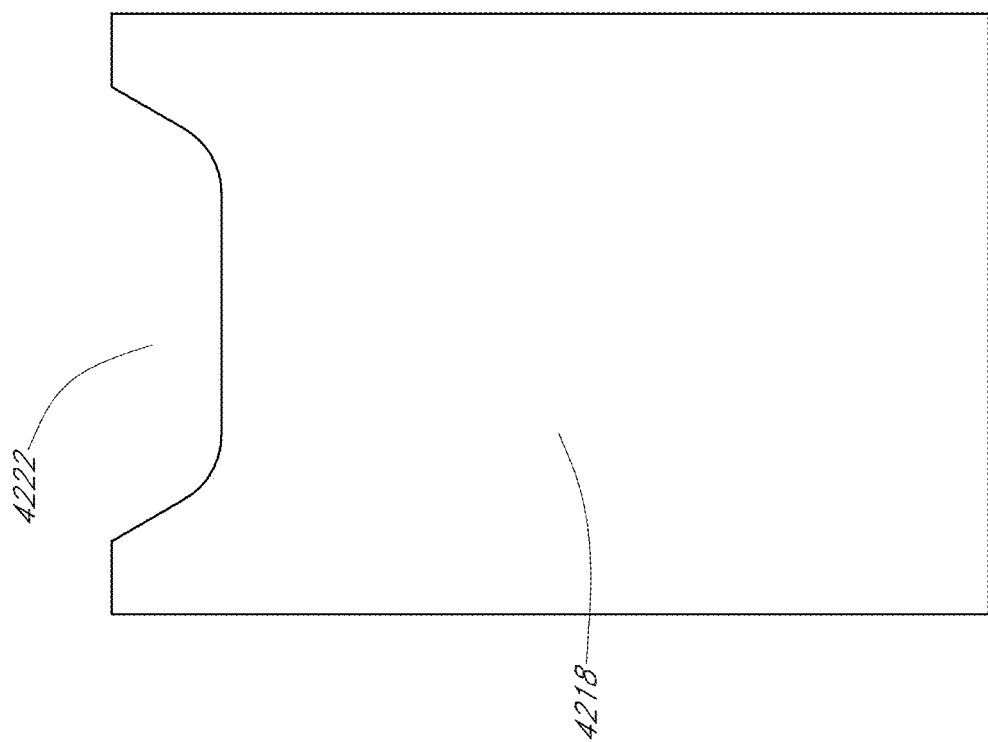
Figure 2F:
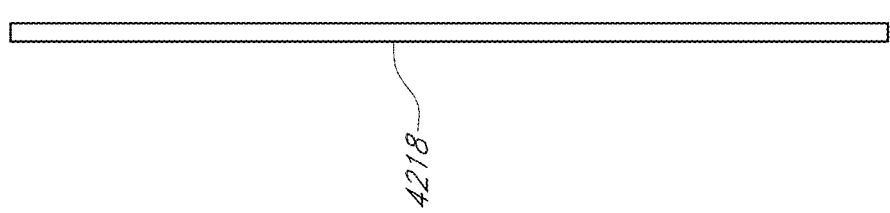

The intervening members 4204 in some embodiments may comprise a first material 4216 with an embedded insert 4218 made of a more rigid material. One embodiment of the embedded insert is illustrated in FIGS. 2E-F. In certain embodiments, the insert 4218 is placed within a female mold and a flexible polymer such as silicone and/or polyurethane is injected around the insert to entomb the insert 4218 within a flexible polymer frame. The inserts 4218 can be inserted into the mold in any desired manner or quantity, allowing for many potential variations of the stabilizing device. In other embodiments, the first material 4216 may be in the form of a sleeve configured to receive the insert 4218. Further, the sleeve 4216 may be configured to allow for the removal of an insert 4218, such as by providing an opening in the top of the sleeve. In a preferred embodiment, the first material 4216 is constructed from a flexible or semi-flexible material such as silicone and/or polyurethane. However, any flexible or semi-flexible material may be suitable. In a preferred embodiment, the insert 4218 is constructed from a rigid or semi-rigid material such as polyvinyl chloride. However, any rigid or semi-rigid material may be suitable.

FIG. 2E illustrates a front view of insert 4218, while FIG. 2F illustrates a side view of insert 4218. The insert in one embodiment may be a flat, plate-like structure having a rectangular shape, with a height greater than its width, and two parallel surfaces. The insert can comprise an indent 4222. The indent is preferably located at the upper portion of the insert, however, the indent 4222 can be positioned on either side of the insert, or on the bottom. The indent 4222 can be configured such that it aids in allowing fluid to flow through the stabilizing structure by providing a flow path. The indent 4222 can improve flexibility of the stabilizing structure 4200 and be configured to allow for a more efficient collapse of the stabilizing structure 4200.

In some embodiments, the stabilizing structure 4200 of FIGS. 2A-B can be configured to include perforations or detachable sections that allow portions of the device to separate from the remainder of the device. For example, perforations may be incorporated into the joints 4206 between various cells contained within the stabilizing structure 4200, allowing for the removal of individual rows or cells to alter the shape of the stabilizing structure 4200. In some embodiments, as described above in relation to FIGS. 2C-D, the sections may be detached along perforations or lines in the elongate strips corresponding to the notches 4220. In some embodiments, the inserts 4218 may be entombed within first material 4216 in a variable number of intervening members 4204 to control the shape and collapse of the stabilizing structure 4200. In other embodiments, the inserts 4218 may be inserted directly into sleeves comprised of first material 4216 within the intervening members 4204 to control the shape and collapse of the stabilizing structure 4200.

For example, the inserts 4218 can be present in at least about 5% of the intervening members, at least about 10% of the intervening members, at least about 15% of the intervening members, at least about 20% of the intervening members, at least about 25% of the intervening members, at least about 30% of the intervening members, at least about 35% of the intervening members, at least about 40% of the intervening members, at least about 45% of the intervening members, at least about 50% of the intervening members, at least about 55% of the intervening members, at least about 60% of the intervening members, at least about 65% of the intervening members, at least about 70% of the intervening members, at least about 75% of the intervening members, at least about 80% of the intervening members, at least about 85% of the intervening members, at least about 90% of the intervening members, at least about 95% of the intervening members, or about 100% of the intervening members.

In certain embodiments, a variable number of supporting segments 4214 may be entombed within elongate strips 4202 to control the collapsibility of the stabilizing structure 4200. In other embodiments, a variable number of supporting segments may be inserted into a pocket contained within the elongate strips 4202 to control the collapsibility of the stabilizing structure. For example, the supporting segments 4214 can be present in at least about 5% of the total length of the elongate strips, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the total length of the elongate strips.

In certain embodiments, the inserts 4218 or supporting segments 4214 may be inserted and/or removed over time to variably control the collapse of the stabilizing structure 4200. For example, although initially all the available sleeves 4216 of the stabilizing structure may contain an insert, after the initial placement of the stabilizing structure in a wound, additional inserts 4218 may be removed over time, thus causing the stabilizing structure 4200 to collapse even further. Inserts can also be added to the stabilizing structure after it is inserted into a wound, thereby decreasing the collapsibility of the stabilizing structure 4200. Thus, the addition and/or removal of the inserts 4216 or supporting segments 4214 allows for variable control of the collapse of the stabilizing structure 4200. In similar fashion, supporting segments 4214 can be inserted and removed from the elongated strips over time to provide variable control over the collapse of the stabilizing structure 4200.

In certain embodiments of the stabilizing structures described in this section or elsewhere in this specification, such as in stabilizing structure 4200 as described in FIG. 2A, the flexibility of various sections of the stabilizing structure is enhanced by thinning of that section. For example, in certain embodiments, rather than using a flexible material for a flexing segment 4212 of elongate strip 4202, instead the flexing segment 4212 can be constructed of a similar material to that used to construct supporting segment 4214. In this embodiment, since supporting segment 4212 is thicker than flexing segment 4212 it will not flex to the degree of flexion that may be experienced by flexing segment 4212. In certain embodiments, the entire stabilizing structure 4200 may be constructed from a single rigid or semi-rigid material, but made to have different rigid and flexible portions by thinning certain areas of the stabilizing structure 4200. In further embodiments, the joints 4206 may be thinned to allow for greater flexibility as compared to the surrounding sections. In certain embodiments, thinning of a section of the stabilizing structure 4200, may allow the thinner portion to be more readily detached from the structure.

Figure 2G:
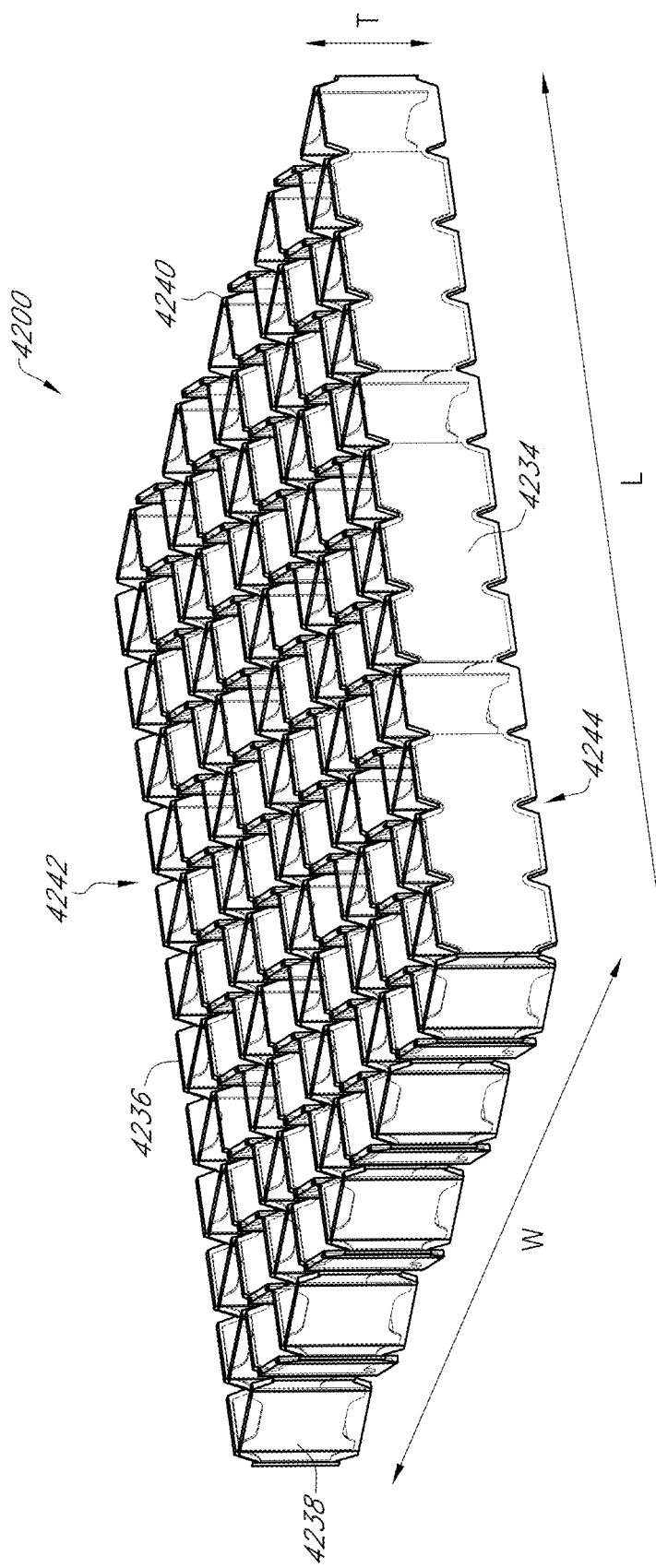
FIGS. 2G-2I illustrate multiple views of another embodiment of a stabilizing structure.
Figure 2H:
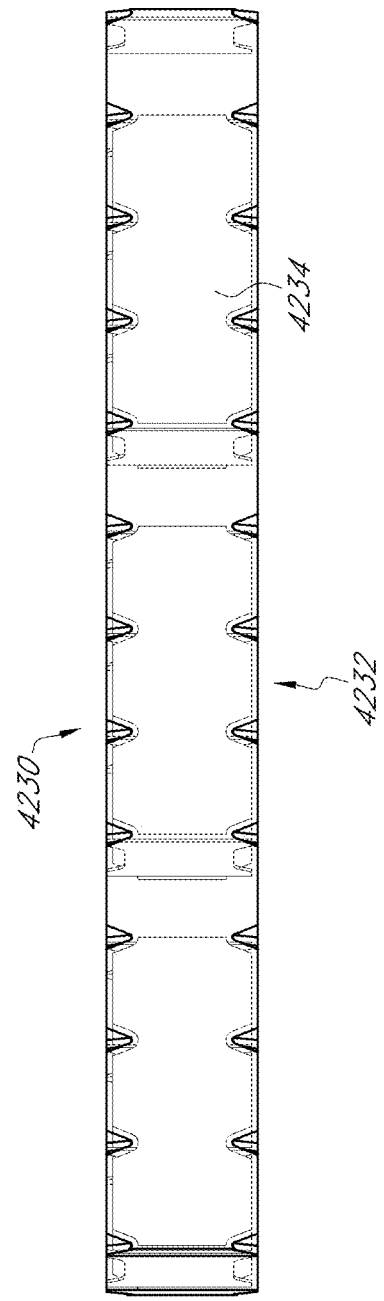
Figure 2I:
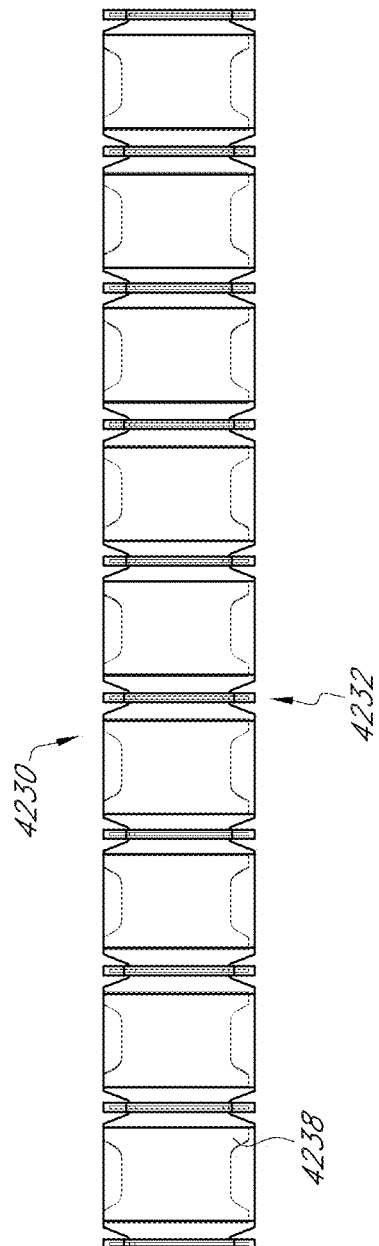

FIGS. 2G-2I illustrate another embodiment of a stabilizing structure 4200 similar to the stabilizing structure described above with respect to FIGS. 2A-2F. In this and other embodiments, the stabilizing structure may have a length L and a width W that extend parallel to a horizontal plane, and a thickness T that may extend vertically and perpendicular to the horizontal plane. As illustrated, the length L and the width W may be greater than the thickness T so that the stabilizing structure forms a generally planar or flat body having an upper surface 4230 and a lower surface 4232 that may be parallel to each other. The thickness T of the structure may be constant between the upper and lower surfaces, or it may vary. The stabilizing structure of FIGS. 2G-2I may further comprise notches 4242 and 4244 in both the upper surface 4230 and lower surface 4232, respectively. These notches may extend through the elongate strips 4202 as well as through supporting segments 4214.

The stabilizing structure of FIG. 2G may define an outer perimeter that is general rectangular in shape, though other shapes are contemplated. In one embodiment, the stabilizing structure has a first side 4234 and a second side 4236 opposite the first side. FIG. 2H illustrates a side view of first side 4234. These sides 4234 and 4236 may be straight in shape and be parallel to each other. These sides also need not be parallel, and can have other shapes such as curved. The stabilizing structure may also have a third side 4238 and a fourth side 4240 opposite the third side. FIG. 2I illustrates a side view of third side 4238. The third and fourth sides may have a zig-zag shape as shown, but may also have other shapes such as straight and curved.

Applicable to all stabilizing structures or wound closure devices described in this section or elsewhere in the specification, a soft polymer could be molded over the entire stabilizing structure 4200 to soften the feel of the device, thereby protecting the surrounding organs and/or other tissues. In other embodiments, the soft polymer could be molded only over the bottom portion of the stabilizing device 4200, while in some embodiments the softer polymer can be molded over the top and/or the sides of the device. In some embodiments, the soft polymer could be molded over particular edges of the stabilizing structure 4200, such as those on the bottom, sides, and/or top. In certain embodiments, the soft polymer could be molded over any side or combination of sides of the stabilizing structure 4200. The soft polymer may act like a softened rim surrounding the hard edges of the stabilizing structure 4200.

Applicable to all stabilizing structures or wound closure devices described in this section or elsewhere in the specification, the stabilizing structure or wound closure device may be tearable such that the stabilizing structure may be shaped into the shape of a wound. In some embodiments the stabilizing structure may be torn at the intersections between intervening members and elongate strips, while in further embodiments, the elongate strips or intervening members may be torn at any suitable position.

Figure 3:
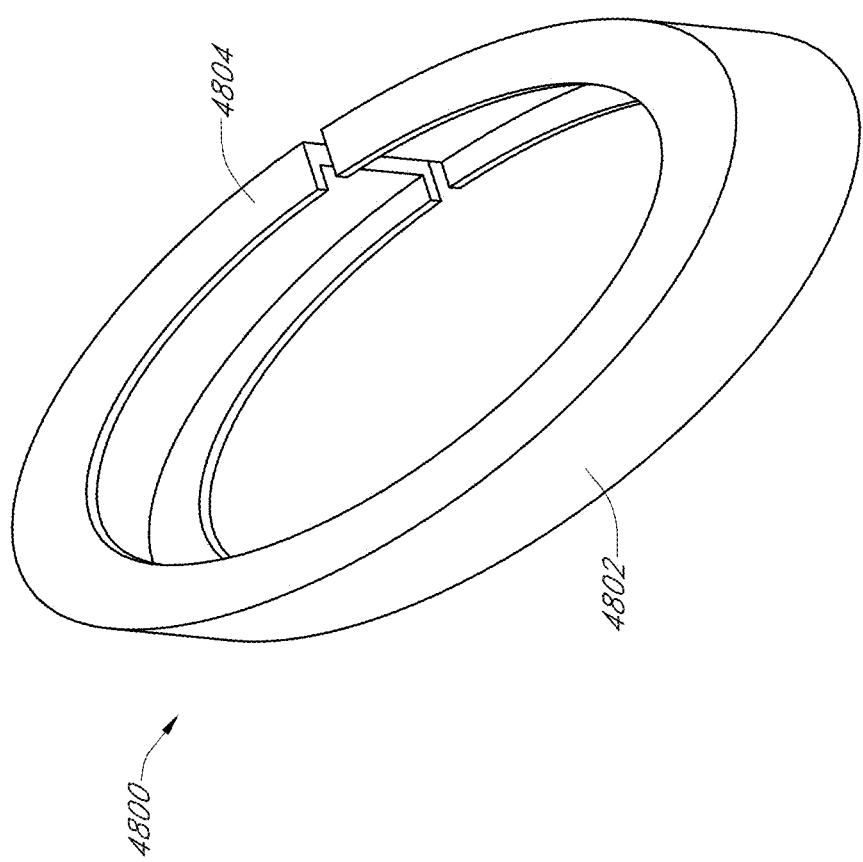
FIG. 3 illustrates an embodiment of a ring that can surround a stabilizing structure.

FIG. 3 illustrates an embodiment of an anchoring layer 4800 that may surround the stabilizing structures as described in this section or elsewhere in this specification. The ring 4800 can comprise a layer of tissue anchors 4802 configured to grip the surrounding edges of a wound. For example, the tissue anchors can be hooks, barbs, prongs, or other structures that serve to attach to the tissue of a wound. In certain embodiments, the tissue anchors comprise hook and loop fasteners such as those used in Velcro technologies. In certain embodiments, the ring 4800 can be comprised of foam, such as those described previously or the ring can be comprised of a combination of a foam layer and a tissue anchor layer 4802. A lip 4804 may extend inward from the ring 4800 and serve to overlap the top and/or the bottom of a stabilizing structure as described in this section or elsewhere in this specification, thereby securing the ring 4800 around the stabilizing structure.

Figure 4:
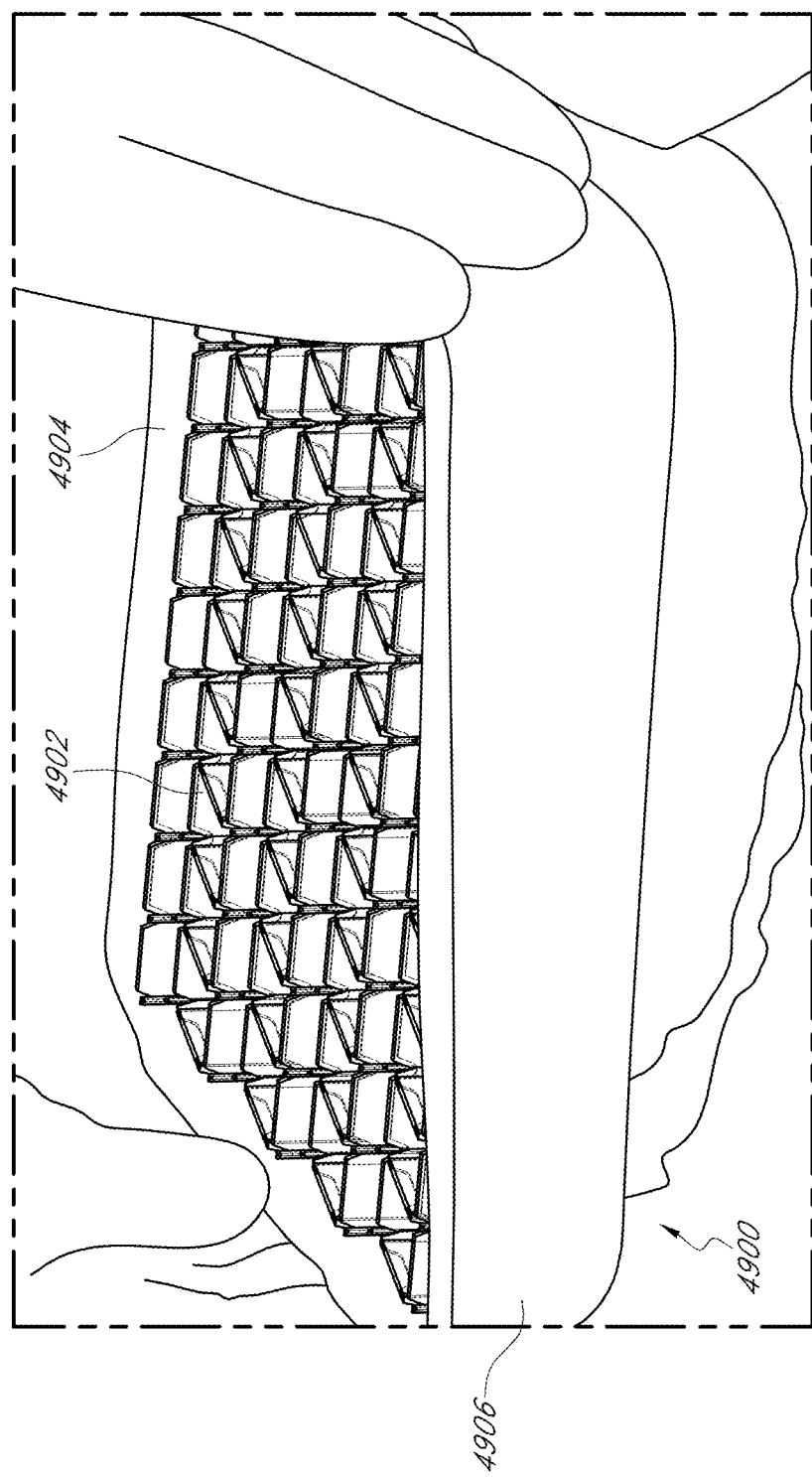
FIG. 4 illustrates an embodiment of a stabilizing structure with surrounding anchoring and foam layers.

FIG. 4 is a photograph of a wound closure device 4900 comprising a stabilizing structure 4902 such as those described in this section or elsewhere in this specification, a foam layer 4904 such as those described in this section or elsewhere in this specification, and an anchoring layer 4906 comprising tissue anchors similar to the ring depicted in FIG. 3. In some embodiments, the wound closure device 4900 may be placed in a wound and sealed with a drape. Similar to the embodiments illustrated in FIGS. 2A-F, the stabilizing structure 4902 can collapse in any manner described in this section or elsewhere in this specification.

The stabilizing structures and/or wound closure devices described in this section or elsewhere in this specification may be used in conjunction with methods or systems for the closure of a wound. In some embodiments of methods of use for closure of a wound, one or more of the stabilizing structures or wound closure devices of any of the embodiments described in this section or elsewhere in this specification is placed into a wound. In some embodiments, an organ protection layer may be provided in the wound before placement of the stabilizing structure. In certain embodiments, foam or other porous material may be placed in the wound along with the stabilizing structure or wound closure device, either below, above, or surrounding the stabilizing structure or wound closure device. Foam or other porous material may also surround the perimeter of the stabilizing structure or wound closure device. The stabilizing structure or wound closure device may be configured to collapse in any manner as described in this section or elsewhere in this specification, for example by having a particular size and shape, or by comprising a certain volume of foam or other porous material within the cells of the structure. The stabilizing structure or wound closure device may further be altered in any manner described in this section or elsewhere in this specification so as to better accommodate the shape of the wound. After placement in the wound, the stabilizing structure or wound closure device can be sealed by a fluid-tight drape. The fluid-tight drape can comprise a port configured for the application of negative pressure. A source of negative pressure may then be connected to the port and negative pressure may be applied to the wound. The stabilizing structure or wound closure device may be replaced over time by stabilizing structures or wound closure devices of various shapes and sizes as desired to best promote wound healing.

FIGS. 5A-D are photographs of a wound closure device 5000 according to another embodiment. The wound closure device 5000 comprises a stabilizing structure 5002 which may be similar to the structures described in FIGS. 2A-I, or may comprise any of the stabilizing structures described elsewhere in this specification. The stabilizing structure 5002 is surrounded by a porous layer 5004 such as a layer of foam, and the porous layer is surrounded by an anchoring layer 5006 comprising tissue anchors such as those anchors produced by Velcro industries, various barbs and/or various hooks. In some embodiments, the tissue anchors are similar to the rings depicted in FIGS. 3-4. In certain embodiments, the porous layer may be in the form of a ribbon. The stabilizing structure 5002, porous layer 5004 and anchoring layer 5006 may be provided as separate components to be attached by the practitioner in use, or they may be pre-attached to each other.

Similar to the embodiments illustrated in FIGS. 2A-I, the stabilizing structure 5002 can collapse in any manner described elsewhere in this specification, for example, horizontally. When the wound closure device 5000 is implanted, the surrounding tissues can be pressed against the tissue anchors to embed them within the tissue and anchor the device. In some embodiments, the wound closure device 5000 may be placed in a wound and sealed with a drape. Although the embodiments further described in this section comprise an anchor layer that surrounds a porous layer, other embodiments may omit the porous layer, such that the anchoring layer directly surrounds or is attached to the stabilizing structure.

In some embodiments, the anchoring layer 5006 comprises an elongate strip of material comprising a plurality of tissue anchors extending from a base layer 5007, wherein the tissue anchors can have different shapes and sizes as described elsewhere in the specification. The tissue anchors may extend from a first planar side of the elongate strip, and the second planar side of the elongate strip may comprise an adhesive covered by an adhesive backing layer. The structure of the anchors can have various forms depending on the tissue they are intended to bind. Longer anchors can be used for loosely bound tissues such as fat or connective tissue, while shorter anchors can be used for denser tissues such as muscle. In other embodiments, depending upon the shape of the anchor, shorter anchors may be more desirable for softer, fatty tissue, while longer anchors are utilized for denser tissues. Anchors with more rigid stems can be utilized to penetrate denser tissues. In some embodiments, anchors can have bilateral prongs that tend to collapse upon insertion in tissue and yet expand when pulled in an opposite direction such that a certain pulling force can be applied to tissue. The characteristics of the anchors or attachment mechanisms, and their resulting force profiles, can vary by a number of parameters, such as the length of the anchor, the shape of the attachment mechanisms, the structure of grasping features, the material(s) used for the attachment mechanisms, the relative flexibility/rigidity of the attachment mechanisms, and the spacing/density of the attachment mechanisms.

The anchors may have various lengths for optimal penetration of the surrounding tissue. For example, the length of the anchors may be at most about 0.01 mm, at most about 0.1 mm, at most about 0.2 mm, at most about 0.5 mm, at most about 1 mm, at most about 2 mm, at most about 3 mm, at most about 5 mm, at most about 10 mm, at most about 20 mm, at most about 30 mm, at most about 40 mm, at most about 50 mm, at most about 75 mm, at most about 100 mm, or more than 100 mm.

Figure 5A:
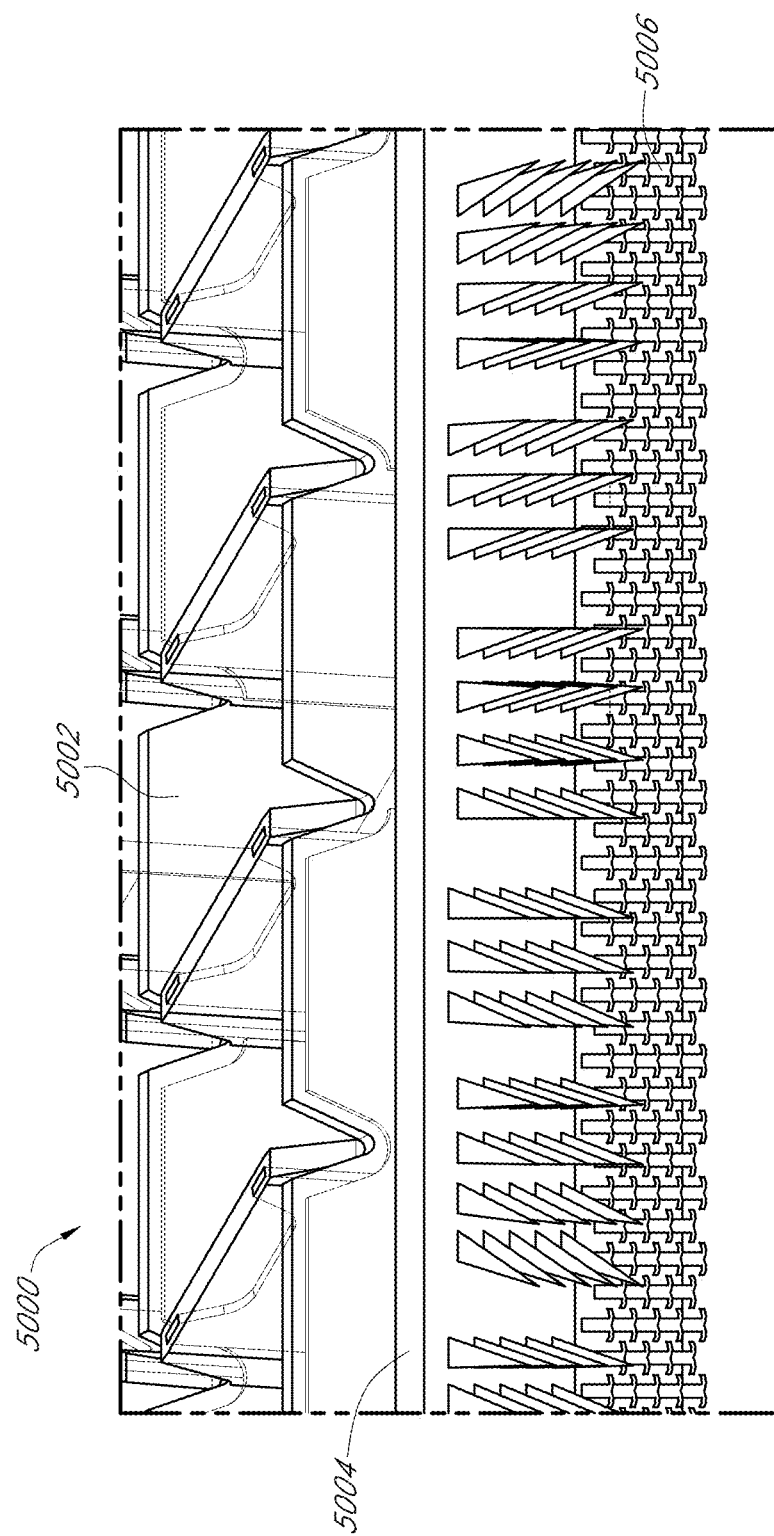
FIGS. 5A-D illustrate another embodiment of a stabilizing structure with surrounding anchoring and foam layers.
Figure 5B:
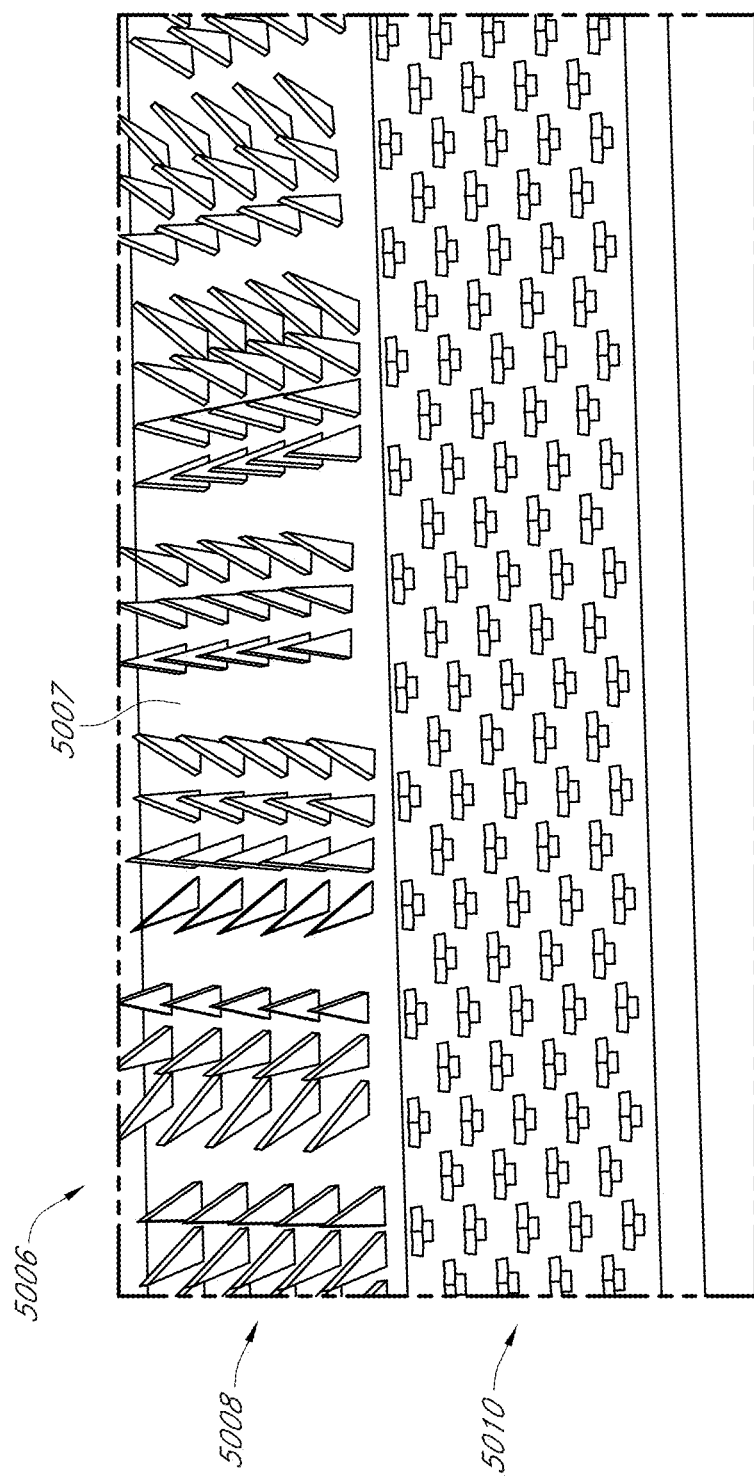

FIG. 5B is a photograph of a closer view of the anchoring layer 5006 of the wound closure device 5002 depicted in FIG. 5A. The anchoring layer may consist of a first band of longer anchors 5008 configured to surround the porous layer 5004 and stabilizing structure 5002, and a second band of shorter anchors 5010 configured to surround the porous layer 5004 and stabilizing structure 5002. As illustrated, the first band 5008 may be disposed above the second band 5010. In some embodiments, there may be additional alternating series of bands vertically relative to each other. In further embodiments, the different bands may have different anchor lengths and shapes, as disclosed herein this section and elsewhere in the specification. For example, instead of 2 types of bands with 2 types of anchors, there may be 3 types of band with 3 types of anchors or 4 types of bands with 4 types of anchors and so on. Preferably, the anchors are selected for the appropriate tissue types. For example, returning to FIG. 5B, the first band 5008 may comprise longer anchors, desirable for penetration into the denser fascia, and thus may be positioned towards the bottom of the device. Similarly, the second band 5010 comprises shorter double hooks, desirable for penetration into denser tissue. Other suitable tissue anchors, as described elsewhere in this specification, include the hook and loop configuration of Velcro, barbs, hooks, spikes, pegs, arrowheads, or any suitable shape. Further examples of surfaces include textured surfaces, such as roughened sandpaper-like surfaces, or nano-textured surfaces that may facilitate tissue adhesion.

In some embodiments, the use of surface anchors can be used in combination with a surgical adhesive, providing a much stronger bond between tissue layers than the adhesive alone, and providing temporary adhesion while the adhesive sets. In some embodiments, the surgical adhesive can be added to the anchors themselves. In certain embodiments, the surgical adhesive may simply be applied between the anchors to coat at least a portion of the anchoring layer. In further embodiments, the anchors may be replaced with a surgical adhesive, and the surgical adhesive may act to anchor the device to the surrounding wound.

In certain embodiments, the anchors may be constructed from a variety of materials, including any materials disclosed elsewhere in the specification, such as: synthetic or natural polymers, metals, ceramics, or other suitable materials. The anchors may be constructed from biodegradable materials such as biodegradable synthetic or natural polymers. Non-limiting examples of biodegradable synthetic polymers include: polyesters such as polylactic acid or polyglycolic acid, polyanhydrides, and linear polymers with biodegradable linkages. Further, the anchors may be constructed of biodegradable biological materials, such as autografts, allografts, and/or xenografts.

Figure 5C:
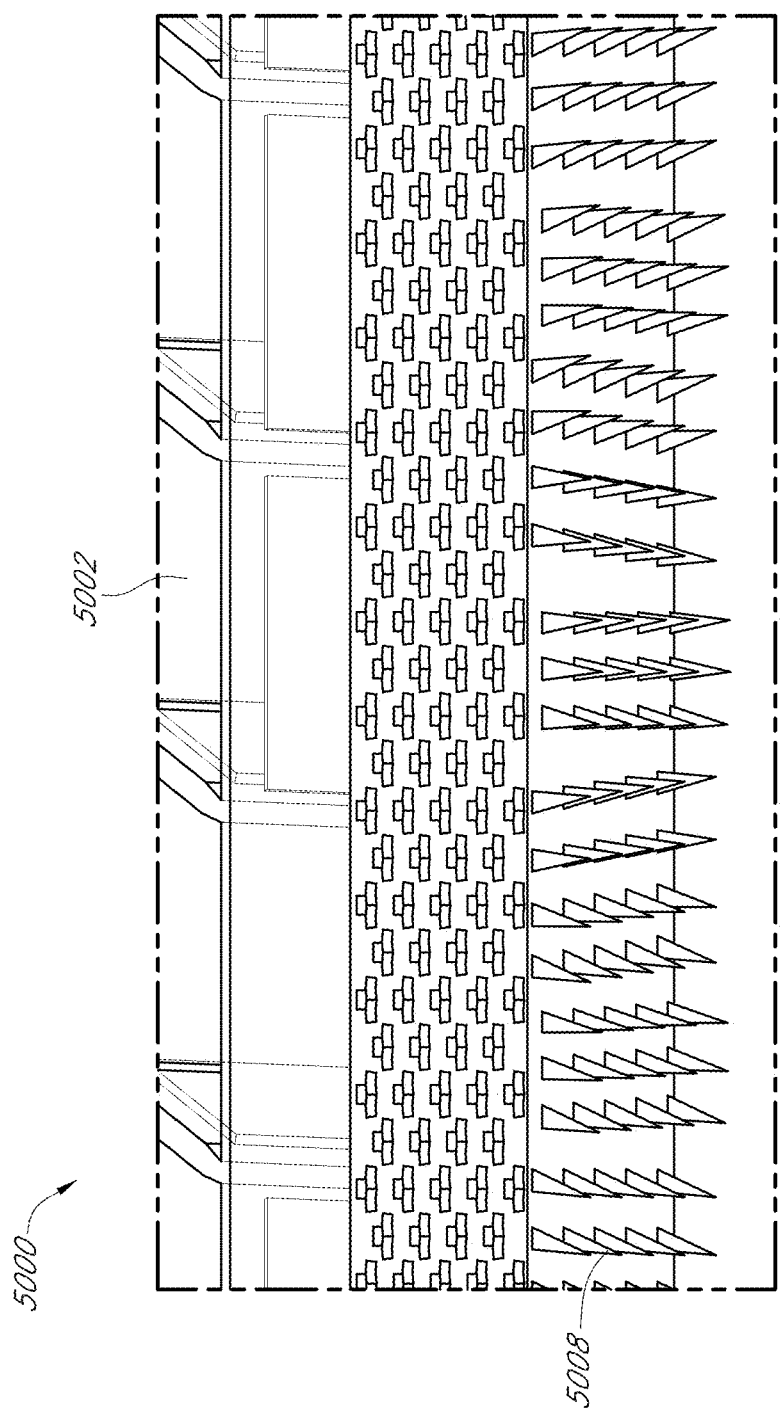
Figure 5D:
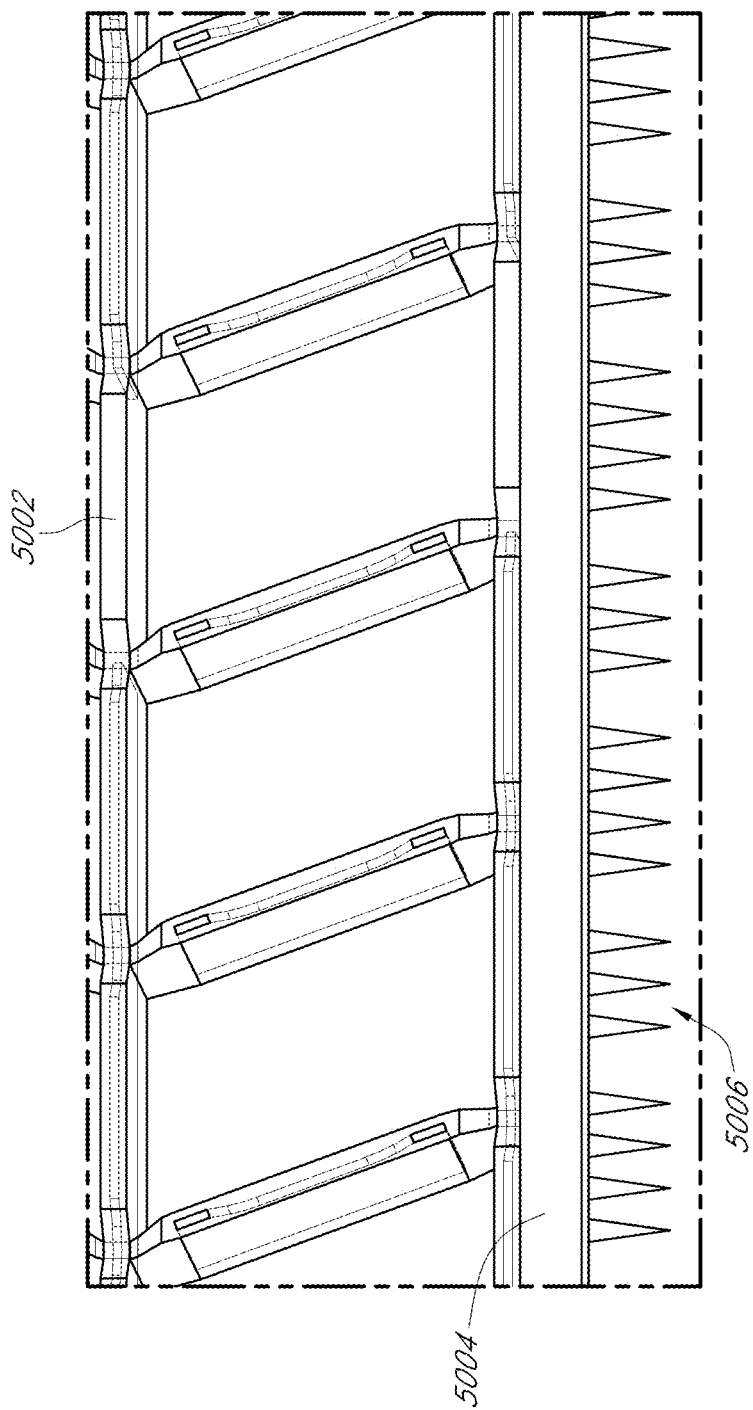

FIG. 5C is a photograph of an embodiment of a wound closure device 5000, similar to the wound closure devices of FIGS. 5A-B. However, in this orientation the first band 5008 of anchors is towards the bottom of the device, while the second band of anchors 5010 is towards the top. As described above, the bands of anchors may be arrayed in any desired manner. FIG. 5D is a top view of an embodiment of a wound closure device 5000, similar to the wound closure devices of FIGS. 5A-C.

Considering the anchoring layer of FIGS. 5A-D, the shape of the anchoring layer is not limited to the ring shape of FIGS. 4-5D. In some embodiments, the anchoring layer is wrapped around the entirety of the stabilizing device, i.e. the top, bottom, and sides. In other embodiments, the anchoring layer is only around a portion of the perimeter of the stabilizing structure. In certain embodiments, the anchoring layer is only attached to discrete portions of the stabilizing structure as needed. In some embodiments, the anchoring layer covers at most about 5%, at most about 10%, at most about 20%, at most about 30%, at most about 50%, at most about 75%, and at most about 100% of the outside of the stabilizing structure.

In some embodiments, the bands of different tissue anchors can be organized in a vertical direction, while in other embodiments, they may be organized in a horizontal direction. They may also be organized in either the horizontal and vertical directions when considered in the xy plane, i.e. facing downward into the wound.

In certain embodiments, the different types of anchors may be interspersed with one another, rather than organized into discrete bands of specific types of anchors. For example, the longer anchors may be surrounded by smaller anchors and vice-versa. In some embodiments, the anchors may be organized randomly across the anchoring layer or in other suitable patterns.

In particular embodiments, the anchoring layer may be disposed on the inner faces of the stabilizing structure. For example, the anchoring layer may cover at most about 5%, at most about 10%, at most about 20%, at most about 30%, at most about 50%, at most about 75%, and at most about 100% of the interior surfaces of the stabilizing structure.

In further embodiments, the entire anchoring layer may be comprised of only one type of anchor, for example the entirety of the anchoring layer may be comprised of the longer hooks 5008 or the shorter hooks 5010 as depicted in FIG. 5B. Some embodiments may call for the anchors to be color coded. For example, the anchors on the bottom may be made to be one color while the anchors on the top may be another so as to identify the proper orientation of the stabilizing structure in the wound.

Wound Closure and Treatment Methods of FIGS. 6-12G

FIGS. 6-10D are photographs and illustrations depicting embodiments of a method for the treatment of a wound that utilizes a wound closure device comprising a stabilizing structure as described herein this section and elsewhere in the specification. To better illustrate a non-limiting embodiment of the method, numbers have been added to each step in FIGS. 10A-D to allow the reader to more easily follow these steps of the method. However, the steps can be performed in any order, and any numbering system is for clarity only. Further, in some embodiments, different steps of this method may be excluded. In other embodiments, additional steps may be added to the method based on methods described herein this section and elsewhere in the specification. The porous layers and structures described in this section may be of any material or structure described elsewhere in the specification, such as foam.

Figure 6:
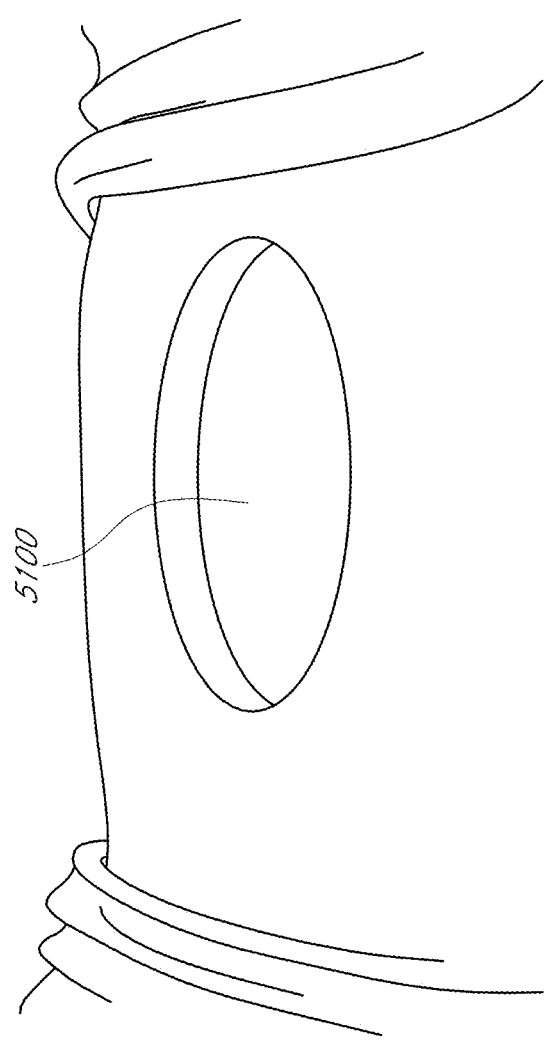
FIG. 6 illustrates an embodiment of an open abdominal wound.

FIG. 6 depicts an embodiment of an open wound 5100 prior to treatment with a wound closure device as will be described in much greater detail below. The open wound of FIG. 6 is similar to the wounds described elsewhere in the specification, particularly as relates to FIG. 1. In some instances, as described elsewhere in the specification, such a wound may be produced via a surgical incision or other means.

Figure 7:
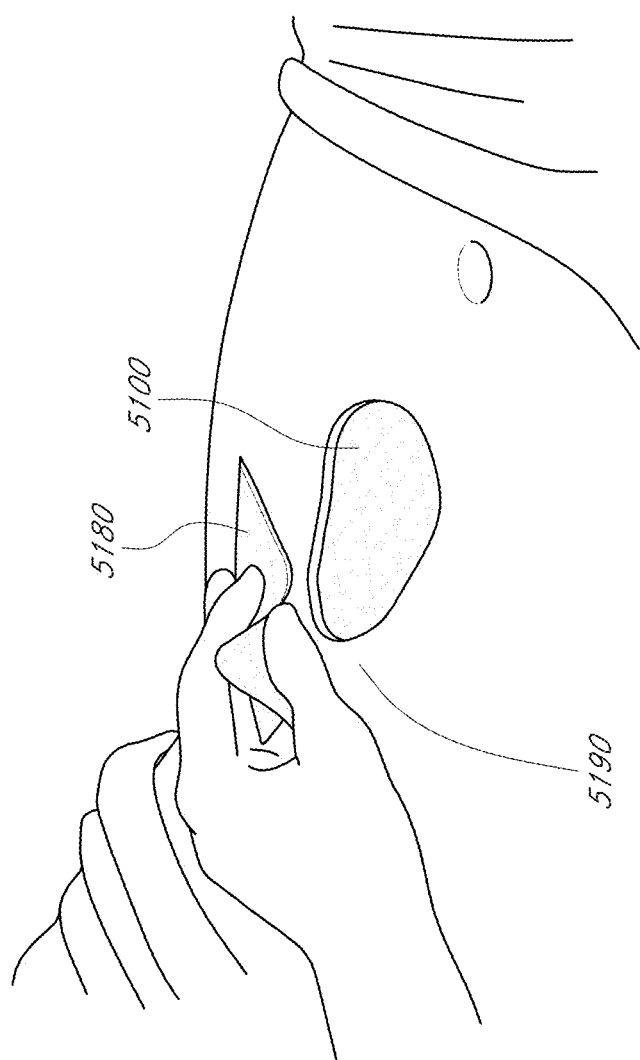
FIG. 7 illustrates an embodiment of a step in a method of treating a wound.

FIG. 7 depicts an embodiment of an initial step in a method for the treatment of an open wound 5100 with a wound closure device. Before treatment, the wound may be cleaned with a pad 5180 and the skin 5190 prepared for application of a wound closure device, such as those described in relation to FIGS. 2A-5D and FIGS. 10A-10C.

Figure 8:
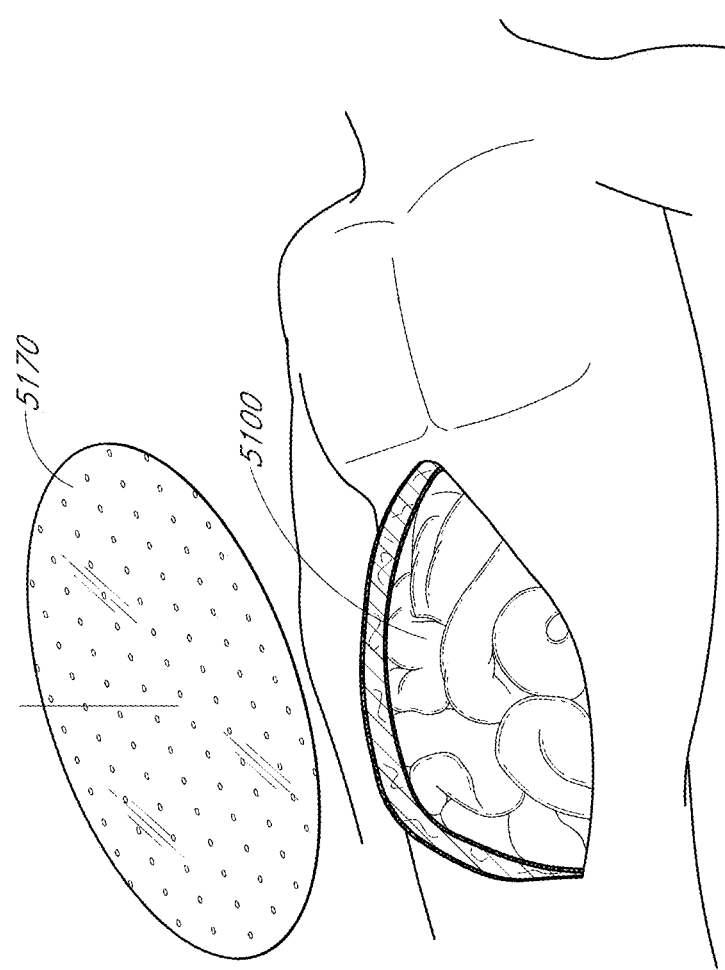
FIG. 8 illustrates an embodiment of a step in a method of treating a wound.

FIG. 8 depicts an embodiment of an early step in a method for the treatment of an open wound 5100. In some embodiments, a tissue protection layer 5170 may be placed over the wound to protect the underlying tissues from the rigors of negative pressure wound therapy or other potential harms. Accordingly, certain embodiments provide for a tissue protection layer 5170 which may be cut to size to be placed over the wound site 5100. The tissue protection layer 5170 can be a material which will not adhere to the wound site or to the exposed viscera in close proximity. Such a tissue protection layer may be constructed from any suitable material such as a biocompatible polymer. For example, organ protection layers manufactured by Smith & Nephew and sold under the brand RENASYS® may act as tissue protection layers and be placed over the abdominal cavity and/or wound bed 5100 and tucked over the peritoneal gutter. In further examples, materials such as the fluoroplymer polytetrafluoroethylene (PTFE) may be applicable as these materials are generally non-adherent and used in surgical grafts. In one embodiment, the tissue protection layer is permeable. For example, the tissue protection layer 5170 can be provided with openings, such as holes, slits, or channels, to allow the removal of fluids from the wound site 5100 or the transmittal of negative pressure to the wound site 5100. In further embodiments, the tissue protection layer may be used over non-abdominal wounds on other areas of the body, such as the leg, arm, shoulder, or back. In certain embodiments, the tissue protection layer may comprise a sensor configured to measure pressures in and around the wound. For example, the sensor may be used to measure the level of negative pressure applied to the wound or to measure the pressure on the underlying organs beneath the abdominal wound.

Figure 9A:
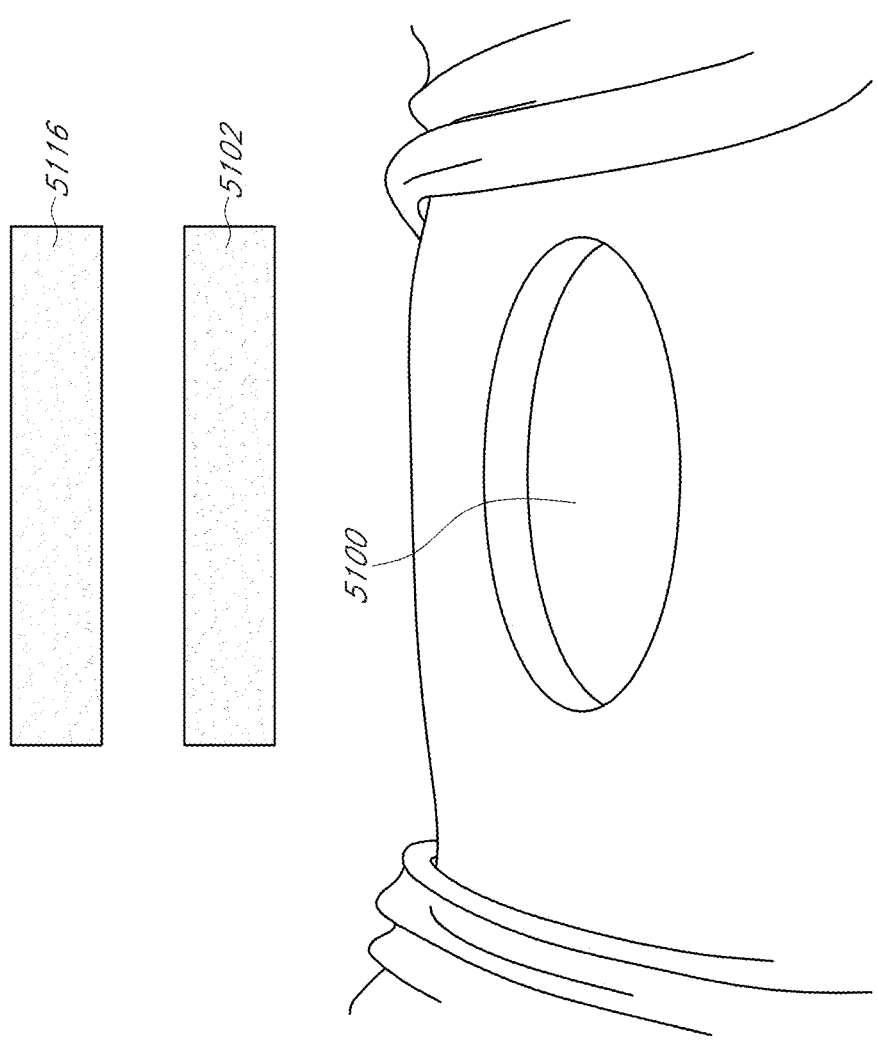
FIGS. 9A-C illustrate an embodiment of steps of a method of treating a wound.
Figure 9B:
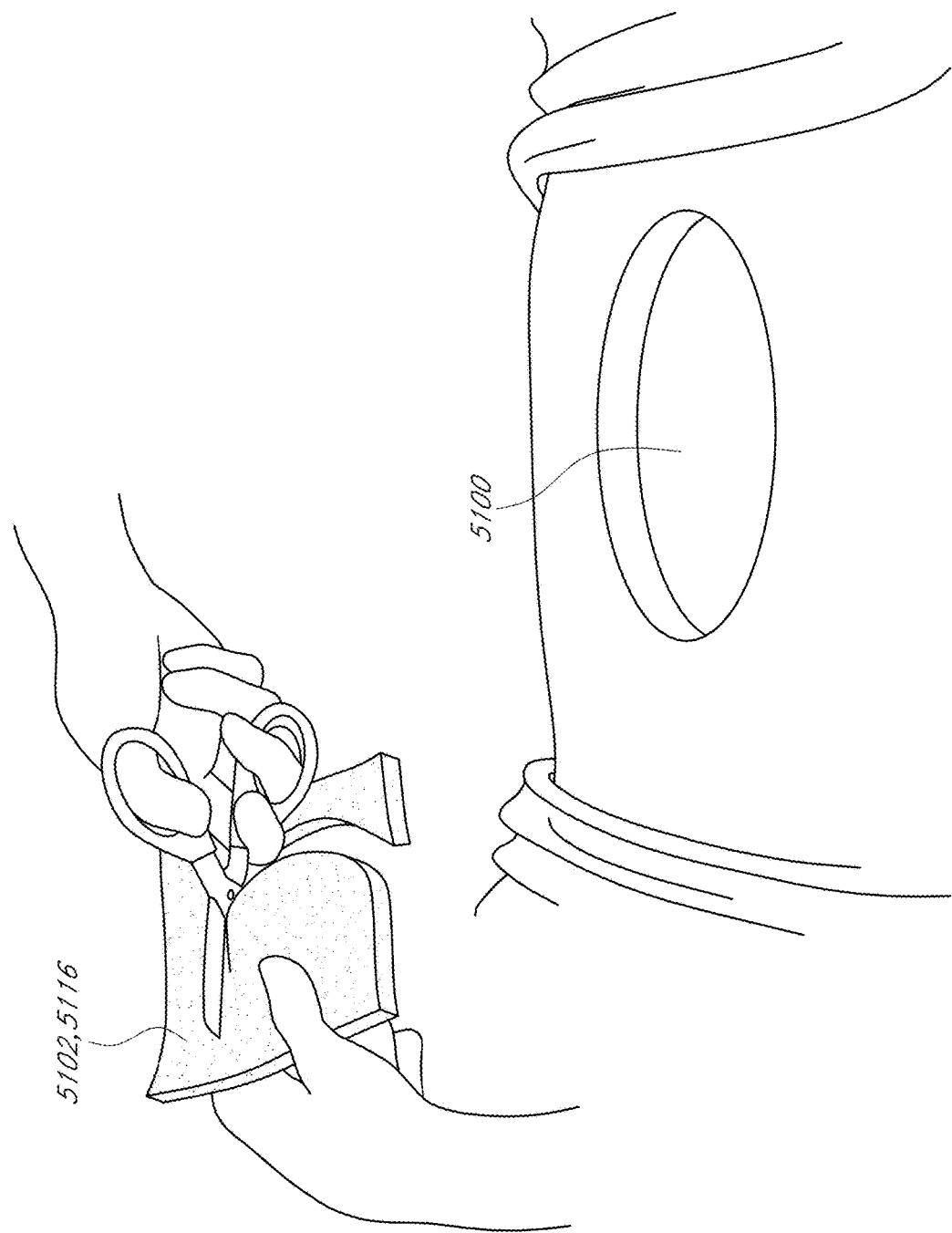
Figure 9C:
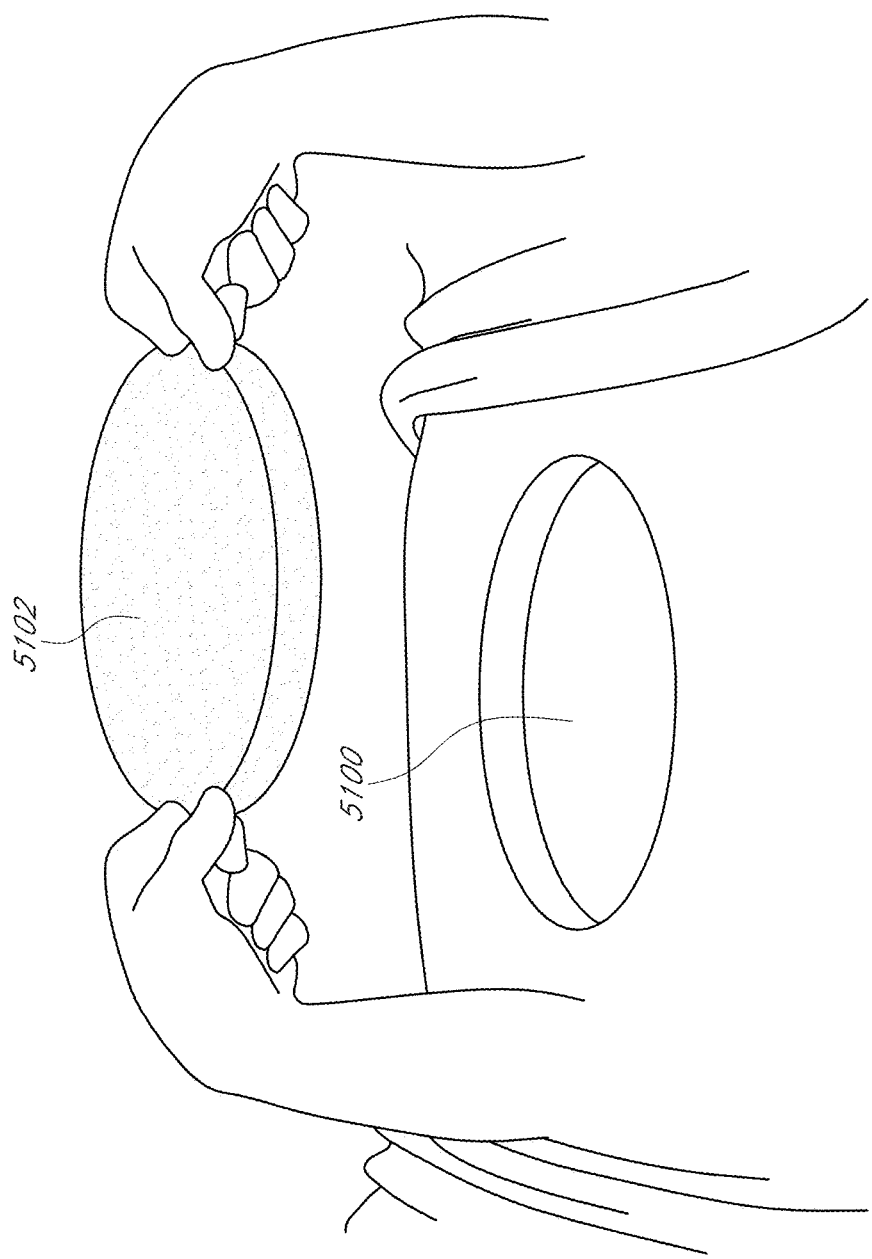

FIGS. 9A-C illustrate embodiments of possible initial steps in a method for the treatment of an open wound. However, as described above, the steps need not be performed in this order and may be performed in any order. In FIG. 9A, two pieces of a porous material such as foam, a bottom piece 5102 and a top piece 5116 are selected so as to approximate the size of the wound 5100. In some embodiments, the top piece and the bottom piece are of identical thickness. However, in certain embodiments, and vice-versa, top piece 5116 may be at least twice as thick, at least four times as thick, at least 10 times as thick or more than ten times as thick as bottom piece 5102. FIG. 9B illustrates an embodiment of additional steps in a method for the treatment of an open wound. Bottom piece 5102 may be shaped via cutting or other suitable means to the shape of the wound and subsequently placed into the wound 5100, as shown in FIG. 9C and depicted further below in FIG. 10A.

Figure 10A:
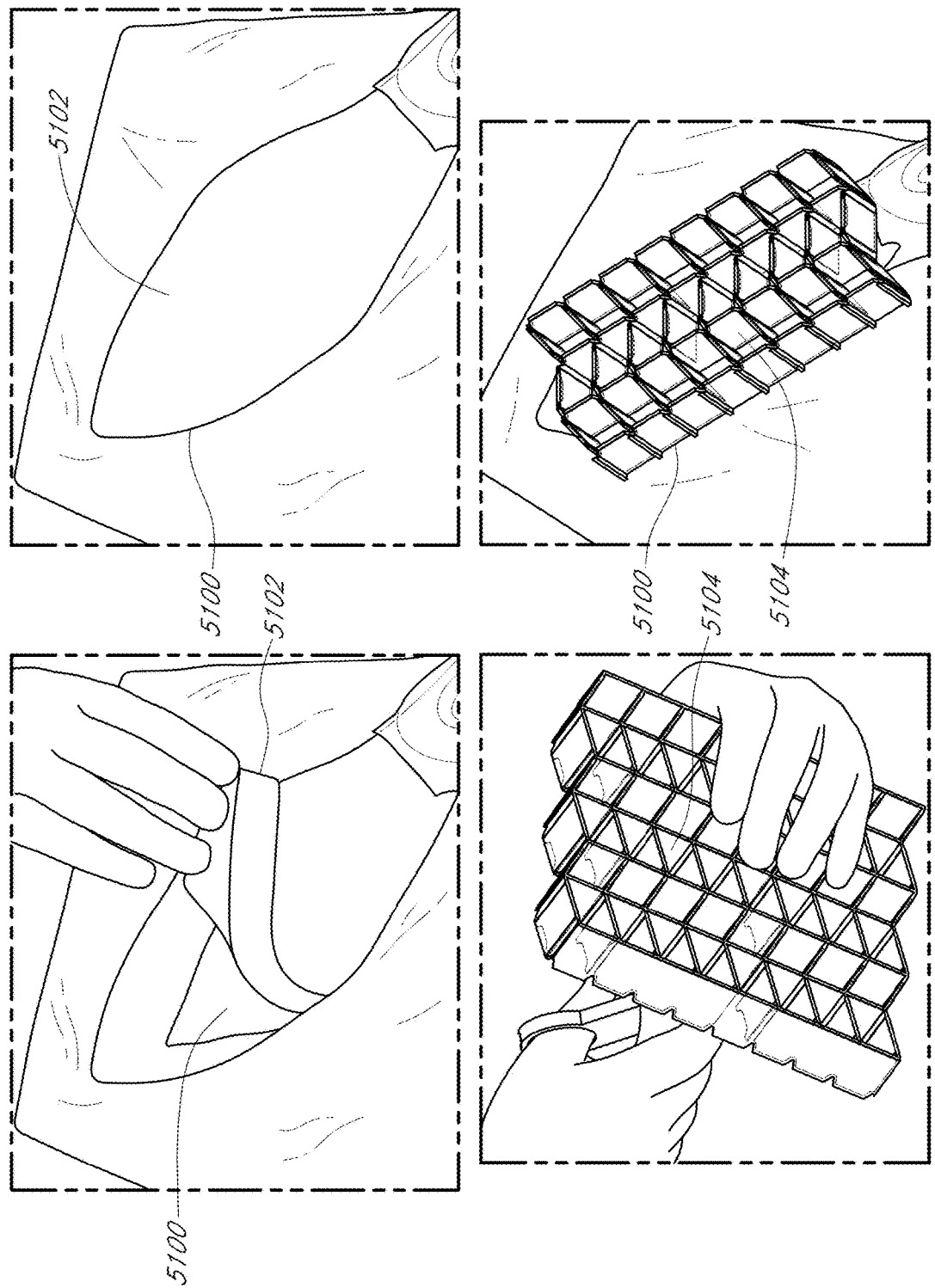
FIGS. 10A-C illustrate an embodiment of steps of a method of treating a wound.

Beginning with steps 1 and 2 of FIG. 10A, after shaping, a foam layer 5102 (for example, a 15 mm layer of foam) is placed in the wound bed 5100. In steps 3-4, a stabilizing structure 5104 similar to the stabilizing structures disclosed in FIGS. 2A-I or any other stabilizing structure described elsewhere in the specification, is shaped to the size of the wound via cutting or other suitable means. In certain embodiments, the matrix may be shaped in such a manner as to ensure that the matrix has flat, longitudinal sides. As displayed in step 4, the stabilizing structure 5104 may be placed in the wound to determine the accuracy of the shaping step. Preferably, when using a stabilizing structure of FIGS. 2A-I, the stabilizing structure is placed such that grooves or notches as described elsewhere in the specification are facing downward. However, in some embodiments, grooves or notches may be present on both the top and the bottom of the stabilizing structure. In steps 5-6 of FIG. 10B, a foam layer 5106, in the shape of a ribbon, is attached to the outer edge of the stabilizing structure 5104 via an adhesive backing tape or other suitable means. The foam layer 5106 may be used to partially or completely surround the perimeter of the stabilizing structure 5104. Excess ribbon can simply be removed from the backing tape and discarded. To allow the backing layer to properly adhere to the stabilizing structure, the foam layer may be held in place for an excess of 30 seconds.

Figure 10B:
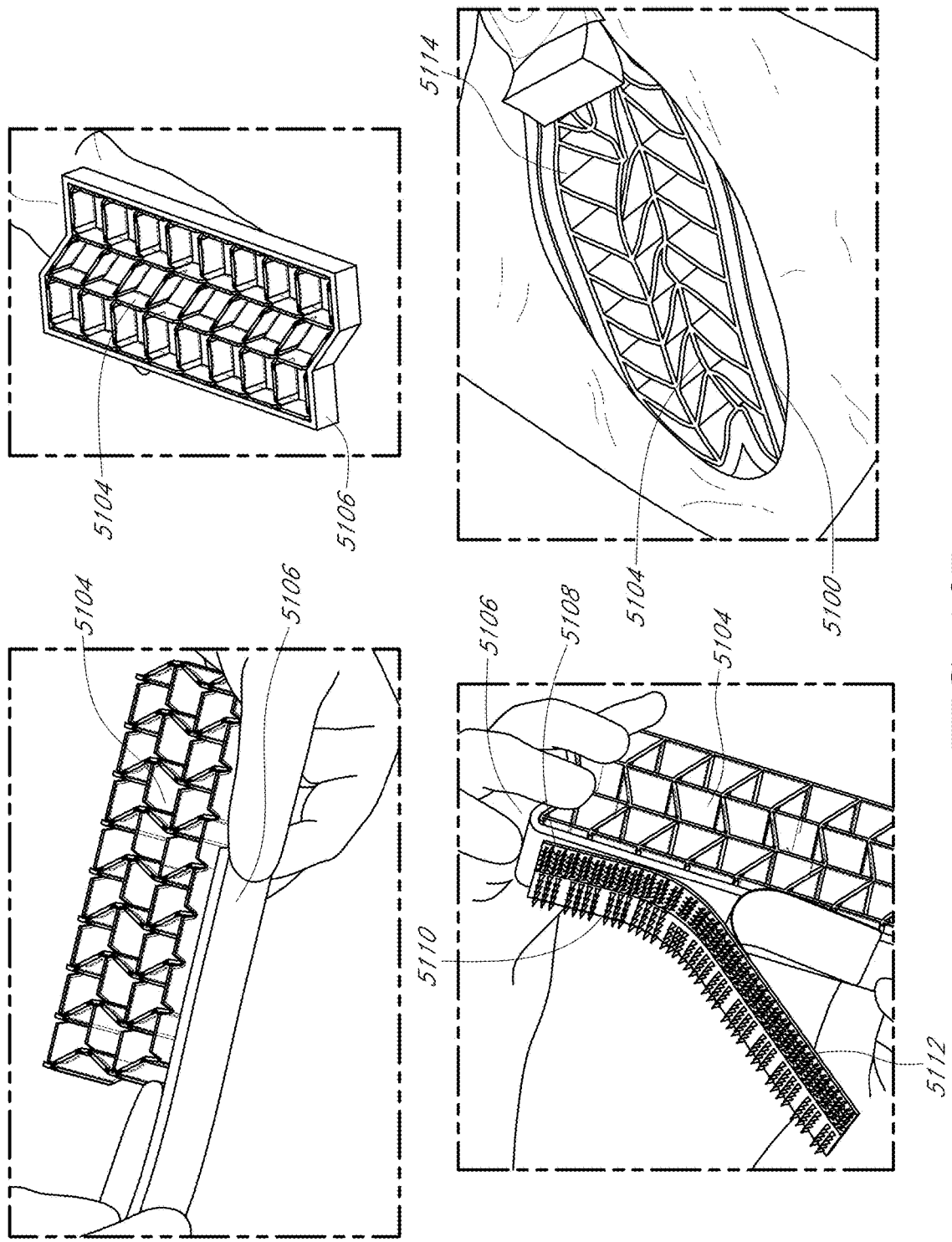

Step 7 of FIG. 10B shows the next step of an embodiment of the method, wherein an anchoring layer 5108 comprising a first band of longer anchors 5110 and a second band of shorter anchors 5112 is attached to the foam layer 5106. The anchoring layer 5108 may be shaped to the size of the perimeter of the stabilizing structure 5104 and adhered to the foam layer 5106 via the removal of an adhesive backing layer covering an adhesive surface on a side of the elongate layer opposite the anchors. The anchoring layer may partially or completely surround the foam layer. To allow the anchoring layer to properly adhere to the stabilizing structure, the anchoring layer may be held in place for a period of time, for example in excess of 30 seconds. Once the anchoring layer has been applied to the foam layer 5106 and stabilizing structure 5104, the entire wound closure device 5114 may be placed into the wound 5100, as displayed in step 8 of FIG. 10B. To assist with the insertion of the device into the wound bed, the device can be deformed slightly inwardly or horizontally to facilitate entrance into the wound site. In some embodiments, the device may be squeezed slightly during insertion and then release upon contact with the walls of the wound. In certain embodiments, the wound closure device 5114 may be placed such that the longitudinal sides of the matrix align with the longitudinal axis of the wound 5100.

In some embodiments, it may be preferable to orient the shorter second anchors 5112 towards the top of the wound and the longer first anchors 5110 towards the bottom of the wound so that the shorter anchors 5112 may engage the fatty tissue of the wound. However, in other embodiments, depending on the shape of the anchors, it may be desirable to orient the combination in the opposite orientation such that the longer anchors 5110 engage the fatty tissue. The anchors may also have the same length. In certain embodiments, the anchors may be color coded, to direct a use to a particular orientation of the stabilizing structure. The anchors also need not cover the entire outer perimeter of the stabilizing structure. In some embodiments, anchors are provided only on the first side 4234 and second side 4236 of the stabilizing structure (for an embodiment such as illustrated in FIG. 2G).

Figure 10C:
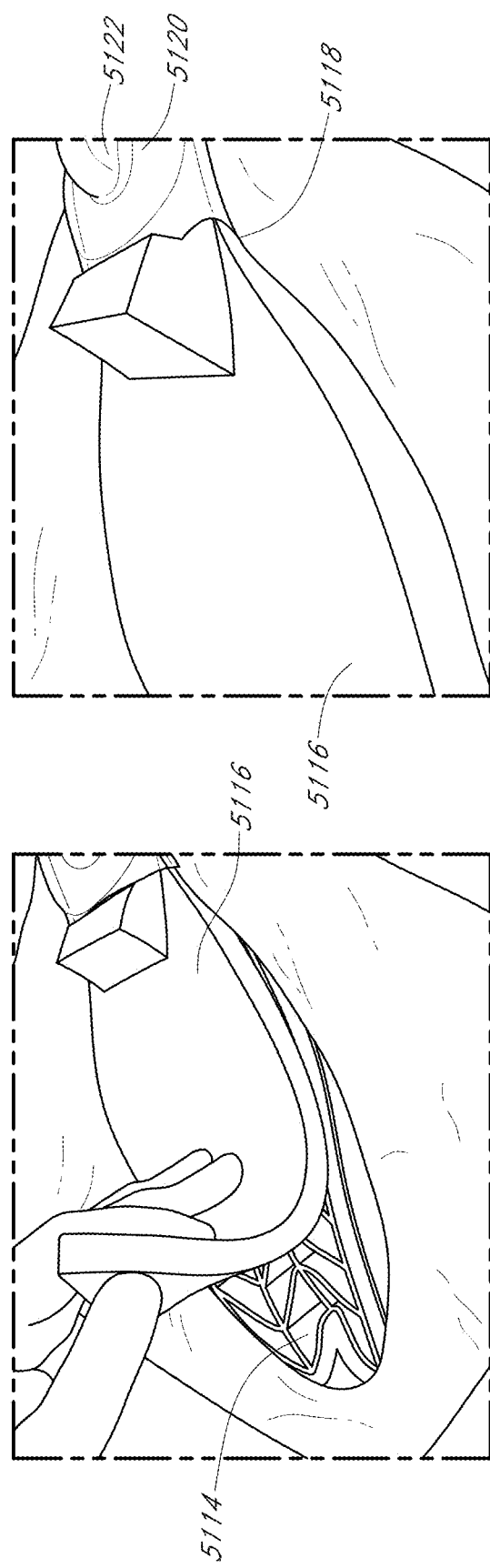

FIG. 10C contains photographs of step 9 and 10 of a method of wound closure and treatment. In step 9, another foam layer 5116 (for example, a 10 mm layer of foam) is placed on top of the wound closure device 5114. As displayed in step 10, a bridging portion of foam 5118 may be placed in intimate contact with the foam layer 5116 at the edge of the wound. The bridging portion of foam 5118 may extend over intact skin, with a piece of drape 5120 placed between it and the intact skin. Further, a suction port 5122 may be connected to the bridging portion 5118 with a section of drape 5120 between. In alternative embodiments, the bridging portion 5118 and suction port 5122 may be placed on the wound during a different step, for example during steps 1 and 2 as depicted in FIG. 10A.

Figure 11:
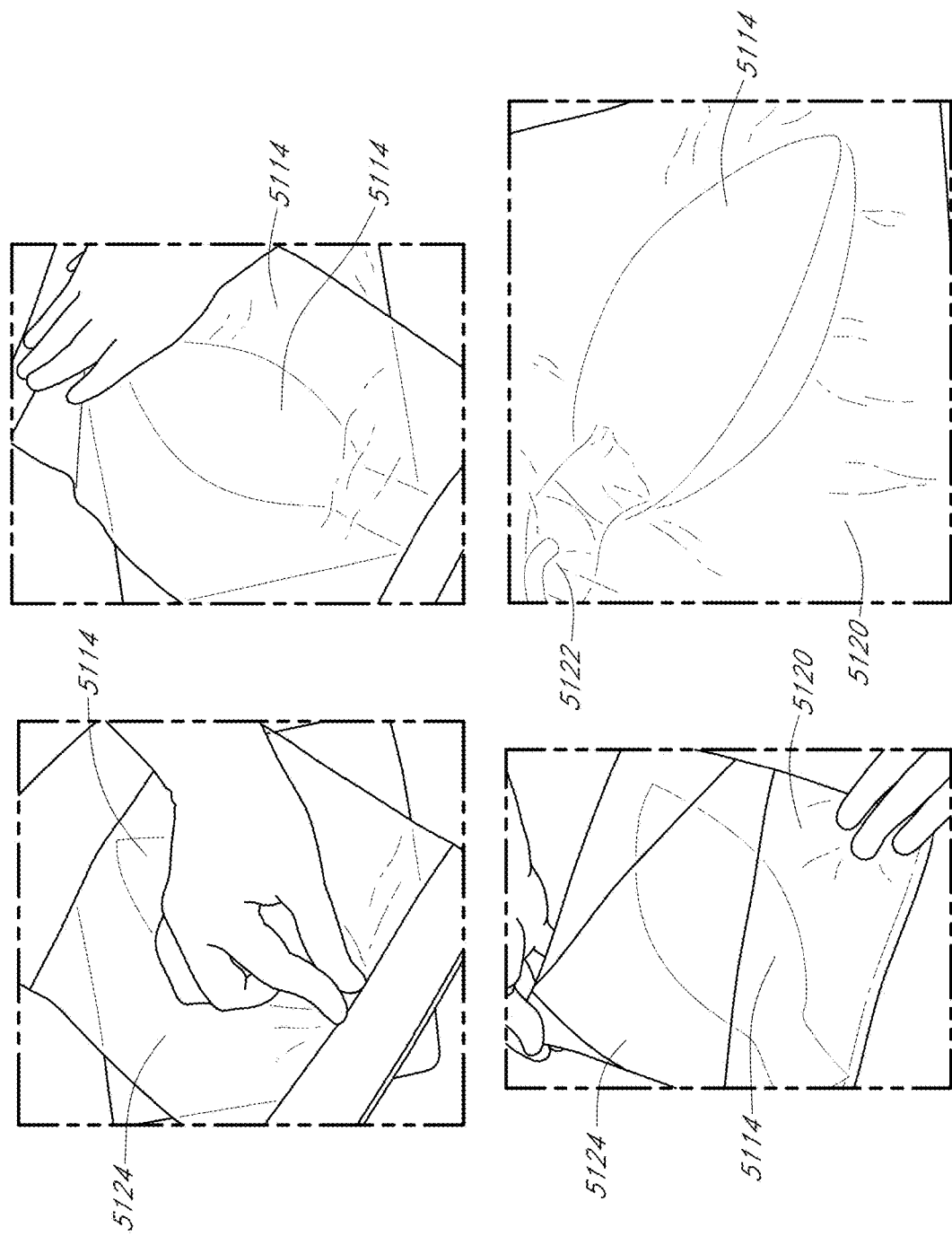
FIG. 11 illustrates an embodiment of steps of a method of treating a wound.

In FIG. 11, as shown by steps 11-14, the device may be covered by one or more drapes 5120. A hole may be made in the drape covering the bridging portion of foam, and a suction port 5122 may be placed over the hole. A protective layer 5124 on the top surface of the one or more drapes may be removed after the drapes 5120 are applied. Once the drapes 5120 are applied and the port is in place, negative pressure may be applied to the wound through the drape from a vacuum source. The negative pressure can cause the stabilizing structure to collapse horizontally as described elsewhere in this specification. The tissue anchors adhered to the stabilizing structure through the porous layer engage tissue of the wound and may facilitate closure of the wound.

Figure 12A:
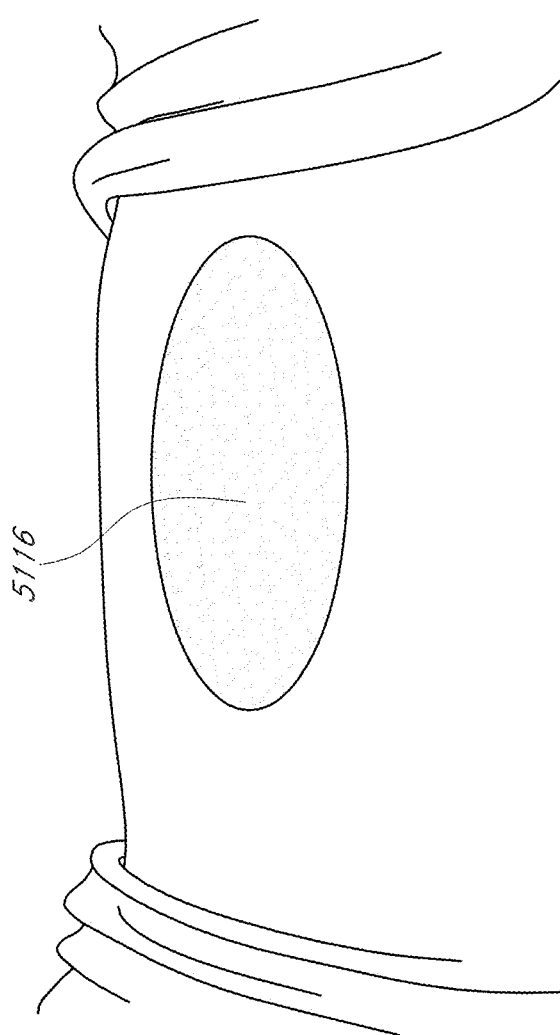
FIGS. 12A-G illustrate an embodiment of steps of a method of treating a wound.
Figure 12B:
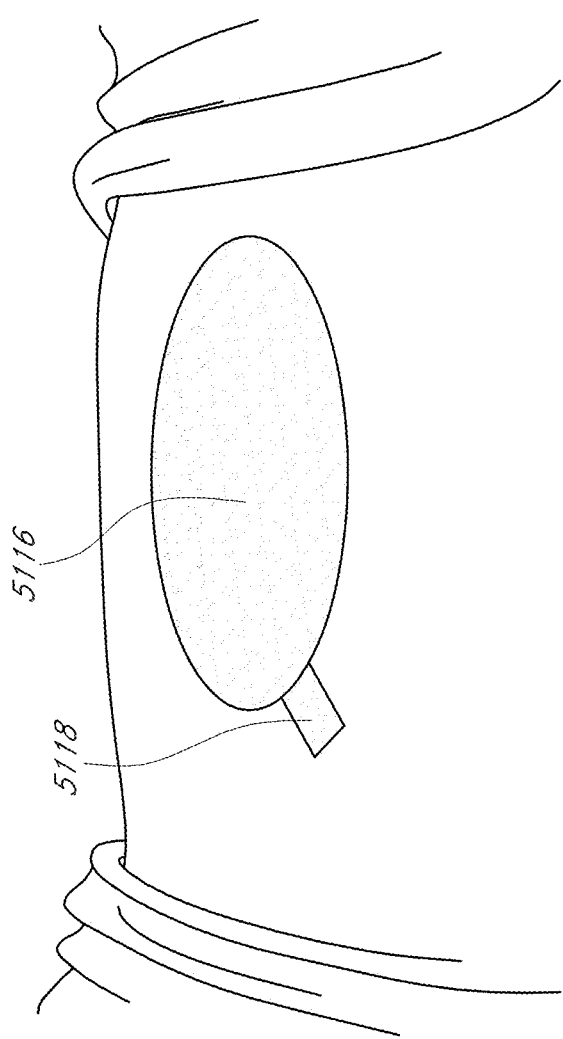
Figure 12C:
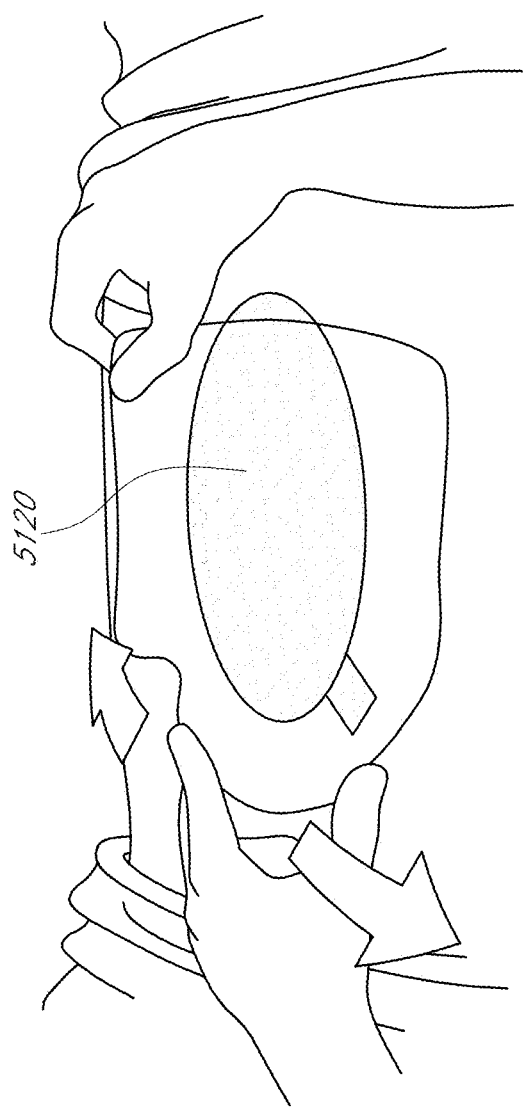
Figure 12D:
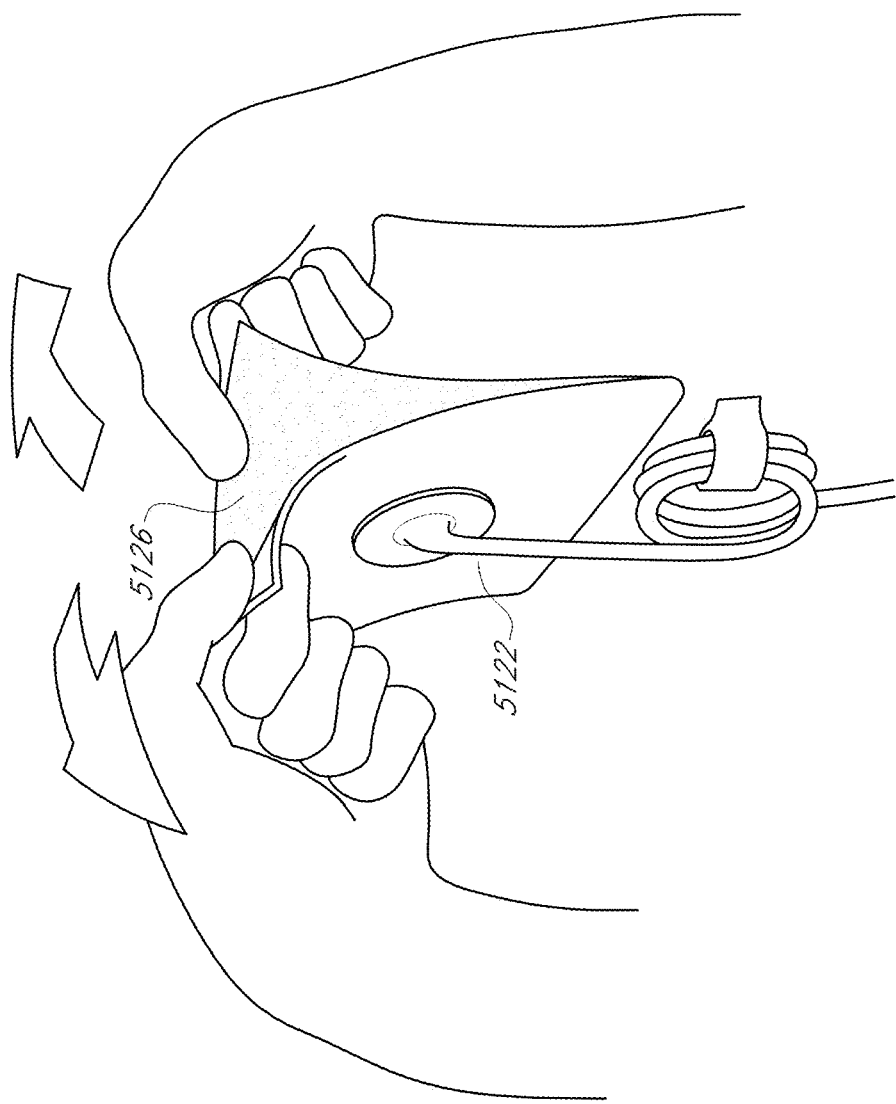
Figure 12E:
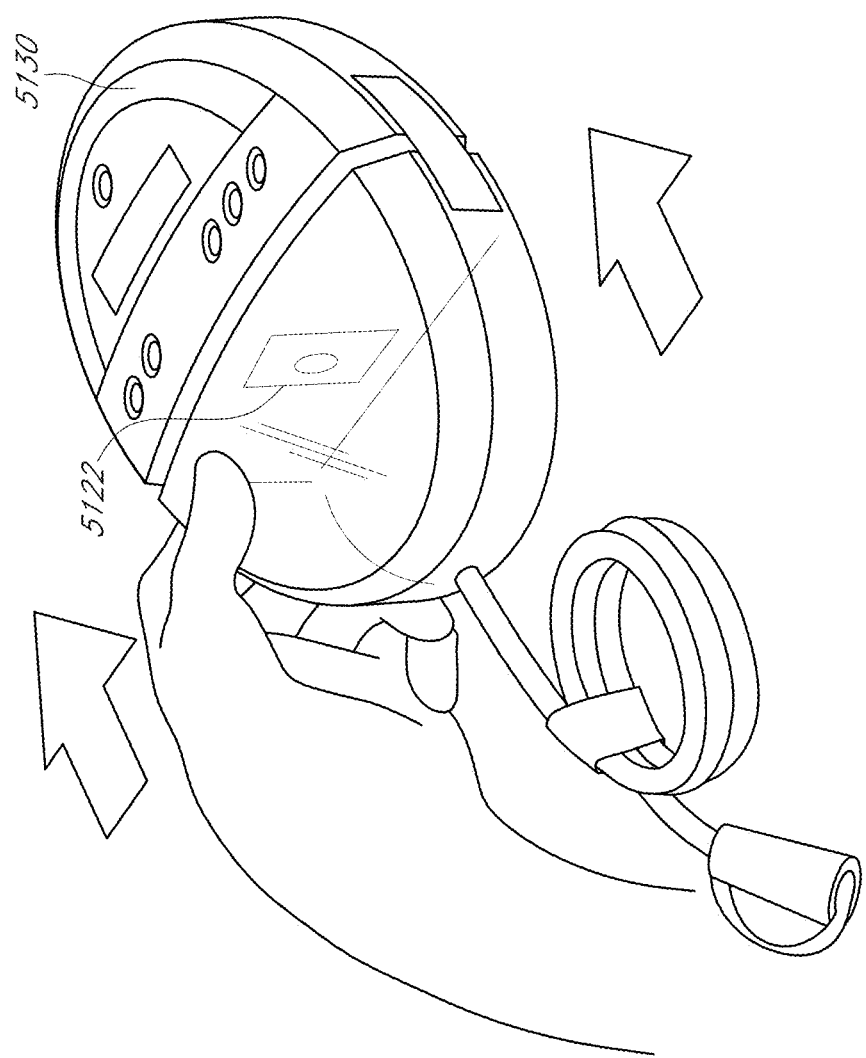
Figure 12F:
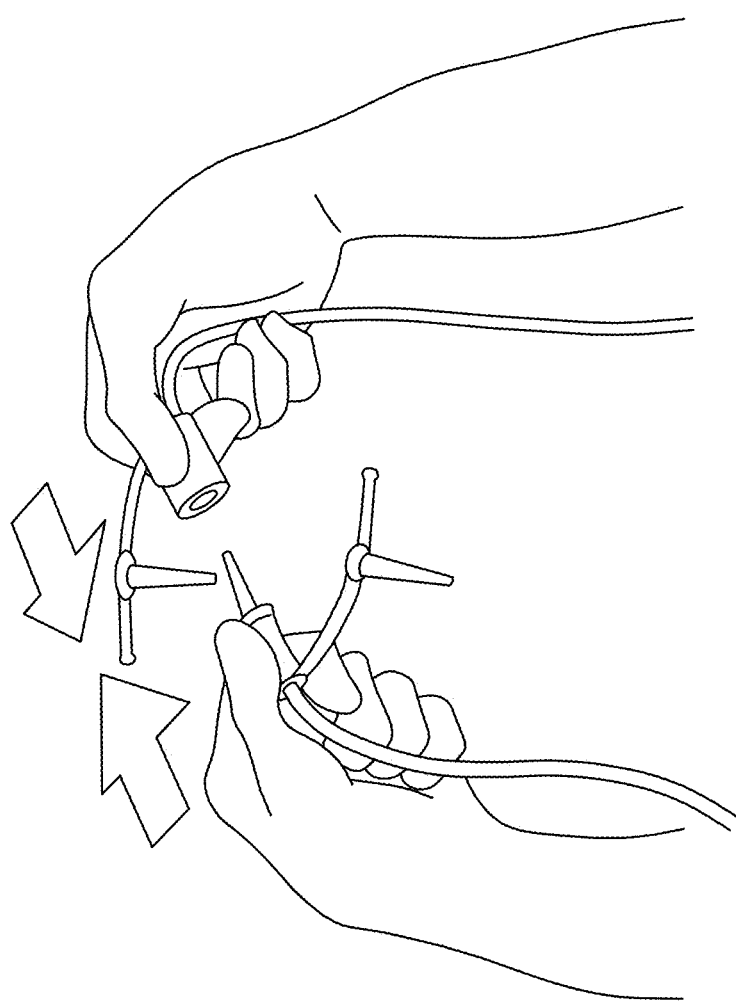
Figure 12G:
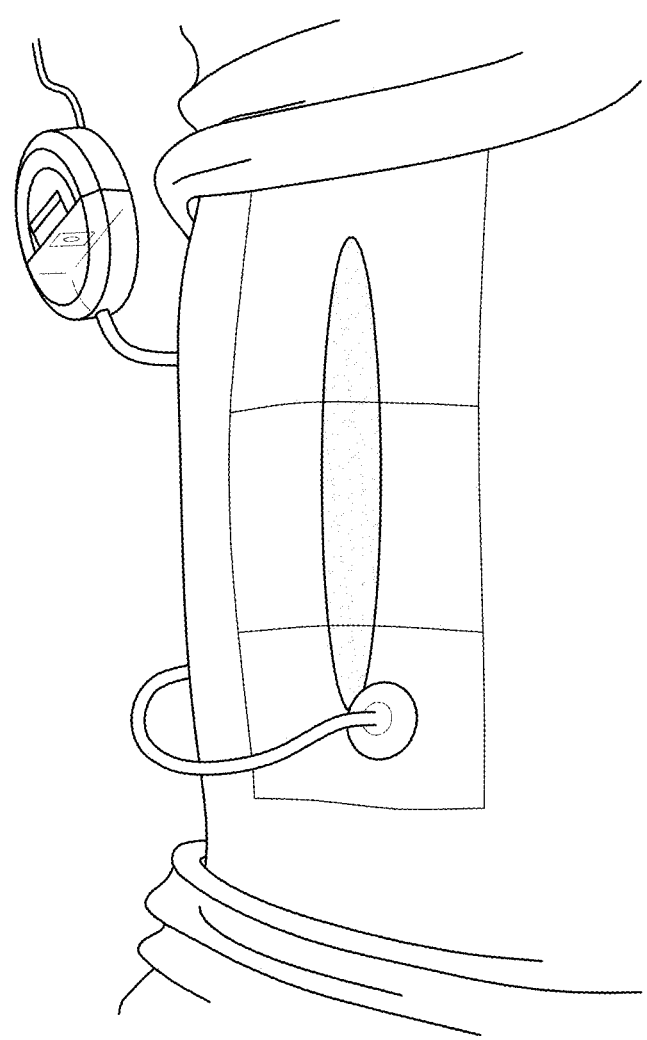

FIGS. 12A-12C provide further illustrations of an upper foam layer 5116 being placed in a wound, followed by placing a bridging portion 5118 and placing one or more drapes or wound covers 5120. FIGS. 12D-12G illustrate an embodiment of several steps in a method for the treatment and closure of a wound. As illustrated in FIG. 12D, a suction port 5122 is separated from a release liner 5126 and later applied to a wound as depicted in FIGS. 10A-11. FIG. 12E illustrates a canister 5128 being inserted into a negative pressure wound therapy device 5130 in preparation for the collection of wound exudate. FIG. 12F illustrates the snap connection between the tubing connected to the suction port and the tubing connected to the negative pressure wound therapy device 5130. Once the connection has been made, negative pressure wound treatment may begin as depicted in FIG. 12G.

Further details regarding the wound closure devices, stabilizing structures, related apparatuses and methods of use that may be combined with or incorporated into any of the embodiments described herein are found elsewhere throughout this specification and in International Application No. PCT/US2013/050698, filed Jul. 16, 2013, published as WO 2014/014922 A1, the entirety of which is hereby incorporated by reference.

Stabilizing Structures and Wound Closure Devices of FIGS. 13A-15E

FIGS. 13A-D illustrate embodiments of a stabilizing structure 6000 that are similar to the embodiments described above in relation to FIGS. 2A-I. In contrast to the stabilizing structures disclosed in FIGS. 2A-I, stabilizing structure 6000 may have an outer perimeter 6002 that defines an at least partially elliptical shape. Similar to the stabilizing structures of FIGS. 2A-I, stabilizing structure 6000 comprises a plurality of cells 6004 provided side-by-side, each cell defined by one or more walls, each cell having a top end and a bottom end with an opening extending through the top and bottom ends. As with the other stabilizing structures described herein this section and elsewhere in the specification, the stabilizing structure 6000 is configured to collapse by collapsing one or more cells 6004. In some embodiments, the cells are all of the same approximate shape and size; however, in other embodiments, the cells are of different shapes and sizes. In some embodiments, the stabilizing structures as described herein this section or elsewhere in the specification may be domed, such that the central portion of the stabilizing structure bulges upward. For example, a lower portion of the stabilizing structure may be concave, while an upper portion of the stabilizing structure is convex. Further description of such an embodiment is found with respect to FIGS. 18A-18C of this specification. The stabilizing structure 6000 comprises a plurality of elongate strips 6006 arranged in parallel or semi-parallel, whose longitudinal length can be aligned with the longitudinal axis of the wound. The elongate strips 6006 may also be arranged in a non-parallel fashion. These elongate strips 6006 may be of similar type to the elongate strips disclosed above in relation to FIGS. 2A-I. For example, elongate strips 6006 may comprise sections of more rigid material and sections of more flexible material as disclosed in relation to FIGS. 2A-I. In some embodiments, the elongate strips 6006 are made from one single material. Further, elongate strips 6006 may be broken up into various segments 6008 to allow flexing of the elongate strips. In certain embodiments, the elongate strips 6006 may be curved along their length so as to facilitate the curved outer perimeter of the stabilizing structure 6000. The elongate strips may be curved along their lengths outward away from a center of the stabilizing structure 6000. The arch of the curves of the elongate strips 6006 may vary considerably, with some strips 6006 being highly curved while other are minimally curved or even straight.

Similarly, the stabilizing structure 6000 can further comprise a plurality of intervening members 6010 connected to the elongate strips 6006. The intervening members 6010 may all be of a similar shape and size or they may be of a variety of shapes and sizes as depicted in FIGS. 13A-D. The intervening members may be similar in construction and function to the intervening members of FIGS. 2A-I, or they may be of different types such as of a single, solid material. In some embodiments, the intervening members 6010 that are located in-line with the bulging section of the elliptical perimeter 6002 may be larger than intervening members 6010 located elsewhere so as to facilitate the outward perimeter 6002 of the ellipse.

Advantageously, such an elliptically shaped stabilizing structure may allow the structure to better accommodate the shape of the wound. Most wounds are in shapes that are more rounded than the square shape of the stabilizing structures depicted in FIGS. 2A-I. Thus, an elliptically shaped stabilizing structure 6000 may better fit into a wound.

Figure 13A:
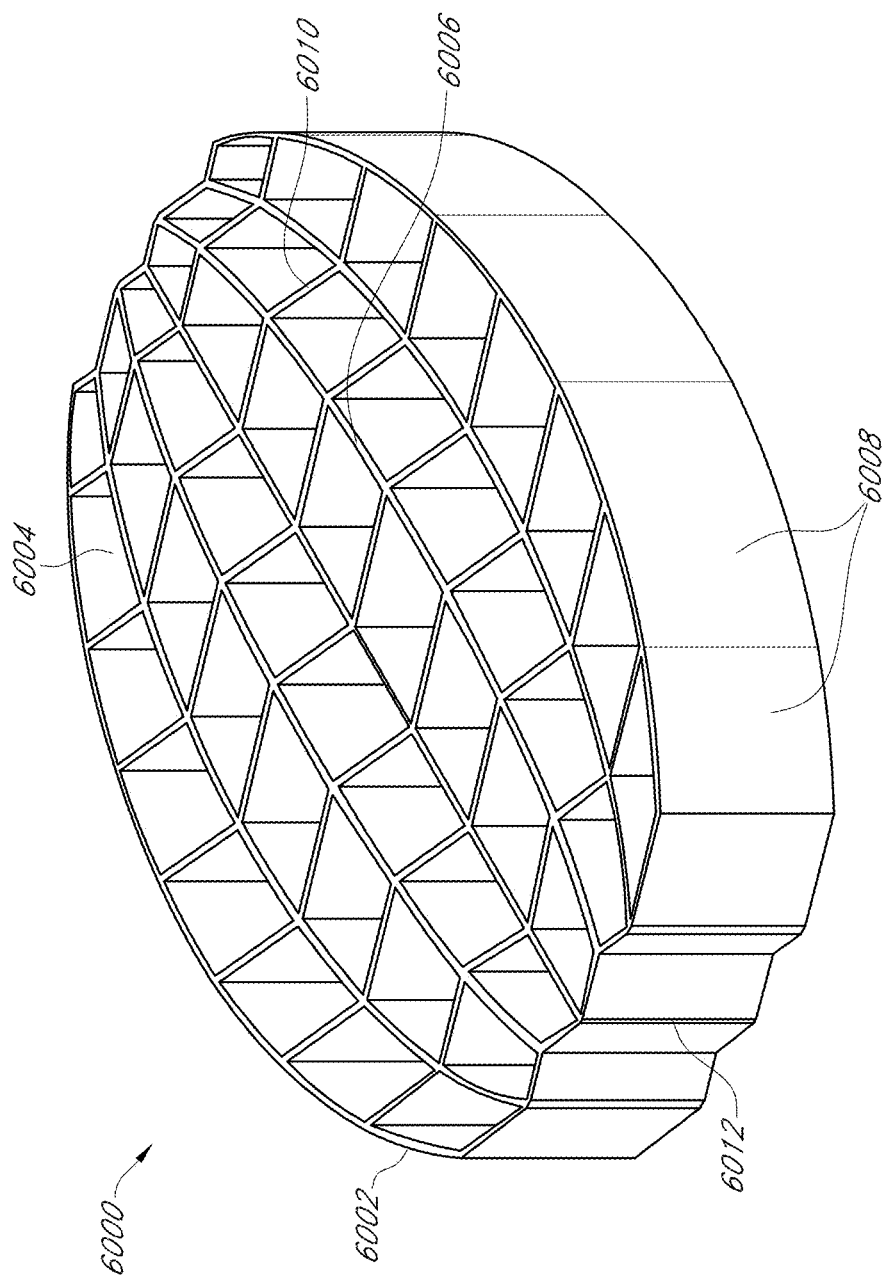
FIGS. 13A-D illustrate embodiments of a stabilizing structures with rounded out walls.
Figure 13B:
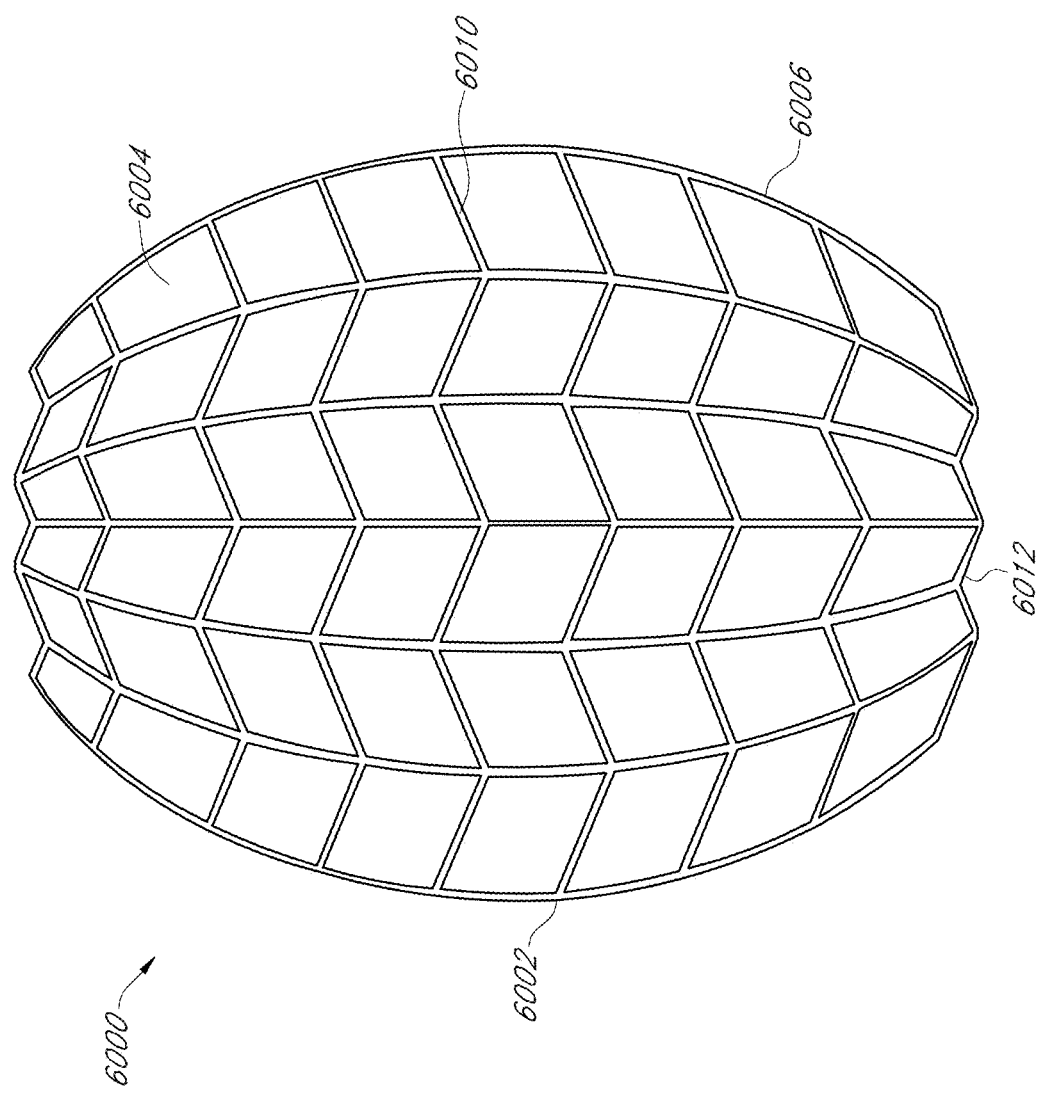

Referring now to the stabilizing structures of FIGS. 13A-B, the outer perimeter 6002 may have a reduced edge 6012 so as to facilitate collapse of the stabilizing structure. By removing mass of the stabilizing structure at reduced edge 6012, the stabilizing structure can collapse more freely at reduced edge 6012, thus allowing for a better fit within the wound. Further, by reduced the mass at reduced edge 6012, there may be less pinching of the surrounding tissue during and after collapse of the stabilizing structure 6000. FIG. 13B depicts a top view of the stabilizing structure of FIG. 13A.

Figure 13C:
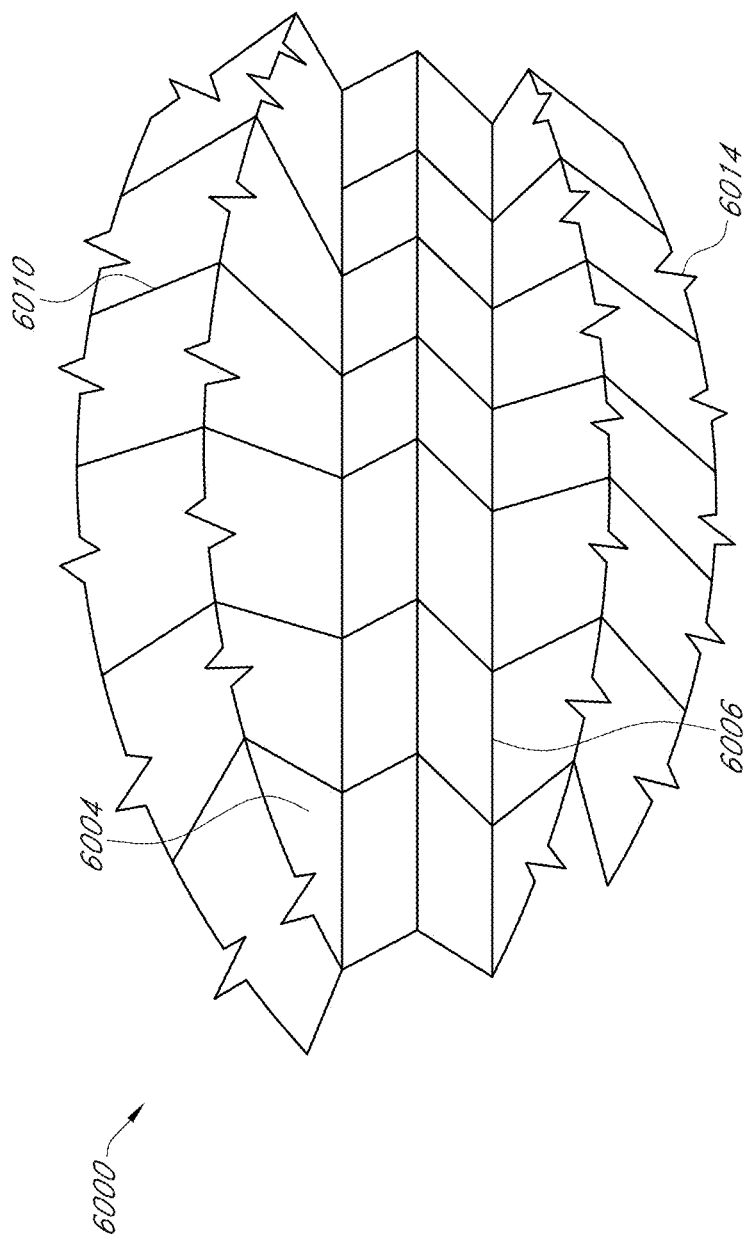

FIG. 13C illustrates an embodiment of a stabilizing structure similar to the structure described in relation to FIGS. 13A-B. However, in this case, some of the elongate strips 6006 may further comprise flexible wall portions 6014 that allow the stabilizing structure 6000 to more easily collapse. When the various cells 6004 of the structure are of different shapes and sizes, as depicted in FIG. 13C, collapse may be limited by the length of the individual segments of the elongate strips 6006. By making the strips 6006 more flexible, complete closure is facilitated. In certain embodiments, the elongate strips 6006 can expand, compress, lengthen, shorten, stretch, and/or tighten. In some embodiments, the flexible wall portions 6014 of the elongate strips 6006 may be replaced by a flexible tube aligned perpendicularly to the plane of the stabilizing structure. In further embodiments, the flexible wall portions 2014 may comprise different materials, thinned sections, a concertina design, a V-edge, or any other suitable design. Where the geometry requires that the elongate strips 6006 adjust as the stabilizing structure 6000 is compressed, flexible wall portions 2014 may be inserted much like the inserts described above in relation to FIGS. 2A-I. In particular embodiments, the outer elongate strips 6006 may comprise flexible wall portions 6014, while the inner may not. One of skill in the art would understand that any suitable combination of elongate strips 6006 with or without flexible wall portions 6014 may be possible.

Figure 13D:
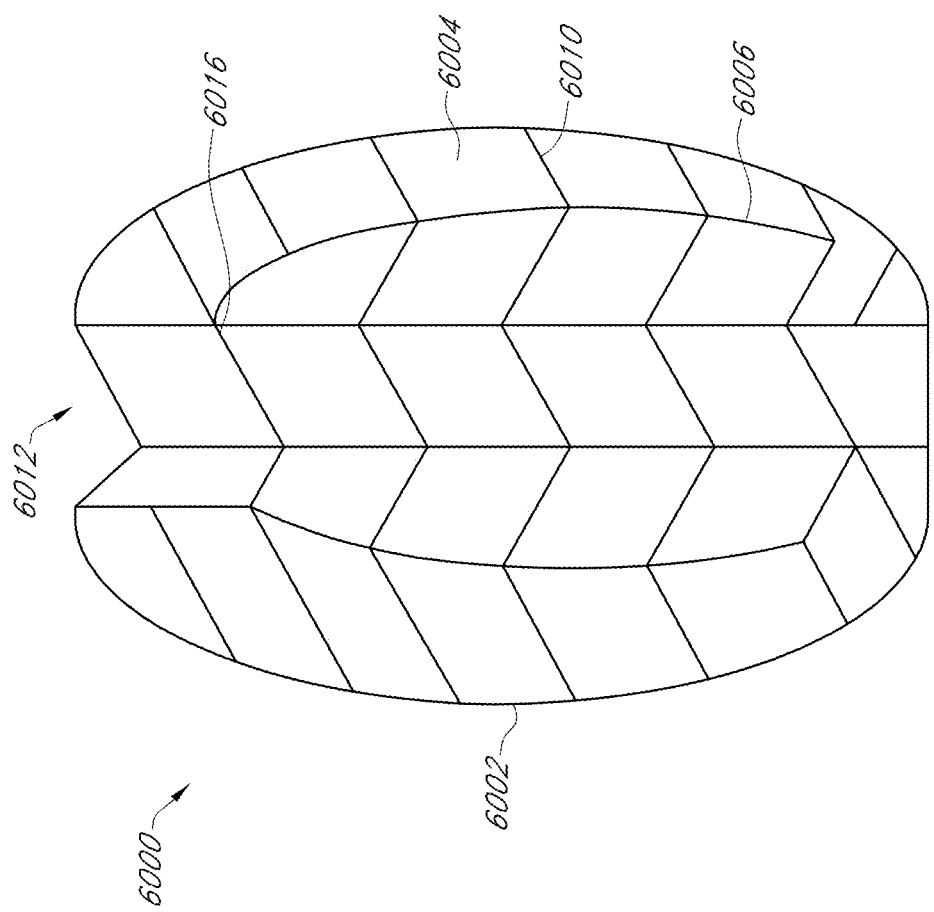

FIG. 13D illustrates an embodiment of a stabilizing structure 6000 similar to the structures of FIGS. 13A-C. However, FIG. 13D depicts a combination of curved and straight elongate strips 6006 and cells 6004 with a variety of shapes and sizes. Further, in some embodiments, the elongate strips 6006 may not extend for the entire length of the stabilizing structure 6000. Further, some of the elongate strips may be joined at their ends.

Figure 14A:
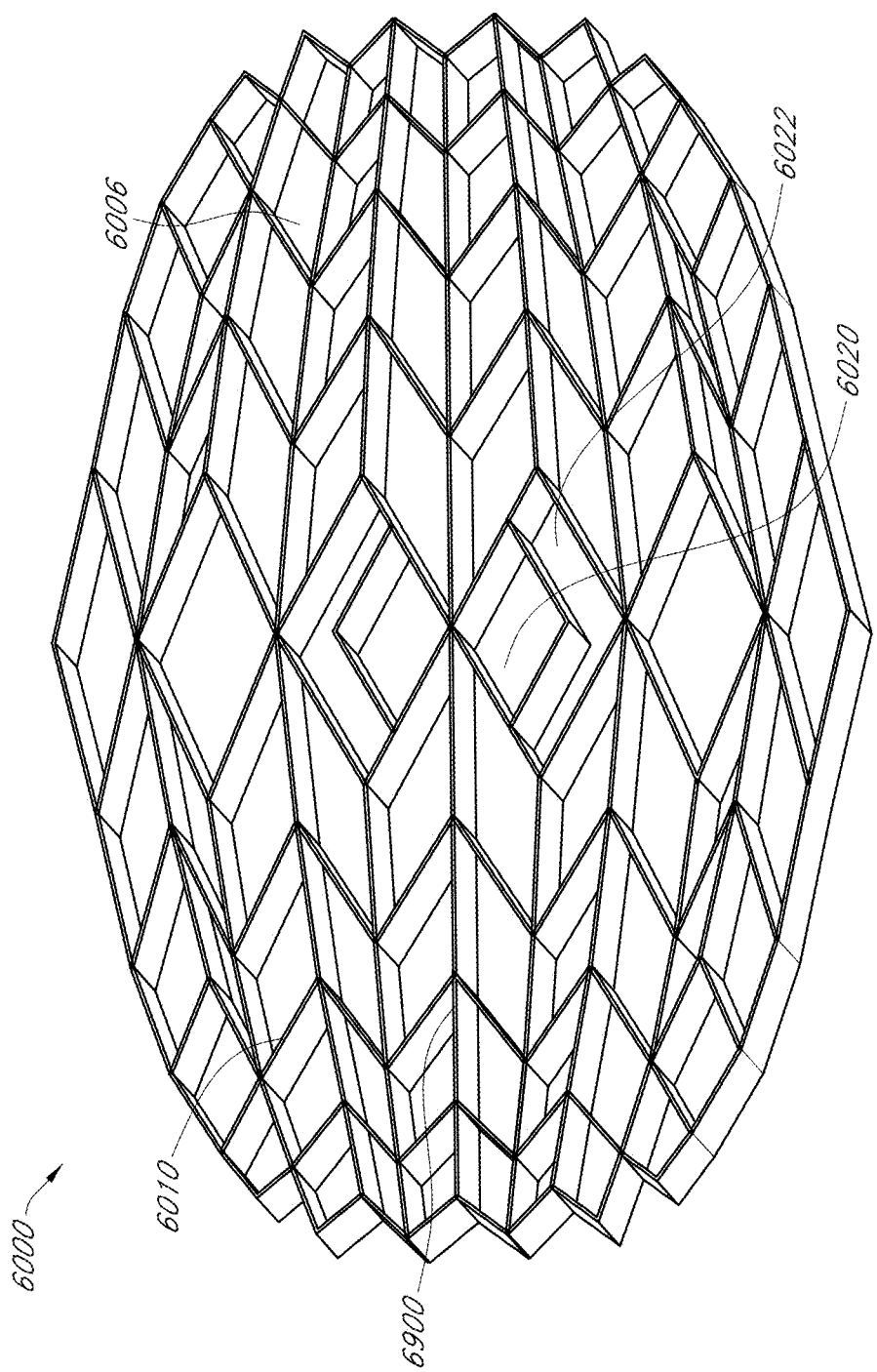
FIG. 14A-C are a photograph and illustrations of embodiments of a stabilizing structure optimized for collapse within a wound.

FIG. 14A is a photograph of an embodiment of a stabilizing structure 6000 similar to the structures of FIGS. 13A-D. As in FIGS. 13A-D, the stabilizing structure 6000 comprises a plurality of elongate strips 6006 arranged in parallel or semi-parallel, whose longitudinal length can be aligned with the longitudinal axis of the wound. Similar to FIG. 13D, the various cells within this stabilizing structure 6000 may have a variety of shapes and sizes. As will be described in greater detail below, the length and shape of the elongate strips 6006, intervening members 6010, and cells 6004 may be designed so as to facilitate greater closure of the stabilizing structure. In certain embodiments, the junctions 6900 between the elongate strips and intervening members may be thinned to better facilitate rotation and closure of the stabilizing structures. In some embodiments, the stabilizing structure is tearable, such that the structure may be shaped into the shape of a wound. As described elsewhere in the specification, tears may be completed at the intersection between intervening members and elongate strips or at any suitable location along the elongate strip or intervening member.

In some embodiments, the pattern of the stabilizing structure is designed in such a way as to facilitate maximum closure of the stabilizing structure. Preferably, maximum closure is in a direction perpendicular to the length of the elongate members and within the horizontal plane. As will be described in greater detail below, greater closure may be achieved by varying the length of the elongate strips 6006, the length of the intervening members 6010, and the shape of the cells 6004. The shape of the cells 6004 may comprise any shape described herein this section or elsewhere in the specification. For example, as depicted in FIG. 14A, the cells 6004 may be diamond-shaped or parallelpiped with smaller diamond-like shapes 6020 located within larger diamonds 6022. Such a construction may provide greater overall closure of the stabilizing device 6000 to provide for maximum closure of the wound. Additionally, the smaller diamond-like shapes 6020 located within larger diamonds 6022 can spread the load over a greater area reducing the chance of damage to the tissue structures below the matrix. This construction can also reduce the likelihood of the foam or the drape being pulled into the matrix and preventing closure of the wound.

Figure 14B:
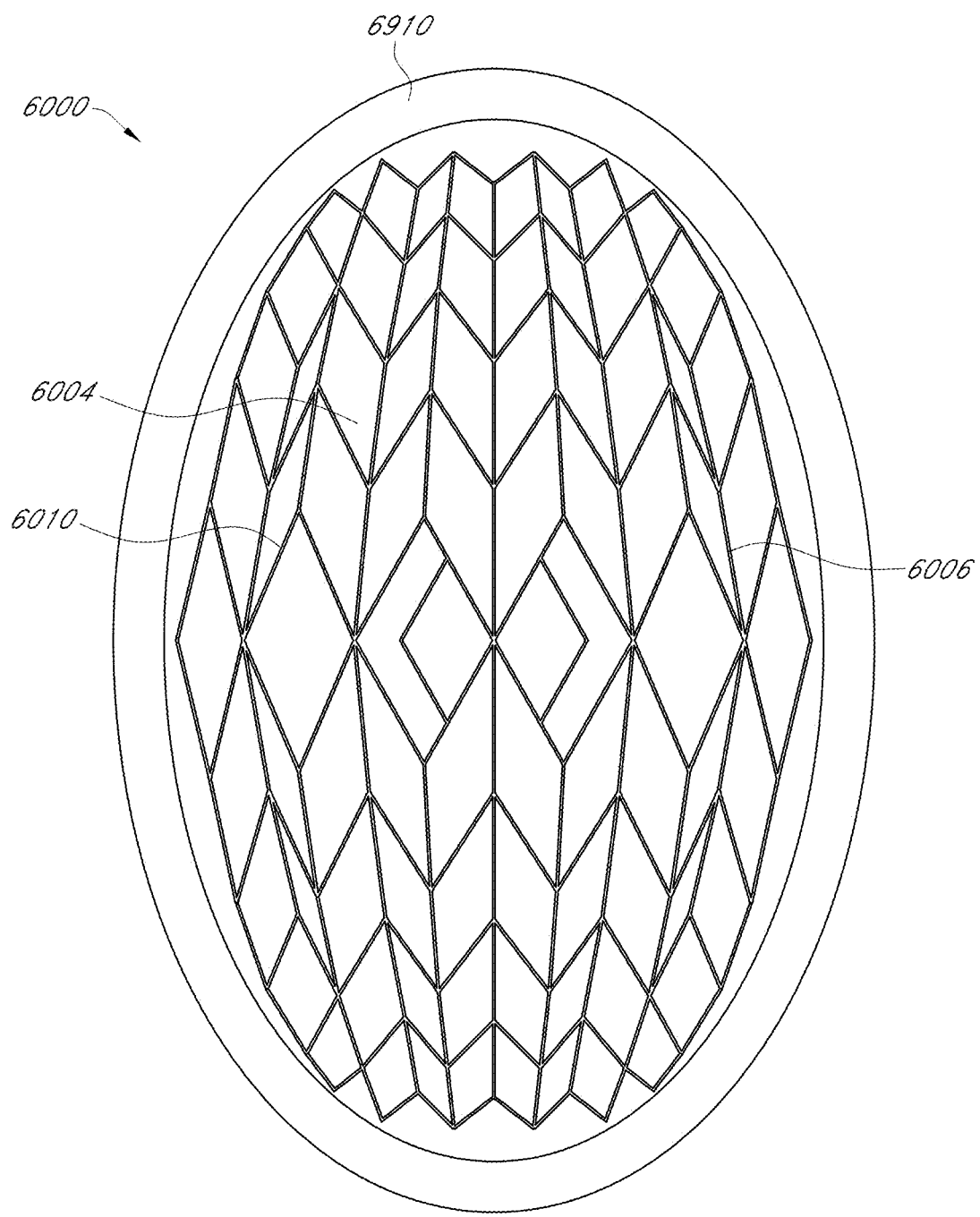
Figure 14C:
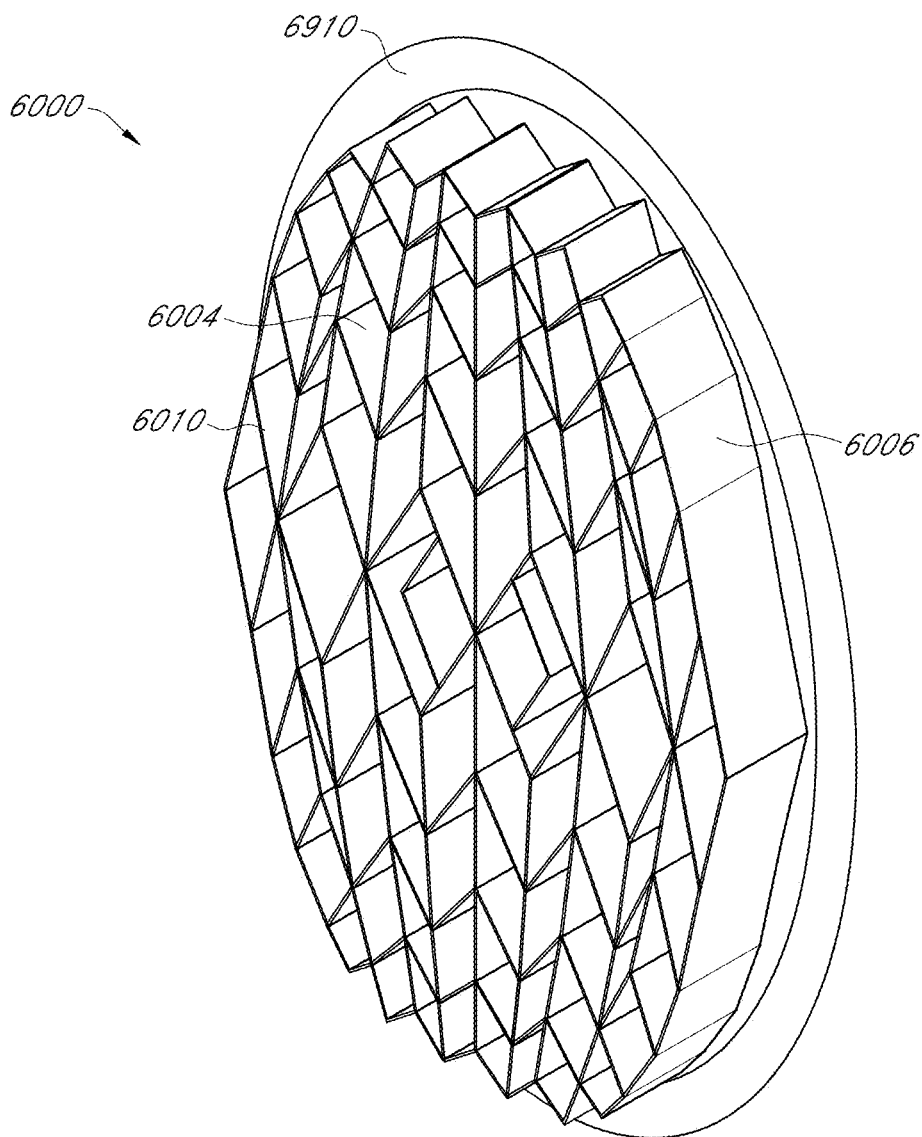

FIGS. 14B-C are illustrations of different views of the stabilizing structure embodiment of FIG. 14A. As described above in relation to FIG. 14A, the stabilizing structure comprises cells 6004, intervening members 6010, and elongate strips 6006; however, here a simulated shape of a wound 6910 is also included for comparison.

Any of the stabilizing structures described herein this section or elsewhere in the specification may be constructed from any suitable means. For example, the stabilizing structures may be constructed via molding or may be printed directly using 3D printing technology. In certain embodiments, the stabilizing structures of FIGS. 14A-C may be constructed from a single polymer via 3D printing. In some embodiments, the stabilizing structures may be constructed from one polymer, two polymers, three polymers, or more than three polymers. The stabilizing structures may be constructed from any material disclosed herein this section or elsewhere in the specification. The stabilizing structure can be made by cutting the structure out of a solid block of material. Methods used for cutting can include, for example, waterjet cutting, laser cutting, or die cutting. The stabilizing structures may be cut to size along the walls of the cells 6004. For example, the intervening members along the outside face of elongate strips 6006 can be cut off to appropriately size the stabilizing structure. The stabilizing structure may be cut along the walls, along any portions of the elongate strips, and/or along any portions of the intervening members.

Figure 15A:
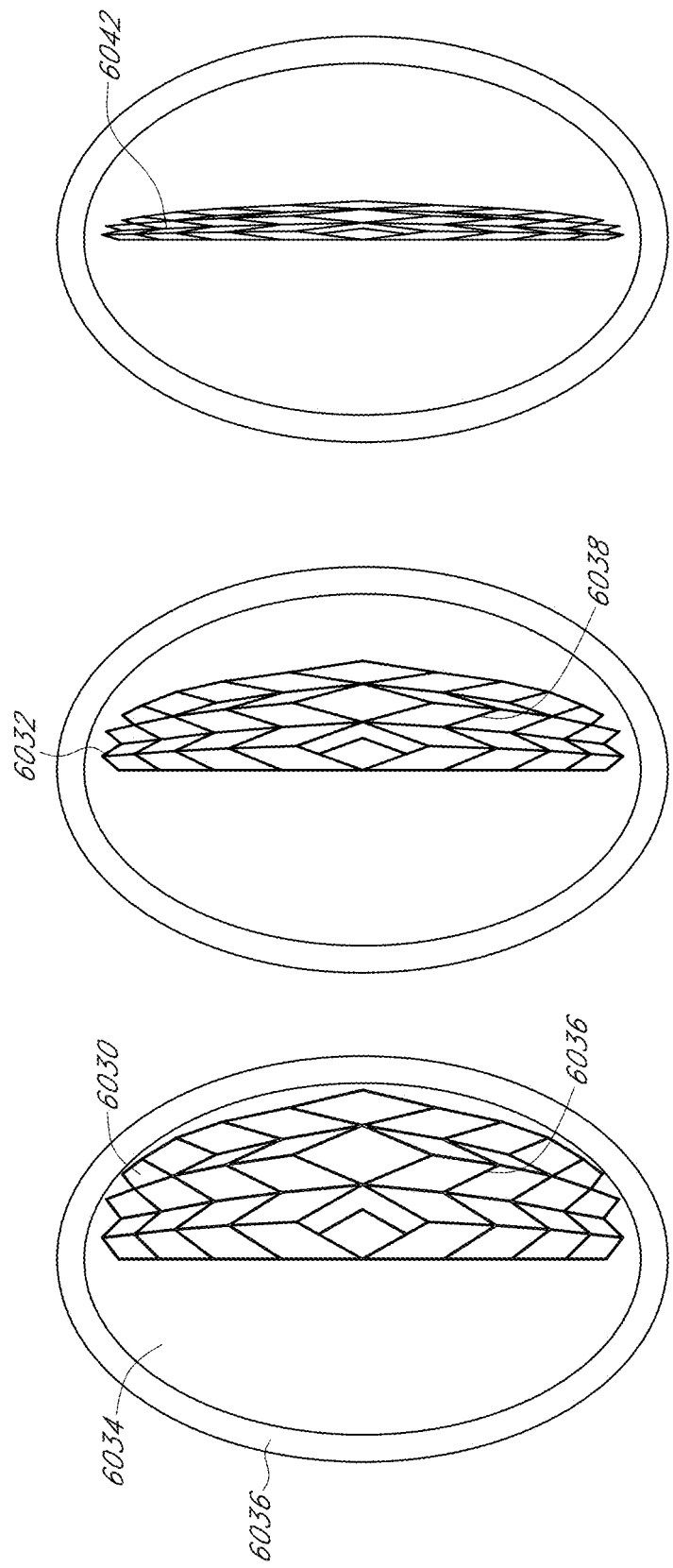
FIGS. 15A-E illustrate embodiments of a method for optimizing the design of a stabilizing structure.

FIGS. 15A-D depict methodologies for generating the design of a stabilizing structure, such as the stabilizing structures of FIGS. 13A-14. To facilitate various types of closure, for example maximum closure, the shape, size, and location of the elongate strips, intervening members, and cells may be determined via various methods. For example, as depicted in FIG. 15A, each collapsible cell 6030 has four sides, and each intersection between an intervening member(s) and/or elongated strip(s) may be modeled via pin-joints 6032. Further, the entirety of stabilizing structure 6034 may be modeled inside of an oval wound model 6036. As depicted in FIG. 15A, the stabilizing structure 6034 may be modeled to collapse from an open state 6038 to a semi-collapsed state 6040, to a fully collapsed state 6042. In some clinical scenarios, maximum closure down to a completely flattened stabilizing structure may be desirable to maximize wound closure by drawing the edges of the wound as close together as possible.

Figure 15B:
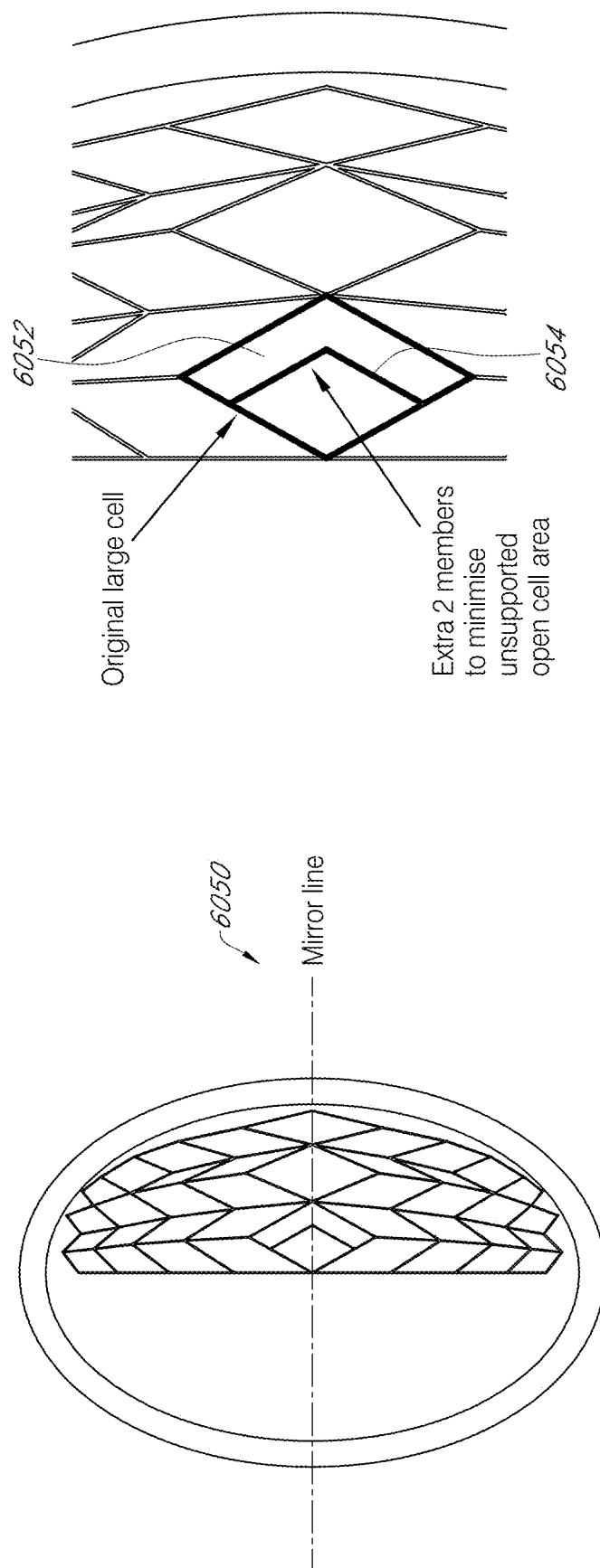

As illustrated in FIG. 15B, in certain embodiments, the process of determining the optimal shape, size, and location of the elongate strips, intervening members, and cells for wound closure may be facilitated by modeling the stabilizing structure as a mirrored pattern on opposite sides of a mirror line 6050 (which may also be referred to as the transverse axis, perpendicular to a longitudinal axis of the stabilizing structure), thereby making the curve and collapse of the stabilizing structure symmetrical. The mirror axis may be along the minor axis or it may be along the major axis of the stabilizing structure. Alternatively, the mirror line may be located in any suitable location within the stabilizing structure, such as diagonally across the stabilizing structure. In certain embodiments, this method may lead to large diamond-shaped cells near the center line. These large diamond-shaped structures 6052 may be further subdivided to further support the stabilizing structure by including smaller diamond shapes 6054 within larger shapes. In some embodiments, these smaller shapes 6054 within a larger shape 6052 may comprise any shape disclosed herein this section or elsewhere in the specification. The larger cells may be further subdivided by two smaller shapes, three smaller shapes, four smaller shapes, or more than four smaller shapes. It will be understood by one of skill in the art that the mirror line need not be confined to a line perpendicular to the longitudinal orientation of the wound. Instead, the mirror line may be located along the longitudinal axis of the wound or at an angle to the longitudinal axis of the wound. In some embodiments, the stabilizing structure may contain multiple mirror lines, thereby having multiple subsections that are symmetrical or different.

Figure 15C:
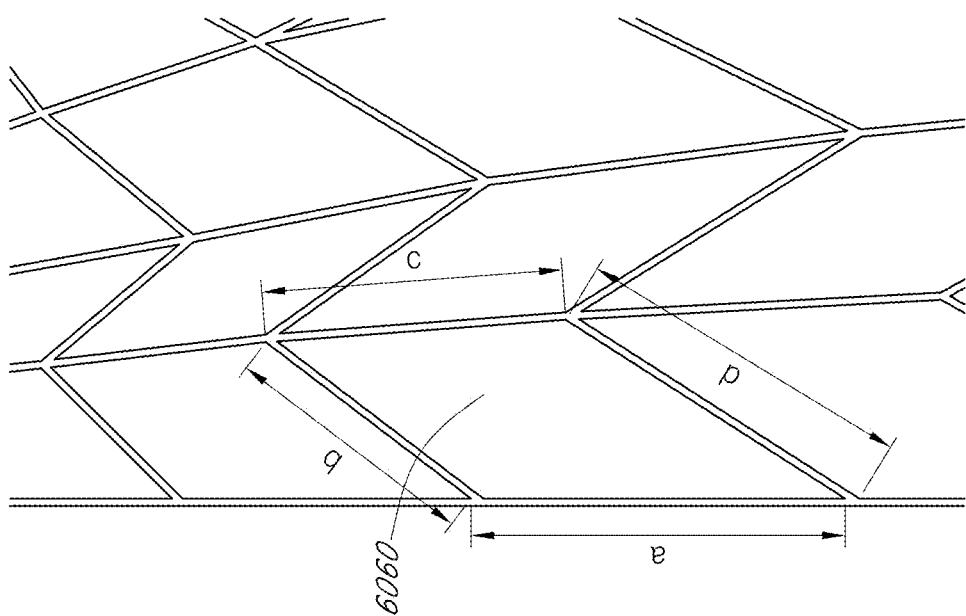

As illustrated in FIG. 15C, for a four-sided cell to collapse, it must follow a simple formula: a+b=c+d, where a, b, c, and d are the lengths of individual sides of a single cell within the stabilizing structure such as the cell 6060 of FIG. 15C. When members c and b collapse together, then d and a collapse together.

Figure 15D:
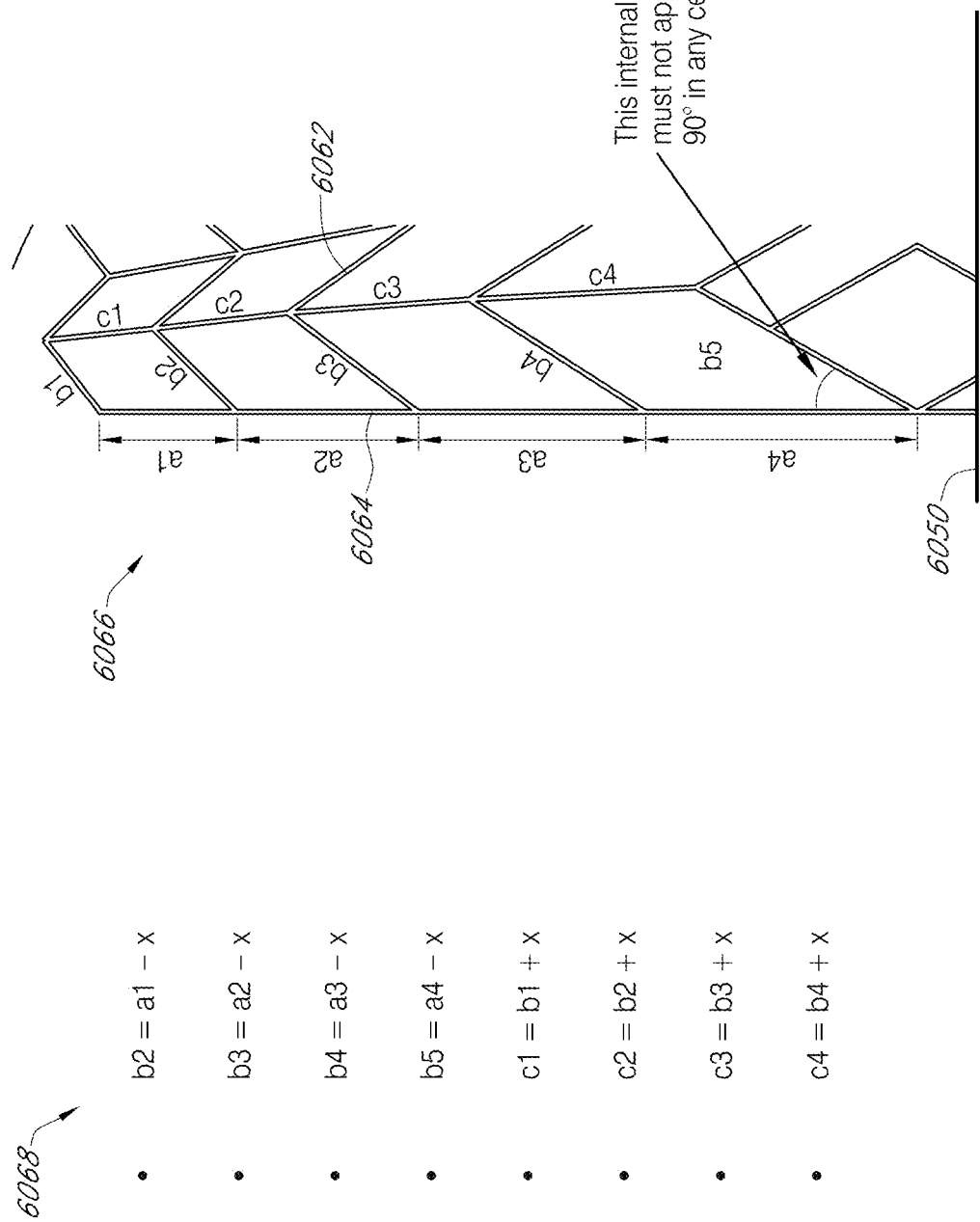
Figure 15E:
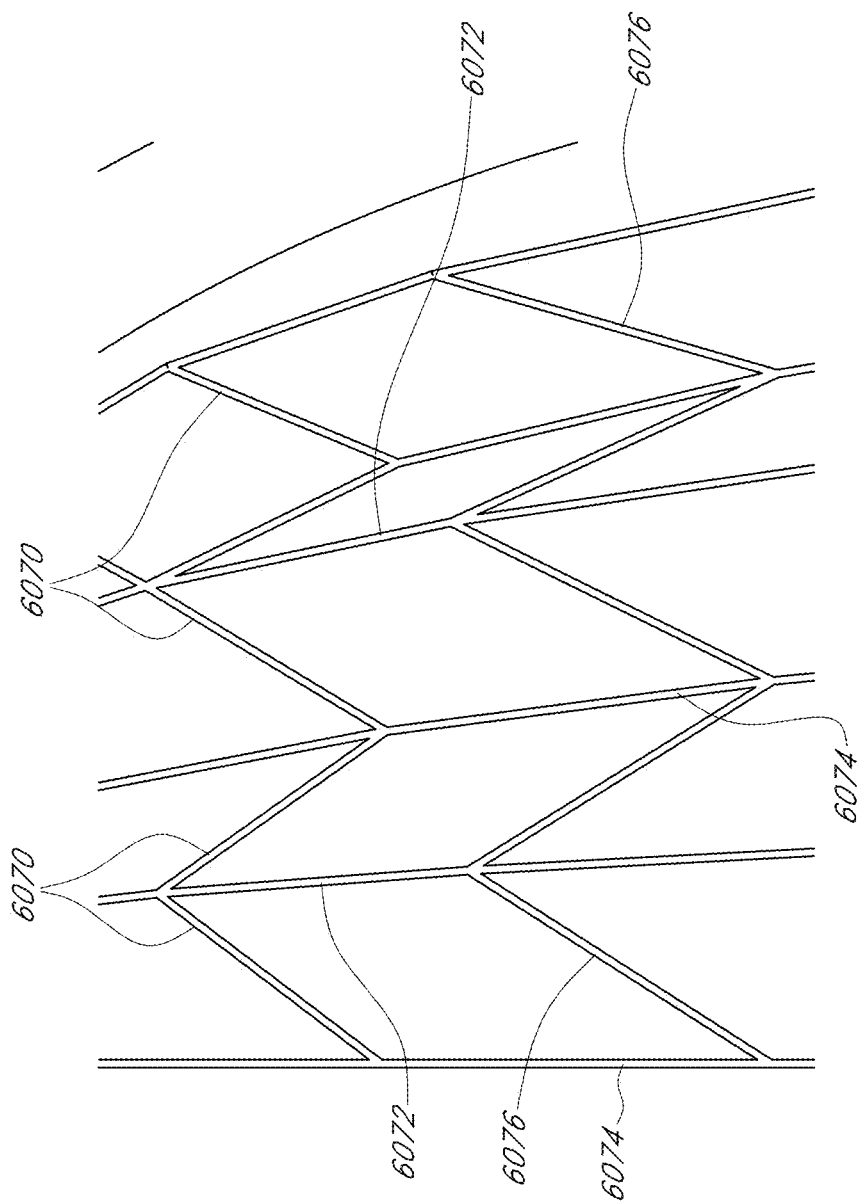

FIG. 15D illustrates an expansion of the concept described in FIG. 15C. By using the base formula a+b=c+d, the elongate strips were progressively lengthened (a4>a3>a2>a1) towards the horizontal mirror line 6032, thereby achieving a curve in the stabilizing structure while preventing any of the intervening members 6062 from becoming perpendicular to the elongate strips 6064 (i.e. having an internal angle of 90 degrees). As illustrated in FIG. 15D, a value for b1 may be chosen, at which point an arbitrary offset value x may also be chosen to ease the construction of the various cell geometries. Using the progressive values for a1 through a4, illustrated visually in FIG. 15D 6066, values for b1-b4 may be calculated 6068. Using calculated values derived from equations 6068 for the various walls of the individual cells allows for the design of a stabilizing structure that collapses completely, such as those depicted in FIGS. 14A-B.

In some embodiments, a method for generating a stabilizing structure design may include steps to speed up the initial geometry construction. For example if all members from left to right in a specific row, as visualized by intervening members 6036 in FIG. 15E, a pattern then emerges where alternating vertical members are also the same length. Walls of the same length are indicated by their respective labels 6070, 6072, 6074, and 6076. Once the initial design is generated then individual cells may be modified by lengthening, shortening, removing or inserted according to the formulas of FIG. 15D to achieve the desired shape of the overall stabilizing structure.

The Elliptical and Domed Structures of FIGS. 16-18B

Figure 16:
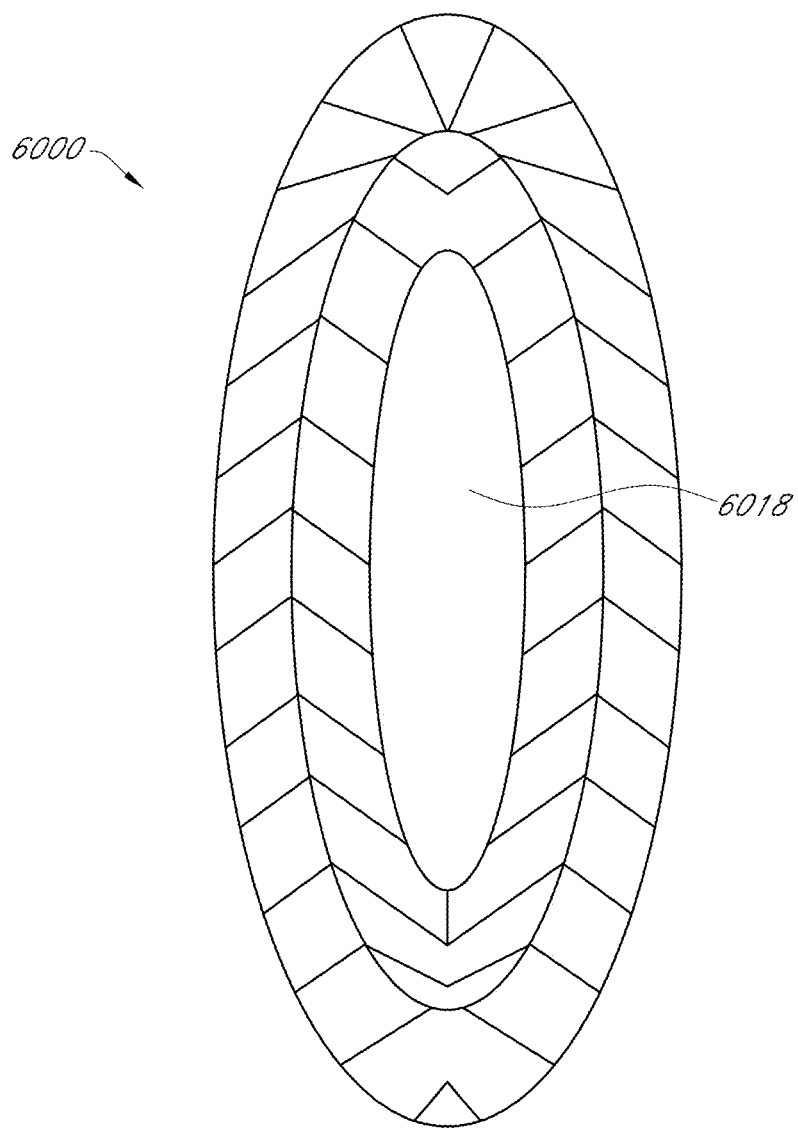
FIG. 16 illustrates an embodiment of a stabilizing structure.

FIG. 16 illustrates a stabilizing structure 6000 similar to the structures disclosed above in relation to FIGS. 13A-D. However, stabilizing structure 6000 may have a gap 6018 removed or having no material. By removing mass from the stabilizing structure, the stabilizing structure may collapse more readily and fully within the wound. In further embodiments, any section of the stabilizing structure may be removed to facilitate closure. For example, a strip of sections may be removed, a side of sections, an inner portion located more closely to one side of the stabilizing structure, etc. Elongate strips shown in FIG. 16 may be joined at their ends to form concentric elliptical shapes, or there may be concentric, continuous strips formed into an elliptical or oval shape, with intervening members as described above in between.

Figure 17:
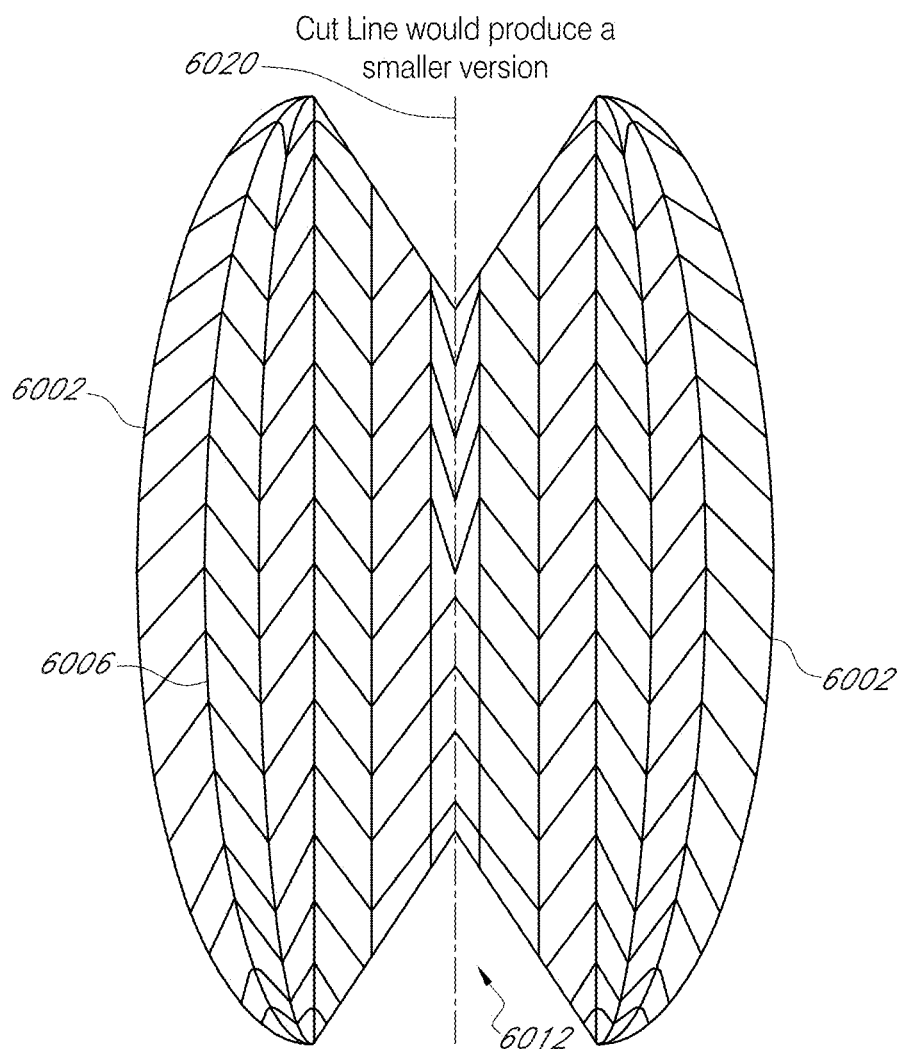
FIG. 17 illustrates an embodiment of a stabilizing structure.

FIG. 17 illustrates another stabilizing structure similar to the structures described in relation to FIGS. 13A-14C. FIG. 17 builds on the concept of FIG. 16, whereas portions of the stabilizing structure are removed to decrease the mass of the structure, thus facilitating closure. Reducing the mass of the stabilizing structure may prove advantageous for wound healing because the mass of the wound may be a rate-limiting step in wound closure. The stabilizing structure 6000 of FIG. 17 may have an outer perimeter 6002 defining a bi-elliptical shape.

Here, reduced edge 6012 allows the stabilizing structure to collapse more readily at the edges of the device to better facilitate placement into the wound, facilitate closure of the wound, and reduce pinching at the edges of the stabilizing structure 6000 as described above. In some embodiments, the elongate strips 6006 may be of various lengths and may be curved or un-curved as depicted in FIG. 17. In particular embodiments, the stabilizing structure 6000 of FIG. 17 may be cut down a centerline 6020 to allow for the creation of multiple smaller stabilizing structures. As will be understood by one of skill in the art, various shapes and sizes of stabilizing structures may be created by this technique.

Figure 18A:
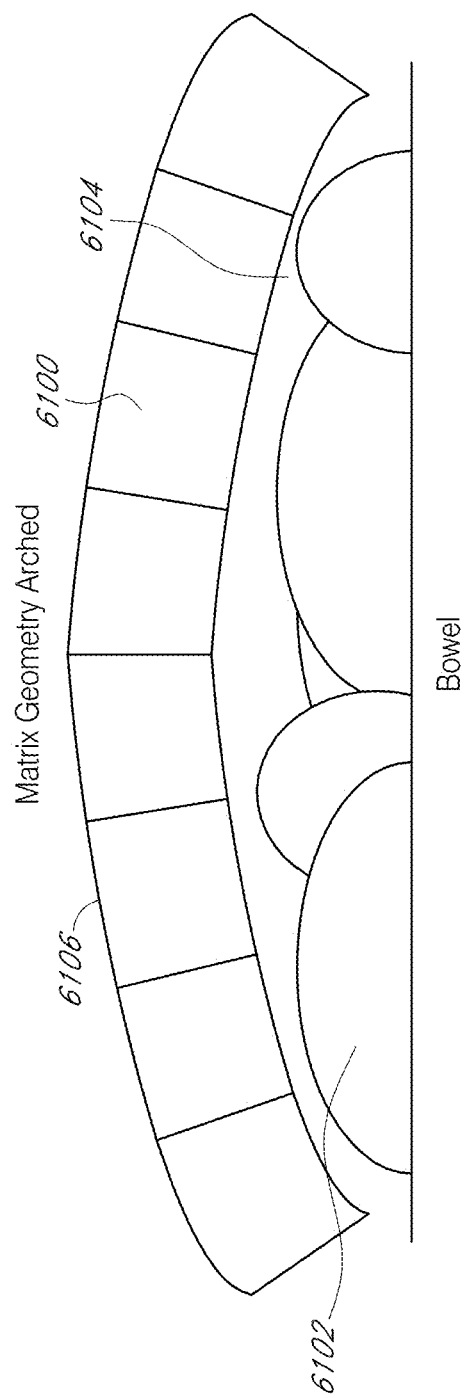
FIG. 18A-C illustrates side views of embodiments of stabilizing structures.
Figure 18B:
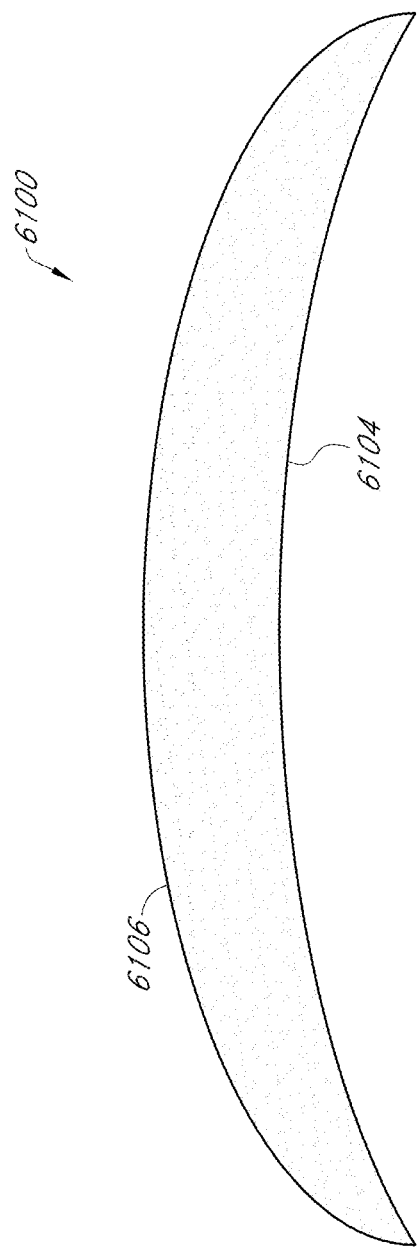
Figure 18C:
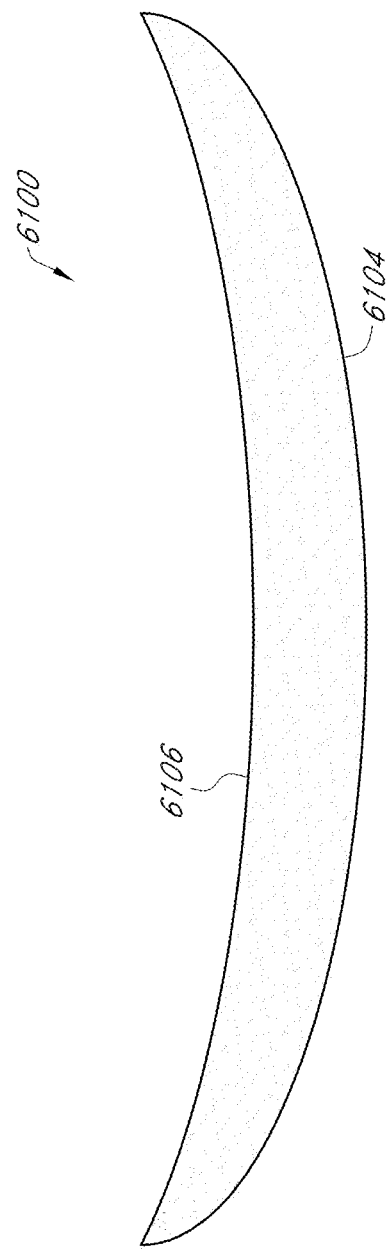

FIGS. 18A-C depict stabilizing structures 6100 similar to the stabilizing structures described herein this section or elsewhere in the specification. However, the stabilizing structures of FIGS. 18A-C are curved upward or downward in a perpendicular direction (e.g., a vertical direction) to the general plane (e.g., the horizontal plane) of the stabilizing structure. As will be understood by one of skill in the art, such an upward or downward curving may be applied to any of the stabilizing structures described herein this section or elsewhere in the specification.

A curved stabilizing structure 6100 such as the structure depicted in FIG. 18A, showing the stabilizing structure from the side, may be advantageous for placement over all wounds, but particularly abdominal wounds. The exposed tissues 6102 of an abdominal wound, such as the bowel, have a tendency to bulge upward and outward from the body. By bulging upward, the bowel creates a convex surface that does not align as closely with a flattened bottom surface, such as the bottom surfaces of the stabilizing structures depicted above in FIGS. 2A-I and 13A-14C.

In some embodiments, a lower portion 6104 of the stabilizing structure 6100 may be concave in a first horizontal direction and/or in a second horizontal direction perpendicular to the first horizontal direction. In certain embodiments, an upper portion 6106 of the stabilizing structure 6100 may be convex along at least an upper portion 6106 of the stabilizing structure 6100, for example in a first horizontal direction and/or a second horizontal direction perpendicular to the first horizontal direction. Accordingly, in some embodiments the stabilizing structure has an arched or domed shape. In other embodiments, only the lower surface may be concave, and the upper surface may be flat or planar.

Such a structure as depicted in FIG. 18A may better fit over a bulging wound and allow for expansion of the tissue. A curved shape with a concave bottom may further serve to relieve discomfort in a patient, as the underlying tissues would not necessarily need to be compressed to the degree that may be required with a flattened surface. Thus, the stabilizing structures of FIGS. 18A-B may be placed into an abdominal wound and conform to the shape of internal organs.

In certain embodiments, an upper portion 6106 of the stabilizing structure is convex in a first horizontal direction and in a second horizontal direction perpendicular to the first horizontal direction. Some embodiments may call for the stabilizing structure to be pre-formed to have either or both of a concave lower surface 6104 and a convex upper surface 6106. However, any combination of concave, convex and flat surfaces may be possible.

In certain embodiments, the top 6106 and/or bottom 6104 portion of the stabilizing structure may be concave/convex while the corresponding top 6106 or bottom 6104 may be flat. Such a design may have a variable thickness over the length of the stabilizing structure 6100.

FIGS. 18B-C illustrate side views of curved stabilizing structures similar to the structure described above in relation to FIG. 18A. In some embodiments, the stabilizing structures may have a shape similar to a contact lens, essentially acting like a bowl. In some embodiments, the bottom portion 6104 may be concave as depicted in FIG. 18B, or it may be convex as depicted in FIG. 18C. One of skill in the art will understand that any combination of convexity and concavity on the top and bottom surfaces may be possible.

Figure 19A:
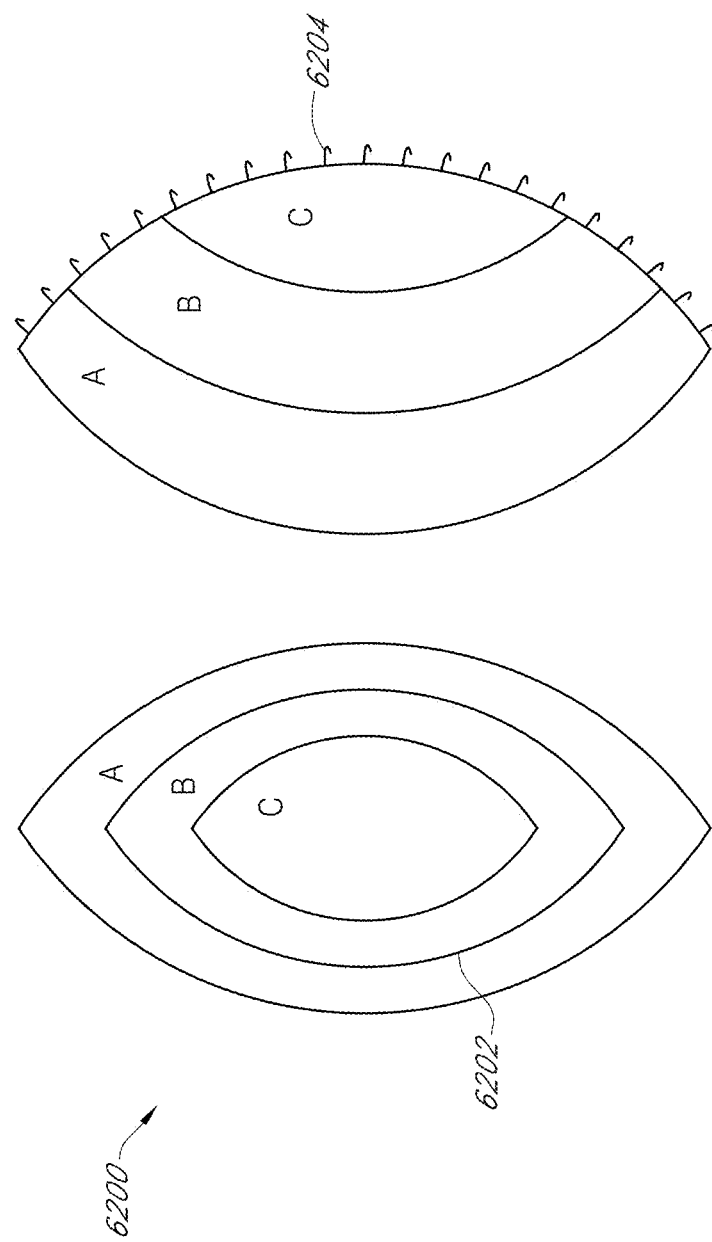

FIGS. 19A-B depict embodiments of modifiable stabilizing structures and/or wound closure devices 6200, similar to the stabilizing structures and wound closure devices described elsewhere in the specification, particularly as relating to FIGS. 2A-I, 13A-18C. Such stabilizing structures 6200 may have a layer or layers of porous material placed on the top and/or bottom to create a sandwich-like wound closure device of the same general shape when viewed from a birds-eye or top view.

The stabilizing structure or wound closure device, with or without the top and bottom porous layers, may be shaped into sections A, B, C to create smaller stabilizing structures or sandwich-like structures. More generally, the shapes shown in FIGS. 19A-19B may be applicable to any suitable wound filler, such as foam or other porous material. Cuts 6202 (which may indicate designated pre-cut lines in the device or may indicate desired cutting locations) may be of any shape, direction, or size. For example, the cuts may be elliptical as depicted in FIGS. 19A-B. Designated pre-cut lines may include, but are not limited to, partial or complete cuts through the thickness of the structure, markings or score-lines to facilitate cutting of the device by the user or removal of certain portions of the device by the user. Providing for such cuts may be advantageous as a manufacturing technique, allowing the production of multiple different modifiable stabilizing structures and/or wound closure devices with just a single pattern of cuts 6202.

In the right-hand drawing of FIG. 19A, one desired cut pattern may provide an elliptical stabilizing structure having a series of cuts 6202 that, rather than forming a complete ellipse as in FIG. 19A, form an arc that may follow the curvature of one side of the elliptical structure (e.g., the left side). For example, these cut lines may be parallel to the left side or have the same or similar curvature. The ends of these cuts lines intersect with the outer perimeter of the structure on the right side of the structure. Accordingly, cutting the structure along the cut line 6202 between sections A and B will leave a structure formed by section B and C forming a smaller elliptical shape than the initial elliptical shape. Similarly, cutting the structure along the line between sections B and C will leave an even smaller elliptical shape.

The stabilizing or sandwich-like structures 6200 may further comprise tissue anchors 6204. In the right-hand drawing of FIG. 19A, by placing the tissue anchors on the outer surface of the right side of the elliptical structure, such that the anchors extend along a portion of the outer perimeters of Sections A, B and C, even if Sections A or B are removed, anchors will remain on the remaining structure. For example, a structure comprising section C, sections B and C, or sections A, B, and C may be placed in different sizes of wounds in a manner such that the perimeter of the stabilizing structure or wound closure device 6200 comprises tissue anchors 6204 which can extend laterally from the stabilizing structure or wound closure device 6200 to engage the surrounding tissue.

In some embodiments, inner tissue anchors may also be provided within the structure, such that once cut, sections A, B, and C have tissue anchors 6204 on additional surfaces than those depicted in FIGS. 19A-B.

FIG. 19B depicts additional or a second set of cuts 6202, which may also be elliptical or curved or may have other shapes, defining further sections D and E. These additional cuts may intersect with the left and right sides of the structure as well as the first cut lines described above. As will be understood by one of skill in the art, a wide variety of possible cuts may be performed to define a wide variety of possible shapes.

Stabilizing Structures and Wound Closure Devices of FIGS. 20A-23

Figure 20A:
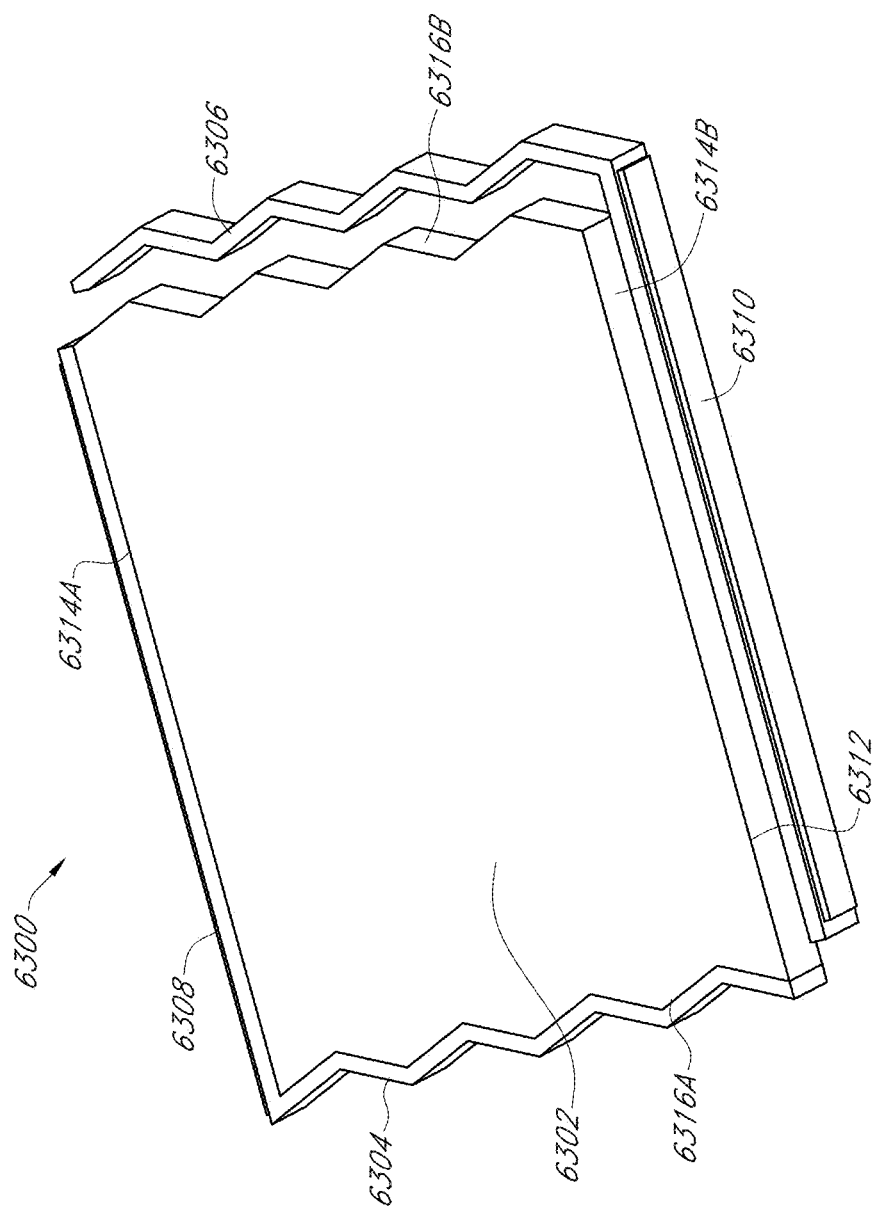
FIGS. 20A-C illustrate embodiments of a stabilizing structure with attachable porous and anchoring layers.
Figure 20B:
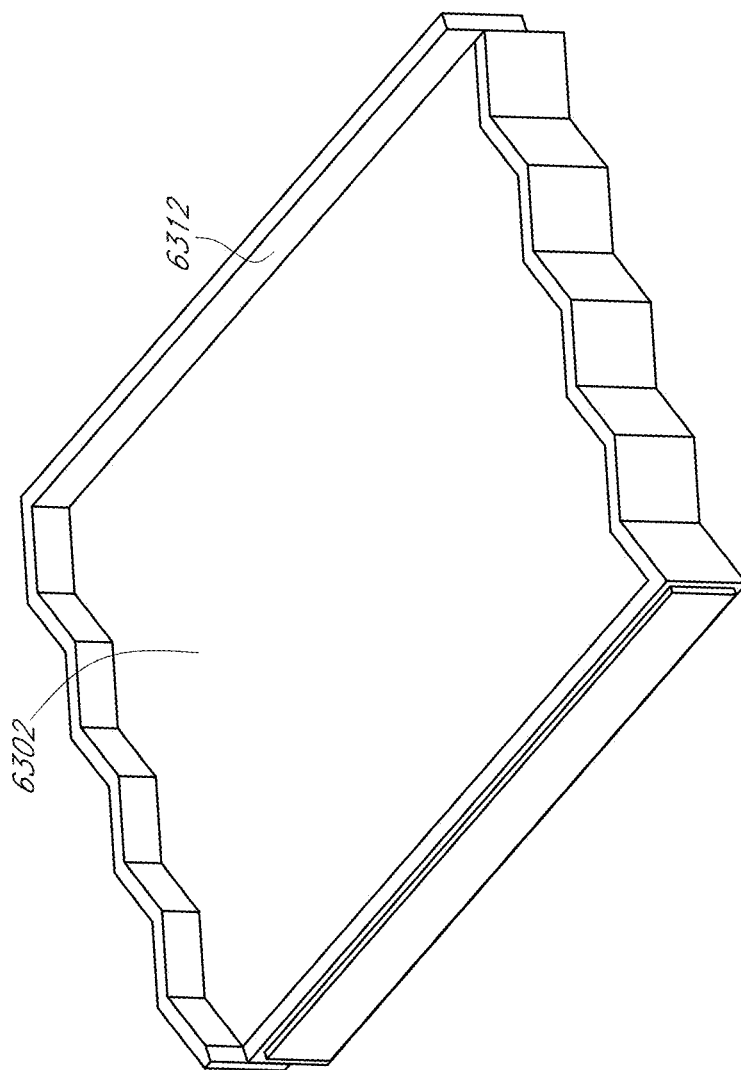

FIGS. 20A-B illustrate a wound closure device 6300 comprising stabilizing structure 6302, first porous layer 6304, second porous layer 6306, first anchoring layer 6308, and second anchoring layer 6310, the anchoring layers comprising tissue anchors such as those described in relation to FIGS. 5A-D. First anchoring layer 6308 is optionally attached to first porous layer 6304, while second anchoring layer 6310 is optionally attached to second porous layer 6306. In some embodiments, the porous layers 6304, 6306 are unattached to anchoring layers 6308, 6310. In certain embodiments the anchoring layers cover at least about 10% of the surface area of one side of the porous layer, at least about 20%, at least about 30%, at least about 40%, at least about 50%, at least about 60%, at least about 70%, at least about 80%, at least about 90%, or about 100% of the surface area of the porous layers.

Stabilizing structure 6302 may be in the form of any stabilizing structure described herein this section or elsewhere in the specification, particularly as relates to FIGS. 2A-I, 5A-D, and 13A-19B. Similar to the other stabilizing structures described herein this section and elsewhere in the specification, stabilizing structure 6302 comprises an outer perimeter 6312 comprising at least one outer wall. For example, the stabilizing structure may have an opposite first side 6314A and second side 6314B extending along the length of the stabilizing structure and an opposite third side 6316A and a fourth side 6316B extending along the width of the stabilizing structure.

Stabilizing structure 6302 may further be shaped in any manner described herein this section or elsewhere in the specification such as is described in relation to Steps 3-4 of FIG. 10A. For example, stabilizing structure 6302 may be shaped in a manner so as to be suitable for placement within a wound.

In certain embodiments, to minimize the sequence of steps required by a clinician to place the wound closure device 6300 within a wound, wound closure device 6300 may be pre-packaged with its complete perimeter 6312 covered with porous foam and/or tissue anchoring layers. However, this embodiment may be disadvantageous because once the stabilizing structure is cut and shaped to the shape of the wound, the outer perimeter 6312 of the device will no longer comprise porous and anchoring layers. Instead, only a portion of the perimeter will still comprise intact porous and anchoring layers. Thus, in particular embodiments as depicted in FIGS. 20A-B, to facilitate the exposure of tissue anchoring layers 6308, 6310 and porous layers 6304, 6306 to the surrounding tissue after shaping, first porous layer 6304 may be pre-attached to only a part of the outer perimeter 6312 of the stabilizing structure 6302. In certain embodiments, the portion of first porous layer 6304 comprising first anchoring layer 6308 may be attached to a first side 6014A of the perimeter of stabilizing structure 6302, while the porous layer unattached to an anchoring layer 6308 may be attached to third side 6316A of the stabilizing structure 6302. In other embodiments, the porous layer 6304 may be applied without an anchoring layer 6308.

As depicted in FIG. 20B, once the stabilizing structure 6302 has been shaped, second porous layer 6306 comprising second anchoring layer may be attached to remaining perimeter 6312 of the stabilizing structure 6302 uncovered by first porous layer 6304, thereby surrounding the entire perimeter of the stabilizing structure with porous layers 6304, 6308. In some embodiments, second porous layer may need to be trimmed to suitably wrap around the entire perimeter of stabilizing structure 6302. During shaping, first porous layer 6304 may be shaped along with the stabilizing structure due to first porous layer's adherence to the stabilizing structure. While shaping first porous layer, first anchoring layer 6308 may also be shaped due to first anchoring layer's attachment to first porous layer. The second layer 6306 may be have second anchoring layer attached to it only in a portion of the second layer 6306 attached to one side of the stabilizing structure (e.g., second side 6314B). Alternatively, the second anchoring layer may be attached to the portion of the second layer 6306 also attached to the fourth side 6316B of the stabilizing structure.

In some embodiments, first porous layer 6304 is only attached to two sides of the stabilizing structure 6302, such as a longitudinal flat side 6314A and a zig-zag side 6316A. However, first porous layer 6304 may also be attached to only one side of the stabilizing structure or to three sides.

Figure 20C:
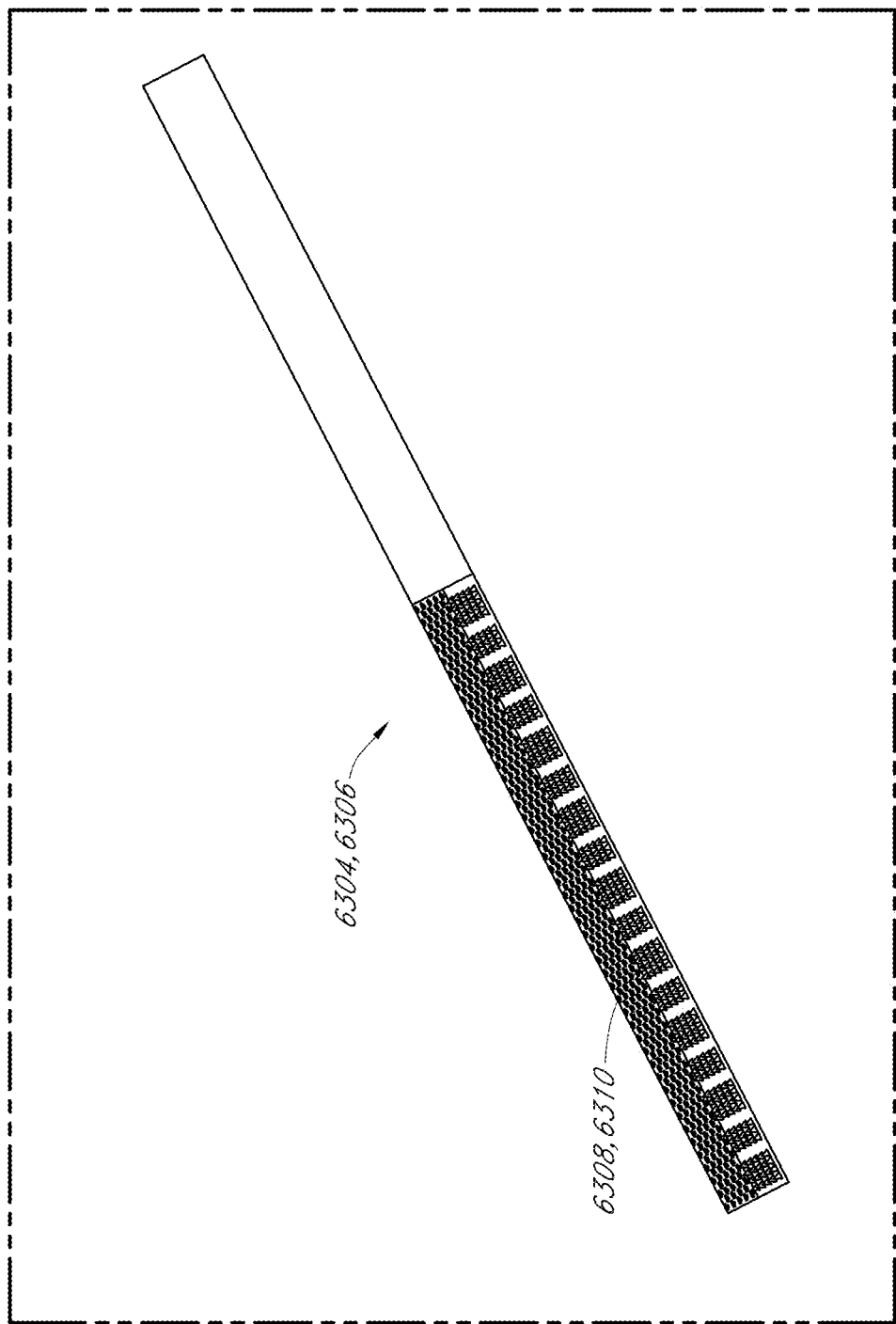

FIG. 20C is a photograph of first porous layer or second porous layer before it is applied to a shaped stabilizing structure. As illustrated, an anchoring layer may only partially cover the porous layer. In some embodiments, anchoring layer 6308, 6310 may comprise different types of anchoring layers such as has been previously described in relation to FIGS. 5A-D.

Figure 21:
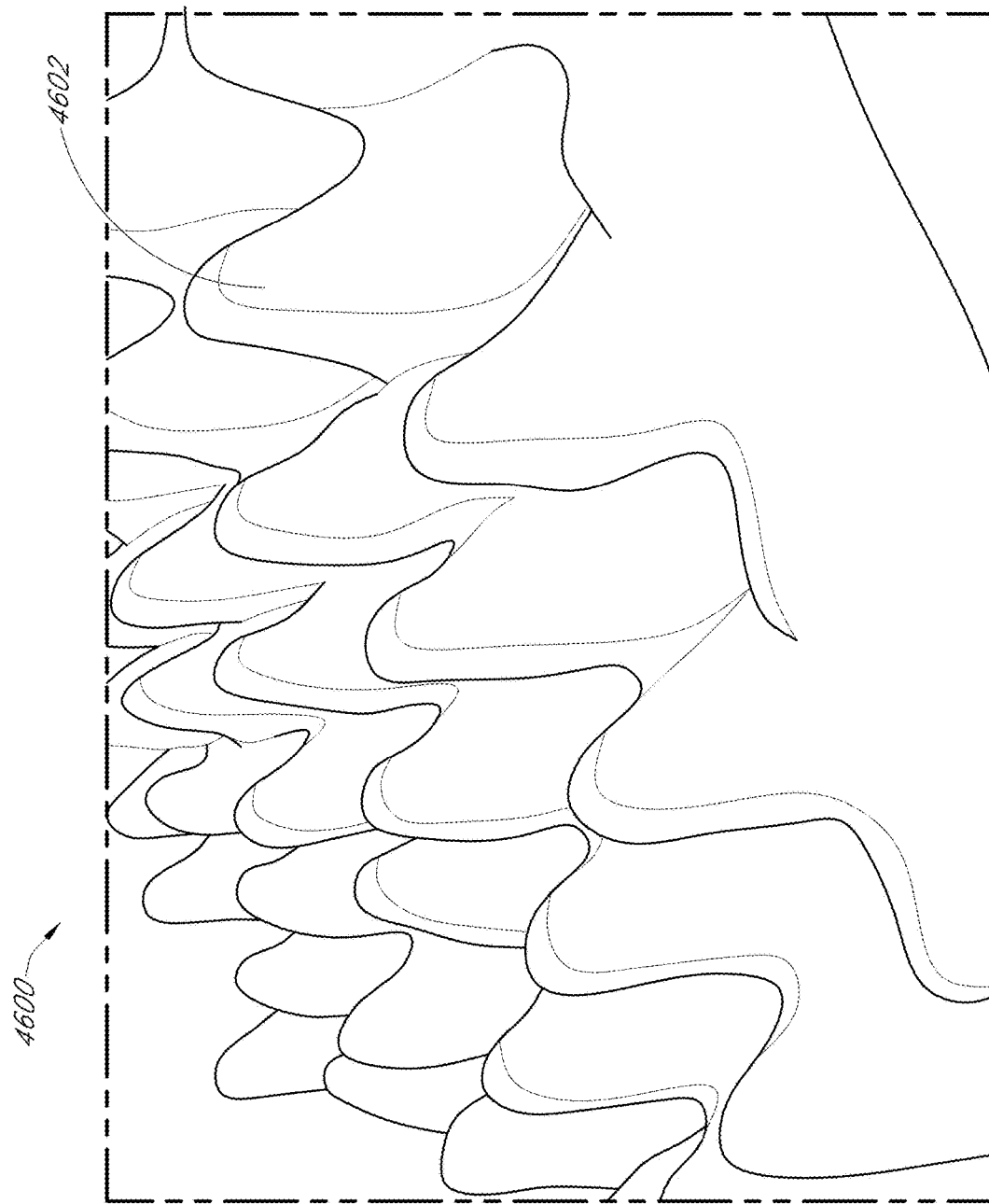
FIG. 21 illustrates an embodiment of a foam layer with fingers.

FIG. 21 is a photograph of an embodiment of a foam layer 4600 that may be used in combination with any of the stabilizing structures or wound closure devices described in this section or elsewhere in this specification. As described above, the foam layer 4600 may be located above or below the stabilizing structure or wound closure device. In some embodiments, the foam layer 4600 is located both above and below the stabilizing structure or wound closure device. The foam layer 4600 can surround the perimeter of the stabilizing structure or wound closure device or completely surround the entirety of the stabilizing structure or wound closure device. The foam layer 4600 can be constructed from absorbent materials, materials configured to distribute fluid, or both.

The foam layer 4600 further comprises fingers 4602, that can extend from the foam layer into the stabilizing structure or closure device. For example, the fingers 4602 may extend into and around the gaps or cells depicted in the stabilizing structures described herein this section or elsewhere in the specification. The fingers 4602 may also extend around the outside of the perimeter of the stabilizing structure. In some embodiments, the fingers 4602 from one foam layer 4600 may extend through the interior or around the outside of the stabilizing structure to meet the fingers 4602 from a second foam layer 4600. Thus, one foam layer will be facing finger-side up, while a second foam layer may be facing finger-side down.

In some embodiments, the foam layer 4600 can have perforations or pre-cuts to allow portions of the foam layer 4600 to be easily torn away to shape the foam for a particular wound. In some embodiments, the fingers 4602 can extend at least about 1 mm from the surface of the foam layer, at least about 3 mm from the surface of the foam layer, at least about 5 mm from the surface of the foam layer, at least about 7.5 mm from the surface of the foam layer, at least about 10 mm from the surface of the foam layer, at least about 12.5 mm from the surface of the foam layer, at least about 25 mm from the surface of the foam layer, at least about 17.5 mm from the surface of the foam layer, at least about 20 mm from the surface of the foam layer, at least about 25 mm from the surface of the foam layer, or more than 25 mm.

Figure 22A:
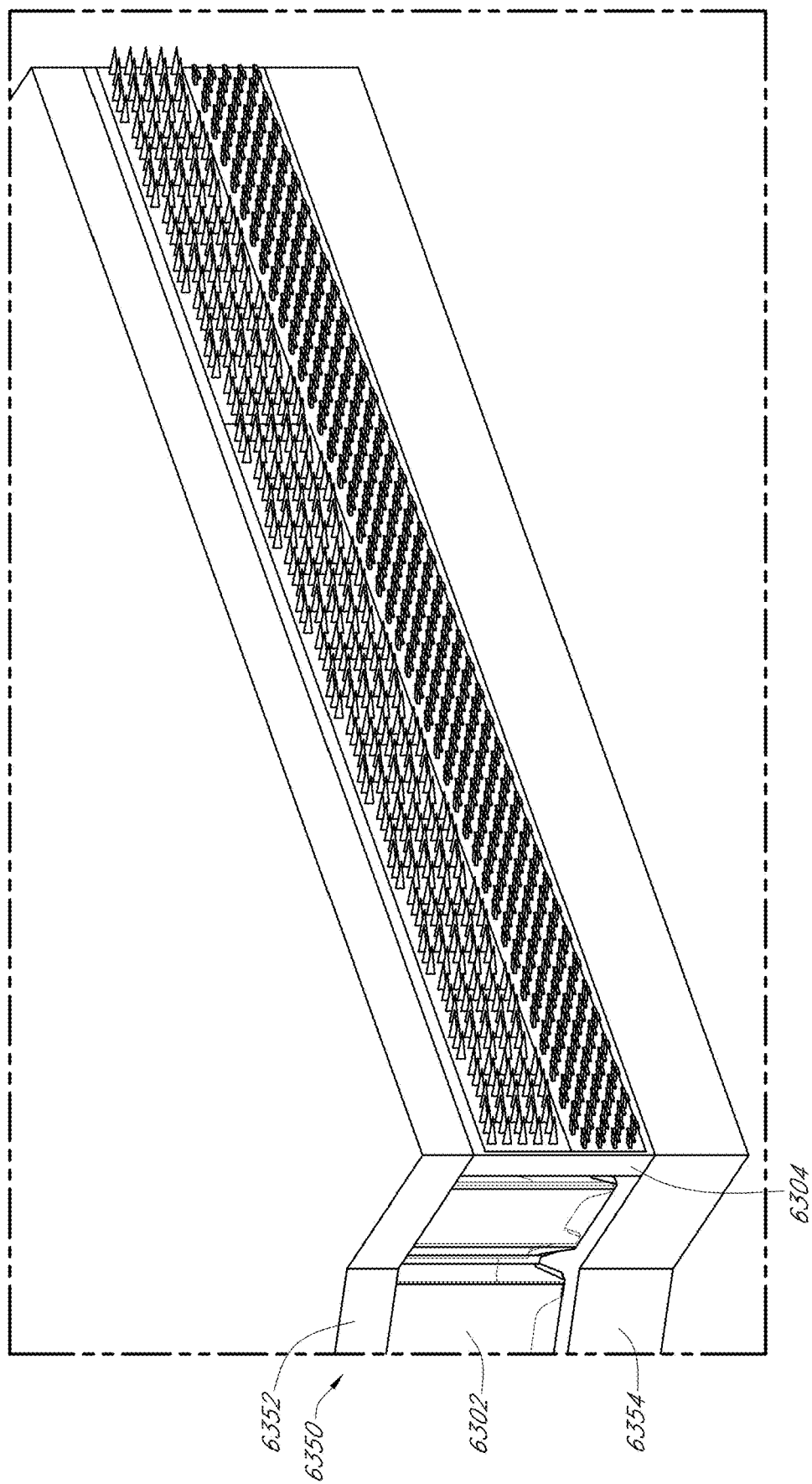
FIGS. 22A-D illustrate embodiments of a stabilizing structure with anchoring and porous layers.
Figure 22B:
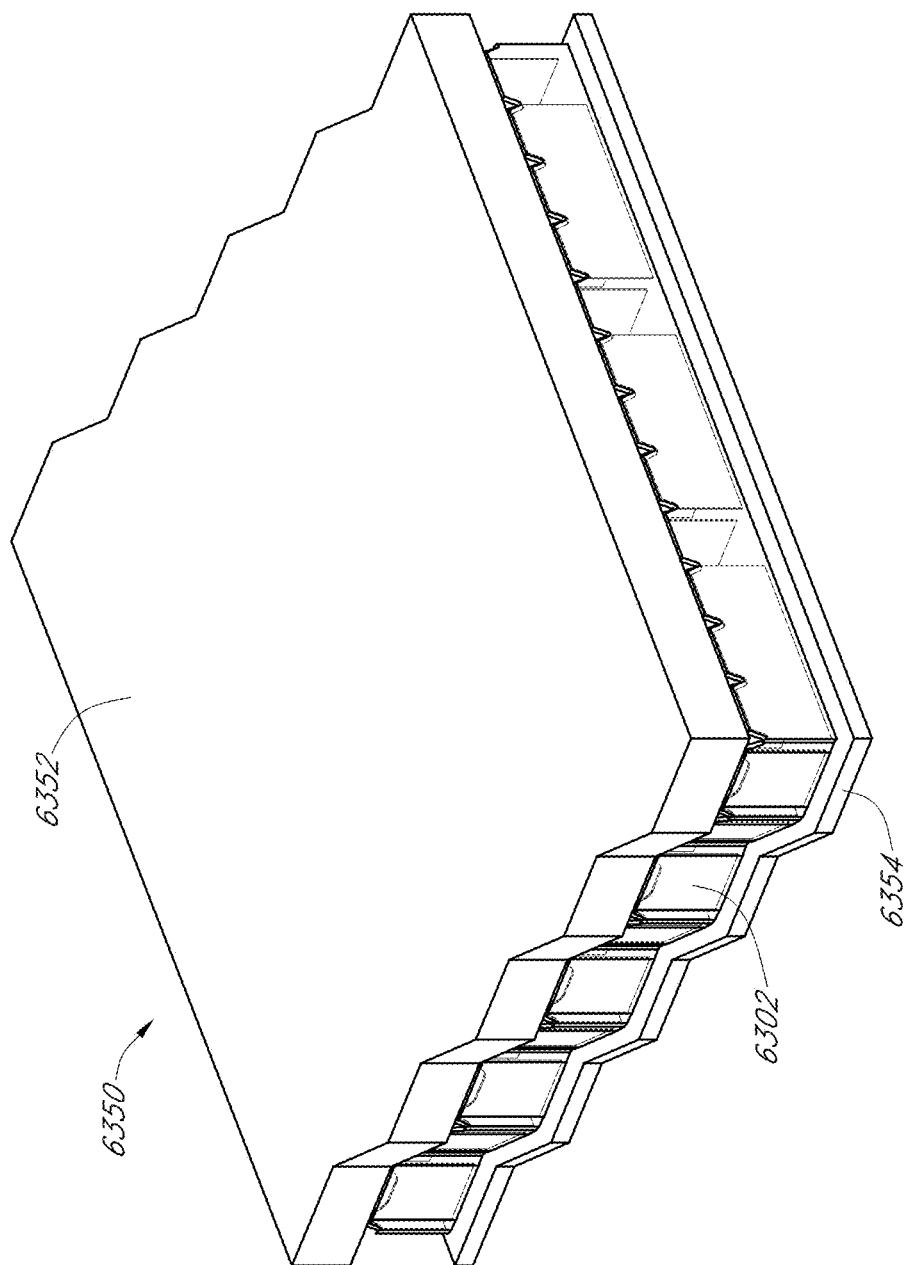
Figure 22C:
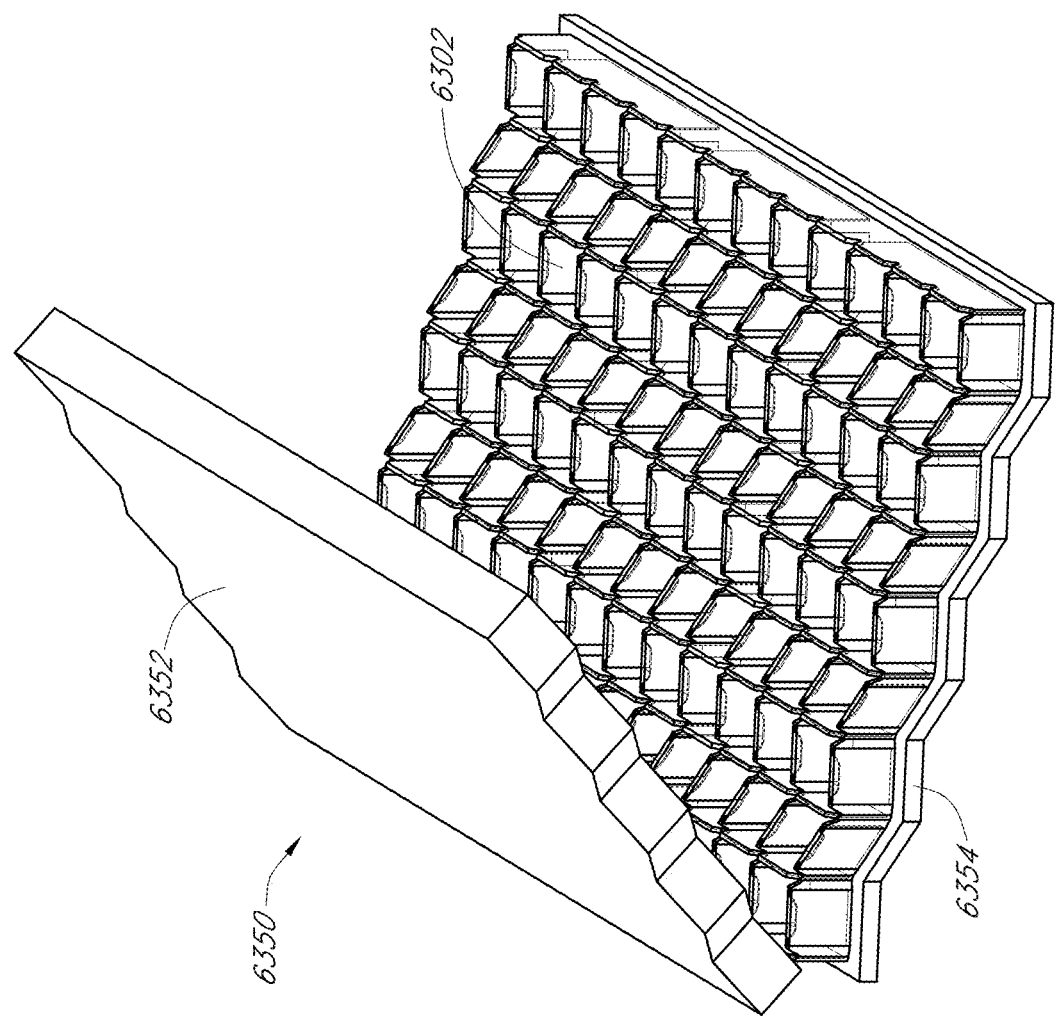
Figure 22D:
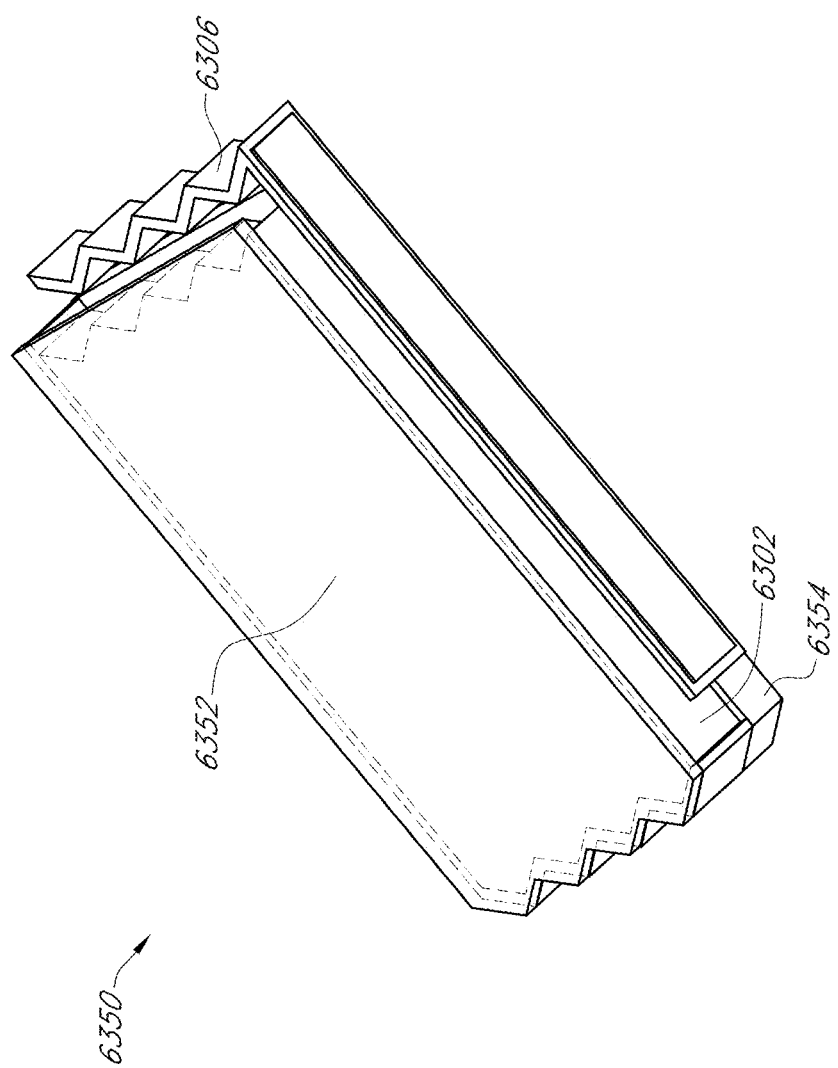

FIGS. 22A-C are photographs of an embodiment of a wound closure device 6350 comprising a stabilizing structure 6302 (similar to the stabilizing structure described above in relation to FIGS. 2A-I and 13A-D), first porous layer 6304 (not shown in FIGS. 22B and 22C), a top porous layer 6352, and a bottom porous layer 6354. Stabilizing structure 6302 in combination with first porous layer 6304 functions as described above in relation to FIGS. 20A-B. However, in this instance, stabilizing structure 6302 can be further encased on the top and bottom by porous layers 6352, 6354, and may be pre-attached to the stabilizing structure 6302. Top and bottom porous layers 6352 and 6354 may be shaped in any desired manner to conform to the shape of stabilizing structure 6302. FIG. 22D illustrates an embodiment where a second porous layer 6306 is attached to the stabilizing structure 6302 after the stabilizing structure having upper and lower porous layers 6352 and 6354 has been appropriately sized.

In some embodiments, top and bottom porous layers 6352, 6354 may be in the form of an egg crate shape, such as the shape described in greater detail above in relation to FIG. 21. In further embodiments, top and bottom layers 6352 and 6354 may be placed about stabilizing structure 6302 in any manner described above in relation to FIG. 21.

In certain embodiments, once the top 6352 and bottom 6354 layers of foam have been applied, wound closure device 6350 may be shaped to the desired shape of the wound, thereby eliminating the step of further shaping the top and bottom porous layers as depicted in FIGS. 9A-10C. In some embodiments, the top and bottom layers may further comprise tissue anchors such as those described elsewhere in the specification such as in relation to FIGS. 5A-5D.

Figure 23:
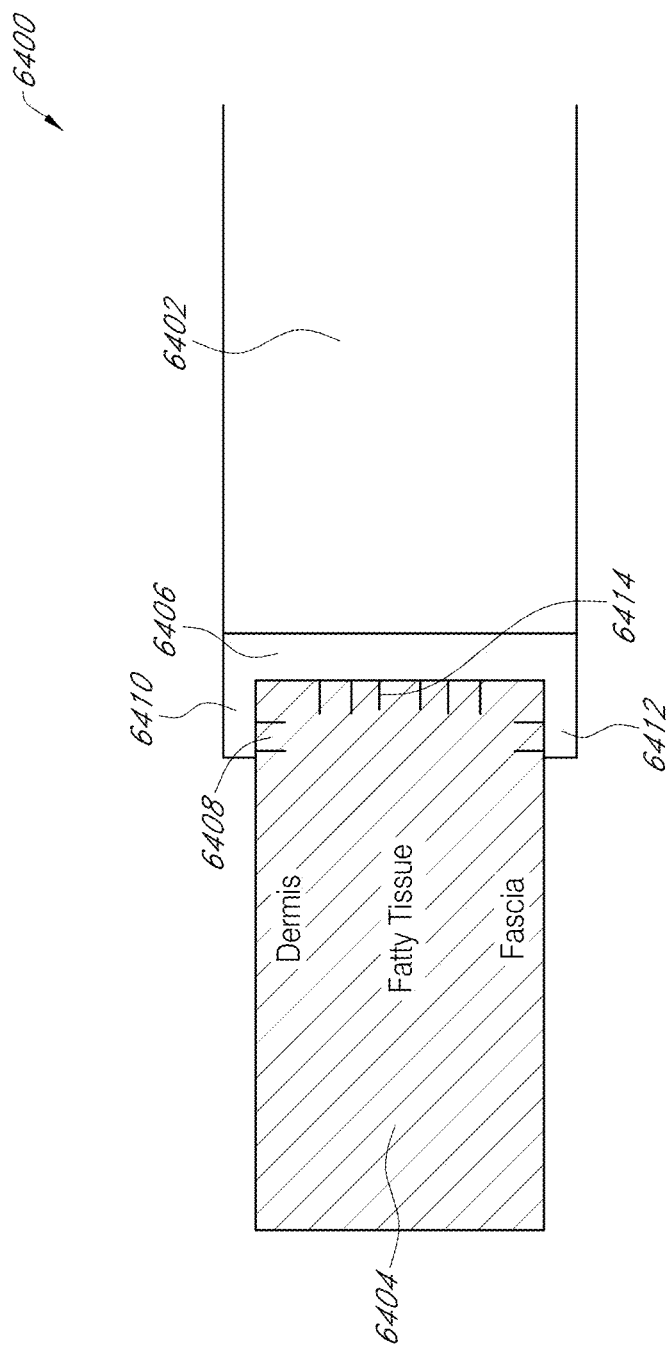
FIG. 23 Illustrates an embodiment of an anchoring layer for adhering a stabilizing structure to the tissues of a wound.

FIG. 23 illustrates an embodiment of a wound closure device 6400 (similar to the wound closure devices depicted in relation to FIGS. 2A-I, 13A-14C, and 16A-18C) comprising a stabilizing structure 6402 and configured to anchor to the surrounding tissues 6404. In certain embodiments, a porous layer 6406, similar to the porous layer described above in relation to FIGS. 20A-C, may be attached to at least a portion of the stabilizing structure 6402. The porous layer comprises a lower lip 6412 that extends outwardly beneath the tissues surrounding the wound such as the fascia, and an upper lip 6410 that extends outwardly from the stabilizing structure over the tissue surrounding the wound, such as the dermis. In certain embodiments, the porous layer comprises tissue anchors 6408, similar to the tissue anchors described above in relation to FIGS. 5A-D. The tissue anchors may allow the porous layer to engage the surrounding tissues and thereby better adhere the stabilizing structure 6402 within the wound. In certain embodiments, the tissue anchors may be present on the upper lip 6410, the lower lip 6412, the central portion 6414, or any combination of the three.

In particular embodiments, some or all of the tissue anchors 6408 may be replaced with an adhesive. For example the lower lip 6412 and central portion 6414 may comprise tissue anchors while the upper lip 6408 comprises an adhesive. In further embodiments, the wound closure device 6400 may further comprise porous layers on the top and bottom, similar to the wound closure device depicted in FIGS. 22A-D.

In some embodiments, the wound closure device 6400 (when viewed from the side as in FIG. 23) may be in shapes that differ from the square shape illustrated in FIG. 23. For example, the device may be a continuous curve such that the outer side has a concave configuration. In some embodiments, portions of the outer perimeter of the stabilizing structure 6402 may be in a concave shape so as to facilitate gripping of the surrounding tissues.

Porous Pads and Stabilizing Structures of FIGS. 24-27B

Figure 24:
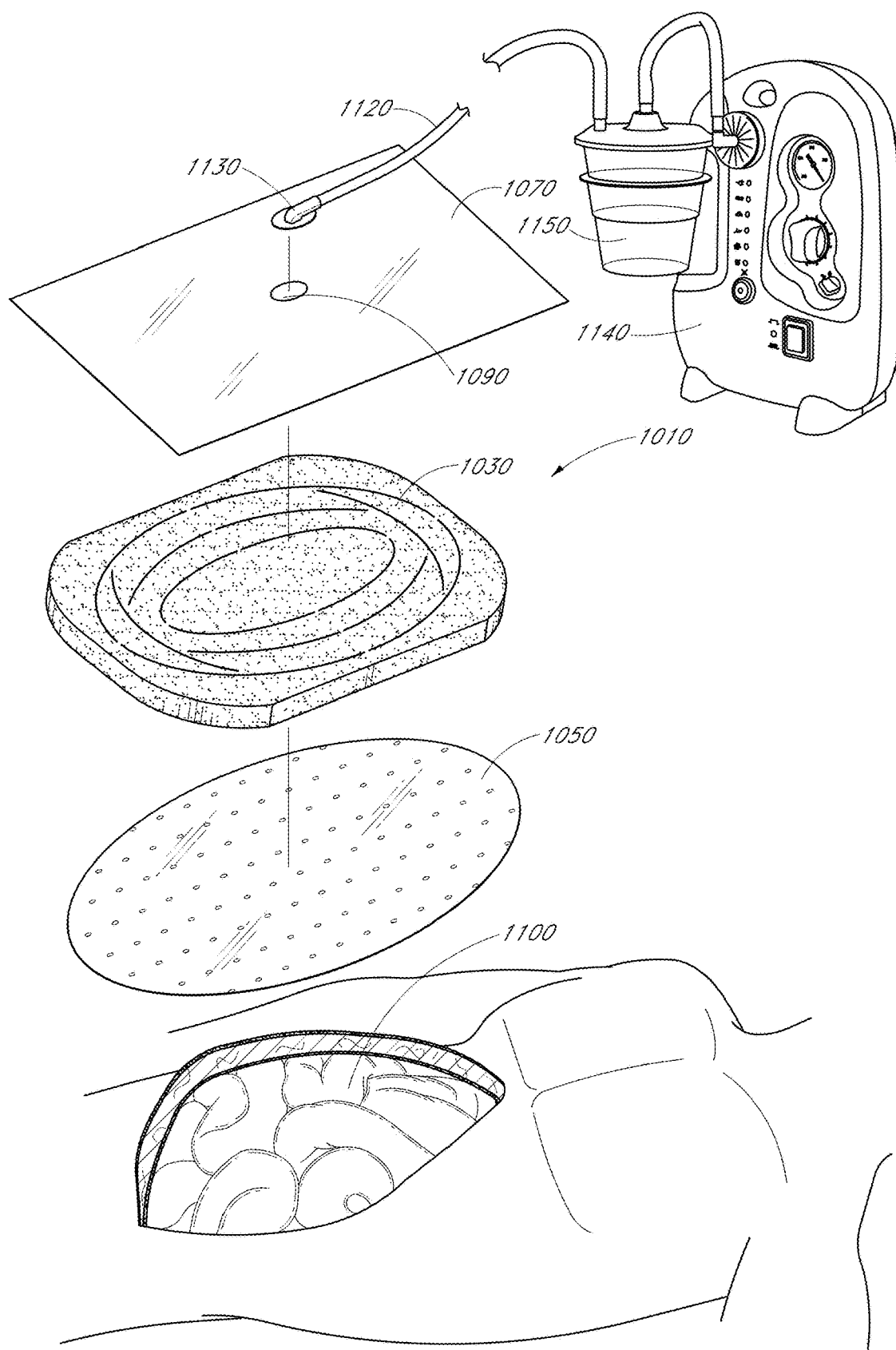
FIG. 24 is a schematic illustration of a system for the treatment of abdominal wounds.

Turning to FIG. 24, similar to the system described above in relation to FIG. 1, treatment of a wound with negative pressure in certain embodiments uses a negative pressure treatment system 1010 as illustrated schematically here. In this embodiment, a wound site 1100, illustrated here as an abdominal wound site, may benefit from treatment with negative pressure. Such abdominal wound sites may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening—particularly in the abdominal cavity—remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound site. The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound site 1100 can be beneficial to a patient.

Accordingly, certain embodiments provide for a wound contact layer 1050 to be placed over the wound site 1100. Preferably, the wound contact layer 1050 can be a thin, flexible material which will not adhere to the wound site or the exposed viscera in close proximity. For example, polymers such as polyurethane, polyethylene, polytetrafluoroethylene, or blends thereof may be used. In one embodiment, the wound contact layer is permeable. For example, the wound contact layer 1050 can be provided with openings, such as holes, slits, or channels, to allow the removal of fluids from the wound site 1100 or the transmittal of negative pressure to the wound site 1100. Additional embodiments of the wound contact layer 1050 are described in further detail below.

Certain embodiments of the negative pressure treatment system 1010 may also use a porous pad 1030, which can be disposed over the wound contact layer 1050. This pad 1030 can be constructed from a porous material, for example foam, that is soft, resiliently flexible, and generally conformable to the wound site 1100. Such a foam can include an open-celled and reticulated foam made, for example, of a polymer. Suitable foams include foams composed of, for example, polyurethane, silicone, hydrophobic materials, hydrophilic materials, open-celled materials, close-celled materials, mixed open and close-celled materials, reticulated materials, polyester, silicone, and/or polyvinyl alcohol. In certain embodiments, the term "open-celled" may refer to a material (such as foam) that comprises just enough open pores to allow fluid to be transmitted when the foam is compressed at pressures of at least about: −350 mmHg, −300 mmHg, −200 mmHg, −150 mmHg, −120 mmHg, −75 mmHg, −50 mmHg, −25 mmHg or −5 mmHg. In some embodiments, the open-celled material may have a wide range of suitable porosities and the pores may be of a variety of suitable sizes. Preferably, this pad 1130 can channel wound exudate and other fluids through itself when negative pressure is applied to the wound. Some pads 1030 may include preformed channels or openings for such purposes. In certain embodiments, the pad 1030 may have a thickness between about one inch and about two inches. The pad may also have a length of between about 16 and 17 inches, and a width of between about 11 and 12 inches. For example, the length of the pad can range from between about 1 to 50 inches, between about 3 to 40 inches, between about 5 to 30 inches, between about 10-20 inches, or between about 14 to 18 inches. Further, for example, the width may range from about 1 to 20 inches, 5 to 15 inches, or 8 to 12 inches. In other embodiments, the thickness, width, and/or length can have other suitable values. Other aspects of the pad 1030 are discussed in further detail below.

Preferably, a drape 1070 is used to seal the wound site 1100. The drape 1070 can be at least partially liquid impermeable, such that at least a partial negative pressure may be maintained at the wound site. Suitable materials for the drape 1070 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. An adhesive layer may be provided on at least a portion the underside of the drape 1070 to secure the drape to the skin of the patient, although certain embodiments may instead use a separate adhesive or adhesive strip. Optionally, a release layer may be disposed over the adhesive layer to protect it prior to use and to facilitate handling the drape 1070; in some embodiments, the release layer may be composed of multiple sections.

The negative pressure system 1010 can be connected to a source of negative pressure, for example a pump 1140. One example of a suitable pump is the Renasys EZ pump available from Smith & Nephew. The drape 1070 may be connected to the source of negative pressure 1140 via a conduit 1120. The conduit 1120 may be connected to a port 113 situated over an aperture 1090 in the drape 1070, or else the conduit 1120 may be connected directly through the aperture 1090 without the use of a port. In a further alternative, the conduit may pass underneath the drape and extend from a side of the drape. U.S. Pat. No. 7,524,315, filed Oct. 28, 2003 discloses other similar aspects of negative pressure systems and is hereby incorporated by reference in its entirety and should be considered a part of this specification.

In many applications, a container or other storage unit 1150 may be interposed between the source of negative pressure 1140 and the conduit 1120 so as to permit wound exudate and other fluids removed from the wound site to be stored without entering the source of negative pressure. Certain types of negative pressure sources—for example, peristaltic pumps—may also permit a container 1150 to be placed after the pump 1140. Some embodiments may also use a filter to prevent fluids, aerosols, and other microbial contaminants from leaving the container 1150 and/or entering the source of negative pressure 1140. Further embodiments may also include a shut-off valve or occluding hydrophobic and/or oleophobic filter in the container to prevent overflow; other embodiments may include sensing means, such as capacitative sensors or other fluid level detectors that act to stop or shut off the source of negative pressure should the level of fluid in the container be nearing capacity. At the pump exhaust, it may also be preferable to provide an odor filter, such as an activated charcoal canister.

Figure 25A:
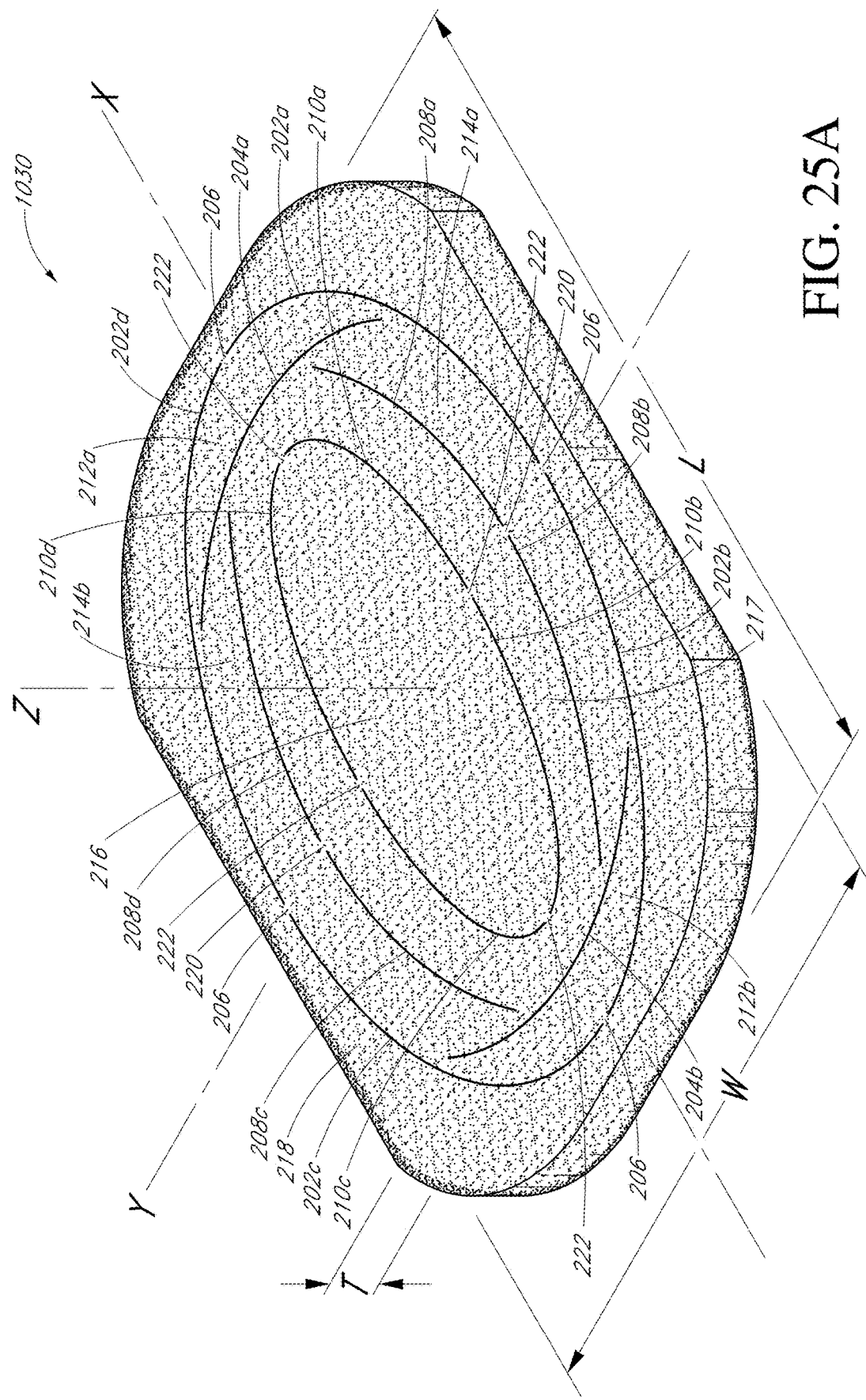
FIG. 25A illustrates a perspective view of one embodiment of a porous pad that can be used in the treatment of wounds.
Figure 25B:
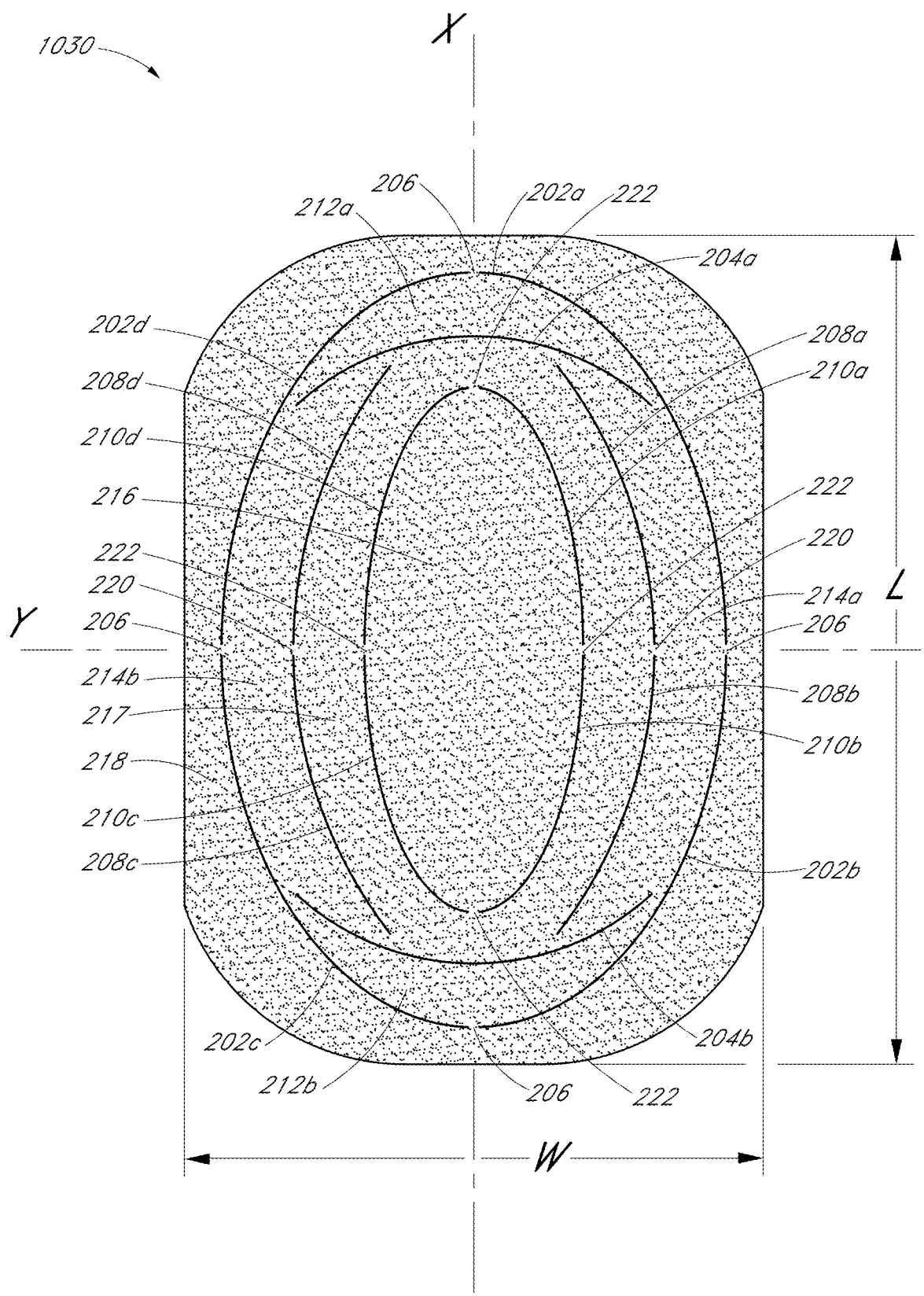
FIG. 25B illustrates a top view of the porous pad of FIG. 2A.

With reference to FIGS. 25A-B, perspective and top views of an embodiment of the porous pad 1030 are shown. The pad 1030 preferably has one or more perforations made thereon, illustrated for example at arcuate cuts 202, 204, 208, and 210. These cuts may be formed on the pad 1030 using any suitable mechanism, including, for example but without, limitation cutting blades, die cutting, or hot wire cutting, and these cuts preferably extend through at least portion of the thickness of the pad 1030. The cuts do not need to be continuous, and may consist, for example, of multiple small perforations. In one embodiment, perforations extend entirely across the thickness of the pad 1030. In order to ensure that the pad 1030 remains structurally intact during handling and use, the cuts made through the pad 1030 preferably retain one or more small bridge portions, such as the bridge portion 206.

In some embodiments, the pad 1030 has a substantially rectangular shape having a length L, a width W, and a thickness T defined about a major axis X, a minor axis Y, and a vertical axis Z, and has four rounded corners. A first series of arcuate outer cuts 202 may be formed in the pad in an elliptical shape. In the illustrated embodiment, there are four outer cuts 202a, 202b, 202c and 202d, each positioned in one of the quadrants defined by the axes X and Y, with four bridge portions 206 positioned at opposite ends along the major and minor axes. Interior to the outer cuts 202 are a series of arcuate inner cuts 210 also having an elliptical shape similarly shaped to the series of arcuate outer cuts 202. As illustrated, in one embodiment there are four inner cuts 210a, 210b, 210c, 210d also each positioned in one of the quadrants defined by the axes X and Y, with four bridge portions 222 positioned at opposite ends along the major and minor axes.

In certain embodiments, located between the outer and inner cuts 202 and 210 may be a series of intermediate cuts 204 and 208. From the top view perspective of FIG. 25B, an upper arcuate cut 204a and a lower arcuate cut 204b are symmetrically arranged about minor axis Y located at opposite ends of the pad 1030. Cuts 204a and 204b extend generally across the width W of the pad, symmetrically about major axis X, with these cuts 204a, 204b having a larger radius of curvature than that of the arcuate cuts 202 near the major axis X. Left and right arcuate cuts 208 are provided between the arcuate cuts 204a, 204b, extending generally length-wise across the pad. As illustrated, there may be four arcuate cuts 208a, 208b, 208c, 208d, each extending generally parallel to the portions of the arcuate cuts 202, 210 that surround them, with bridge portions 220 located on the minor axis Y. It will be appreciated that the shape and number of cuts may be varied, and that there may be more than one series of intermediate cuts between the inner and outer cuts 210, 202.

Advantageously, cuts made on the pad 1030 can be used to selectively size the pad 1030 to the wound site in which the pad 1030 is to be placed. For example, the pad 1030 can be sized by removing detachable sections from the pad 1030, for example, outer section 218 that surrounds outer cuts 202, inner sections 212a, 212b located between the outer cuts 202 and intermediate cuts 204a and 204b, and inner sections 214a, 214b between the outer cuts 202 and intermediate cuts 208. Although additional and different cuts from the cuts 202, 204, 208, and 210 may be made on the pad 1030, these cuts represent examples of types and locations of cuts that can be used to size a pad in a dimensionally-independent manner. Types of cuts that can be made on the pad 1030 include, for example, arcuate, circular, ovoid, zigzag, and/or linear cuts. Further, although the cuts shown here are along the length L and width W of the pad, similar cuts may be made along the thickness T of pad 1030, such that a thinner pad can be used in a wound site. Cuts may also be made at an angle not aligned with either of the X, Y, or Z axes, for example diagonally across the pad 1030.

In use, the pad 1030 may be too large for the wound site 110, and may need to be sized by removing the detachable area 218 encompassed by the edges of the pad 1030 and the cuts 202 made thereon. For smaller wounds, detachable areas 212a, 212b, 214a, and 214b may all be removed to leave only the detachable areas 216 and 217. In even smaller wounds, the remainder of the pad 1030 may be removed to leave only the central detachable area 216. Typically, such sizing can be performed manually, for example using scissors, but such methods incur concomitant disadvantages such as difficulties in manipulating a cutting utensil in a busy operating room, uneven and imprecise cuts, and the possibility of shedding foreign particles into a wound site. Instead, the premade cuts on the pad 1030 may be detached by hand or with minimal cutting along the various bridge portions 206, 220, 222.

With continued reference to FIGS. 25A-B, certain embodiments permit sizing of a pad 113 in a dimensionally-independent manner. Here, sections from the pad 1030 can be detached or cut along the delineations between the various cuts, for example the sections 212a, 212b and 214a, 214b. These cuts 204 and 208 can permit sizing of the pad 1030 as desired to more closely tailor the actual dimensions of a wound site. For example, sizing a pad 1030 for fitting in a wound that is wider on the left side and narrower on the right side may be effectuated by removing a pad section 214a delineated between the cuts 208a, 208b and 202a, 202b. In another example, where the pad 1030 is longer along its top portion than the wound site 110, a pad section 212a, delineated between cuts 202a, 202b, and 204a can be removed from one end of the pad 1030. In these preceding examples, the outer detachable portion 218 has preferably already been removed, although this is not necessarily required. Consequently, dimensionally-independent sizing of the pad 1030 (e.g., modifying the length of the pad without altering the width of the pad, and vice-versa) may be achieved by detaching sections 212, 214 delineated by cuts 204 or 208. Additional detachable sections encompassed by additional cuts so as to permit dimensionally-independent sizing of the pad 1030 are contemplated, and the embodiments illustrated herein are not intended to be limiting. Obviously, for smaller wound sites, the removal of symmetric sections of the pad 1030 may still be useful, and embodiments of the pad 113 may provide such sections, illustrated here as sections 218, 217, 216. For example, removal of the outer section 218 of the pad 1030 along the cuts 202 may be necessary. Similarly, for smaller incisions only the inner section 216 delineated inside cuts 210 may be required.

Figure 25C:
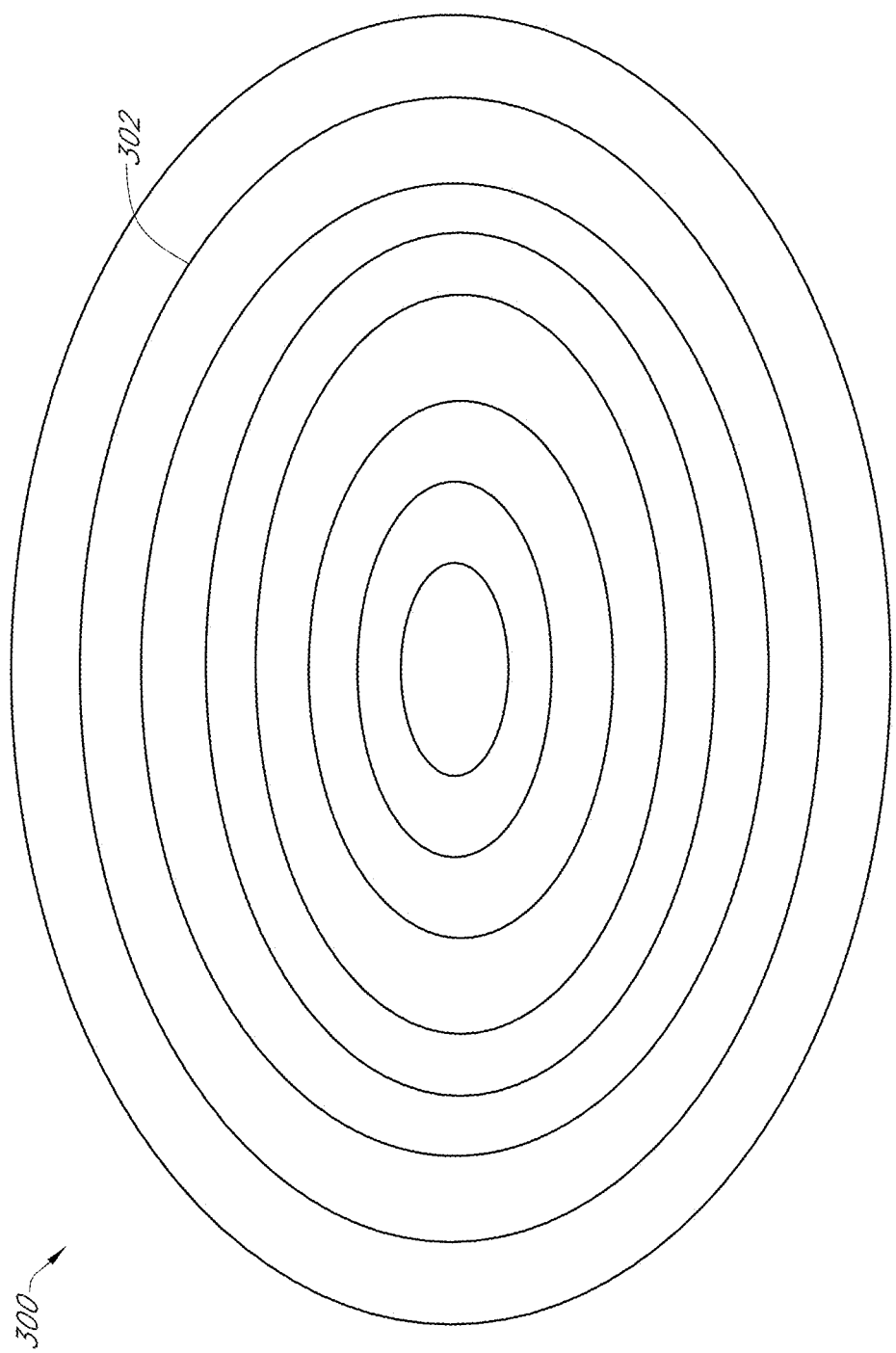
FIG. 25C illustrates another embodiment of the porous pad that can be used in the treatment of wounds.

FIG. 25C illustrates an alternative embodiment of a foam pad 300, similar to the pads depicted in FIGS. 25A-B, however, the pattern of cuts 302 depicted in FIG. 3 may differ from the cuts depicted in FIGS. 25A-B. In certain embodiments, the pad 300 may comprise multiple concentric elliptical cuts 302. The cuts may encompass a complete 360 degree ellipse or they can encompass a partial cut that does not comprise the entirety of an ellipse. For example, a cut may comprise less than at least 10 degrees, at least 10 degrees, at least 30 degrees, at least 60 degrees, at least 90 degrees, at least 120 degrees, at least 180 degrees, at least 240 degrees, at least 300 degrees, or at least 360 degrees. In particular embodiments, the pad may contain at least one elliptical cut, at least two elliptical cuts, at least three elliptical cuts, at least four elliptical cuts, at least five elliptical cuts, at least ten elliptical cuts, or more than 10 elliptical cuts. As with the pad embodiments and methods depicted in relation to FIGS. 25A-B, the cuts may allow for sections of foam to be removed from the pad to allow the pad to be shaped to the form of a wound.

Figure 26:
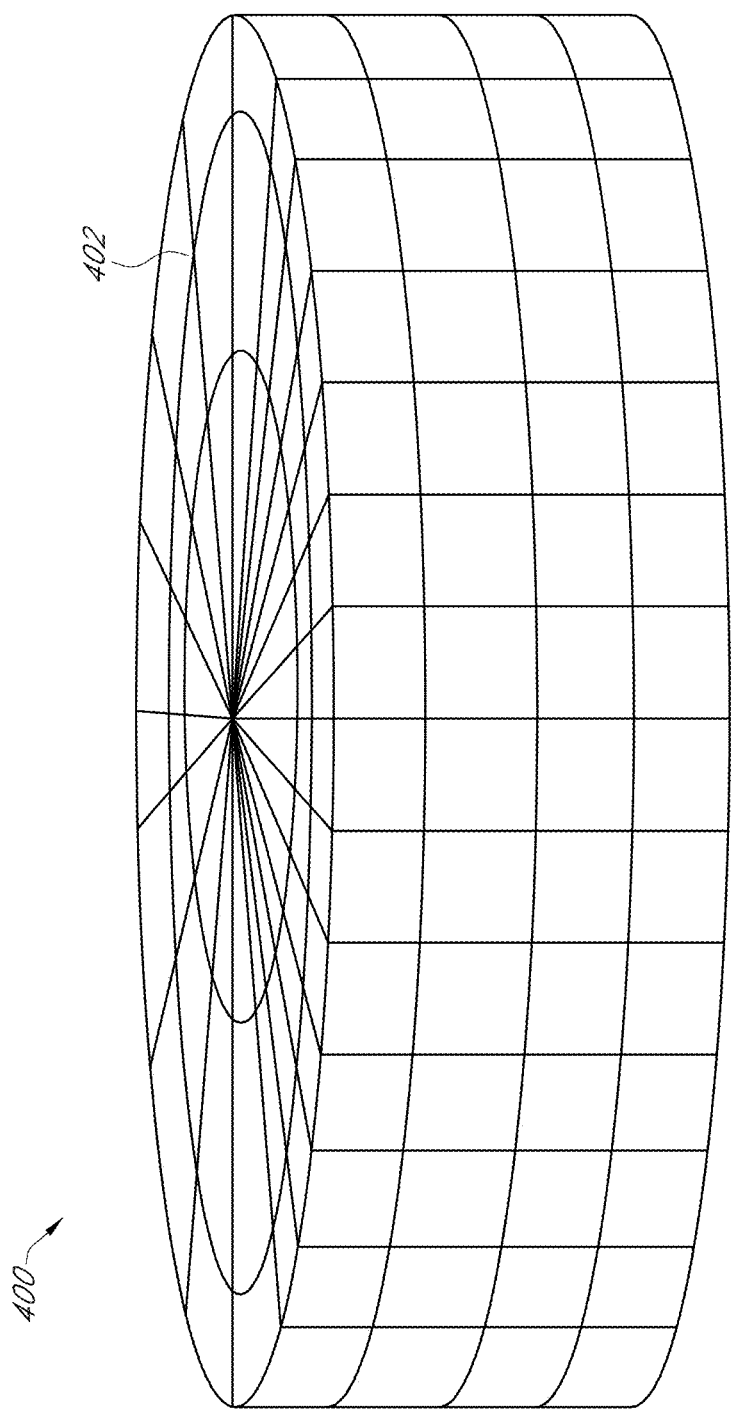
FIG. 26 illustrates an embodiment of a foam structure that can be used in the treatment of wounds.

FIG. 26 depicts an embodiment of a three-dimensional foam structure 400, similar to the foam pads depicted in FIGS. 25A-C. The foam structure may comprise a foam material with a number of cuts or perforations 402 in the x, y, and z dimensions. The cuts or perforations may create frangible regions within the structure that can be selectively removed from the structure. Such cuts or perforations 402 may allow the foam structure 400 to be modified in a dimensionally-independent manner, similar to the dimensionally-independent modification of the foam pads depicted in FIGS. 25A-C. For example, the frangible regions of the structure 400 may be selectively removed to alter the structure in the x dimension, the y dimension, and the z dimension, to shape the structure into the shape of a wound. Further details regarding the shaping of a three-dimensional to the shape of a wound may be found in U.S. application Ser. No. 13/201,427, titled WOUND PACKING, filed Sep. 14, 2011, and published as US 2011/0319804. This application is hereby incorporated by reference in its entirety.

In certain embodiments, the foam structure may be in the form of an ovoid, a cube, or other suitable three-dimensional shape. The foam structure 400 may be used in combination with any suitable negative pressure wound therapy system or apparatus described herein this section or elsewhere in the specification.

Figure 27A:
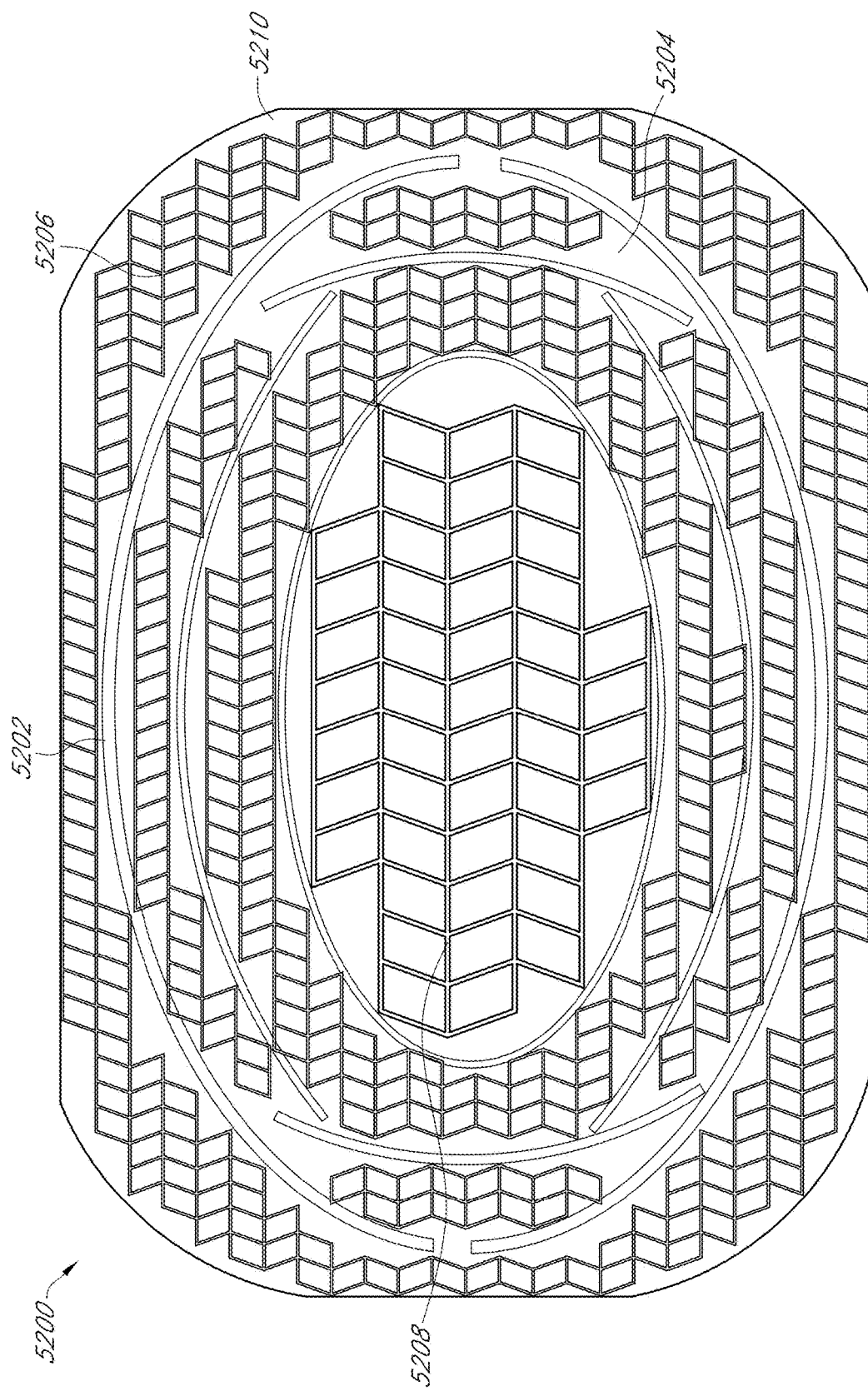
FIGS. 27A-B illustrate embodiments of stabilizing structures within a porous material.
Figure 27B:
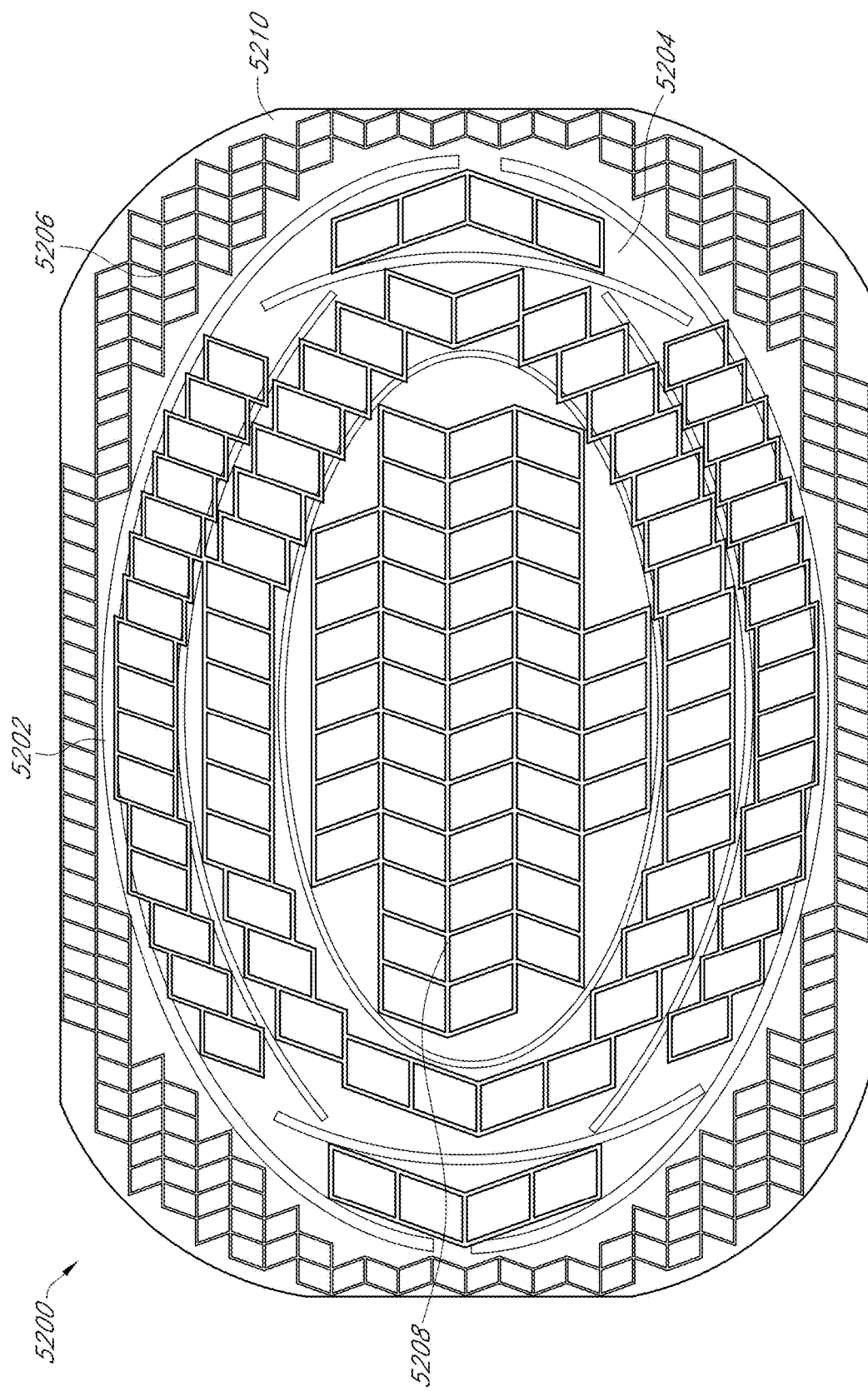
Figure 28:
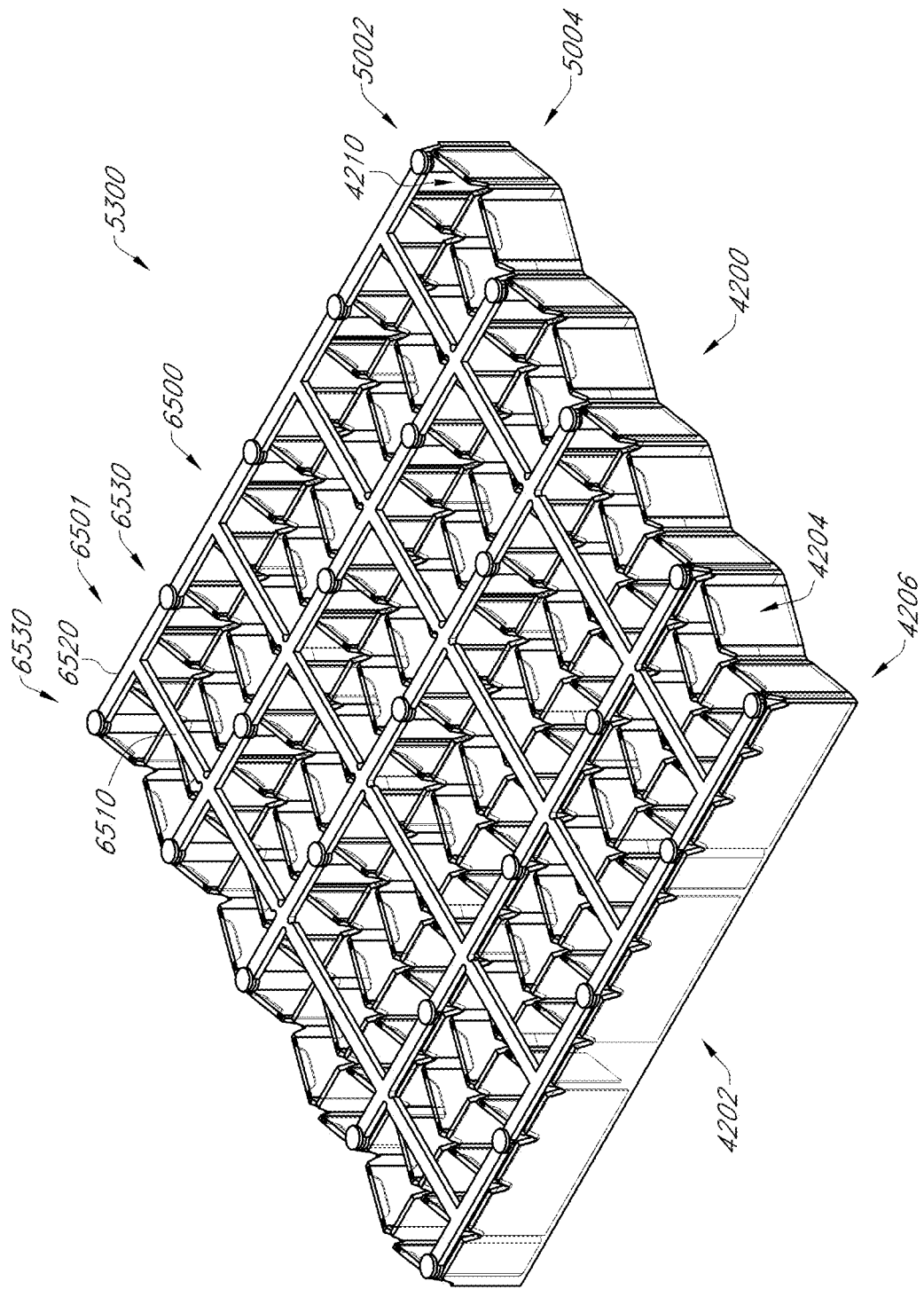
FIG. 28 is a perspective view of one embodiment of a wound closure device for negative pressure wound therapy with one embodiment of a stabilizing structure and support structure attached to the stabilizing structure.
Figure 29:
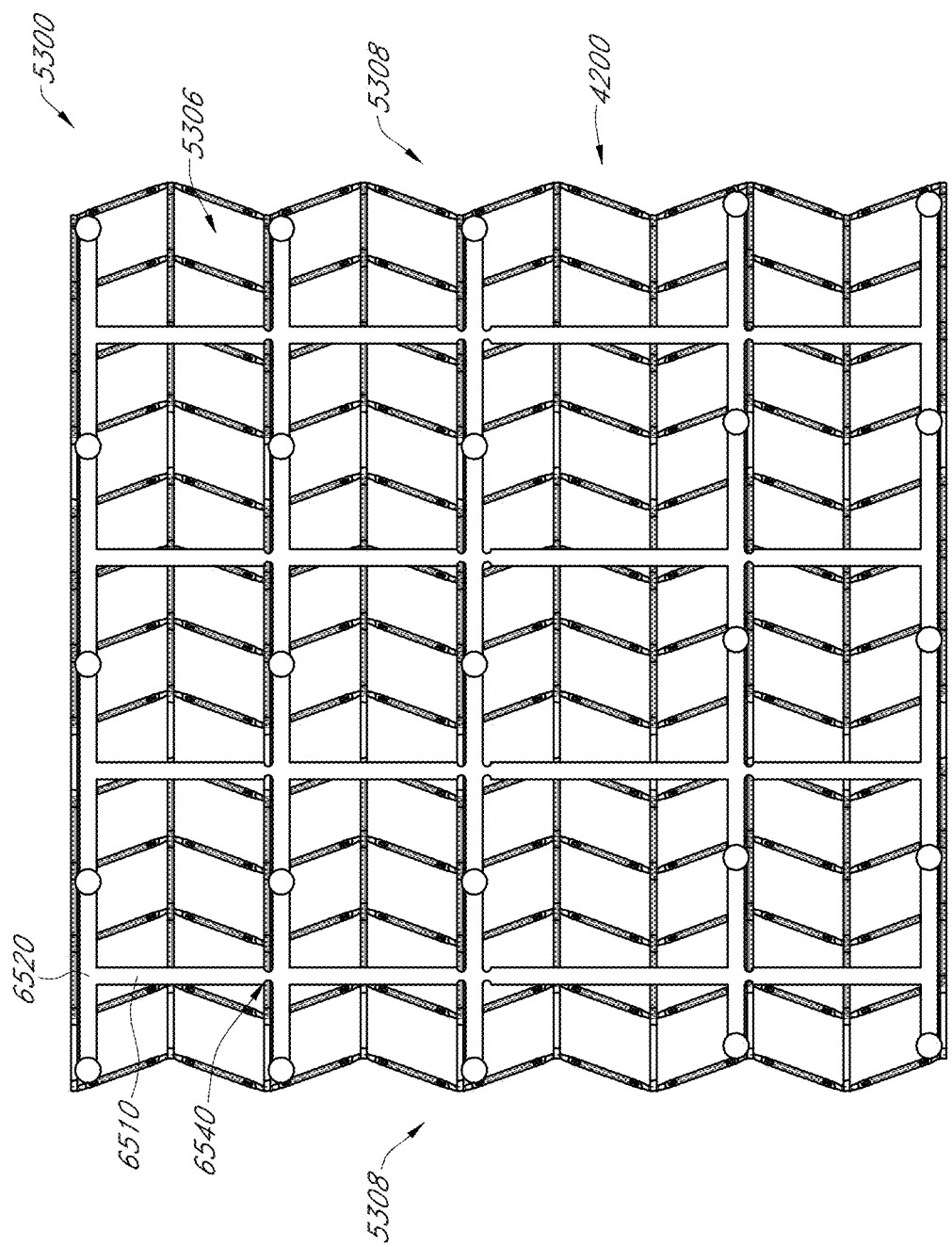
FIG. 29 is a top view of the wound closure device of FIG. 28.
Figure 30:
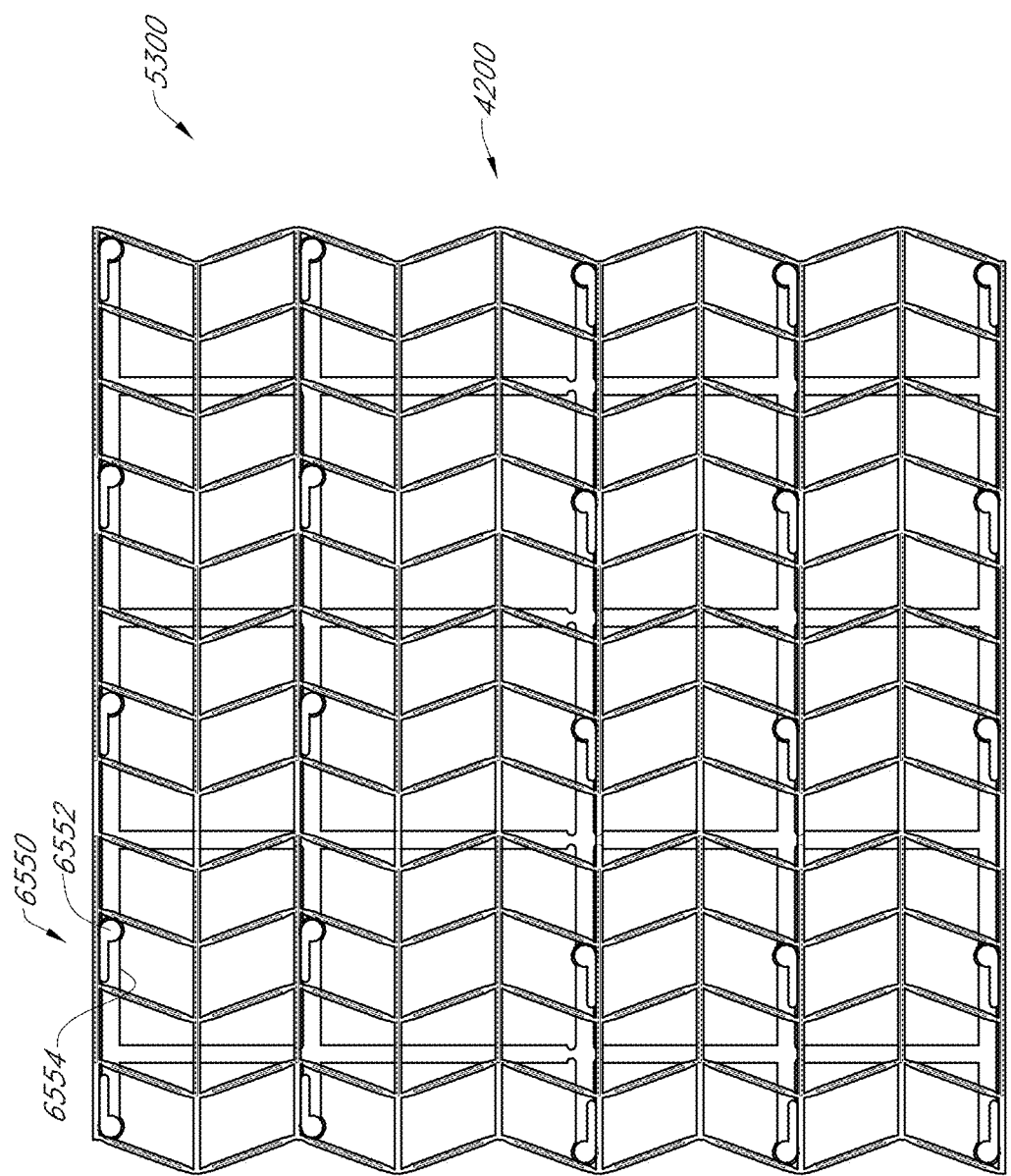
FIG. 30 is a bottom view of the wound closure device of FIG. 28.

FIGS. 27A-B depict embodiments of a porous pad 5200, similar to the pads and structures described above in relation to FIGS. 24-26. Although the word "pad" 5200 will be used in this section, any description relating to the pad is also applicable to the three-dimensional "structure" 400 described in FIG. 26.

In certain embodiments, the porous pad 5200 of FIGS. 27A-B may comprise a series of cuts or perforations 5202, similar to the cuts described in relation to FIGS. 25A-26. The pad may be comprised of a porous material 5204, such as those materials described in relation to FIGS. 25A-26, and other materials described herein this section and elsewhere in this specification. The pad may further comprise one or more stabilizing structures 5006, 5008 embedded within the porous material 5204. Such stabilizing structures are similar to the structures described above in relation to FIGS. 2A-2I, 13A-14C, and 16-18C. The stabilizing structures may be completely encased within the surrounding porous material 5204, such that the stabilizing structures are completely surrounded by the porous material in all directions. In certain embodiments, portions of the stabilizing structures may protrude from the porous material. For example, the stabilizing structures may protrude from the top, bottom, or sides of the porous material.

As will be understood by one skilled in the art, the stabilizing structures are not limited to a side by side arrangement in a two-dimensional plane. Instead, with reference to the three-material structure embodiments described elsewhere in reference to FIG. 26, the stabilizing structures may also be arranged along the height of the structure in three dimensions.

In certain embodiments, the cuts or perforations 5202 in pad 5200 through porous material 5204 may be of any type described herein this section or elsewhere in the specification, particularly as relates to FIGS. 25A-26. As described elsewhere, particularly in relation to FIGS. 25A-26, the cuts or perforations may allow frangible regions of the pad 5200 or three-dimensional structure to be detached so as to shape the pad or three-dimensional structure to the shape of a wound. In certain embodiments, the stabilizing structures 5206 and 5208 are completely contained within the detachable regions. In other embodiments, the stabilizing structures may extend between frangible regions, and thus the stabilizing structures themselves may be separable. For example, the stabilizing structures may have cuts or perforations similar to those cuts or perforations in the porous material 5204. In particular embodiments, the frangible stabilizing structures may not be surrounded by any porous material, instead they may be shaped to the shape of a wound without the use of an encasing porous material. Further, any of the stabilizing structure embodiments described herein this section or elsewhere in the specification may be frangible and capable of being shaped even in the absence of an encasing porous material. In certain embodiments, frangible regions of the stabilizing structure may be adhered to one another via an adhesive.

The stabilizing structures may be of a variety of shapes and sizes such as those described herein this section or elsewhere in the specification. Further, different types of stabilizing structures may be incorporated into a single porous pad 5200. For example, as depicted in FIG. 27A, the porous pad 5200 may be comprised of two types of stabilizing structures, a smaller-celled stabilizing structure 5206, and a larger-celled stabilizing structure 5208. As illustrated in FIG. 27A, the larger-celled structure may be contained within the central portion of the porous pad 5200, while the smaller-celled stabilizing structure can be contained throughout the outer regions. In certain embodiments, the larger-celled structures may be contained within the outer regions of the porous pad 5200, while the smaller-celled structures may be contained within the central portions. The porous pad may be surrounded by a flexible annular outermost region 5210. In some embodiments, there may be additional similar regions, allowing for further frangible regions.

In particular embodiments, a portion of the pad containing only porous material may extend beyond the sections of the pad that comprise a stabilizing structure. This extending porous material-only portion of the pad may extend above, beneath or between layers of surrounding tissue, such as the skin, fatty tissue, fascia, muscle, or other suitable tissues. In some embodiments, this porous material-only portion of the pad may extend for less than one inch, at least 1 inch, at least 2 inches, at least 4 inches, at least 8 inches, at least 12 inches, at least 15 inches, or more than 15 inches.

As depicted in FIG. 27B, the porous pad 5200 may be comprised of larger-celled stabilizing structures 5208 within the central region and surrounding regions, while the smaller-celled stabilizing structures 5206 are contained only within the flexible outermost region 5210. In further embodiments, the porous pad may comprise more than two types of stabilizing structures. For example, the porous pad may comprise at least three types of stabilizing structures, at least four types of stabilizing structures, at least five types of stabilizing structures, at least six types of stabilizing structures, or more than six types of stabilizing structures. In certain embodiments, all of the stabilizing structures are of the same type, i.e. have cells of the same size.

The stabilizing structures 5206, 5208 may be configured to collapse in any manner described herein this section or elsewhere in the specification such as in relation to FIGS. 2A-2I, 13A-14C, and 16-18C. Briefly, as described in detail elsewhere, the stabilizing structures 5006 and 5008 can be configured to collapse more readily under negative pressure in a first direction, while not collapsing to a significant degree in a second direction. Further, various stabilizing structures may have different collapsibility properties as described herein this section or elsewhere in the specification.

In certain embodiments, the stabilizing structure may be of any type described herein this section or elsewhere in this specification. Further, the stabilizing structure may be comprised of any of the materials described herein this section or elsewhere in the specification. In some embodiments, the porous pads 5200 depicted in FIGS. 27A-B may be surrounded by an anchoring layer such as those described in relation to FIGS. 4-5D. The anchoring layer may be attached to the porous pad in any manner described herein this section or elsewhere in the specification. For example, the anchoring layer may be attached by an adhesive and/or via tape.

In some embodiments, the porous pad 5200 may further comprise tissue anchors similar to those described in relation to FIGS. 4-5D. Similar to the embodiments described in relation to FIGS. 4-5D, the tissue anchors can be hooks, barbs, prongs, or other structures that serve to attach to the tissue of a wound. In some embodiments, the tissue anchors comprise hook and loop fasteners such as those used in Velcro technologies. The anchors may extend from the stabilizing structures or from the foam portions of the porous pad.

In some embodiments, the porous pads 5200 may be manufactured by forming a porous material around the stabilizing structures and then creating cuts and/or perforations via any method described herein this section or elsewhere in the specification. In certain embodiments, the porous pad may contain a single internal pocket or multiple internal pockets for insertion of the stabilizing structures.

For example, each frangible region may have a pocket to allow for insertion of a stabilizing structure. In some embodiments, the porous material may be initially sliced in two, such that the stabilizing structure is placed within once portion of the porous material and then covered by a second portion of the porous material.

Mechanism for Preventing Collapse of Wound Closure Device (FIGS. 28-39)

In some embodiments, the stabilizing structure used in wound closure devices as described herein comprises a plurality of cells provided side-by-side in a plane, each cell defined by one or more walls, each cell having a top end and a bottom end with an opening extending through the top and bottom ends in the direction perpendicular to the plane. The stabilizing structure is configured to collapse more within the plane than along the direction perpendicular to the plane. The plane may extend in a horizontal direction parallel with a tissue surface, and the walls extend in a vertical direction perpendicular to the tissue surface. In certain embodiments, the stabilizing structure comprises a plurality of elongate strips, and a plurality of intervening members connecting the elongate strips, wherein the plurality of intervening members are configured to pivot relative to the strips to allow the plurality of elongate strips to collapse relative to one another.

FIGS. 28-32 show one embodiment of a wound closure device 5300. The wound closure device 5300 can have a stabilizing structure 4200 with one or more strips 4202 interconnected by one or more intervening members 4204 joined to the one or more strips 4202 via joints 4206. As discussed above, the strips 4202 and intervening members 4204 define a plurality of cells 4210 side by side in a plane 5308 (e.g., defined by page in FIG. 29), each of the cells 4210 defined between two adjacent strips 4202 and two adjacent intervening members 4204 and having an opening 5307 that extends from a top end 5303 to a bottom end 5305 of the stabilizing structure 4200 in a direction perpendicular to the plane 5308. As described above, the stabilizing structure 4200 can collapse along the plane such that the one or more strips 4202 move toward each other (e.g., adjacent each other) as the intervening members 4204 pivot relative to the strips 4202 (e.g., as the cells 4210 collapse).

With continued reference to FIGS. 28-32, the wound closure device 5300 can also include a support structure 6500. The support structure 6500 can attach to the stabilizing structure 4200. The support structure 6500 can at least partially inhibit or prevent the collapse of the stabilizing structure (e.g., when a negative pressure is applied to the wound closure device 5300).

In one embodiment, the support structure 6500 can include a plurality of support elements 6501 that can couple to each other to define the assembled support structure 6500. The support structure 6500 is thus modular and the size of the support structure 6500 can be varied at least by varying the number of support elements 6501 that are coupled to each other.

Each of the support elements 6501 can optionally include one or more beams 6510 that (e.g., together) define a length of the support element 6501 and one or more cross-beams 6520 that define a width of the support element 6501, where each beam 6510 extends between and attaches to a pair of cross-beams 6520. In one embodiment, the beams 6510 and cross-beams 6520 can be perpendicular to each other (e.g., form a T-shape). However, in other embodiments, the beams 6510 and cross-beams 6520 can be at other suitable angles relative to teach other. Each cross-beam 6520 can have a pair of opposite ends 6530, wherein each of the ends 6530 of one support element 6501 of the support structure 6500 can couple to an end 6530 of another support element 6501 of the support structure 6500, as further discussed below.

In one embodiment the one or more beams 6510 can have a frangible portion or joint 6540 (e.g., portion of reduced thickness), that allows the beam 6510 to be detached (e.g., broken, torn, cut) from the rest of the support element 6501 via the frangible portion 6140. Therefore, the size (e.g., length) of the support element 6501 can be adjusted at least by detaching one or more beams 6510 therefrom via the frangible portion 6540, for example, in addition to being adjusted by the number of support elements 6501 that are coupled to each other. In one embodiment, the frangible portion 6540 is defined at the junction of the beam 6510 and cross-beam 6520. However, in other embodiments, the frangible portion 6540 can be defined in another portion of the beam 6510 (e.g., midway along the beam). In one embodiment, only one end of the beam 6510 has the frangible portion 6540. In another embodiment, both ends of the beam 6510 have the frangible portion 6540.

Figure 31:
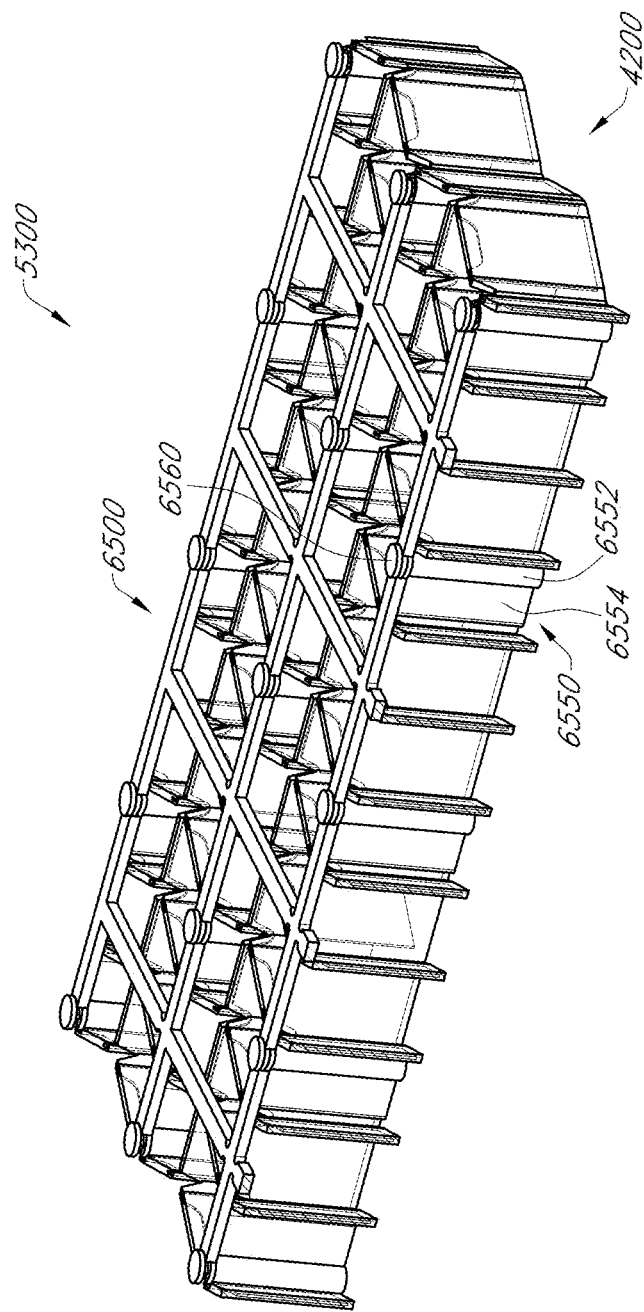
FIG. 31 is a cross-sectional view of the wound closure device of FIG. 28.
Figure 32:
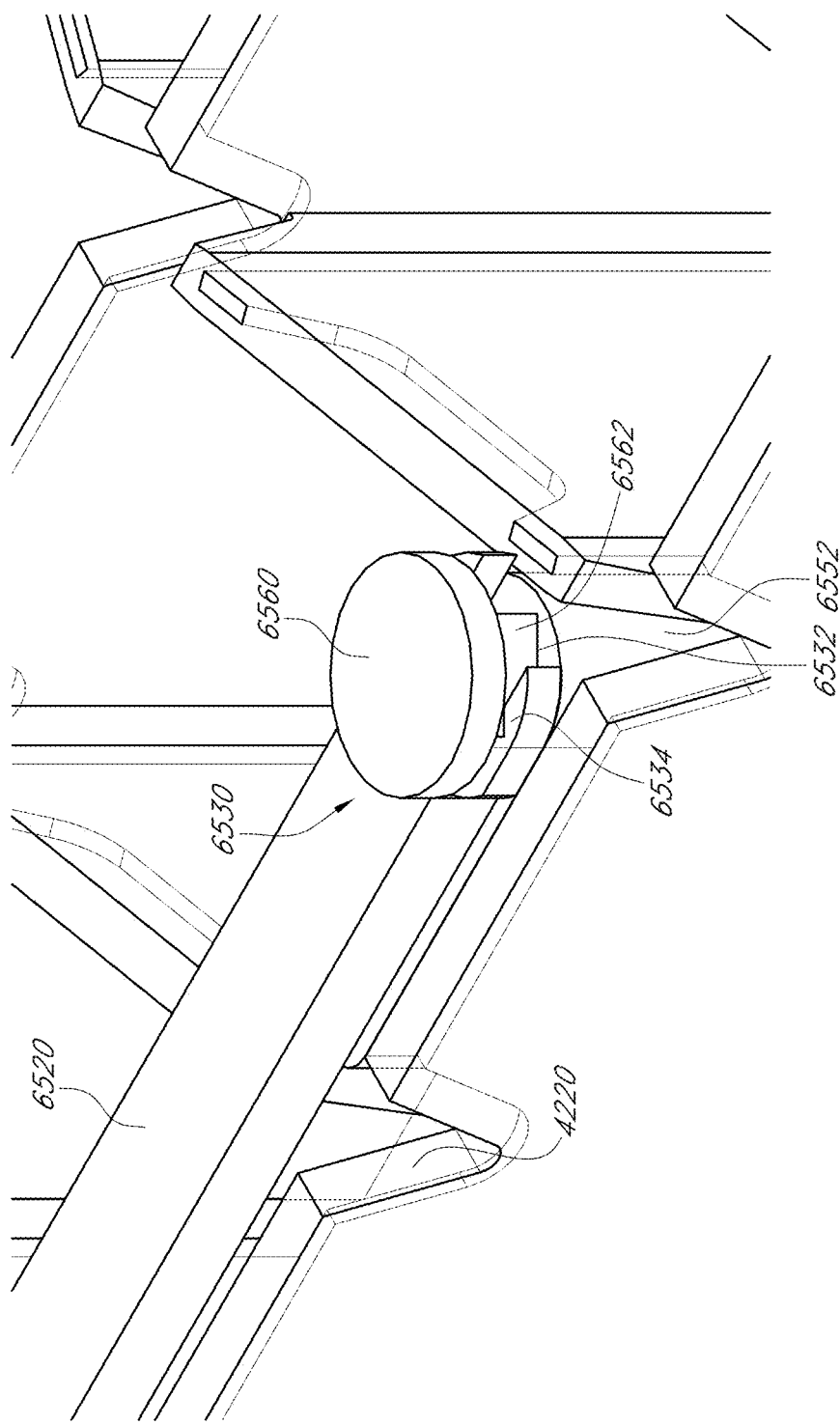
FIG. 32 shows a partial view of the wound closure device of FIG. 28, showing a portion of the support structure.
Figure 33:
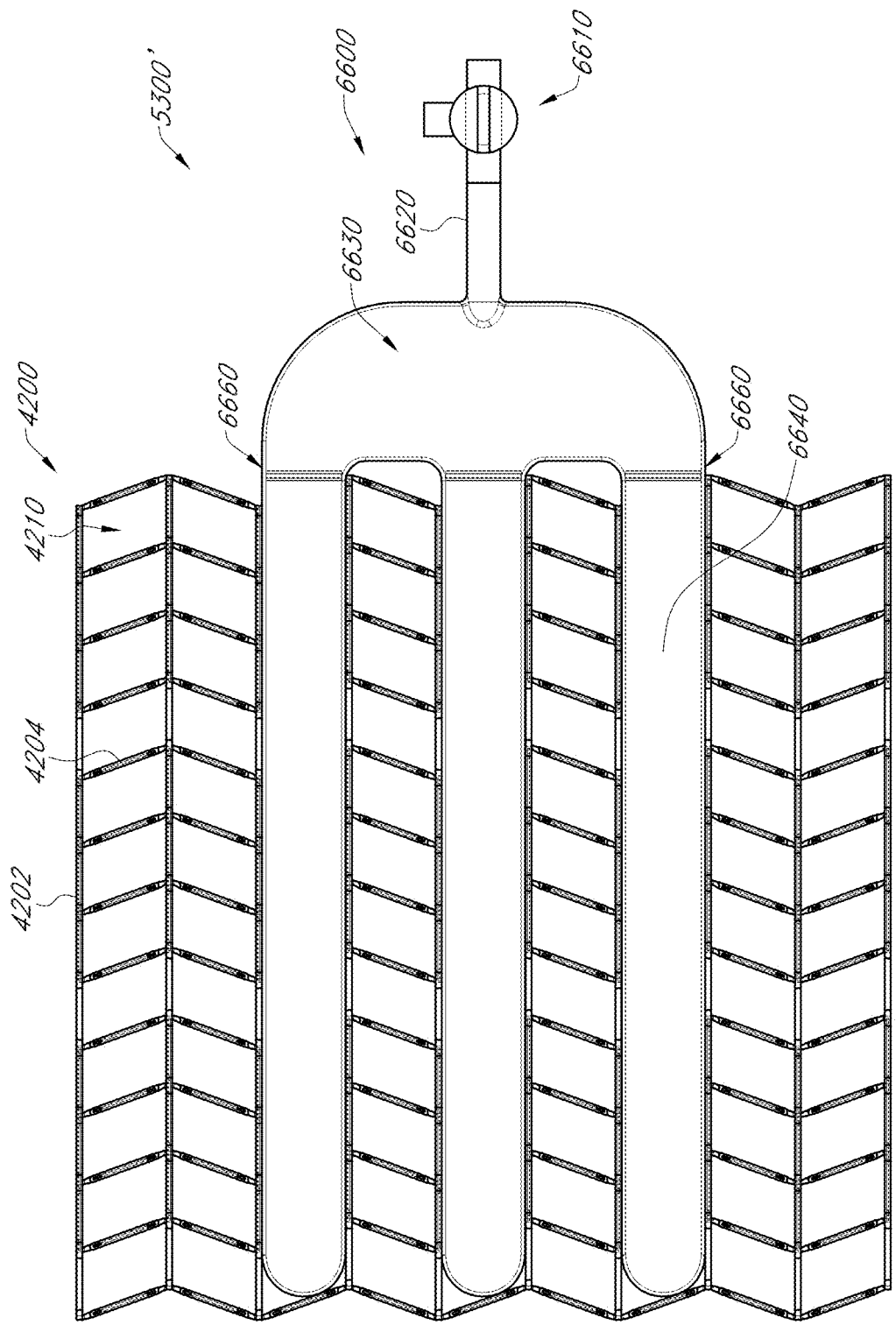
FIG. 33 is a schematic top view of another embodiment of a wound closure device for negative pressure wound therapy with another embodiment of a stabilizing structure and support structure attached to the stabilizing structure.
Figure 34:
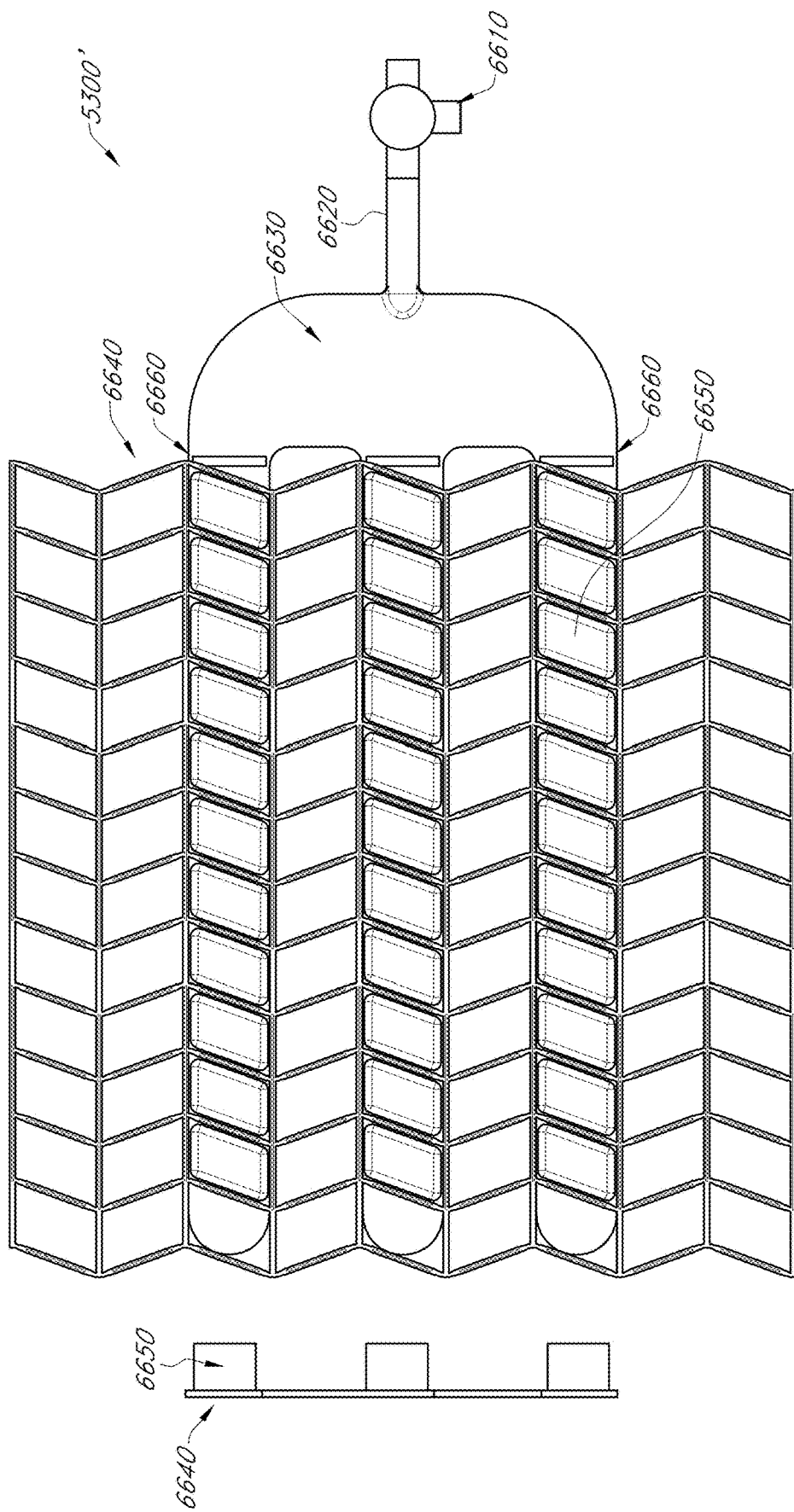
FIG. 34 is a schematic bottom view of the wound closure device of FIG. 18.
Figure 35:
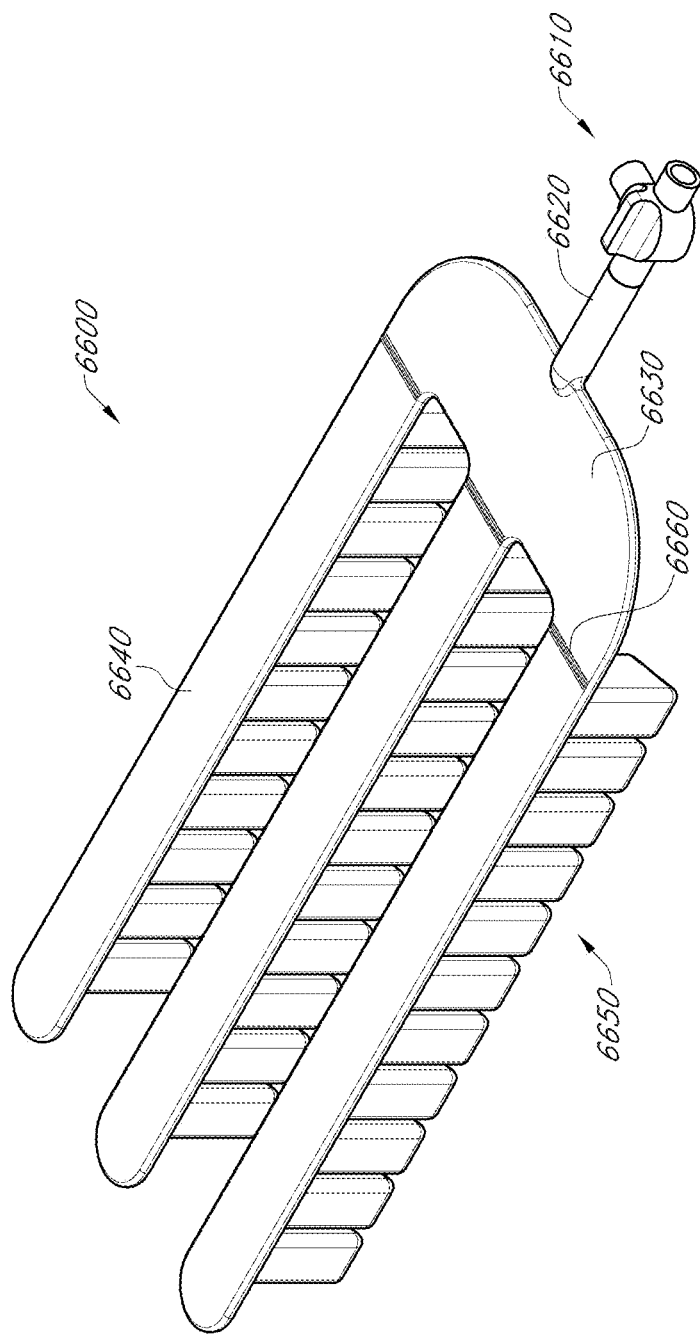
FIG. 35 is a perspective top view of the support structure of FIG. 33 that attaches to the stabilizing structure.
Figure 36:
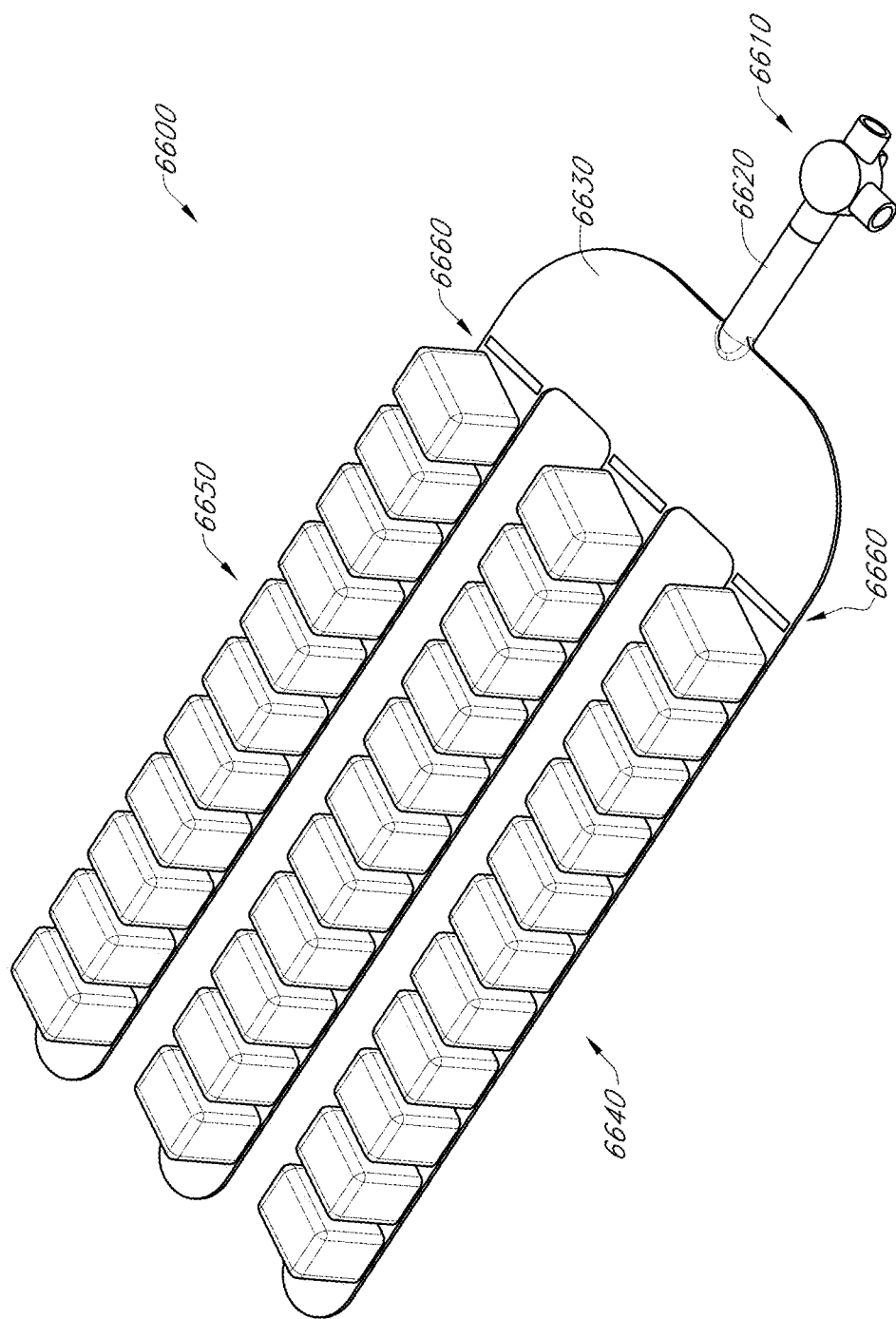
FIG. 36 is a perspective bottom view of the support structure of FIG. 33.
Figure 37:
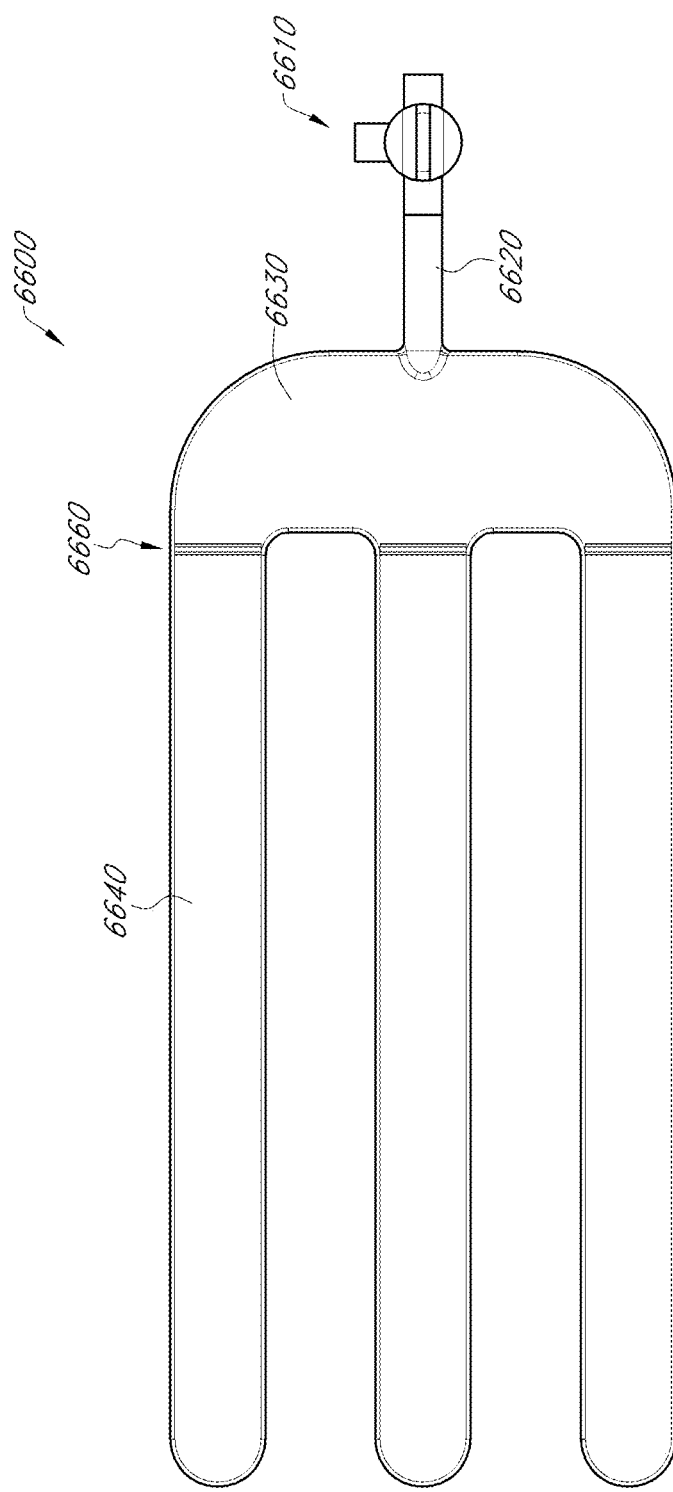
FIG. 37 is a top planar view of the support structure of FIG. 33.
Figure 38:
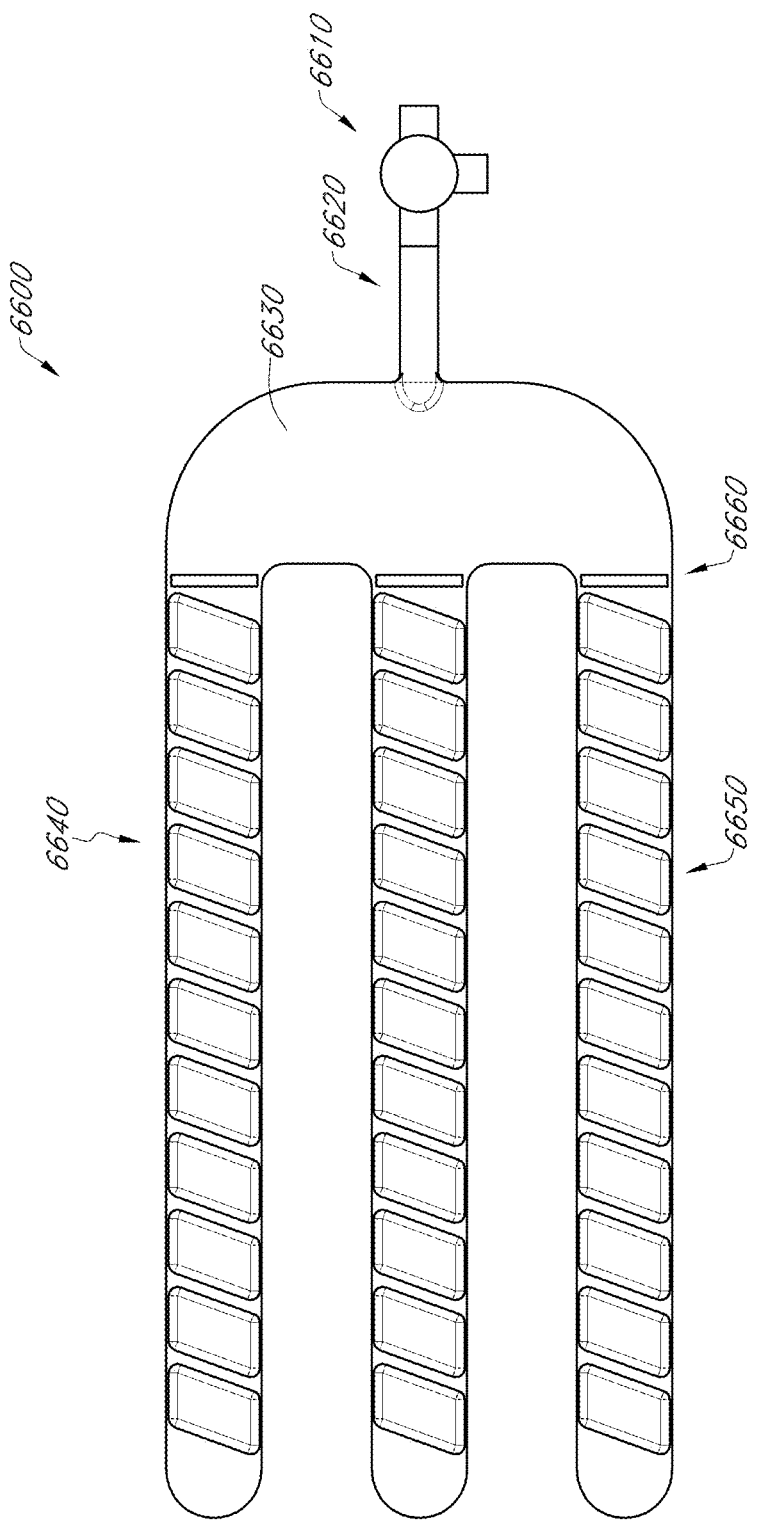
FIG. 38 is a bottom planar view of the support structure of FIG. 33.
Figure 39:
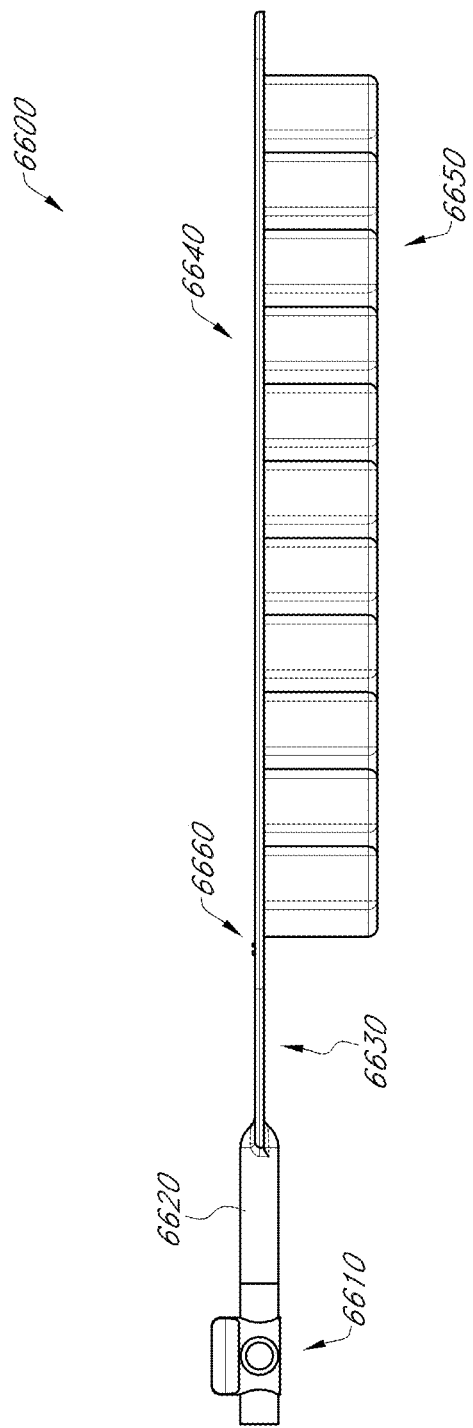
FIG. 39 is a side elevational view of the support structure of FIG. 33.
Figure 40:
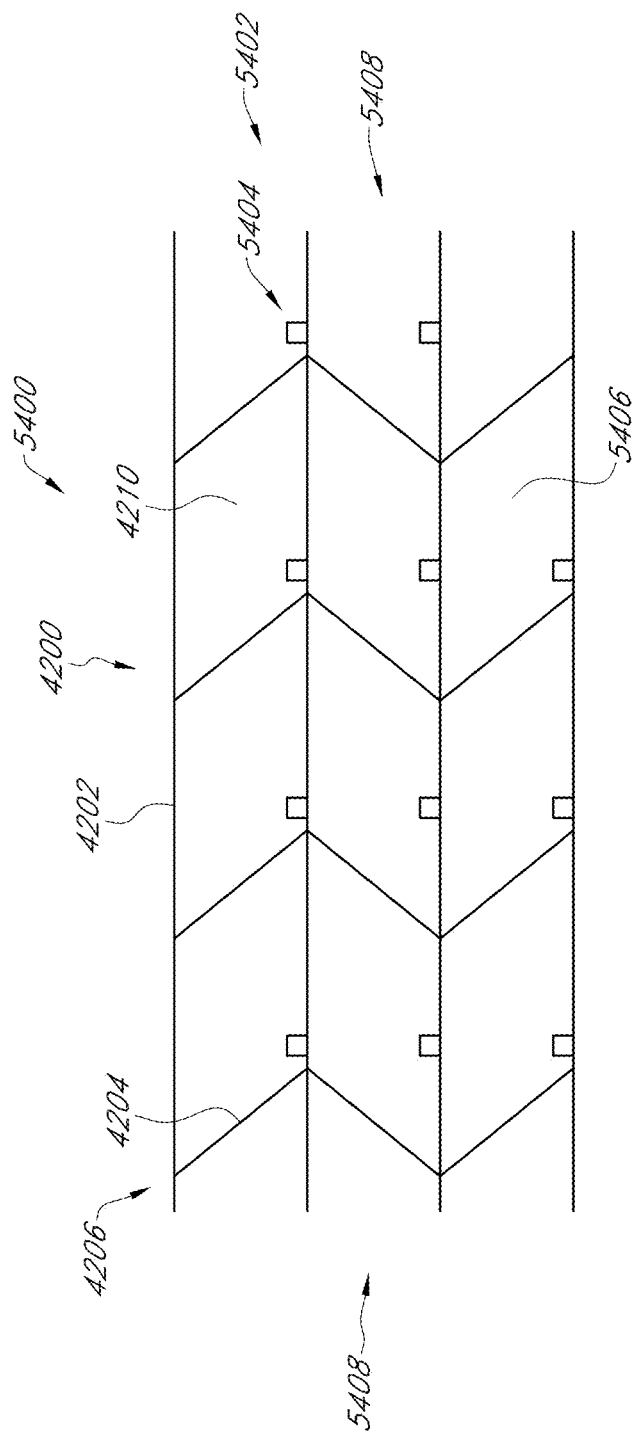
FIG. 40 is a schematic view of one embodiment of a stabilizing structure for a wound closure device with a mechanism for latching the stabilizing structure when in a collapsed configuration.

As discussed above, a plurality of support elements 6501 can be coupled together to form the support structure 6500 by coupling the ends 6530 of the cross-beams 6520 of adjacent support elements 6501 together. With reference to FIGS. 31-32, the ends 6530 of the cross-beams 6520 can in one embodiment have a C-shaped opening 6532 and one or more notches 6534 that couple (e.g. clip) onto a boss portion 6562 of a pin 6560 attached to a cylinder member 6552 of an insert 6550 that extends into a cell 4210 of the stabilizing structure 4200. In one embodiment, the boss portion 6562 can be square shaped and have a length sized to allow two ends 6530 of cross-beams 6520 of adjacent support elements 6501 to couple thereto. However, in other embodiments, the boss portion 6562 can have other suitable shapes (e.g., round). In one embodiment, the pin 6560 and cylinder member 6552 can be one piece (e.g., monolithic). In another embodiment, the pin 6560 can be removably inserted into a corresponding opening in the cylinder member 6552.

The insert 6550 can also include a wall 6554 attached to the cylinder member 6552, where the wall 6554 can contact (e.g., bear against) a surface of an adjacent strip 4202. The support structure 6500 can include a plurality of inserts 6550 attached to the support elements 6501 via the pins 6560 and ends 6530 of the cross-beams 6520, as discussed above.

In one embodiment, the support structure 6000 can be made of a rigid or semi-rigid material. For example, in one embodiment, the support structure 6000 can be of a rigid polymer material. However, other suitable materials (e.g., plastic materials) can be used.

During use, the size stabilizing structure 4200 can be adjusted or varied in the manner described above. The support structure 6000 can then be sized (e.g., by the number of support elements 6501 that are coupled together and/or the beams 6510 removed via the frangible portions 6540) and attached to the stabilizing structure 4200. In one embodiment, the one or more inserts 6550 of the support structure 6000 are inserted into one or more cells 4210 of the stabilizing structure 4200 so that support elements 6501 contact the top end 5302 of the stabilizing structure 4200 (e.g., extend a long a plane parallel to the plane 5308). In another embodiment, the one or more inserts 6550 of the support structure 6500 are inserted into one or more cells 4210 of the stabilizing structure 4200 so that support elements 6501 contact the bottom end 5005 of the stabilizing structure 4200. In one embodiment, the top end 5302 of the stabilizing structure 4200 has a plurality of notches 4220 on an edge of one or more strips 4202 to allow the removal of fluids from the wound site (e.g., when negative pressure is applied). In another embodiment, the plurality of notches 4220 are instead defined on the bottom end 5304 of the stabilizing structure 4200.

In one embodiment, the support structure 6500 can attach to the stabilizing structure 4200 by inserting the one or more inserts 6550 into the cells 4210 of the stabilizing structure 4200 and so that the support elements 6501 are adjacent (e.g., contact) an end of the stabilizing structure 4200. In another embodiment, the support structure 6500 couples onto the stabilizing structure 4200 via one or more clip members (not shown) such that the support structure 6000 locks onto the stabilizing structure 4200.

In one embodiment, the support structure 6500 can be sized to correspond to the size of the stabilizing structure 4200, such that when attached to the stabilizing structure 4200 the support structure 6500 inhibits (e.g., prevents) the collapse of substantially the entire (e.g., all) stabilizing structure 4200 (e.g., when negative pressure is applied to the wound closure device 5300).

In another embodiment, the support structure 6500 can be sized to correspond to a size smaller than the size of the stabilizing structure 4200, such that when attached to the stabilizing structure 4200 the support structure inhibits (e.g., prevents) the collapse of a portion of the stabilizing structure 4200 while another portion of the stabilizing structure 4200 (to which the support structure 6500 is not attached) is allowed to collapse (e.g., when negative pressure is applied to the wound closure device 5300).

FIGS. 33-39 show another embodiment of a wound closure device 5300'. The wound closure device 5300' can have a stabilizing structure 4200, which can be similar in structure as the stabilizing structure 4200 described above in connection with FIGS. 28-32 (e.g., have one or more strips 4202 interconnected by one or more intervening members 4204 via joints 4206 and that define a plurality of cells 4210 side by side in a plane 5008).

The wound closure device 5300' can include a support structure 6600 that is expandable (e.g., by introduction of a fluid, such as air, into the support structure 6600). In one embodiment, the support structure 6600 can include a control valve 6610 in fluid communication with a header member 6630 (e.g., via a conduit or tube 6620). The header member 6630 can be in fluid communication with one or more support elements 6640 (e.g., a plurality of support elements 6640). In one embodiment, the one or more support elements 6640 extend parallel to each other. Each of the support elements 6640 can have one or more inserts 6650 (e.g., a plurality of inserts 6650) that extend from one side of the support element 6640 and are expandable (e.g., via fluid delivered via the header member 6630 and support elements 6640 into the inserts 6650. The inserts 6650 can be sized to fit within the cells 4210 of the stabilizing structure 4200, such that the inserts 6650 can extend into the cells 4210 and can contact one or more surfaces of the cell 4210 (e.g., walls defined by the strips 4202 and intervening members 4204).

In the illustrated embodiment, the support structure 6600 has three support elements 6640. However, in other embodiments, the support structure 6600 can have more or fewer support elements 6640.

With continued reference to FIGS. 33-39, the support structure 6600 can have one or more seals 6660 to seal off at least a portion of the one or more support elements 6640. In one embodiment, the one or more seals 6660 can be disposed between the header member 6630 and the one or more support elements 6640. However, in other embodiments, the one or more seals 6660 an additionally, or alliteratively, be disposed between adjacent inserts 6650 of a support element 6640. In one embodiment, the seals 6660 can be plastic zipper type seals or sliderless plastic zipper type seals. The seals 6660 advantageously allow the size of the support structure 6600 to be adjusted while allowing the remaining portion of the support structure 6600 (e.g., the remaining inserts 6650) to be expanded via the introduction of a fluid (e.g., air) therein. To adjust the size of the support structure 6600, a user can actuate the seal 6660 adjacent the location of the support structure 6600 to be removed to seal (e.g., close) fluid flow at said location. The desired portion of the support structure 6600 downstream of said seal 6660 can then be removed (e.g., cut, torn) and the remaining inserts 6650 of the support structure 6600 expanded via the introduction of said fluid. The closing of said seal 6660 will inhibit (e.g., prevent) loss of fluid therethrough.

In one embodiment, the support structure 6600 can be sized to correspond to the size of the stabilizing structure 4200 (e.g., by choosing a support structure 6600 with a number of support elements 6640 and inserts 6650 corresponding to the number of rows of cells 4210 and number of cells 4210 in the stabilizing structure 4200). When the support structure 6600 is attached to the stabilizing structure 4200 such that the inserts 6650 extend into the cells 4210, the support structure 6600 inhibits (e.g., prevents) the collapse of substantially the entire (e.g., all) stabilizing structure 4200 (e.g., when negative pressure is applied to the wound closure device 5300'.

In another embodiment, the support structure 6600 can be sized to correspond to a size smaller than the size of the stabilizing structure 4200, such that when attached to the stabilizing structure 4200 the support structure 6500 inhibits (e.g., prevents) the collapse of a portion of the stabilizing structure 4200 while another portion of the stabilizing structure 4200 (to which the support structure 6500 is not attached) is allowed to collapse (e.g., when negative pressure is applied to the wound closure device 5300').

Mechanism for Maintaining Closure of Wound Closure Device (FIGS. 40-46)

FIGS. 40-46 show one embodiment of a wound closure device 5400. The wound closure device 5400 can have a stabilizing structure 4200 and have one or more strips 4202 interconnected by one or more intervening members 4204 joined to the one or more strips 4202 via joints 4206. As discussed above, the strips 4202 and intervening members 4204 define a plurality of cells 4210 side by side in a plane 5408 (e.g., defined by page in FIG. 40), each of the cells 4210 defined between two adjacent strips 4202 and two adjacent intervening members 4204 and having an opening 5406 that extends from a top end to a bottom end of the stabilizing structure 4200 in a direction perpendicular to the plane 5408. As described above, the stabilizing structure 4200 can collapse along the plane such that the one or more strips 4202 move toward each other (e.g., adjacent each other) as the intervening members 4204 pivot relative to the strips 4202 (e.g., as the cells 4210 collapse).

With continued reference to FIGS. 40-44, the wound closure device 5400 can also include a mechanism 5402 that can latch, lock or otherwise hold portions of the stabilizing structure when in a collapsed configuration to thereby maintain the stabilizing structure 4200 in the collapsed configuration, for example, after negative pressure to the wound closure device 5400 is ceased. In one embodiment, the mechanism 5402 can include one or more latching members 5404 attached to at least one of the one or more strips 4202. In the illustrated embodiment, a plurality of latching members 5404 are attached to one or more strips 4202 of the stabilizing structure 4200 such that a portion of the latching member 5204 extends into the opening 5406 of each cell 4210.

Figure 41:
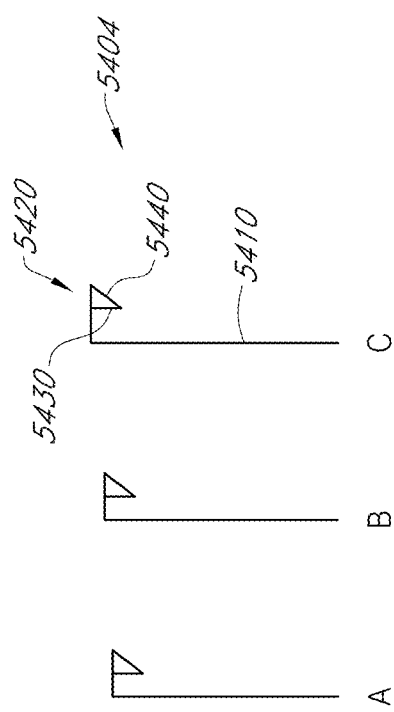
FIG. 41 is schematic view of one embodiment of a latching mechanism.

FIG. 41 shows one embodiment of a latching member 5404. The latching member 5404 can have an elongate member 5410, where one surface of the elongate member 5410 can attach to a surface of the one or more strips 4202 (e.g., via an adhesive). The latching member 5404 can also include a latching element 5420 that can optionally be spaced apart from the elongate member 5410 and can extend at an angle relative to the elongate member 5410. In one embodiment, the latching element 5420 can extend substantially perpendicular (e.g., at 90 degrees) to the elongate member 5410. However, in other embodiments, the latching element 5420 can extend at other suitable angles relative to the elongate member 5410, such as at an angle of less than 90 degrees, or an angle of more than 90 degrees.

The latching element 5404 can have an inner surface 5430 and an outer surface 5440. In one embodiment, as shown in FIG. 41A, the inner surface 5430 can be curved and the outer surface 5440 can be substantially planar. In the illustrated embodiment, the curved inner surface 5430 can be concave facing the elongate member 5410. However, in other embodiments, the inner surface 5430 can be convex facing the elongate member 5410. In another embodiment, as shown in FIG. 41B, the inner and outer surfaces 5430, 5440 can be generally planar, where the inner surface is angled away from the elongate member 5410 and the outer surface is angled toward the elongate member 5410. In still another embodiment, as shown in FIG. 41C, the inner and outer surfaces 5430, 5440 can be curved. In the illustrated embodiment, both the inner and outer surfaces 5430, 5440 can be concave. However, in other embodiments, one or both of the inner and outer surfaces 5430, 5440 can be convex.

Figure 42:
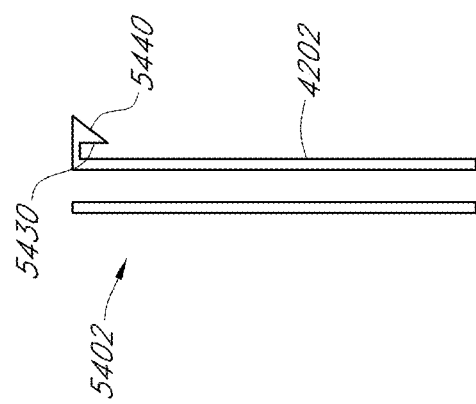
FIG. 42 is a schematic view of the latching mechanism of FIG. 41 coupled to a portion of the stabilizing structure when the stabilizing structure is in a collapsed configuration.

FIG. 42 shows one embodiment of the latching member 5404 coupled to a wall of the stabilizing structure 4200, for example, when the stabilizing structure 4200 is in the collapsed configuration. The latching member 5404 can be attached to the one or more strips 4202 so that the latching element 5420 is proximate a top end of the strip 4202. As the stabilizing structure 4200 moves to the collapsed configuration (e.g., via application of negative pressure to the wound closure device 5400, the outer surface 5440 of the latching element 5420 comes in contact with a top edge of the adjacent strip 4202. As the stabilizing structure 4200 continues to collapse, the top edge of the strip 4202 moves past the outer surface 5440 and the apex of the latching element 5420 and moves into the space between the inner surface 5430 and the elongate member 5410. The inner surface 5430 can contact the top edge of the strip 4202 and inhibit the strip 4202 from moving past the inner surface 5430 and apex of the latching element 5420, thereby acting to maintain the stabilizing structure 4200 in a collapsed configuration, even after application of negative pressure to the wound closure device 5000 has ceased.

As discussed above, the inner and outer surfaces 5430, 5440 of the latching element 5420 can have various configurations, at least one of which can make it easier (e.g., require less force) for the latching element 5420 to latch onto the strip 4202, make it more difficult (e.g., require a greater force) for the strip 4200 to unlatch from the latching element 5420, or both.

In one embodiment, as described above, the latching member 5404 can be attached to the one or more strips 4202 of the stabilizing structure 4200. In another embodiment, the one or more latching members 5404 and at least a portion (e.g., a supporting segment 4214) of a corresponding strip 4202 can be a single piece (e.g., molded as one piece or monolithic).

Figure 43:
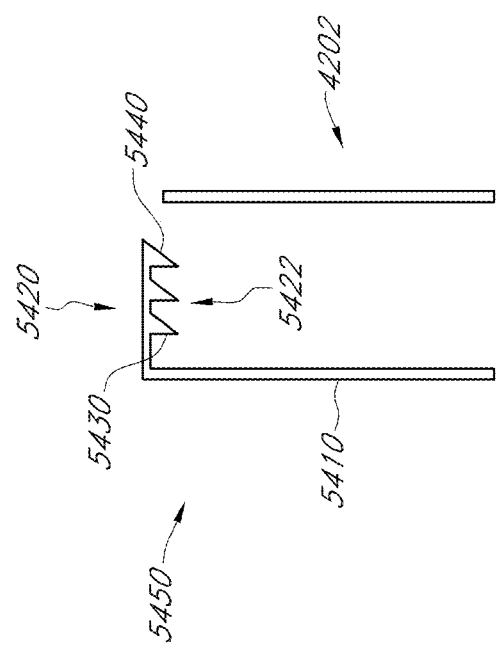
FIG. 43 is a schematic view of another embodiment of a latching member of a latching mechanism.

FIG. 43 shows another embodiment of a latching member 5450 of a mechanism 5402. The latching member 5450 that can latch, lock or otherwise hold portions of the stabilizing structure when in a collapsed position to thereby maintain the stabilizing structure 4200 in said collapsed position, for example, after negative pressure to the wound closure device 5000 is ceased. The latching member 5450 is similar to the latching member 5404, except as described below.

The latching member 5450 can have an elongate member 5410 and a latching element 5420. In the illustrated embodiment, the latching element 5420 has more than one tooth 5422 (e.g., a plurality of teeth 5422), each of the teeth having an inner surface 5430 and an outer surface 5440, as described above in connection with the latching member 5450. The multiple teeth 5422 advantageously allow the mechanism 5402 to latch, secure or otherwise hold the stabilizing structure 4200 in more than one compressed state. For example, the latching member 5450 can hold the stabilizing structure 4200 in a first compressed state (e.g., 60% compressed) when the strip 4202 latches to a first tooth 5422A, can hold the stabilizing structure 4200 in a second compressed state (e.g., 40% compressed) when the strip 4202 latches to a second tooth 5422B, and can hold the stabilizing structure 4200 in a third compressed state (e.g., 20% compressed) when the strip 4202 latches to a third tooth 5422C. Accordingly, where the stabilizing structure 4200 is unable to completely collapse upon the application of negative pressure, or where different portions of the stabilizing structure 4200 collapse to different positions, the latching members 5450 of the mechanism 5402 can latch, secure or otherwise hold the stabilizing structure 4200 or portions of the stabilizing structure 4200 in their compressed positions, for example once negative pressure has been removed.

Figure 44:
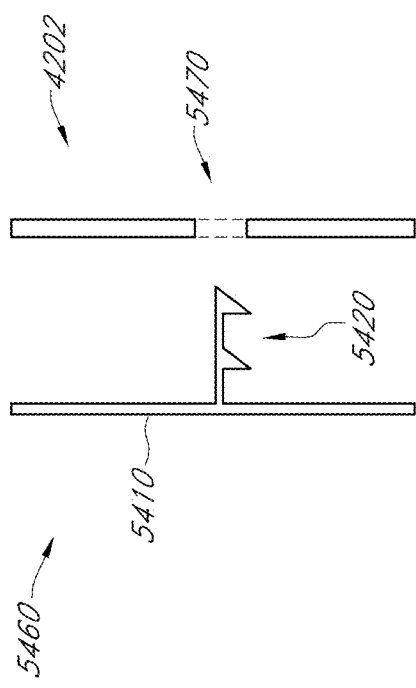
FIG. 44 is a schematic view of another embodiment of a latching member of a latching mechanism.

FIG. 44 shows another embodiment of a latching member 5460 of a mechanism 5402. The latching member 5460 that can latch, lock or otherwise hold portions of the stabilizing structure when in a collapsed position to thereby maintain the stabilizing structure 4200 in said collapsed position, for example, after negative pressure to the wound closure device 5400 is ceased. The latching member 5460 is similar to the latching member 5450, except as described below.

The latching member 5460 can have an elongate member 5410 and a latching element 5420. In the illustrated embodiment, the latching element 5420 has more than one tooth 5422 (e.g., a plurality of teeth 5422), each of the teeth having an inner surface 5430 and an outer surface 5440, as described above in connection with the latching member 5450 and allowing the mechanism 5402 to latch, secure or otherwise hold the stabilizing structure 4200 in more than one compressed state, as discussed above. In the illustrated embodiment, the latching element 5420 is disposed at an intermediate position between a bottom end and a top end of the latching member 5460. The latching element 5420 can extend through an opening 5470 in a portion of the stabilizing structure 4200, such as a strip 4202, so that stress provided by the coupling of the latching element 5420 and the strip 4202 can be centralized in the stabilizing structure 4200 such that coupling the latching members 5460 to the corresponding portions (e.g., strips 4202) of the stabilizing structure 4200 does not cause a curvature (e.g., deformation away from the plane) of the stabilizing structure 4200.

In another embodiment, the latching elements can be disposed along the face of the elongate member 5410 and can be hook members that couple to loop members on the corresponding surface (e.g., strip 4202) of the stabilizing structure 4200, such that the mechanism 5402 includes a hook-and-loop latching mechanism.

Figure 45:
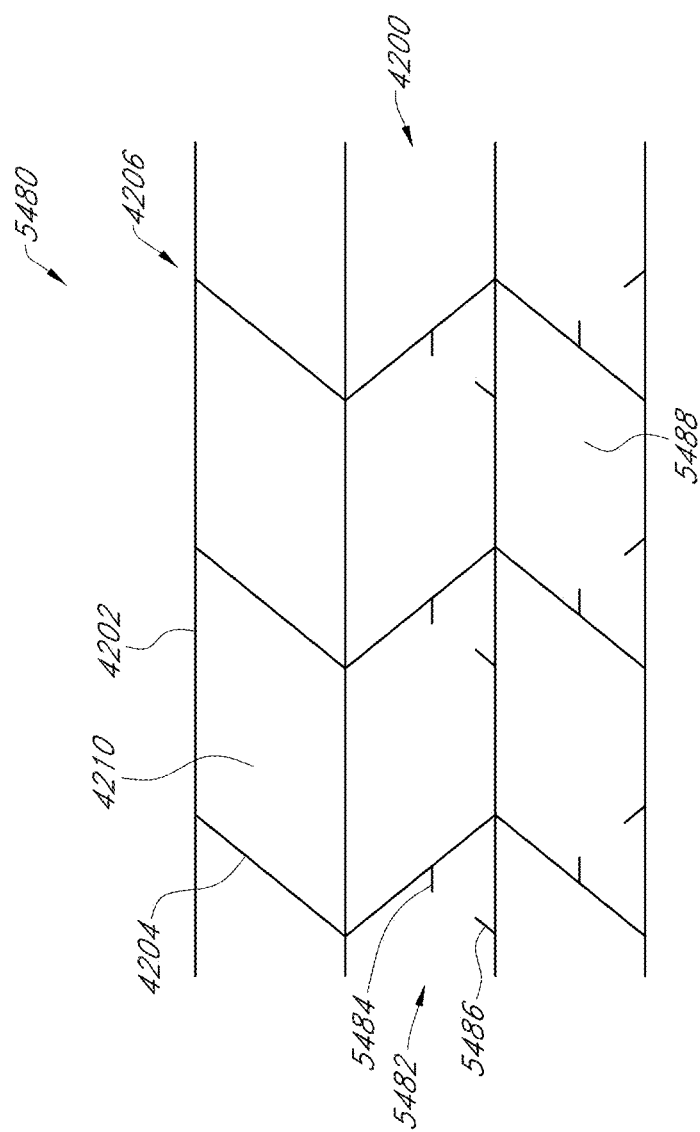
FIG. 45 is a schematic view of another embodiment of a stabilizing structure for a wound closure device with a mechanism for latching the stabilizing structure when in a collapsed configuration.

FIG. 45 shows another embodiment of a wound closure device 5480. The wound closure device 5480 can have a stabilizing structure 4200 and have one or more strips 4202 interconnected by one or more intervening members 4204 joined to the one or more strips 4202 via joints 4206. As discussed above, the strips 4202 and intervening members 4204 define a plurality of cells 4210 side by side in a plane (defined by the page in FIG. 43), each of the cells 4210 defined between two adjacent strips 4202 and two adjacent intervening members 4204 and having an opening 5488 that extends from a top end to a bottom end of the stabilizing structure 4200 in a direction perpendicular to the plane. As described above, the stabilizing structure 4200 can collapse along the plane such that the one or more strips 4202 move toward each other (e.g., adjacent each other) as the intervening members 4204 pivot relative to the strips 4202 (e.g., as the cells 4210 collapse).

With continued reference to FIG. 45, the wound closure device 5480 can also include a mechanism 5482 that can latch, lock or otherwise hold portions of the stabilizing structure when in a collapsed configuration to thereby maintain the stabilizing structure 4200 in the collapsed configuration, for example, after negative pressure to the wound closure device 5480 is ceased. In one embodiment, the mechanism 5482 can include one or more first latching members 5484 attached to at least one of the one or more intervening members 4204 and one or more second latching members 5486 attached to at least one of the one or more strips 4202. In the illustrated embodiment, a plurality of first latching members 5484 are attached to a plurality of intervening members 4204, and a plurality of second latching members 5486 are attached to a plurality of strips 4202 such that a first latching member 5484 and a second latching member 5486 extend into the opening 5488 of the cell 4210. In one embodiment, the first latching member 5484 extends at a non-perpendicular angle (e.g., an acute angle) relative to its corresponding intervening member 4204, and the second latching member 5486 extends at a non-perpendicular angle (e.g., an acute angle) relative to its corresponding strip 4202. In one embodiment, the angle of the first and second latching members 5484, 5486 relative to their corresponding intervening member 4204 and strip 4202 is the same.

As the stabilizing structure 4200 moves to the collapsed configuration (e.g., via application of negative pressure to the wound closure device 5480), the intervening member 4204 folds toward the strip 4202 so that the first latching member 5484 comes in contact with the second latching member 5486. In one embodiment, the first latching member 5484 slidably contacts the second latching member 5486 as the intervening member 4204 folds onto the corresponding strip 4202. In one embodiment, the first and second latching members 5484, 5486 maintain the intervening member 4204 and strip 4202 (and therefore the stabilizing structure 4200) in the collapsed configuration via at least the friction force between the first and second latching members 5484, 5486. In another embodiment, the latching members 5484, 5486 can have latching elements, such as the latching elements 5420 described above. For example, one or both of the first and second latching members 5484, 5486 can have a curved surface (e.g., convex surface) that slides past a corresponding latching surface (e.g., convex surface) on the other of the first and second latching members 5484, 5486.

In one embodiment, the first and second latching members 5402, 5482 can be attached (e.g., adhered) to their corresponding intervening member 4204 and strip 4202. In another embodiment, the first latching member 5484 and intervening member 4204 can be a single piece (e.g., molded together, monolithic), and the second latching member 5486 and the corresponding strip 4202 can be a single piece (e.g., molded together, monolithic).

In one embodiment, the mechanism 5482 can have a reset or release mechanism that can be actuated to unlatch the one or more latching members 5404, 5450, 5460, 5484, 5486 from corresponding portions (e.g., strips 4202) of the stabilizing structure 4200. For example, if the mechanism 5482 inadvertently or accidentally latches at least portions of the stabilizing structure 4200 as the stabilizing structure 4200 is first placed over or within the wound site. In another embodiment, if the surgeon wants to move at least a portion of the stabilizing structure 4200 from a collapsed configuration, for example after negative pressure has been removed, the surgeon can actuate the rest or release mechanism to allow said at least a portion of the stabilizing structure 4200 to be moved to an expanded configuration. An operator (e.g., surgeon) can actuate the reset of release mechanism (e.g., via an actuator, such as a lever) to unlatch the one or more latching members 5404, 5450, 5460, 5484, 5486 from the corresponding strips 4202. For example, the reset or release mechanism can move the latching element 5420 of the engaged latching member 5450, 5460 away (e.g., axially away) from the strip 4202 so that the strip 4202 can move past the latching element 5420 allowing the stabilizing structure to be expanded from a collapsed configuration. In one embodiment, each latching member 5404, 5450, 5460, 5484, 5486 can have a separate reset or release mechanism. In another embodiment, the reset or release mechanism can be actuated to unlatch a plurality of latching members 5404, 5450, 5460, 5484, 5486 at the same time.

Figure 46:
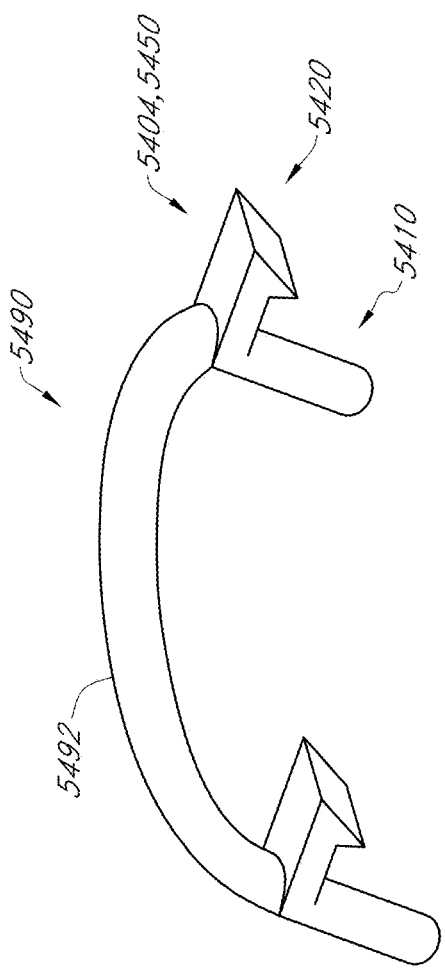
FIG. 46 is a schematic view of one embodiment of a reset or release mechanism for one or more latching members of a mechanism for latching the stabilizing structure when in a collapsed position.

FIG. 46 shows one embodiment of a reset or release mechanism 5490 that can be used, for example, with the one or more latching members 5450, 5450. In the illustrated embodiment, the reset or release mechanism 5490 can include an arch portion 5492 that can interconnect two latching members 5404, 5450. An operator (e.g., surgeon) can actuate the reset or release mechanism 5490 to unlatch the one or more latching members 5404, 5450 from portions (e.g., strips 4202) of the stabilizing structure 4200 by applying an upward force on the arch portion 5492 (e.g., via a surgical instrument inserted underneath the arch portion 5492, such as forceps or other surgical instruments in the operating room, or via the operator's fingers), thereby lifting the latching element 5420 of the interconnected latching members 5404, 5450 from engagement with the portion (e.g., strips 4202) of the stabilizing structure 4200.

In one embodiment, two latching members 5404, 5450 can be interconnected by the arch portion 5492. In another embodiment, more than two latching members 5404, 5450 can be interconnected by arch portions 5492 disposed between adjacent latching members 5404, 5450. For example, where the reset and release mechanism 5490 is to be operated by using the operator's fingers, three or four arch portions 5492 could interconnect adjacent latching members 5402, 5450, to allow facilitate lifting of the arch portions 5492 as described above. In one embodiment, the arch portion 5492 can be proud of (e.g., can protrude from) the end (e.g., top end) of the stabilizing structure 4200 by an amount sufficient to allow an operator to insert either a surgical instrument or the operator's finger(s) under the arch portion 5492 to lift the latching members 5404, 5450 from engagement with the portion (e.g., strips 4202) of the stabilizing structure 4200, as discussed above. In one embodiment, the profile of the arch portion 5492 can be as low as possible while allowing an operator to insert at least a portion of a surgical instrument, or the user's finger(s), under the arch portion 5492 so as not to impede the dynamic contraction or collapse of the stabilizing structure 4200 (e.g., via drag exerted by the arch portions 5492 on a foam portion disposed above the stabilizing structure 4200). Though the reset or release mechanism 6201 is described above in connection with the latching members 5404, 5450, one of skill in the art will recognize that the reset or release mechanism 5490 described above could also be used with the latching members 5404, 5450.

The latching members described above can be made of a resilient material, such as a plastic or polymer material. However, other suitable materials can be used.

Stabilizing Structures and Wound Closure Devices of FIGS. 47-51

In certain embodiments, it may be advantageous to minimize the number of steps needed for a clinician to position a stabilizing structure as described above and other components into a wound. For example, it may be desirable to eliminate one or more steps relating to placement of the porous layers 5102, 5116, the porous layer 5106 and/or the anchoring layer 5108, as depicted above in FIGS. 10A-10C.

In some embodiments, while the porous layers 5102, 5116 and/or 5106 of FIGS. 10A-10C may be useful for transmitting fluid between upper and lower surfaces of the stabilizing structure, in another embodiment with or without one or more of such layers, the stabilizing structure itself may include a system of pores, channels or grooves running from the lower surface to the upper surface, e.g., along some or all of the vertical walls within some or all of the cells to allow liquids to bridge the stabilizing structure using capillary action. For example, channels or grooves may be moulded, etched or deposited onto surfaces of the stabilizing structure. For example, channels could be made by deposition as described in PCT Publication No. WO 2008/150542 A1, the entirety of which is hereby incorporated by reference. For example, referring now to FIGS. 2A-2I above, the material 4216 may be molded so as to contain vertical tubes running from the lower to the upper surface of the stabilizing structure either within the elongate strips 4202 or within the intervening members 4204, allowing fluid transfer. For example the system of pores, channels or grooves could be present on the individual supporting segments so as to allow liquid to travel from the lower surface to the upper surface if the soft polymer is selectively molded over only parts of the stabilizing structure thus leaving these pores, channels or grooves exposed.

Essentially, using such an approach will provide a route with a working capillary cross-section. Providing such pathways either along the surfaces of the stabilizing structure or within it will mean that even after cutting of the stabilizing structure to a desired size, these pathways will still exist in the as-sized structure. In one embodiment, the one or more pathways provided by the pores, channels or grooves of the stabilizing structure can be hydrophilic to facilitate capillary action by liquid (e.g., from the wound side), thereby allowing said liquid to bridge the stabilizing structure, as discussed above. For example, said soft polymer discussed above can be a soft hydrophilic polymer (e.g., acrylic polymer with hydrophilic groups, such as ethyl hydroxyl), hydrophilic silicone, etc. However, other suitable hydrophilic materials known in the art can be used. Such hydrophilic materials are described, for example, in Mechanical Properties of a Hydrophilic Acrylic Polymer, W. J. O'Brien, J. Hermann, & T. H. Shepherd, J. Biomed. Mater. Res. Vol. 6, PP. 15-24 (1972). In other embodiments, a hydrophilic coating (e.g., hydrophilic silicone) can be applied to one or more surfaces of the stabilizing structure. Any suitable hydrophilic coating know in the art can be used.

Other examples of such soft polymers include copolymeric polymers such as hybrids derived from two or more monomeric species, including alternating, periodic, statistical, random, block, linear, branched, star, graft and pendant copolymers. Entangled systems include interpenetrating networks (IPNs) and semi-interpenetrating networks (SIPNs). These polymers can incorporate both organic and inorganic moieties. Examples of hybrid organic-inorganic polymeric systems that have used both siloxane and organic units include: acrylate functionalized siloxane copolymers; hybrid grafts where organic polymers are grafted onto a polysiloxane chain or where siloxanes are grafted onto organic polymers, for example in silane graft technology for cross linkable high density polyethylene (HDPE) where hybrid grafts have been used to allow the cross linking of organic polymers through siloxane bond formation; hybrid block copolymers, for example silicone-polycarbonate block copolymers; and copolymers of hybrids of silicone and ethylene copolymers, cross-linked with vinyl-containing silicone copolymers.

IPNs represent a class of hybrid polymeric systems that use a combination of mechanical entanglement and cross-linking in which one polymer is cured about another. These include thermoplastics entangled with platinum catalyzed addition cure silicones, such as silicone-urethane IPNs and semi-IPNs including silicone-urethane and silicone-polyamide systems; hydrophilic components immobilized in a silicone polymer; and silicone polymer cured about a nonreactive polymer of comparable adhesion.

In another embodiment the soft polymer described above, molded over part or all of the stabilizing structure 4200 of FIGS. 2A-2I may be selected so as to retain the required material properties with regards to the required feel and function of the device but also to function as the porous material.

Examples of suitable elastomers may be found in U.S. Publication No. 2010/0075056, the entirety of which is hereby incorporated by reference. For example, porous polymers synthesized within high internal phase emulsions (HIPE), sometimes referred to as "polyHIPE" within the scientific literature, can be used. In another example, highly porous elastomer-silsesquioxane nanocomposites synthesized within high internal phase emulsions or polydimethylsiloxane (PDMS) elastomerformed with three-dimensional (3D) micro-channels, can be used.

In another embodiment the porous materials such as the foam described above, wicking layers, acquisition distribution layers (ADLs), elastomers or other materials may be provided on internal surfaces and or on the external surfaces of the stabilizing structure. Wicking or acquisition distribution layers (ADLs) are able to wick fluid such as wound exudate and would serve to transport liquid from the lower face to the upper face of the stabilizing structure. Some embodiments of the ADL may comprise viscose, polyester, polypropylene, cellulose, or a combination of some or all of these, and the material may be needle-punched. Some embodiments of the ADL may comprise polyethylene in the range of 40-150 grams per square meter (gsm). Examples of ADLs may include: Dry Web TDL2 from Libeltex BVBA with a basis weight of 55 gsm, SlimCore TL4 from Libeltex BVBA with a basis weight of 150 gsm & 90 gsm, Dry Web T28F from Libeltex BVBA with a basis weight of 50 gsm & MH080.121 from Glatfelter with a basis weight of 80 gsm.

Advantages of these approaches is that they may overcome the requirement to use foam or other porous material on the outer perimeter of the stabilizing structure, especially foam or porous material applied after sizing of the stabilizing structure, to allow fluid transfer and would also allow for transfer across all (or selected) vertical members or walls within the stabilizing structure.

In any of these embodiments, anchors or an anchor layer may further be provided on internal (as well as external) surfaces of the stabilizing structure, alone or in combination with the embodiments described above. For example, anchors may be provided inside cells of the stabilizing structure on elongate strips extending lengthwise across the stabilizing structure. Thus, when the stabilizing structure is cut the resulting structure would have anchors on the two lengthwise surfaces on the resulting outer perimeter.

In another embodiment, anchors may be incorporated into the individual supporting segments 4214 described above in relation to FIG. 2A-2I which comprise part of the longitudinal strips 4202. In such embodiments, the base of the anchors may serve as the individual supporting segments 4214, the base optionally encapsulated or partly encapsulated within a flexible polymer.

Figure 47:
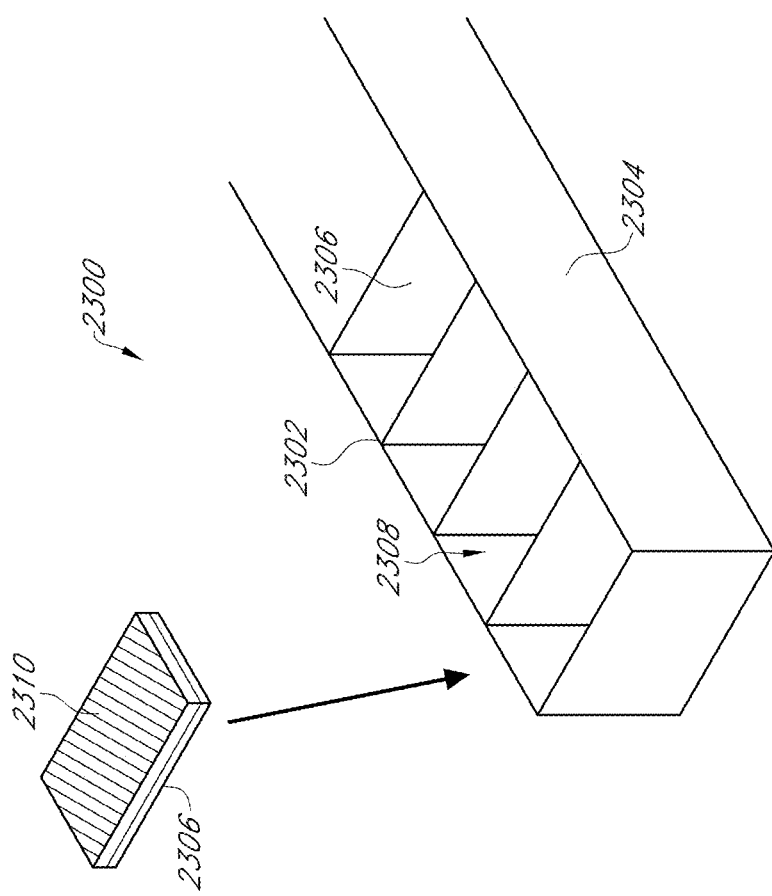
FIG. 47 illustrates a portion of a stabilizing structure with a foam layer configured to be attached to one or more walls within a cell of the stabilizing structure.
Figure 48:
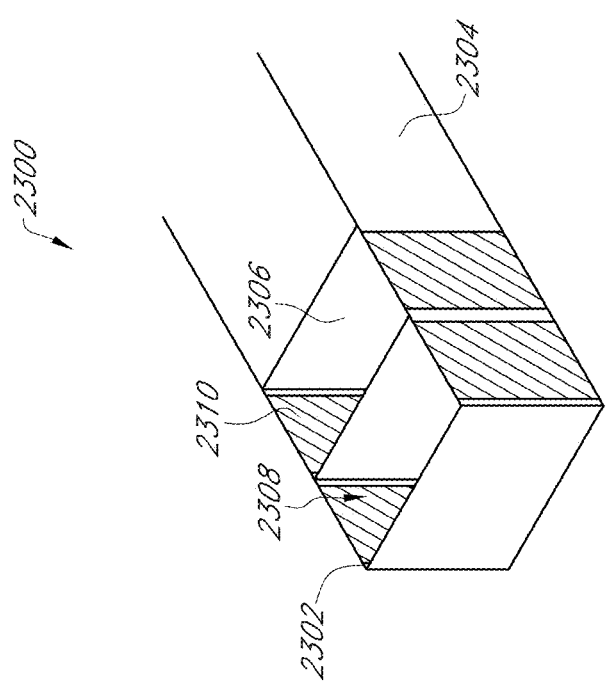
FIG. 48 illustrates a portion of a stabilizing structure with a foam layer attached to internal walls of cells of a stabilizing structure.

FIG. 47 illustrates one embodiment wherein a section of a stabilizing structure (which may be any of the stabilizing structures described herein) comprises at least two elongate strips 2302 and 2304 separated by intervening members 2306 to define a plurality of cells 2308. One, two, three or all of the vertical walls of the cells 2308 defined by the strips and intervening members may be covered by a porous material such as foam, an elastomer, or other material or structure described above to provide for fluid transfer. Preferably, even though internal walls or covered, the cells are still open between the upper surface and lower surface of the stabilizing structure in order to facilitate to collapse of the structure. As illustrated in FIG. 48, a layer of porous material 2310 such as foam can be applied to internal surfaces of the stabilizing structure using an adhesive layer 2306. The porous layer 2310 may further have anchors or an anchoring layer attached to all or portion thereof, or not at all.

As illustrated in FIG. 48, the porous layer 2310 may be applied to internal surfaces of adjacent cells. FIG. 48 also illustrates that the porous layer 2310 may be applied to an external surface of strip 2304, if strip 2304 defines an outer perimeter of the structure. In some embodiments where the cells have four internal walls, two defined by strips 2302 and 2304 and two defined by adjacent intervening members 2306, one embodiment provides for one of the four internal walls to be covered with the porous layer 2310. In other embodiments, the porous layer may have an "n" shape covering three of four walls, for example an intervening member wall and the two adjacent walls formed by the strips 2302 and 2304. Other variations are also possible. Accordingly, even if the stabilizing structure 2300 is cut to an appropriate size, the structure advantageously will have a resulting outer perimeter that includes at least a portion thereof covered by a porous material.

Figure 49A:
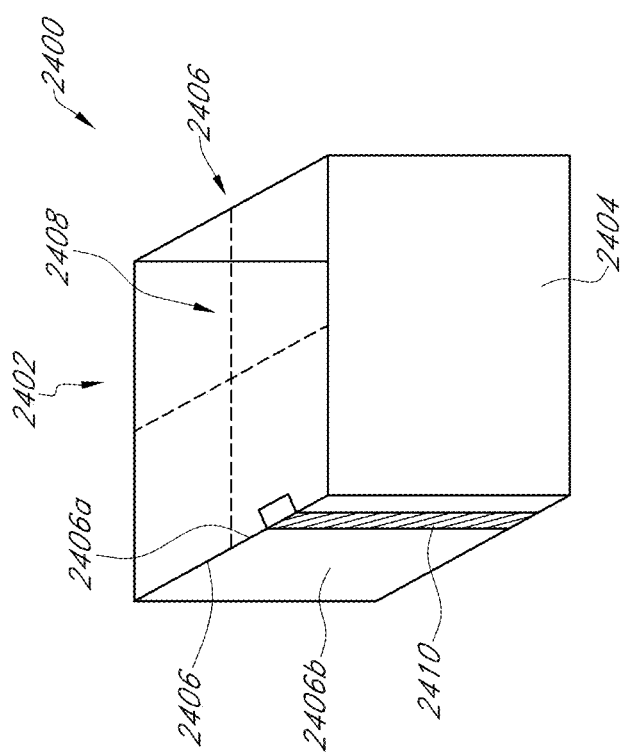
FIG. 49A illustrates a cell of a stabilizing structure with a porous layer, channels or grooves disposed on a portion of one or more walls of the cell, with the cell in a first orientation.
Figure 49B:
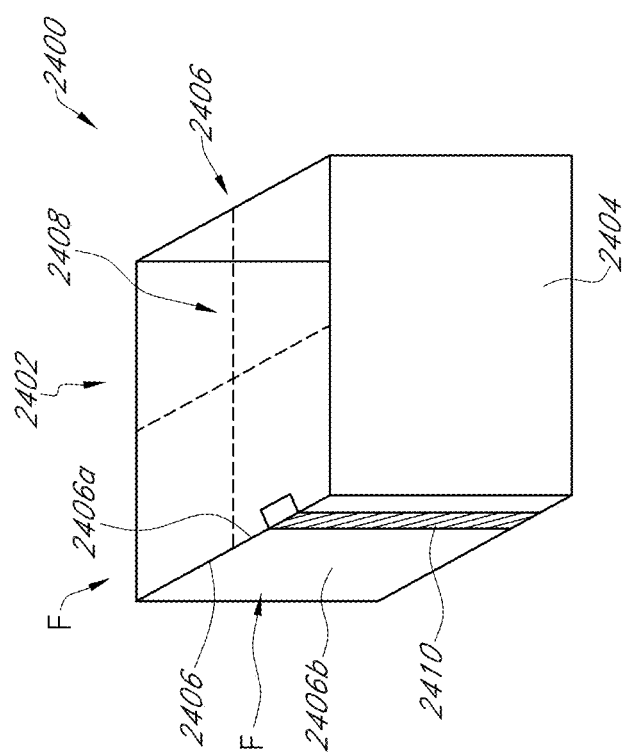
FIG. 49B illustrated the cell of FIG. 15A moving toward a collapsed position.

FIGS. 49A-49B illustrate one cell 2408 of a stabilizing structure 2400, which can be similar to the stabilizing structure 2300 and can have a plurality of cells 2408 arranged in rows as described above, the cell 2408 having wall portions that define portions of two elongate strips 2406, and intervening members 2402, 2404 that interconnect the elongate strips 2406. A strip 2406 can have a medial surface 2406a and a lateral surface 2406b. Medial or medially-facing as used herein refers to a direction toward a center of the stabilizing structure, and lateral or laterally-facing (sometimes also referred to herein as distal or distally-facing) as used herein refers to a direction outward from a center of the stabilizing structure.

In one embodiment, a porous layer 2410, which can be similar to the porous layer 2310 described above, can be disposed on at least a portion of the medial surface 2406a. Accordingly, when the size of the stabilizing structure 2400 is adjusted (e.g., by cutting one or more strips) to better fit over or within the wound site, the lateral surface (e.g., distal surface) 2406b of the one or more cells 2408 of the stabilizing structure 2400 can have a substantially flat or planar (and in some embodiments smooth) surface.

In one embodiment, the porous layer 2410 can be disposed over less than the entire (e.g., less than 90%, less than 80%, less than 70%, less than 50%, less than 30%, less than 20%, less than 10%) width of the medial surface 2406a, and can extend from a bottom end to a top end of the medial surface 2406a. In one embodiment, the porous layer 21410 can be disposed on a portion of said medial surface 2406a that defines one quadrant (or less than one quadrant) of the cell 2408.

With continued reference to FIG. 49A, the porous layer 2410 can be disposed on the medial surface 2406a so as to not restrict movement of the one or more walls of the cell 2408 as the cell 2408 collapses when the stabilizing structure 2400 moves toward a collapsed position, such as during the application of negative pressure thereto. For example, the porous layer 2410 can be disposed on a portion of the medial surface 2406a that defines an obtuse angle (e.g., between strip 2406 and intermediate member 2404) as the cell 2408 collapses, thereby avoiding restricting the collapsing movement of the cell 2408. It will be appreciated that the porous layer 2410 can be placed in other locations, such as on an inwardly-facing surface of one of the intervening members 2402, 2404.

FIG. 49B shows the cell 2408 moving toward a collapsed position, where the cross-section of the cell 2408 is shaped like a parallelogram. Said collapsing motion can occur as a force F (e.g., due to negative pressure applied to the stabilizing structure 2400) is applied on the lateral face 2406b and the face of the intervening member 2402. In the illustrated embodiment, as the medial surface 2406a moves toward the intervening member 2402, the porous layer 2410 facilitates the flow of fluid therethrough while not interfering or restricting the collapsing movement of the cell 2408.

Figure 50:
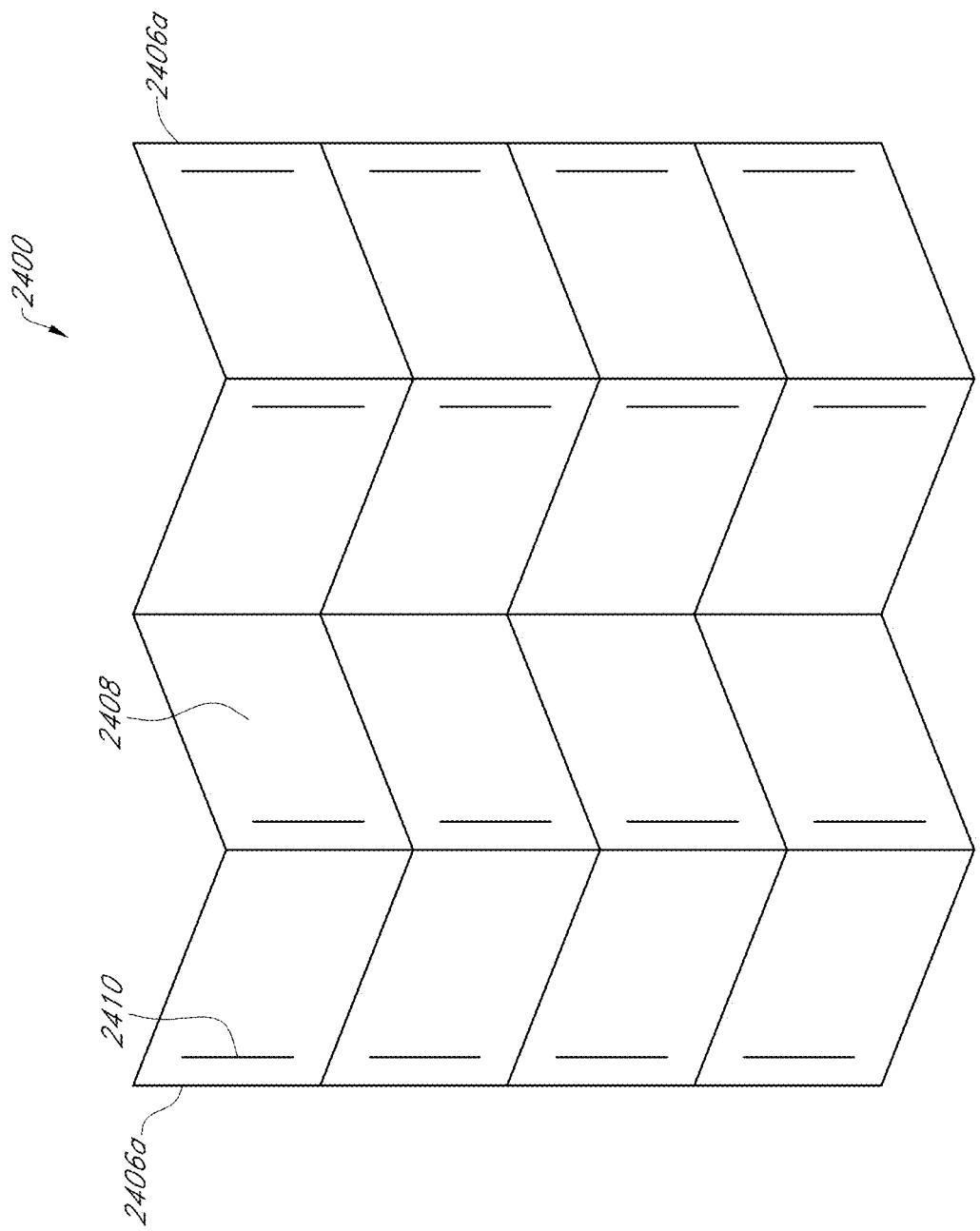
FIG. 50 illustrates a portion of a stabilizing structure with a porous layer, channels or grooves disposed on medial surfaces of one or more cells of the stabilizing structure.

FIG. 50 schematically illustrates a bird-eye view of a plurality of cells 2408 of the stabilizing structure 2400, where porous layers 2410 are disposed on the medial surfaces 2406a (e.g., proximal surfaces) of the strips 2406 of the stabilizing structure 2400. When strips 2406 are removed (e.g., cut), along with associated intervening members, from the stabilizing structure 2400, the lateral surface 2406b (see FIG. 51) of the remaining strips 2406 can be substantially flat or planar while the medial surface 2406a of the strips 2406 has the porous layer 2410 (e.g., disposed in one or more of the cells 2408 of the stabilizing structure 2400). That is, if certain elongate strips (and corresponding intervening members) are removed from lateral portions of the stabilizing structure, more medial strips will remain that include the porous layers 2410. After sizing of the stabilizing structure shown in FIG. 16, elongate strips 2406 may remain having flat or substantially smooth outer or lateral surfaces. Such surfaces may not include a porous layer 2410, and may be used for attachment of an anchoring layer as described above thereto.

Figure 51:
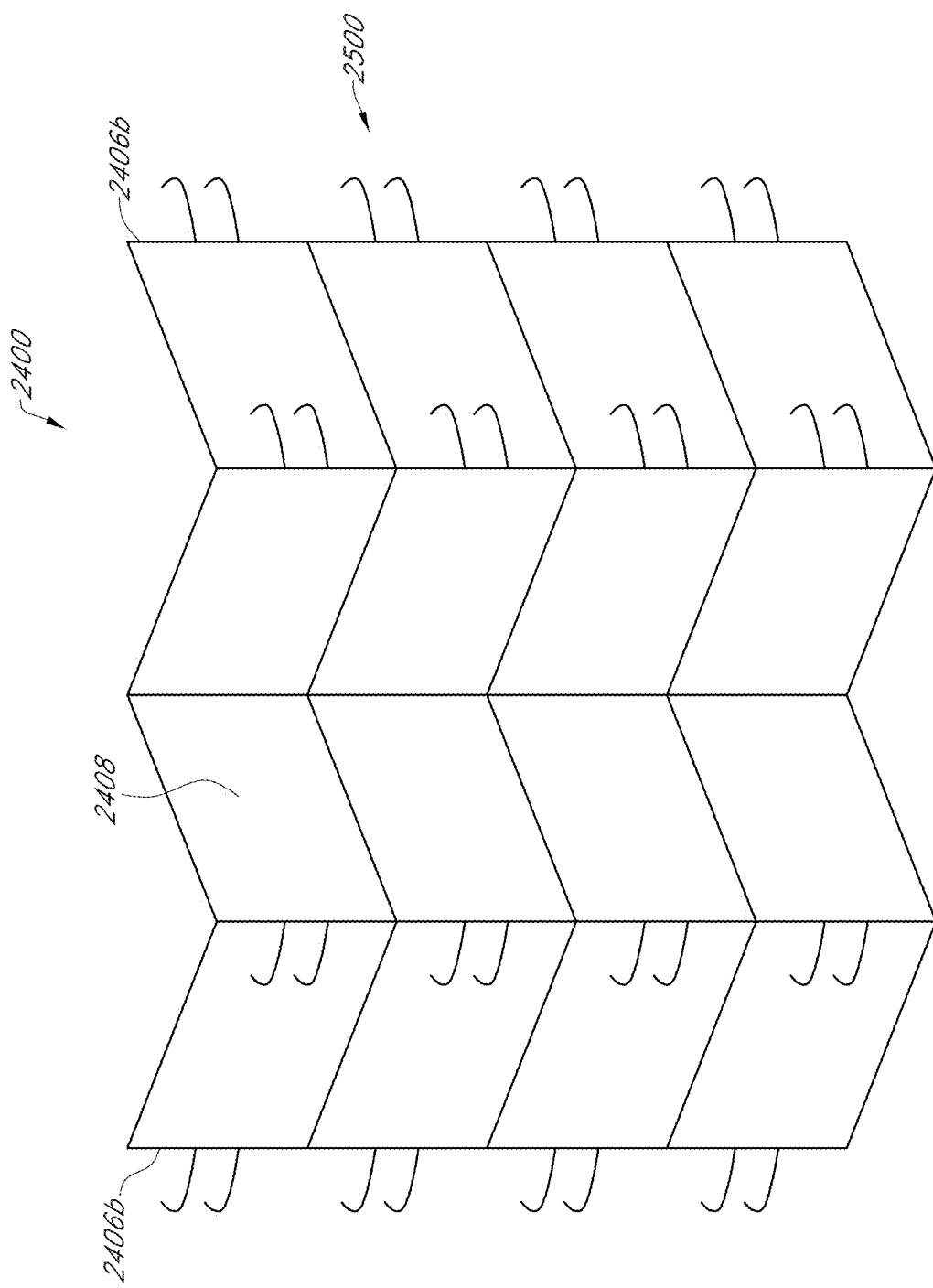
FIG. 51 illustrates a portion of a stabilizing structure with one or more anchoring members disposed on lateral or distal surfaces of one or more cells of the stabilizing structure.

FIG. 51 schematically illustrates the stabilizing structure 2400, where one or more anchors (e.g., an anchor layer) 2500 is disposed on at least a portion of lateral surfaces (e.g., distal surfaces) 2406*b* of the strips 2406. Accordingly, when strips 2406 are removed (e.g., cut) from the stabilizing structure 2400, the lateral surfaces 2406*b* (e.g., distal surfaces) of the strips 2406 will have said anchors thereon, thereby avoiding having to attach an anchor layer to said lateral surfaces 2406*b* following the resizing of the stabilizing structure 2400. Said anchors 2500 can be tissue anchors, as described above.

In one embodiment, the one or more anchors or anchor layer 2500 can be disposed on the lateral surfaces (e.g., distal surfaces) 2406*b* of the strips 2406 so as to not restrict movement of the one or more walls of the cells 2408 of the stabilizing structure 2400 as the cells 1408 collapse when the stabilizing structure 2400 moves toward a collapsed position, such as during the application of negative pressure thereto. For example, the anchors 2500 can be disposed on a portion of the lateral surface 2406*b* that defines an obtuse angle (e.g., between strip 1406 and intermediate member 2404, 2402) as the cell 2408 collapses, thereby avoiding restricting the collapsing movement of the cell 2408.

In one embodiment, the one or more anchors or anchor layer 2510 can be disposed over less than the entire (e.g., less than 90%, less than 80%, less than 70%, less than 50%, less than 30%, less than 20%, less than 10%) of the lateral surface 2406*b*. In one embodiment, the anchor layer 2500 can be disposed on a portion of said lateral surface 2406*b* that defines one quadrant (or less than one quadrant) of the cell 2408.

In one embodiment, the stabilizing structure 2400 can have both one or more porous layers 2410 on medial surfaces 2406*a*, and one or more anchors 2500 on lateral surfaces 2406*b* of the strips 2400. Accordingly, when strips 2406 are removed (e.g., cut) from the stabilizing structure 2400, the lateral surfaces 2406*b* (e.g., distal surfaces) of the strips 2406 will have said anchors thereon and the medial surfaces 2406*a* (e.g., proximal surfaces) will have porous layers 2410 thereon, thereby avoiding having to attach an anchor layer 2500 to said lateral surfaces 2406*b* or a porous layer 2410 to said medial surfaces 2406*a* following the resizing of the stabilizing structure 2400.

The Anchoring Clips of FIGS. 52A-58B

Figure 52A:
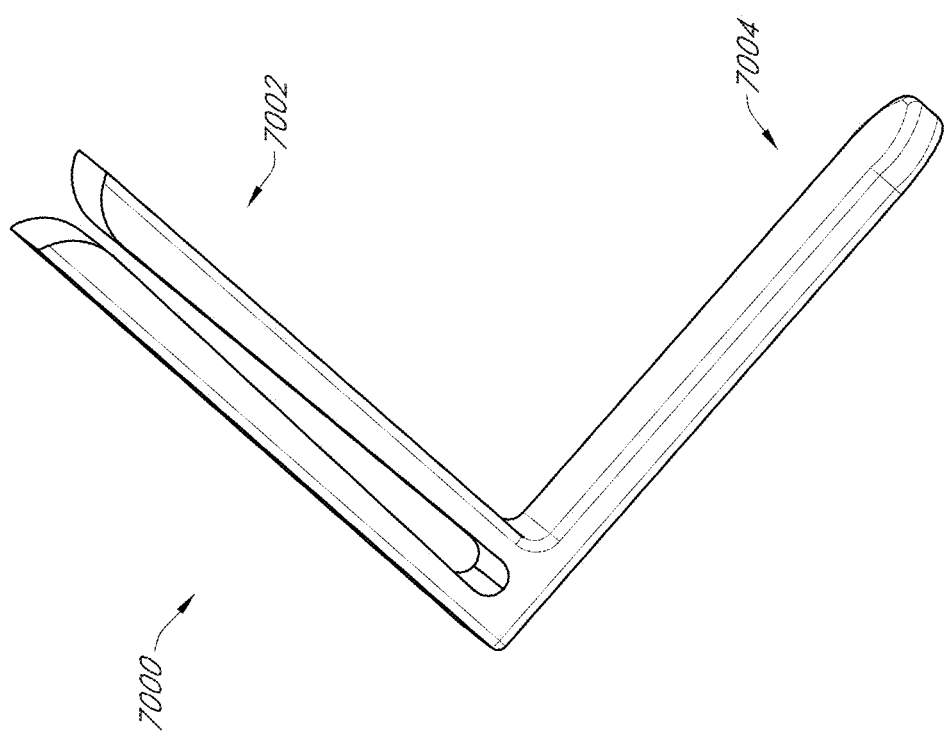
Figure 52B:
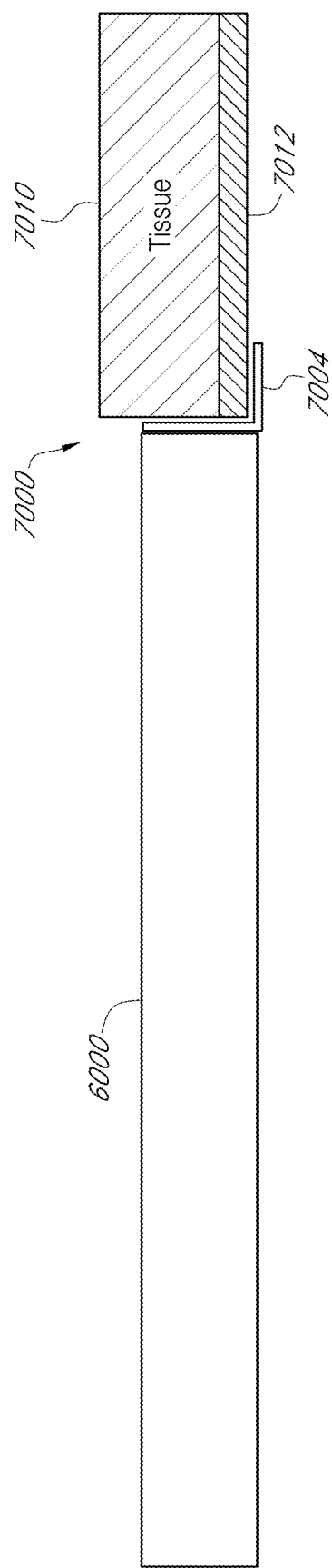

FIGS. 52A-52E illustrate multiple views of stabilizing clips that may be attached to the stabilizing structures of FIGS. 2A-5D, 13A-14C, and 16-18C or other embodiments described herein. As illustrated in FIG. 52A, in some embodiments, stabilizing clip 7000 may comprise an attachment portion 7002 that allows it to "clip" onto a wall of a stabilizing structure, such as upon an elongate member or an intervening member. Stabilizing clip 7000 may also comprise a securing portion 7004 that can extend above or below tissue layers to aid in securing the stabilizing structure 6000 to the surrounding tissue. The securing portion 7004 may extend from a lower end of the attachment portion 7002, at the closed end of the attachment portion. For example, when a stabilizing structure, such as stabilizing structure 6000 of FIG. 14A, is placed into an abdominal wound, the underlying viscera may tend to expand and push the stabilizing structure upwards and out of the abdominal wound. Such an occurrence is undesirable because, as described above, the stabilizing structure is suited to be placed within an abdominal wound whereby the stabilizing structure can draw the edges of the wound together. To alleviate the outward pressure of the expanding viscera, in some embodiments as illustrated by FIG. 52B, before placing the stabilizing structure within the wound, the stabilizing clips 7000 may be attached to the underside of the stabilizing structure 6000. The securing portion 7004 of the stabilizing structure 6000 may then extend outward from the stabilizing structure and under the surrounding tissue 7010, for example the fascia 7012.

In some embodiments, the clips are rigid, therefore once the securing portion 7004 is extended below the fascia 7012, the securing portion can absorb upward force from the swelling viscera while maintaining the stabilizing structure 6000 in place within an abdominal wound. In further embodiments, the securing portion may be semi-rigid or soft. In some embodiments, the clip can be made from any suitable material including, for example, plastics, ABS, PU, PE, PP, PET, silicone, Nylon, or other suitable materials known in the art. Further, the clip can be made of metals including, for example, titanium, stainless steel, Inconel, or other suitable material known in the art. Additionally, the clip can be made of composites including, for example, carbon fiber, Kevlar, reinforced plastics, or other suitable material known in the art.

The stabilizing clip may be clipped to the top or the bottom of the stabilizing structure, thereby extending the securing portion over the top or below the surrounding tissue. In some embodiments, an anchoring layer such as those described elsewhere in the specification, particularly in FIGS. 3-5D, may be attached to the stabilizing clip. One of skill in the art with recognize that such an anchoring layer may be applied to the stabilizing clip in any suitable manner, such as around or under the stabilizing clip.

In some embodiments, the stabilizing clips are radiopaque, such that they are easily identifiable if lost within the body. To further make the stabilizing clips easier to find, the stabilizing clips may be attached or tied together in a suitable manner. In some embodiments two stabilizing clips are attached together, three stabilizing clips, four stabilizing clips, or more than four stabilizing clips attached together.

In embodiments, the stabilizing structure may have notches such that the stabilizing clips may be help more firmly over the notch. The stabilizing clip may further have an additional protrusion that serves to prop open the stabilizing structure such that the stabilizing structure cannot fully close. Instead of or in tandem with a protrusion, the stabilizing clip may have a loop that acts to prop open the stabilizing structure. In some embodiments, the stabilizing clip props open the stabilizing structure at least: 10%, 20%, 30%, 40%, 50%, or more than 50%.

Figure 52C:
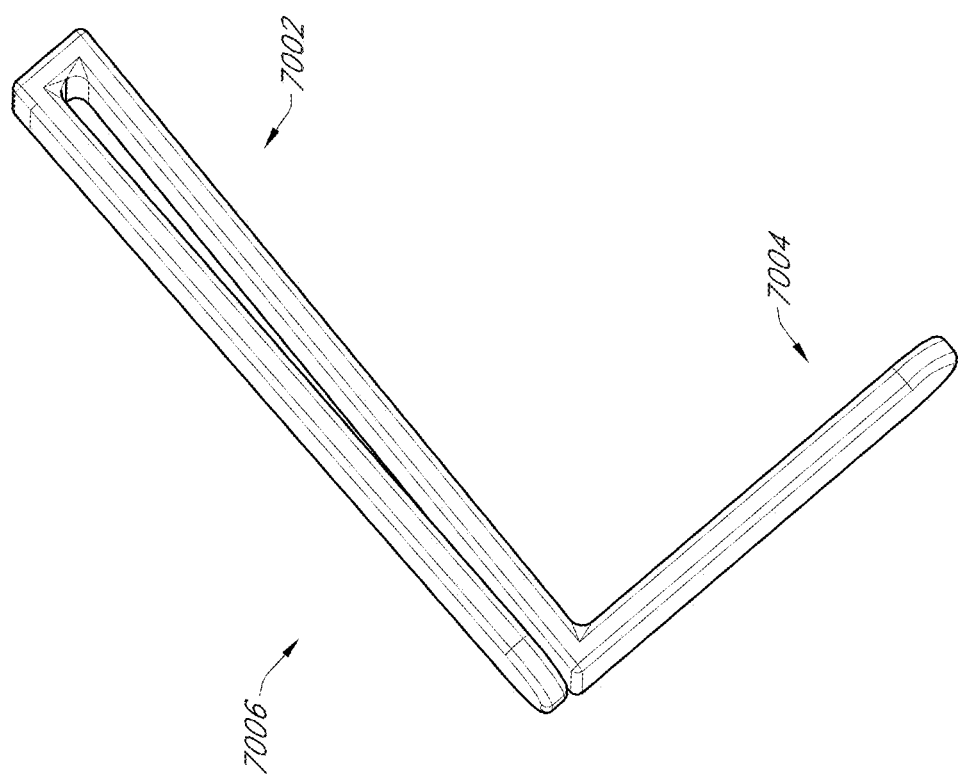

FIG. 52C illustrates an embodiment of stabilizing clip 7006, similar to the stabilizing clip of FIG. 52A. Stabilizing clip 7000 may comprise an attachment portion 7002 that loops over the top of a wall of a stabilizing structure. In this way, the stabilizing clip 7000 will be more difficult to dislodge from the stabilizing structure. As with the other stabilizing clip embodiments illustrated in FIG. 52A, the stabilizing clip of FIG. 52B may comprise a securing portion 7004 that extends below a layer of tissue such as the fascia, to maintain the stabilizing structure in place. The securing portion 7004 may extend from a lower end of the attachment portion 7002, however, in this instance the lower end of the attachment portion is the open end because the stabilizing clip "clips" onto the stabilizing structure from the top.

Figure 52D:
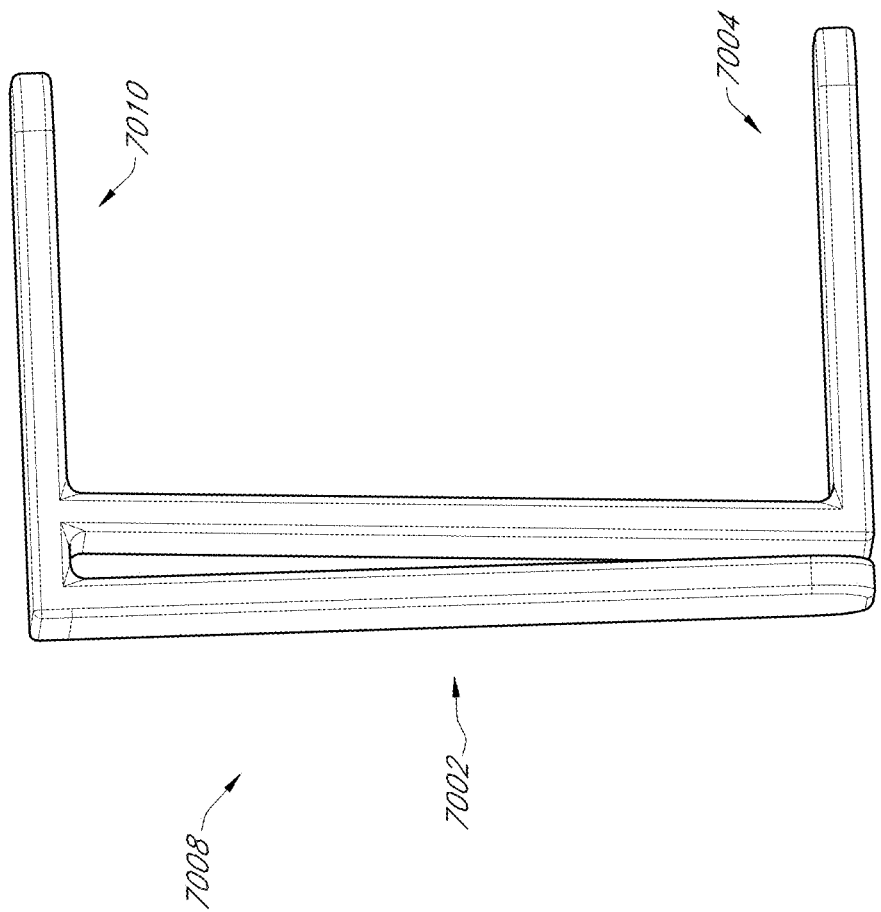
Figure 52F:
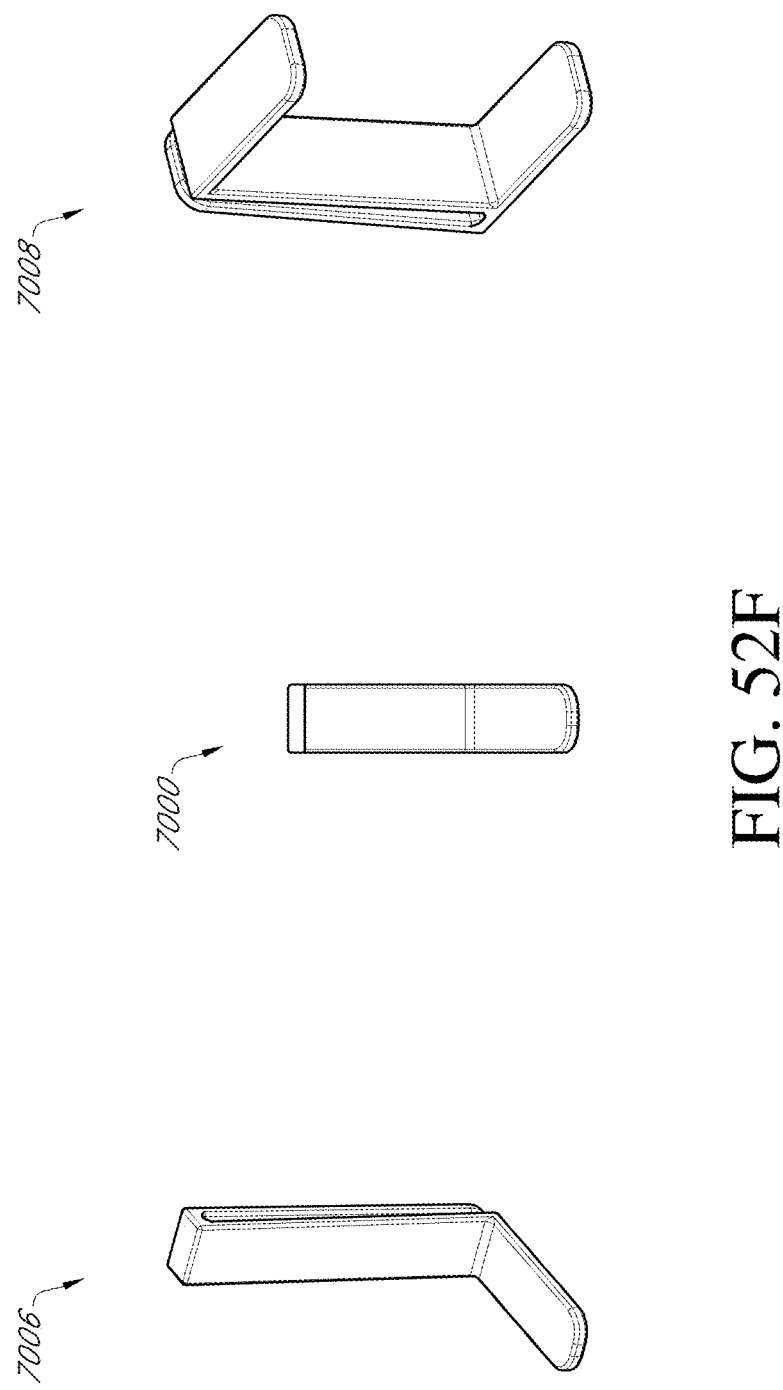

FIG. 52D depicts another embodiment of a stabilizing clip 7008, similar to the stabilizing clip embodiments of FIGS. 52A-B. Stabilizing clip 7008 has securing portions 7004, 7010 on both the upper and lower portions of the stabilizing clip. The stabilizing clip may have a first securing portion 7010 extending outward from an upper end of the attachment portion and a second securing portion 7004 extending outward from a lower end of the attachment portion. Therefore, once attached to a stabilizing structure, stabilizing clip 7008 may more tightly secure the stabilizing structure in place because the securing portions extend both above and below various tissue layers such as the fascia. FIG. 52E shows side views of stabilizing clips 7000, 7006, and 7008, while FIG. 52F shows a top front view of stabilizing clips 7000, 7006, and 7008.

Figure 53A:
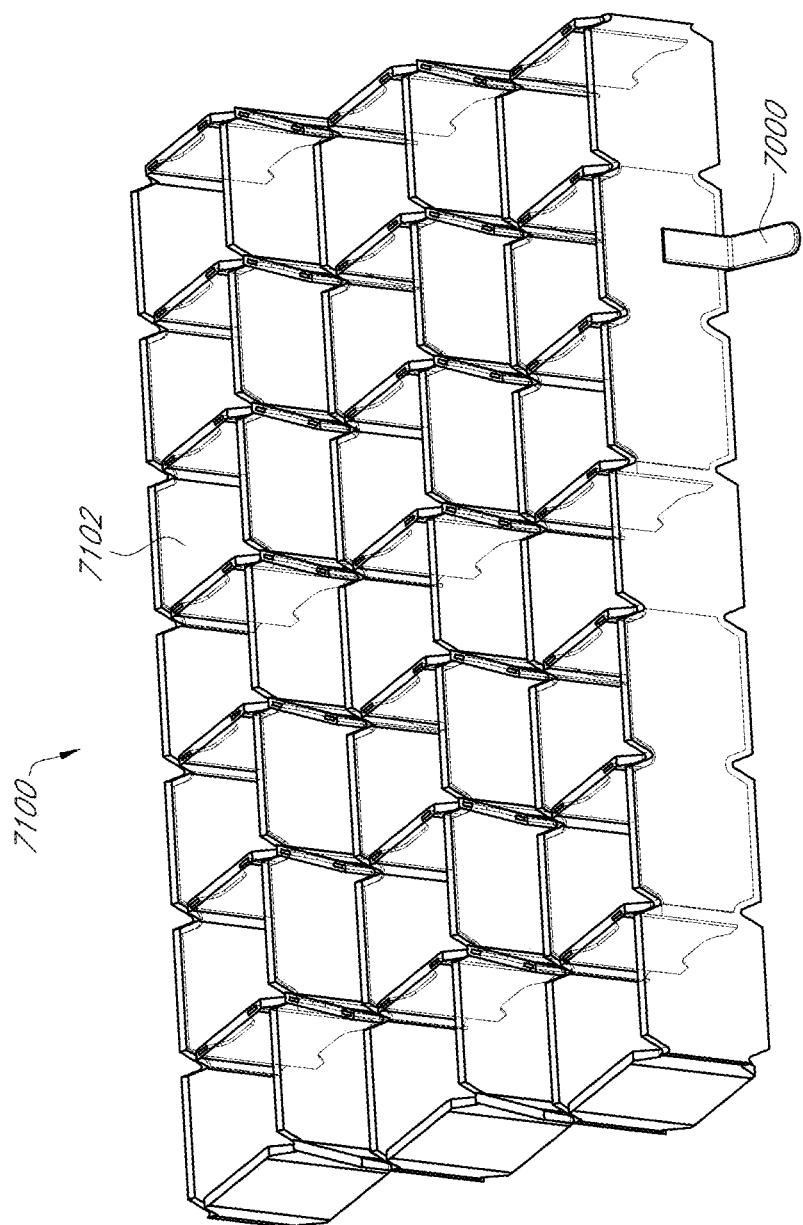
FIGS. 53A-C are photographs of embodiments of stabilizing structures with attached stabilizing clips.
Figure 53B:
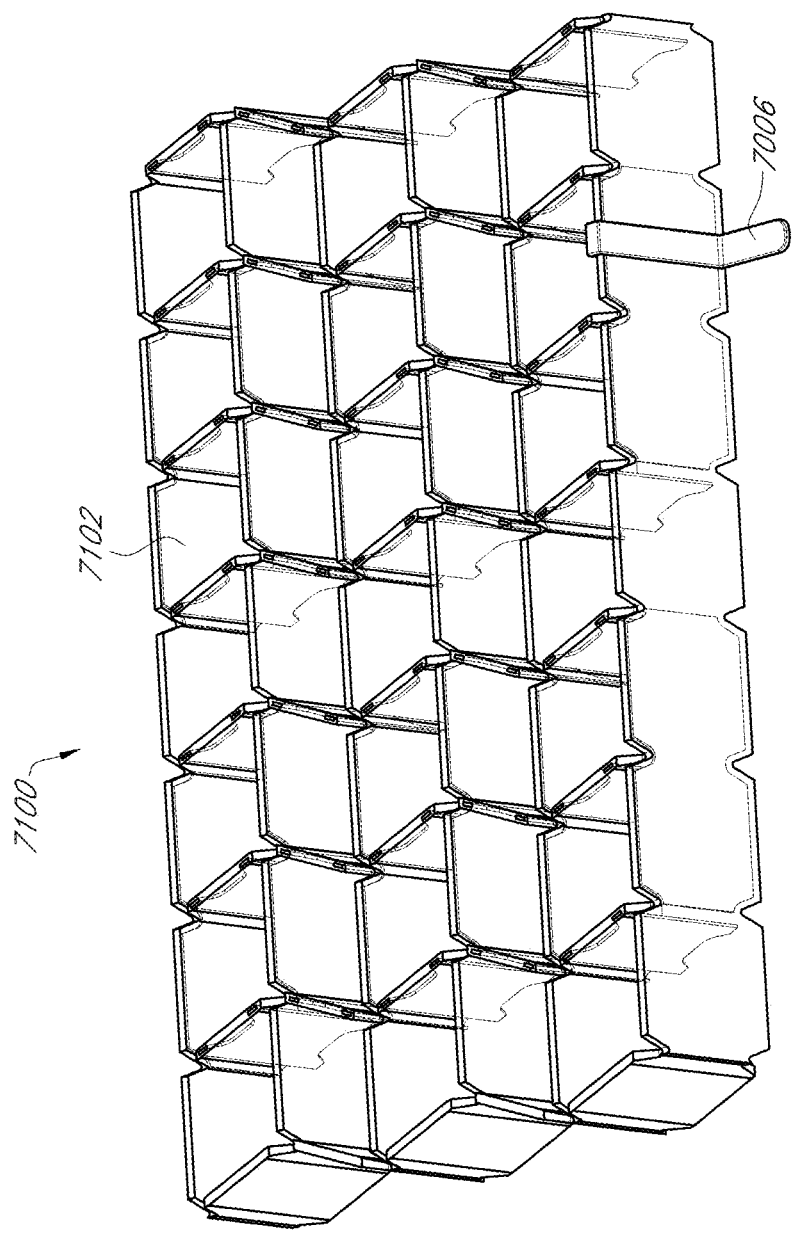
Figure 53C:
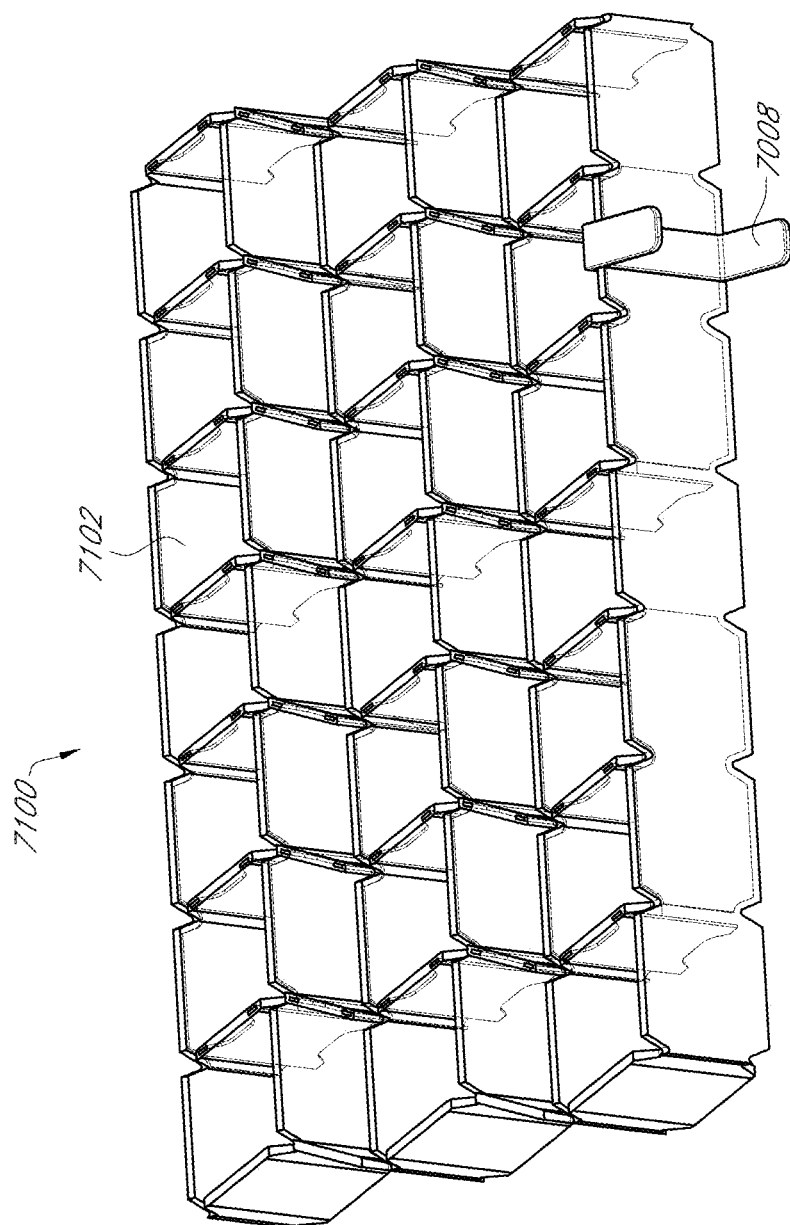

FIGS. 53A-C illustrate embodiments of stabilizing clips, similar to the stabilizing clips depicted in FIGS. 52A-F, attached to a stabilizing structure 7100 similar to the stabilizing structures of FIGS. 2A-2I and 5A-5D. Here the stabilizing clip 7000, 7006, 7008 may be attached to the bottom of a stiffer portion 7102 of the stabilizing structure. However, the stabilizing clip may also be attached to the softer portion of the stabilizing structure. In some embodiments, more than one stabilizing clip will be used. For example, a single stabilizing structure may contain 2 or more of one type of stabilizing clip on one side, three or more stabilizing clips, four or more stabilizing clips, five or more stabilizing clips, six or more stabilizing clips, or more than six stabilizing clips. Sometimes when using more than one clip, only one type of clip is used, however, at other times more than one type of clip may be used. In certain embodiments, there will only be one stabilizing clip per wall of the stabilizing structure; however, further embodiments may call for multiple stabilizing clips per wall of the stabilizing structure.

FIGS. 54A-54E are pictures of embodiments of stabilizing structures 8000 similar to the stabilizing structures of FIGS. 14A-C. Similar to FIGS. 53A-C, stabilizing clips 8002 may be attached to the stabilizing structure to secure the stabilizing structure within the wound. As described herein this section and elsewhere in the specification, the stabilizing clips 8002 may extend outward from the stabilizing structure into the surrounding tissue and hold the stabilizing structure in place within the abdominal wound.

Figure 54A:
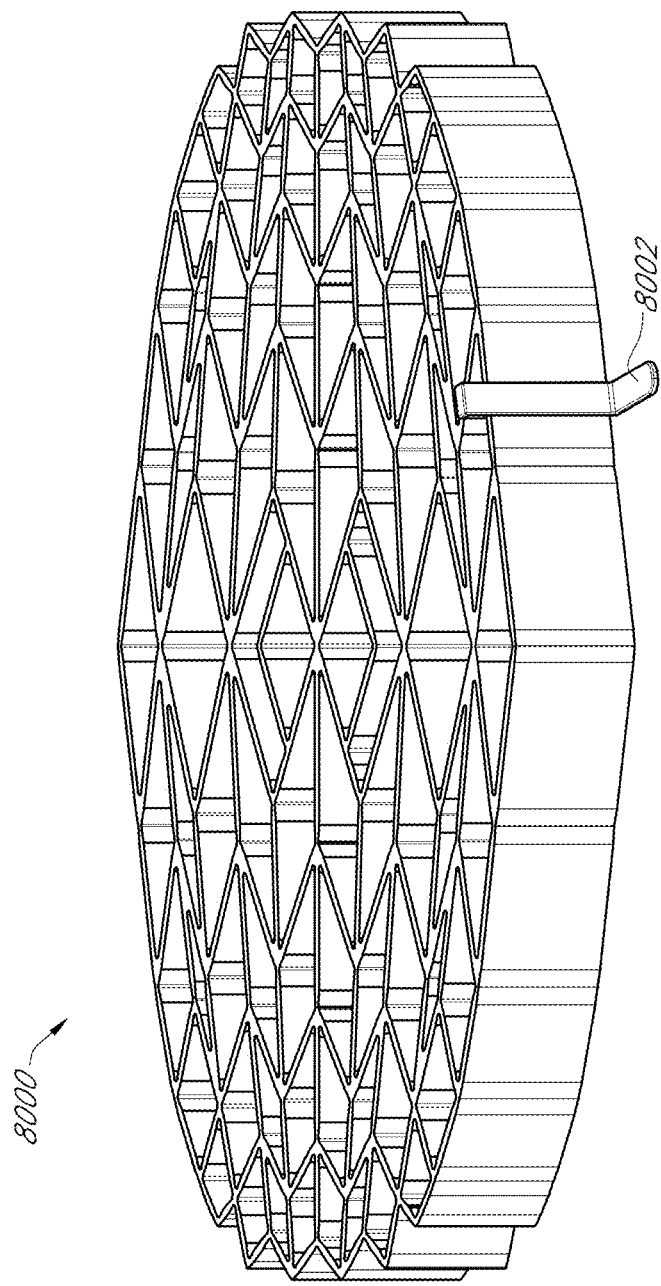
FIGS. 54A-G are photographs and illustrations of embodiments of an elliptical stabilizing structure with attached stabilizing clips.
Figure 54B:
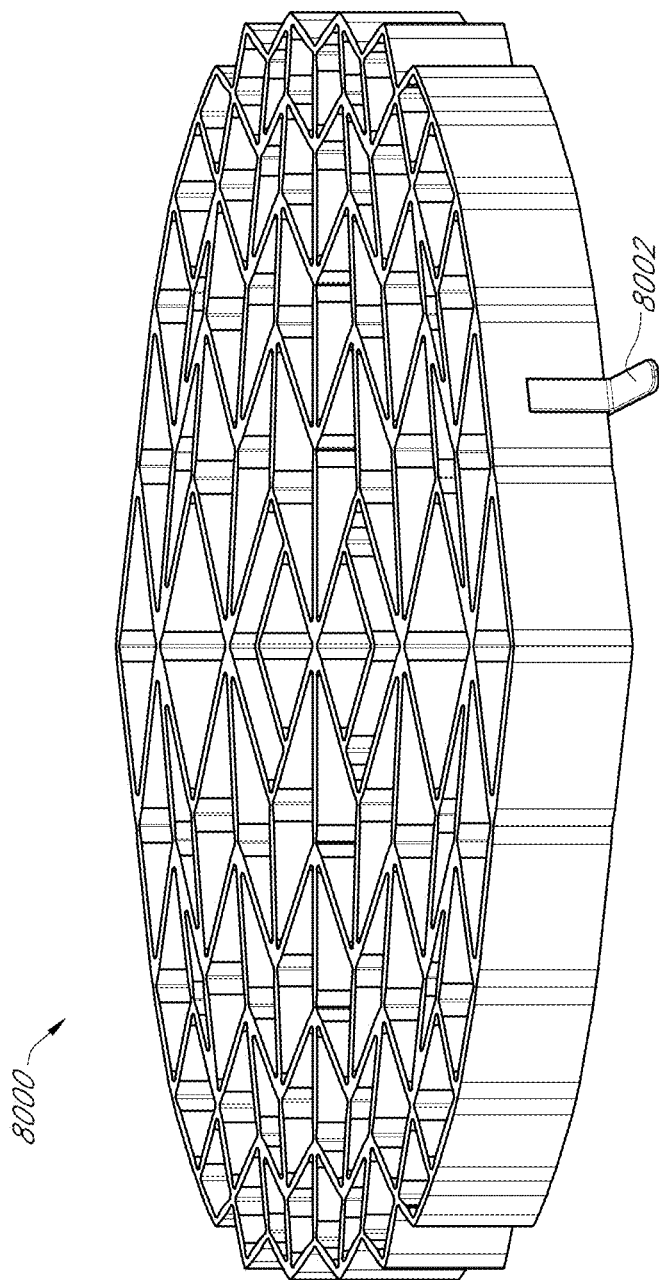
Figure 54C:
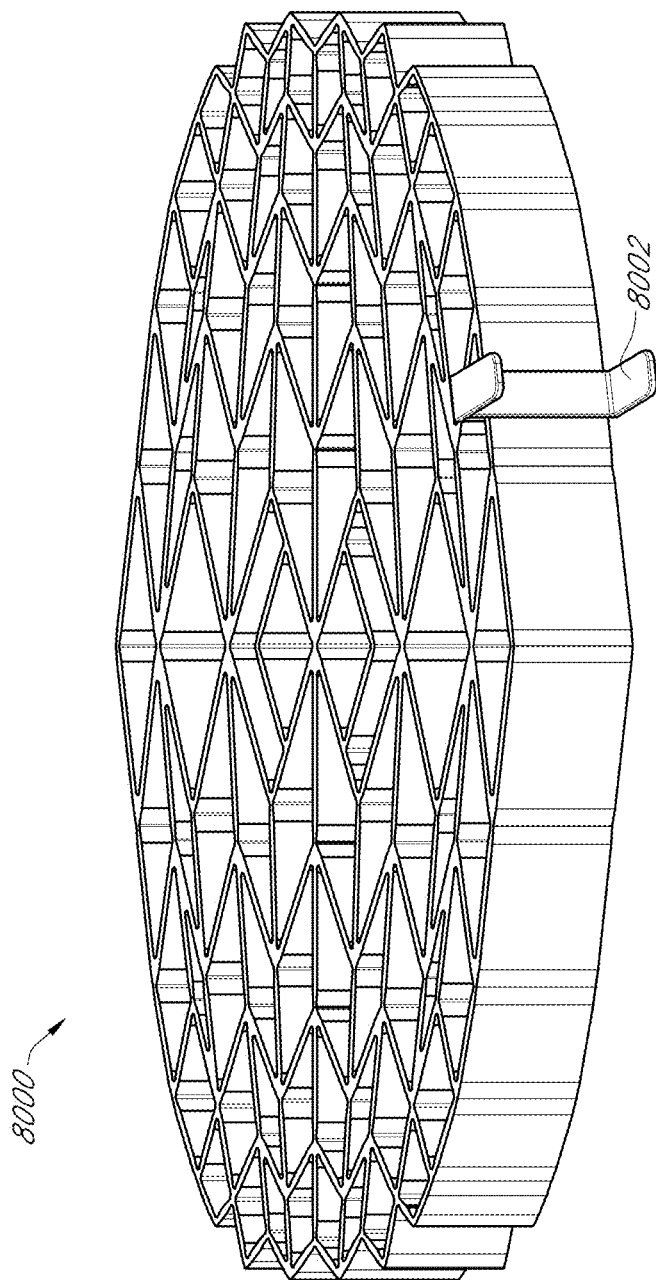
Figure 54D:
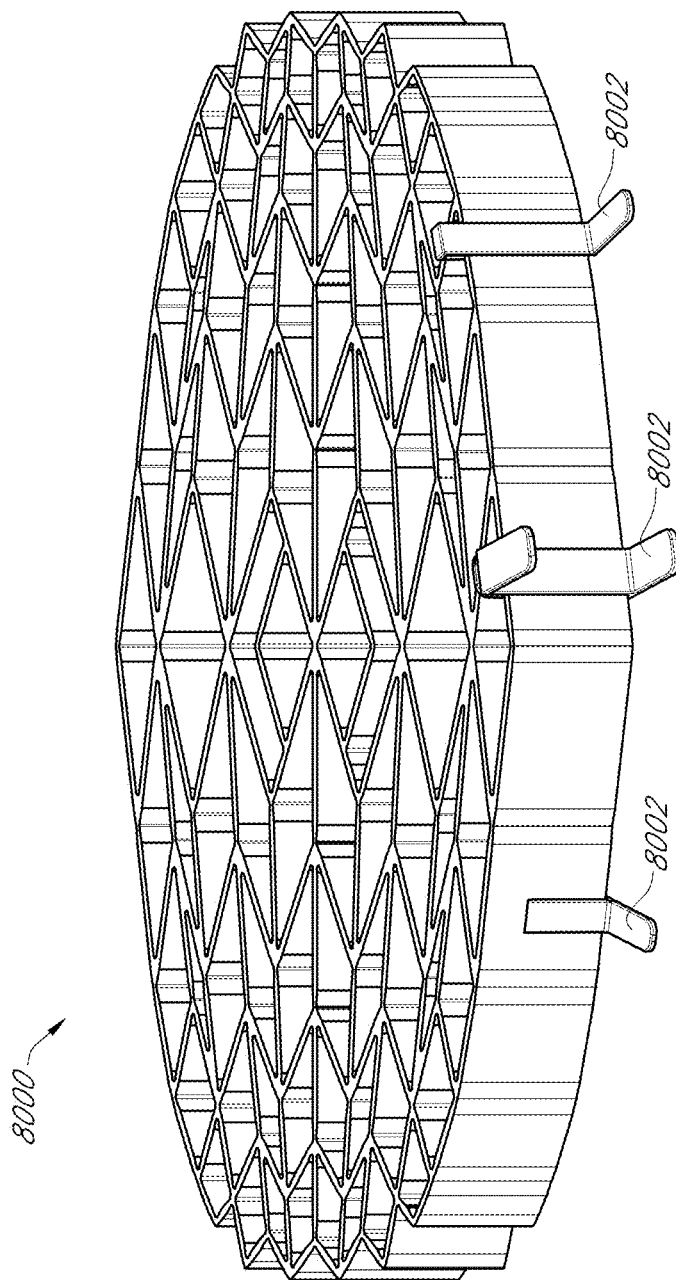
Figure 54E:
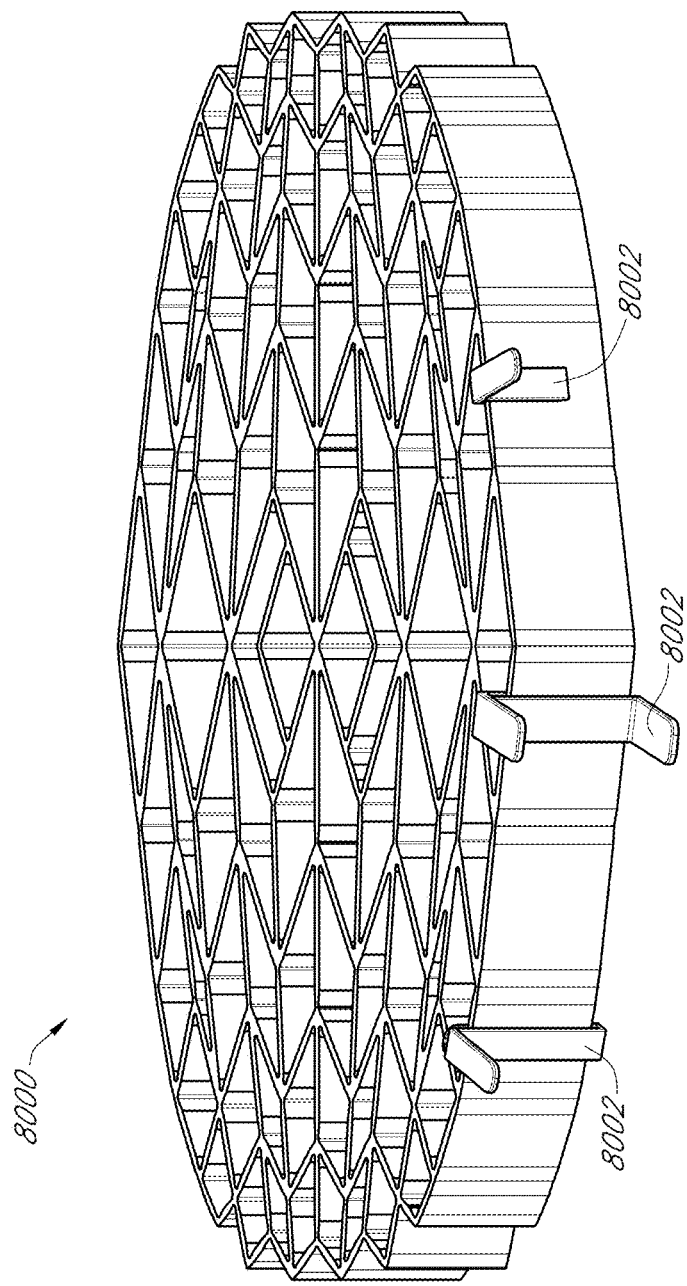
Figure 54F:
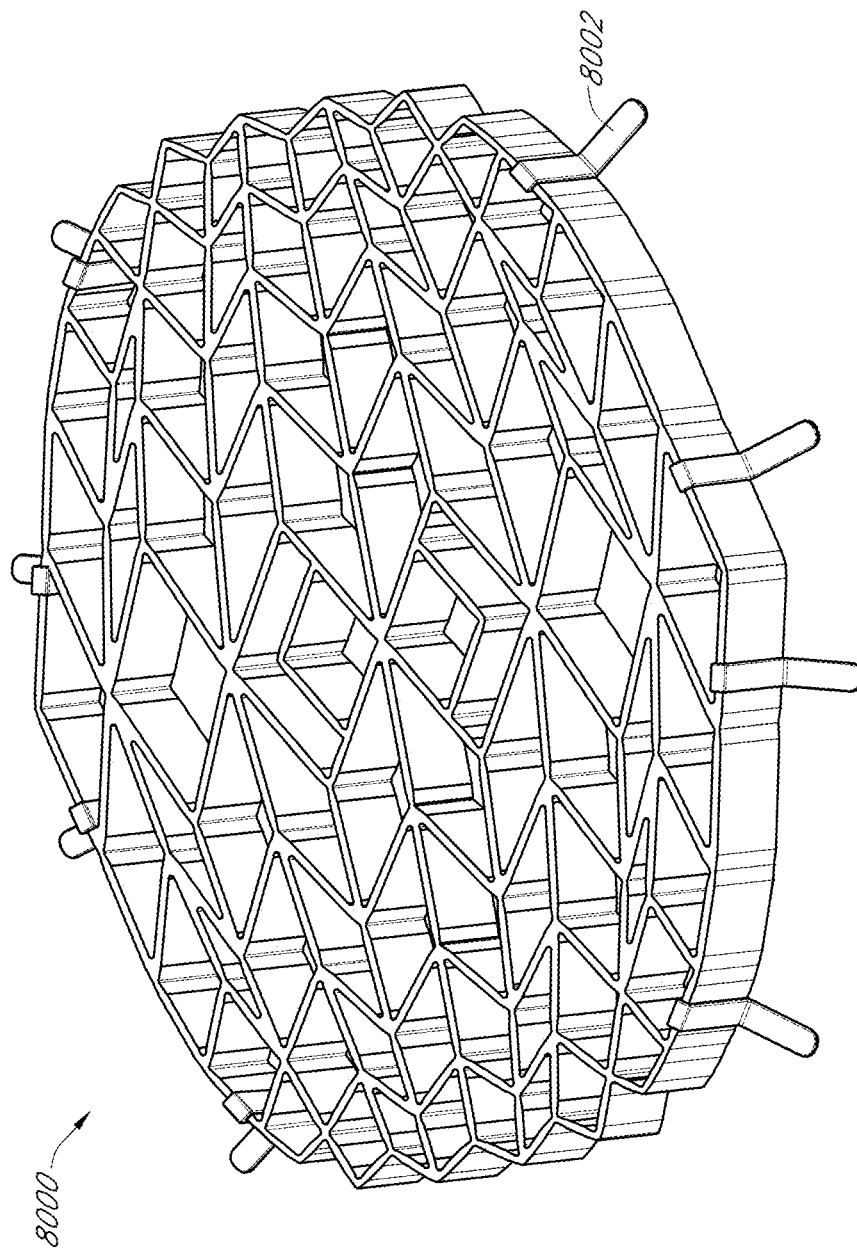
Figure 54G:
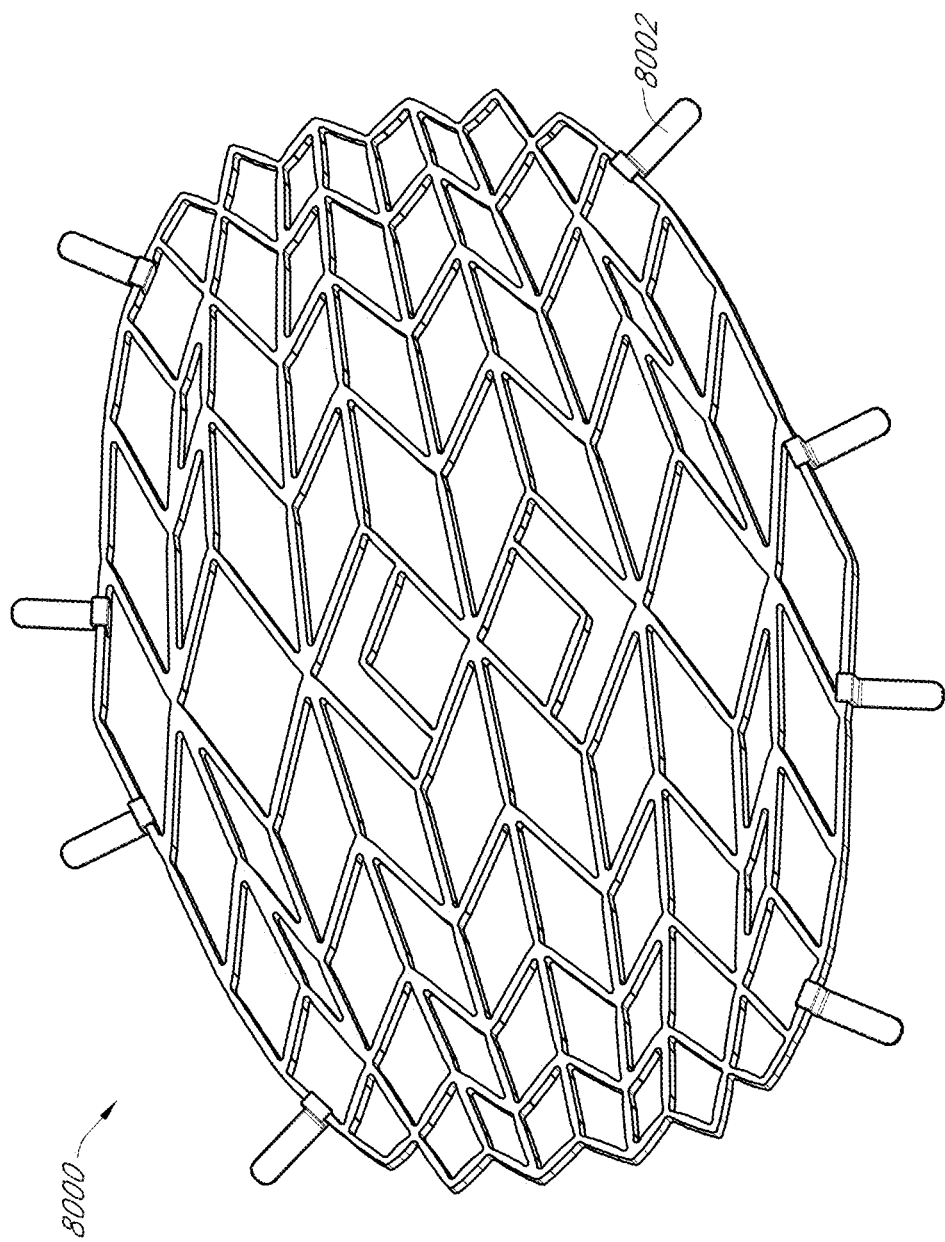
Figure 55A:
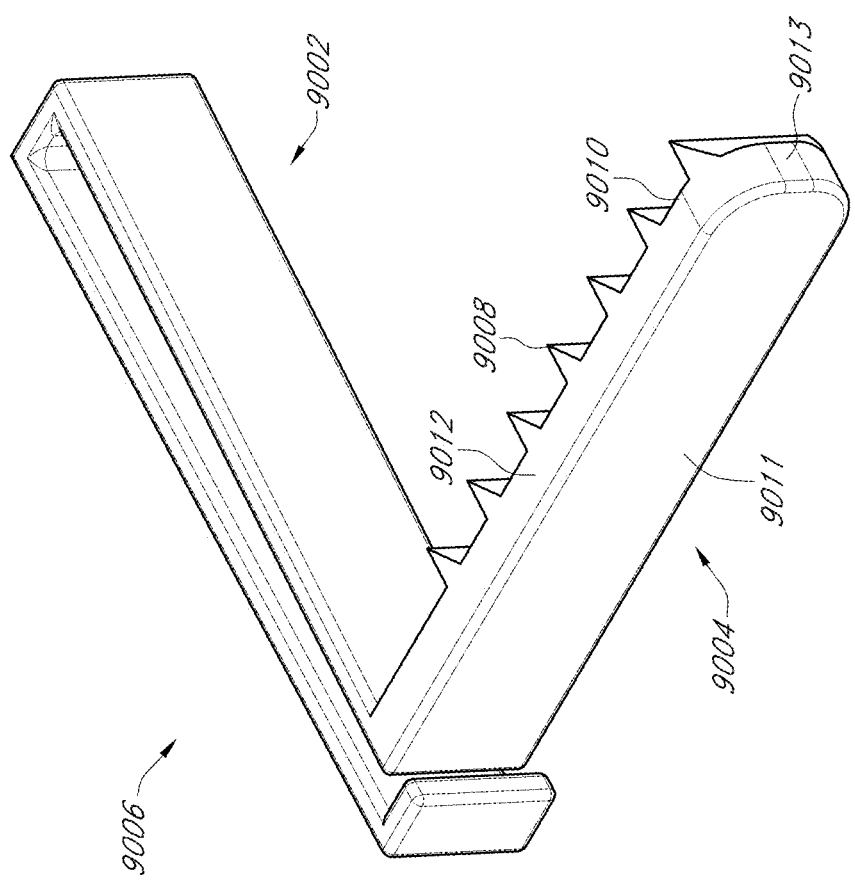
Figure 55B:
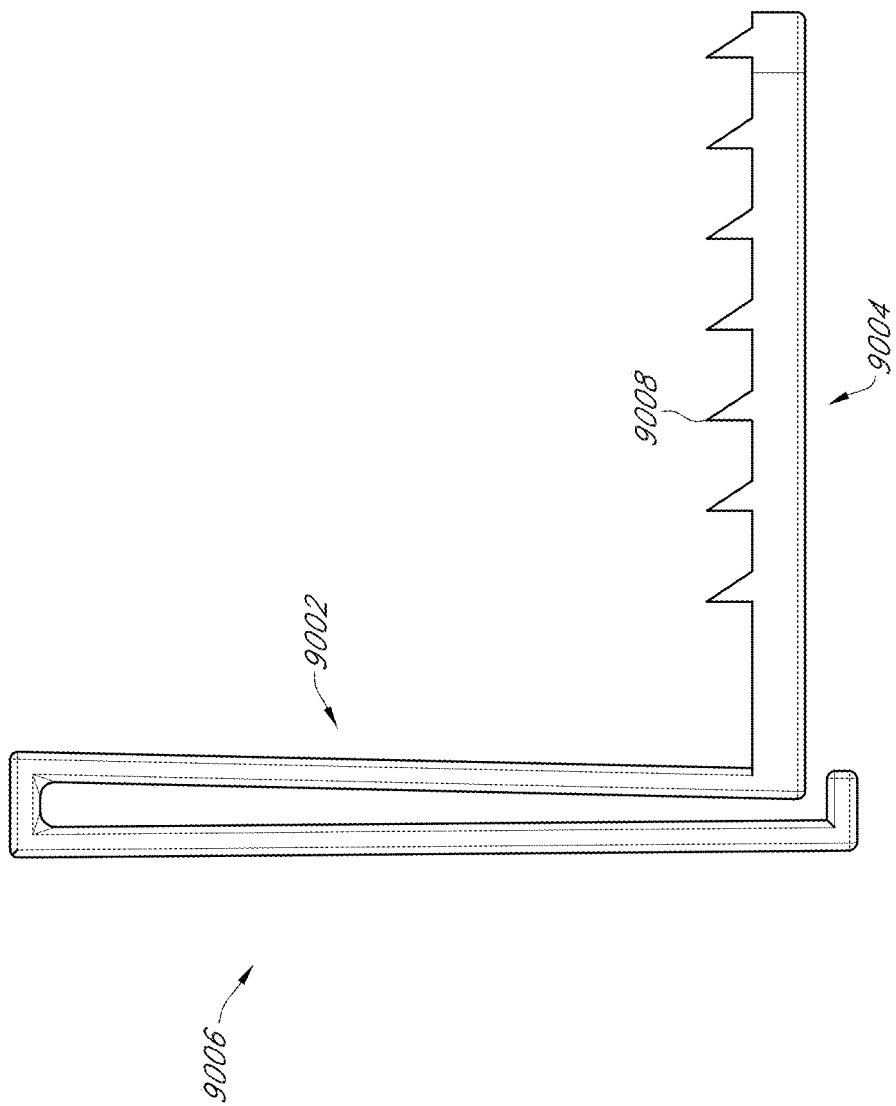
Figure 55C:
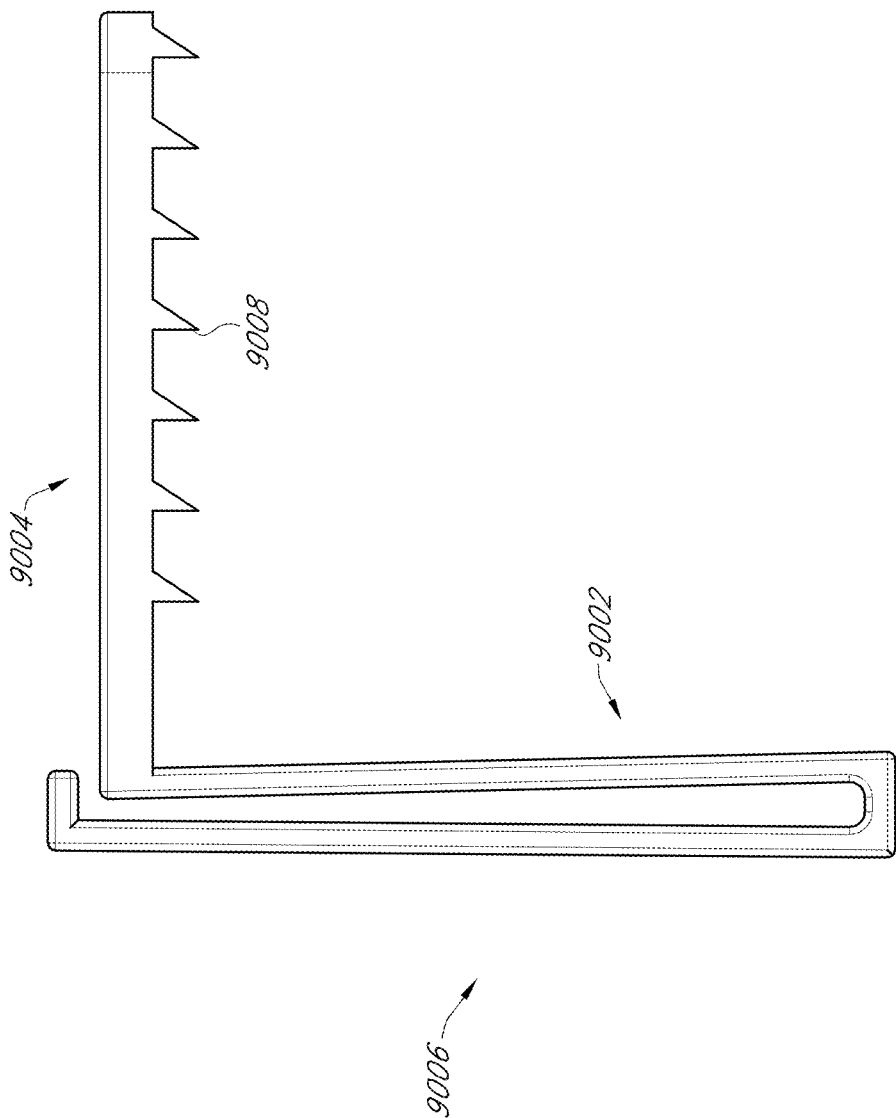
Figure 55D:
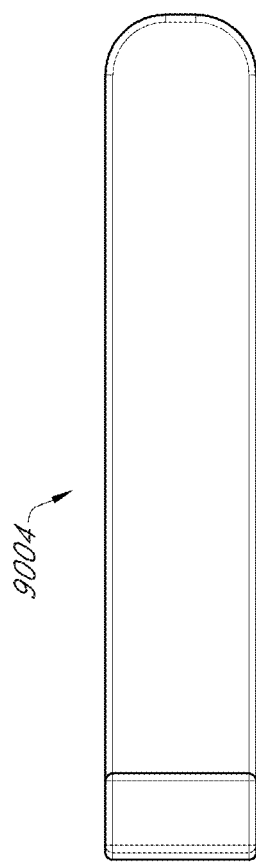
Figure 55E:
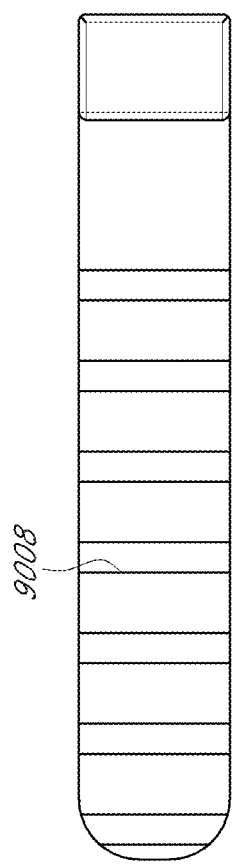
Figure 55F:
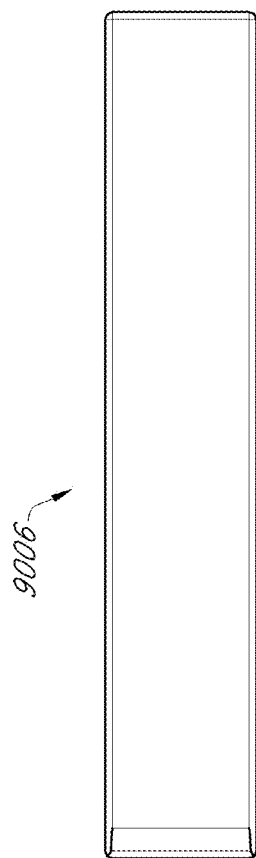

FIGS. 54F-G are illustrations of the stabilizing structure embodiments of FIGS. 54A-18E, however, the embodiments within these illustrations includes a larger number of stabilizing clips.

FIGS. 55A-G illustrate an embodiment of stabilizing clip 9006, similar to the stabilizing clip of FIG. 52C. Stabilizing clip 9006 may comprise an attachment portion 9002 that loops over the top of a wall of a stabilizing structure. As with the other stabilizing clip embodiments illustrated in FIG. 52C, the stabilizing clip of FIGS. 55A-G may comprise a securing portion 9004 that extends below a layer of tissue such as the fascia, to maintain the stabilizing structure in place. The securing portion 9004 may extend from a lower end of the attachment portion 9002. The securing portion 9004 can include grippers 9008. The grippers 9008 can assist in attaching the securing portion to the surrounding tissue. The securing portion 9004 and the grippers 9008 extend below a layer of tissue such as the fascia, to maintain the stabilizing structure in place. The tissue grippers 9008 can be similar to the tissue anchors described with reference to FIGS. 5A-D. The tissue grippers 9008 can be formed of the same material as the stabilizing clip. In some embodiments, the grippers 9008 can be formed of a different material than the material used for construction of the stabilizing clip. FIGS. 55A-G illustrate grippers 9008 on a top surface 9010 of the securing portion 9004. In some embodiments, the grippers 9008 may be provided on the bottom surface 9011, sides 9012, or front surface 9013 of the securing portion. Further, in some embodiments, the attachment portion of the stabilizing clips may include grippers that can assist in securing the stabilizing structure.

FIGS. 56A-J illustrate an embodiment of stabilizing clip 10006, similar to the stabilizing clip of FIGS. 55A-G. Stabilizing clip 10006 may comprise an attachment portion 10002 that loops over the top of a wall of a stabilizing structure. As with the other stabilizing clip embodiments illustrated in FIGS. 55A-G, the stabilizing clip of FIGS. 56A-J may comprise a securing portion 10004 that extends below a layer of tissue such as the fascia, to maintain the stabilizing structure in place. The securing portion 10004 may extend from a lower end of the attachment portion 10002. The stabilizing clip 10006 can include a step or recess 10010 at the intersection of the securing portion 10004 and the attachment portion 10002 or where the securing portion 10004 extends horizontally from the attachment portion 10002. In some embodiments, as depicted in FIGS. 56A-J, the securing portion 10004 may include grippers 10008 to assist in attaching the securing portion to the surrounding tissue. In other embodiments, the stabilizing clip 10006 with the step or recess 10010 may be used with a securing portion 10004 without grippers 10008 on the surface of the securing portion 10004. The step 10010 can provide a step or recess in the stabilizing clip to accommodate a foam and/or other material positioned below the matrix, similar to foam layer 5102 described with reference to FIG. 10A or other embodiments described herein. The step 10010 allows the stabilizing clip 10006 attached to the matrix stabilizing structure 10013 to fit around a piece of foam that is placed below the stabilizing structure 10013 which may be slightly larger than the stabilizing structure 10013. In some embodiments, the size of the step can be changed to accommodate the various foam sizes.

Figure 56A:
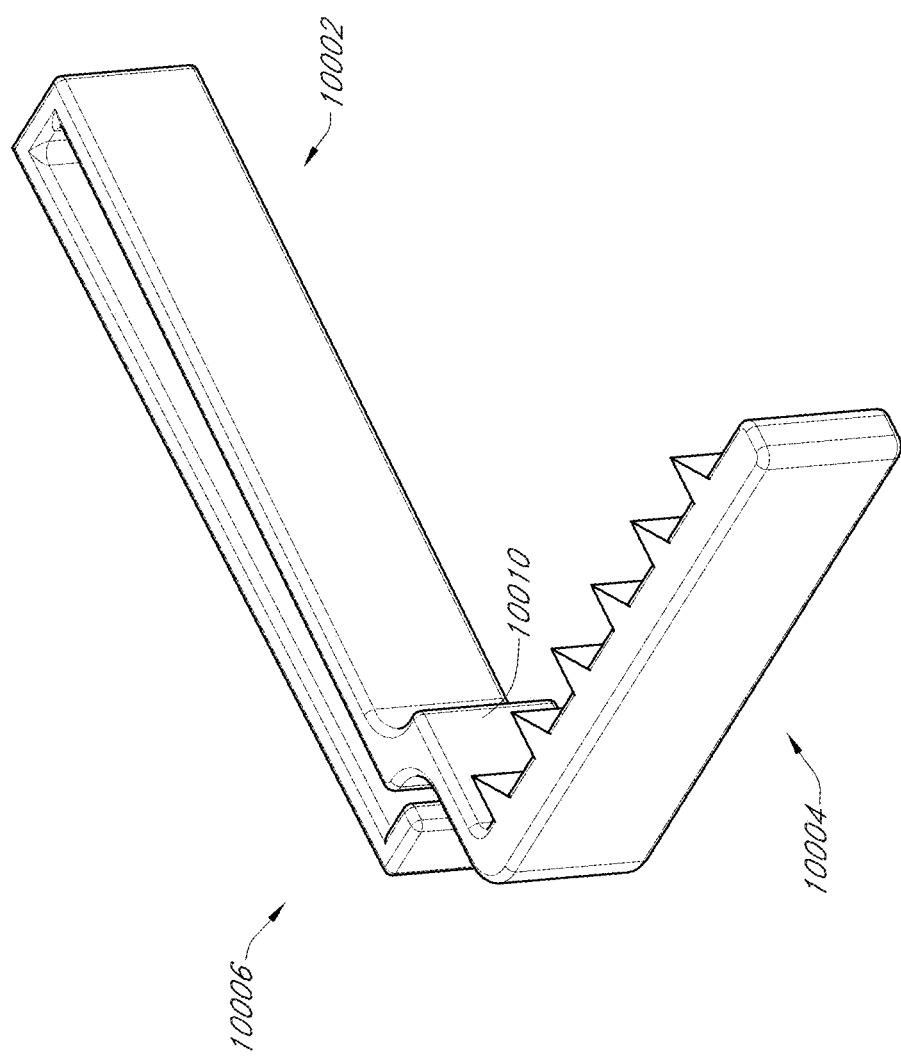
FIGS. 56A-J illustrate embodiments of stabilizing clips for attachment to a stabilizing structure with a step or recess at the intersection of the securing portion and the attachment portion.
Figure 56B:
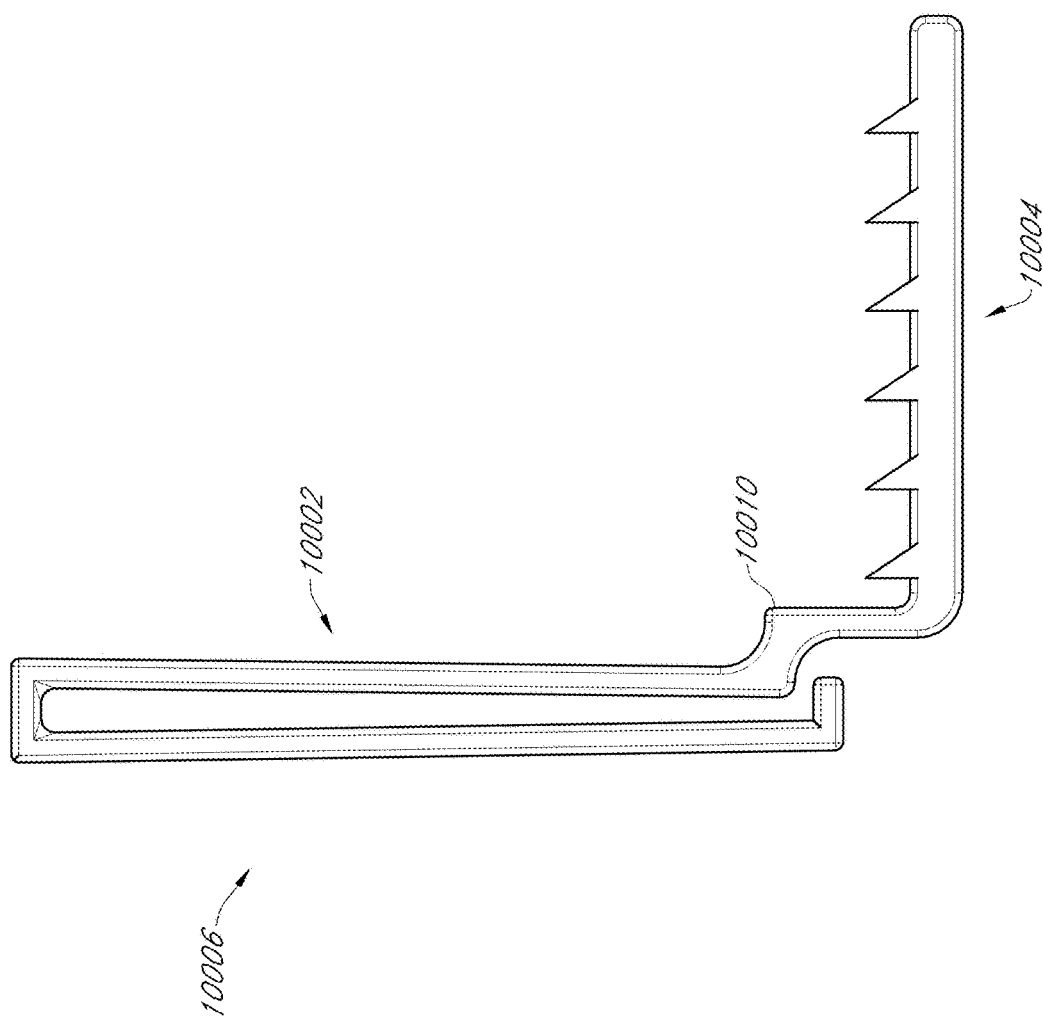
Figure 56C:
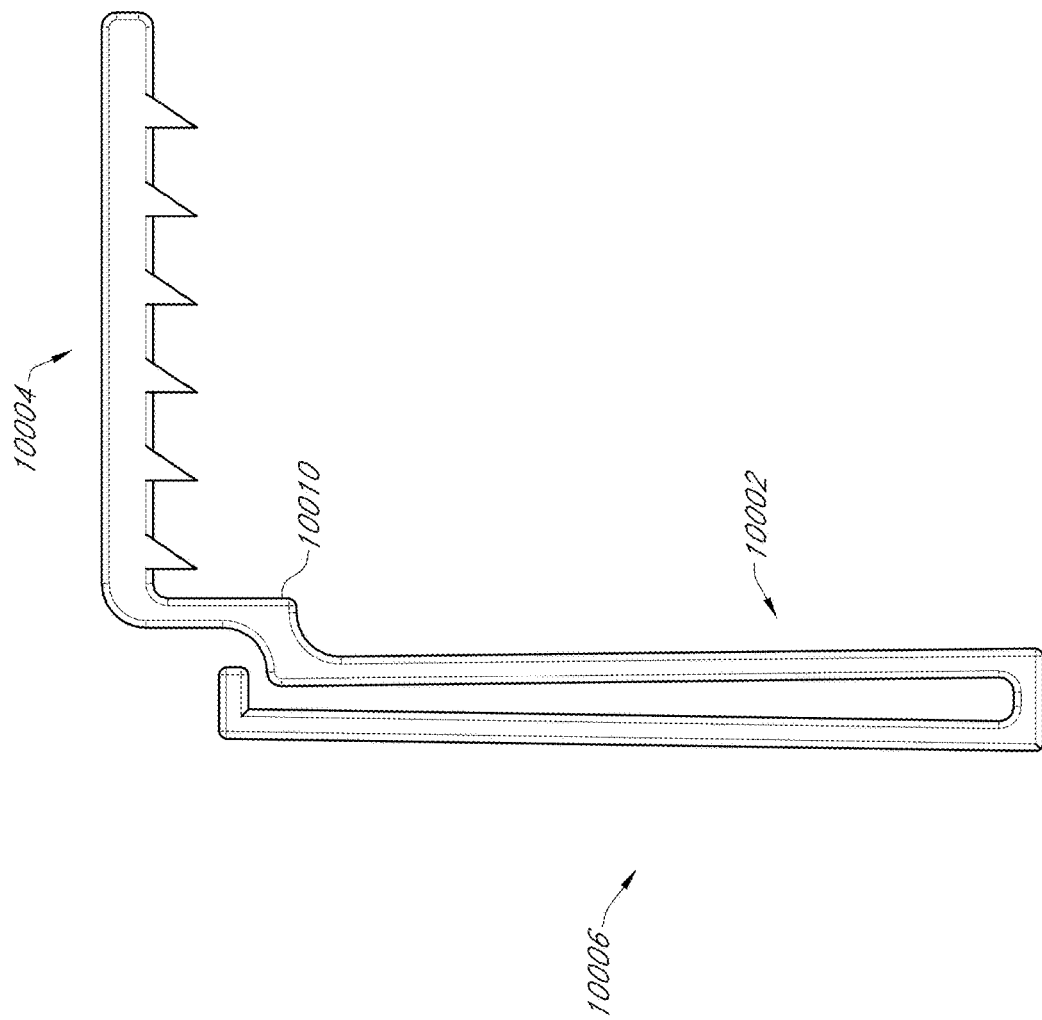
Figure 56D:
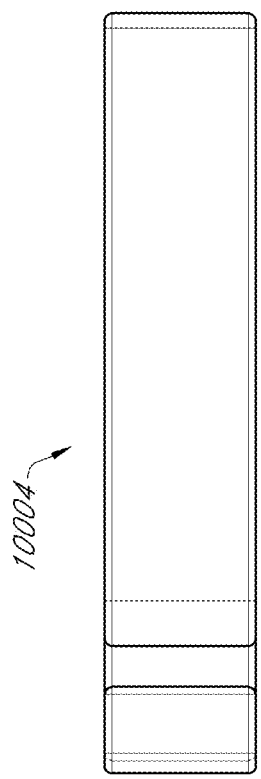
Figure 56E:
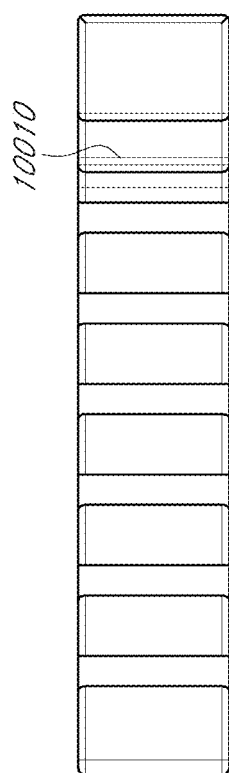
Figure 56F:
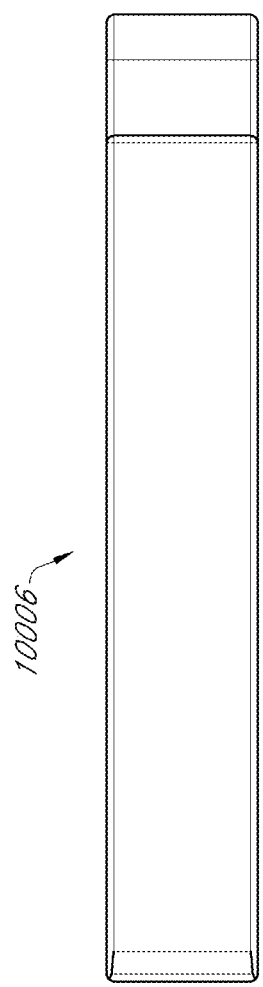
Figure 56G:
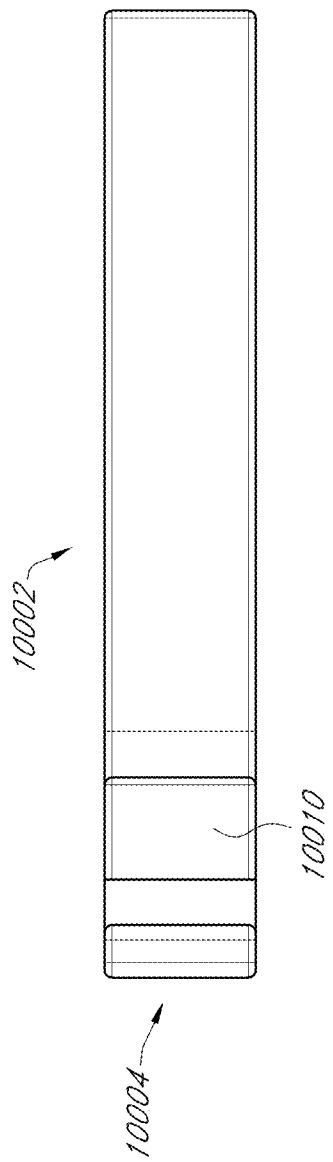
Figure 56H:
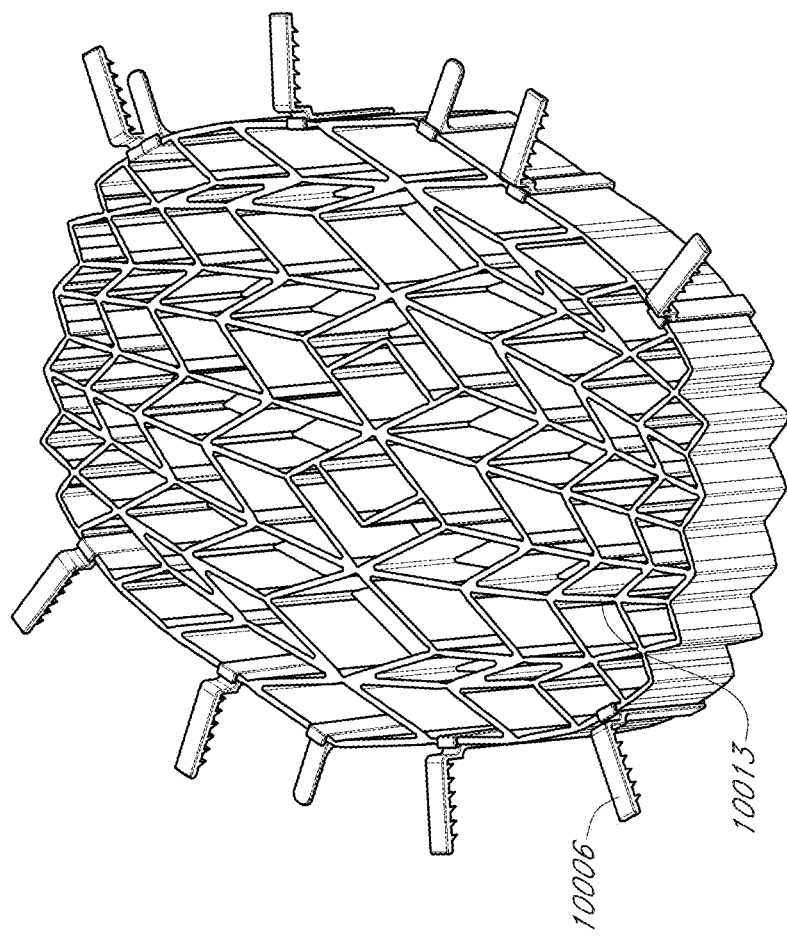
Figure 56I:
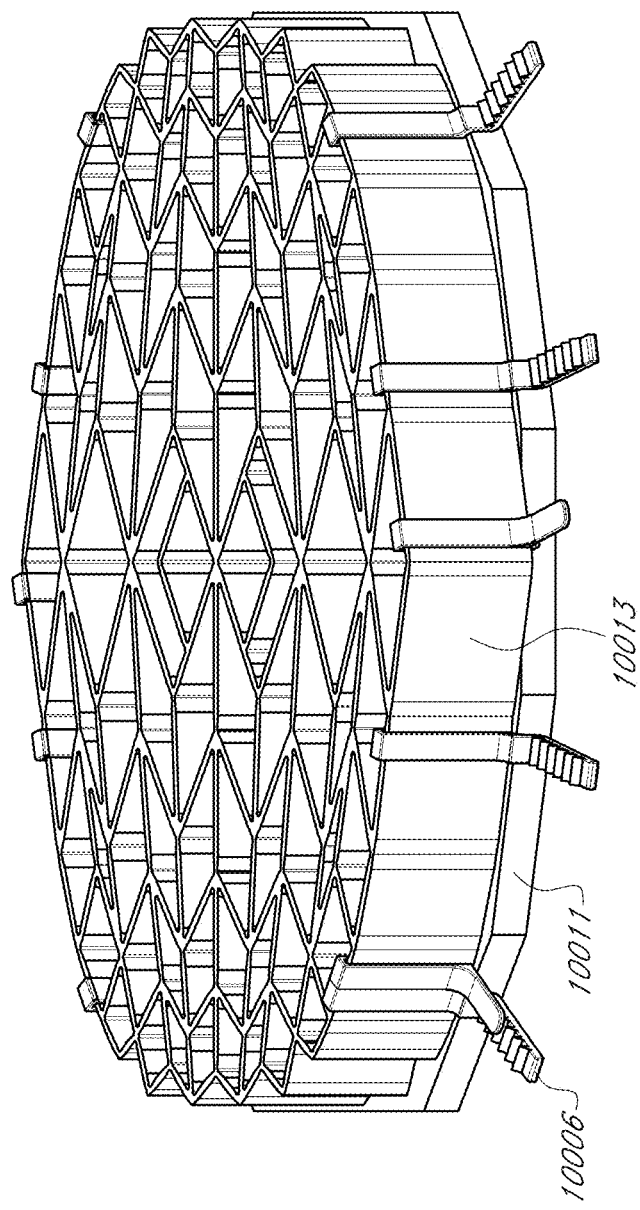
Figure 56J:
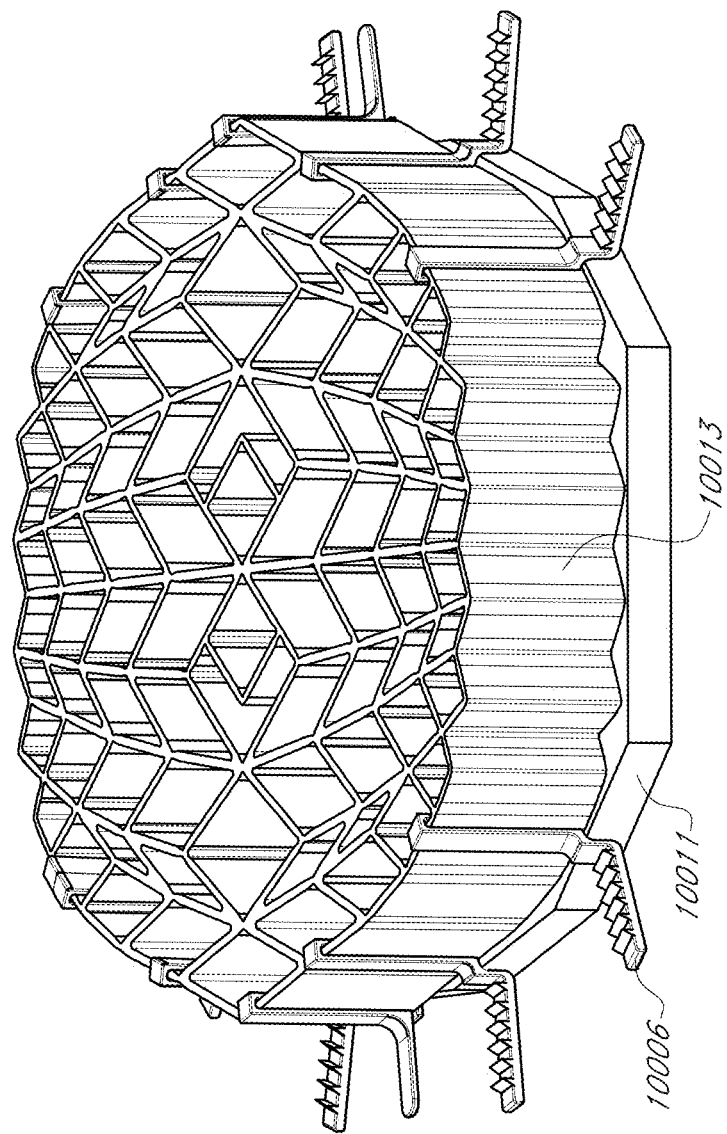

FIGS. 56H-J are pictures of the stabilizing clip 10006 attached to a stabilizing structure or matrix support 10013. The stabilizing structure 10013 is positioned above a foam layer 10011. The foam layer 10011 is larger than the stabilizing structure 10013. The step or recess 10010 of the stabilizing clip fits around the larger foam layer 10011. The step or recess 10010 may allow the stabilizing clip to secure the stabilizing structure within the wound without applying excess pressure on the foam layer that is slightly larger than the stabilizing structure. The step or recess may be provided at any vertical position along the attachment portion of the stabilizing clip to accommodate various depths of foams, stabilizing structures, and/or stabilizing clips.

Figure 57A:
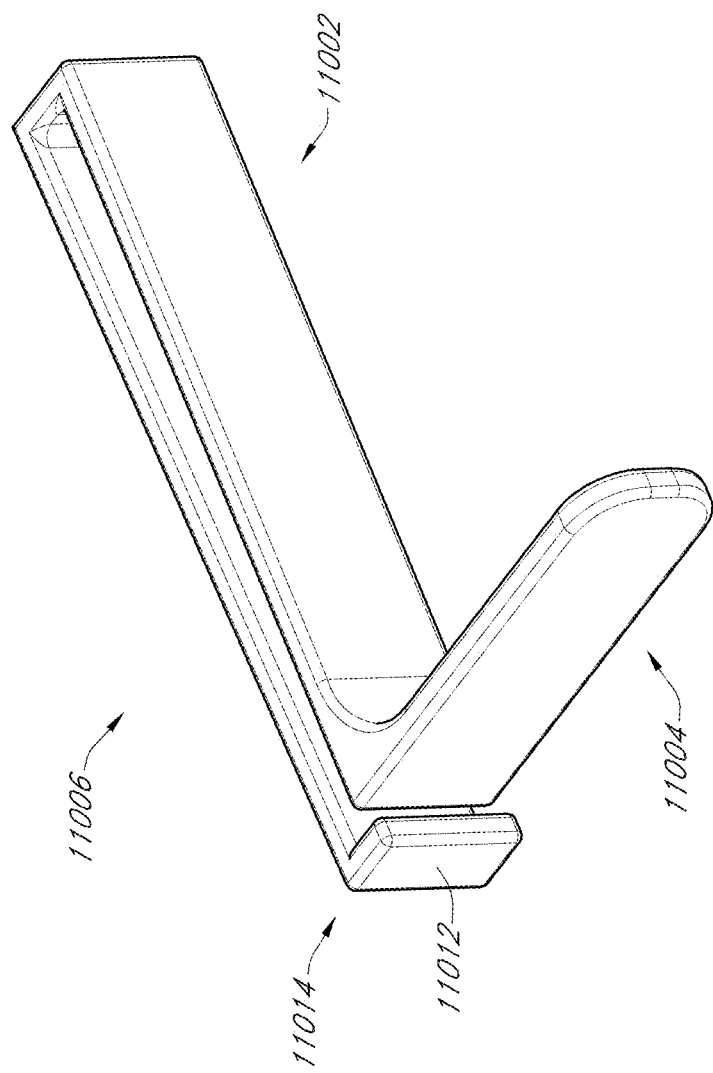
FIGS. 57A-J illustrate embodiments of stabilizing clips for attachment to a stabilizing structures with a foot.
Figure 57B:
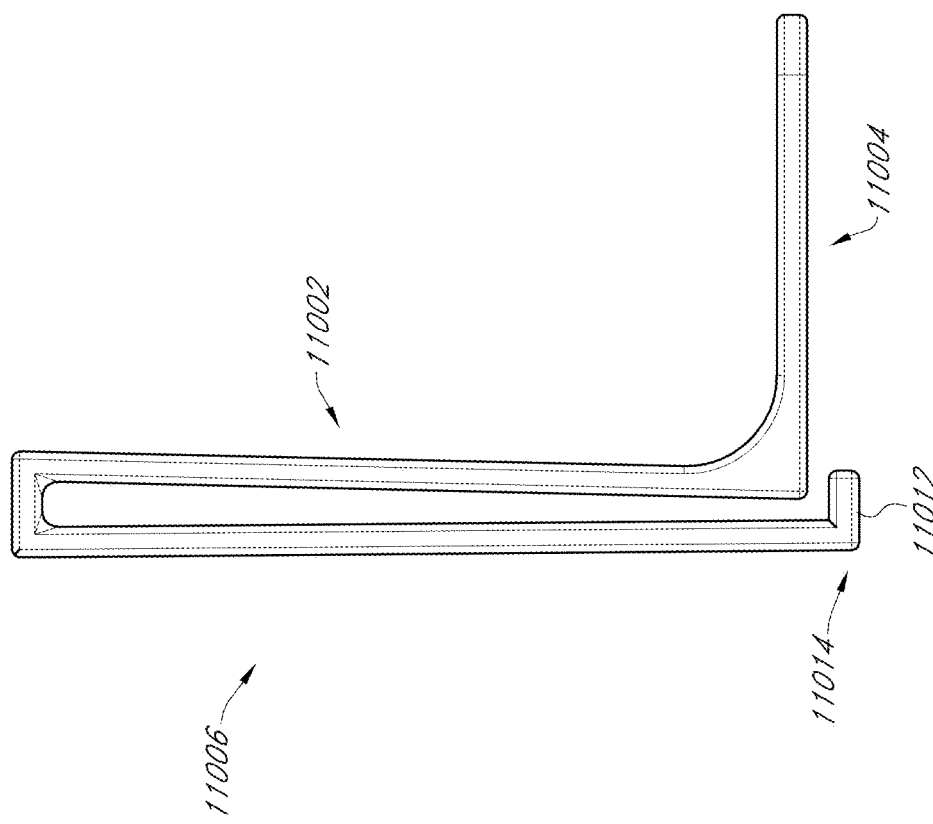
Figure 57C:
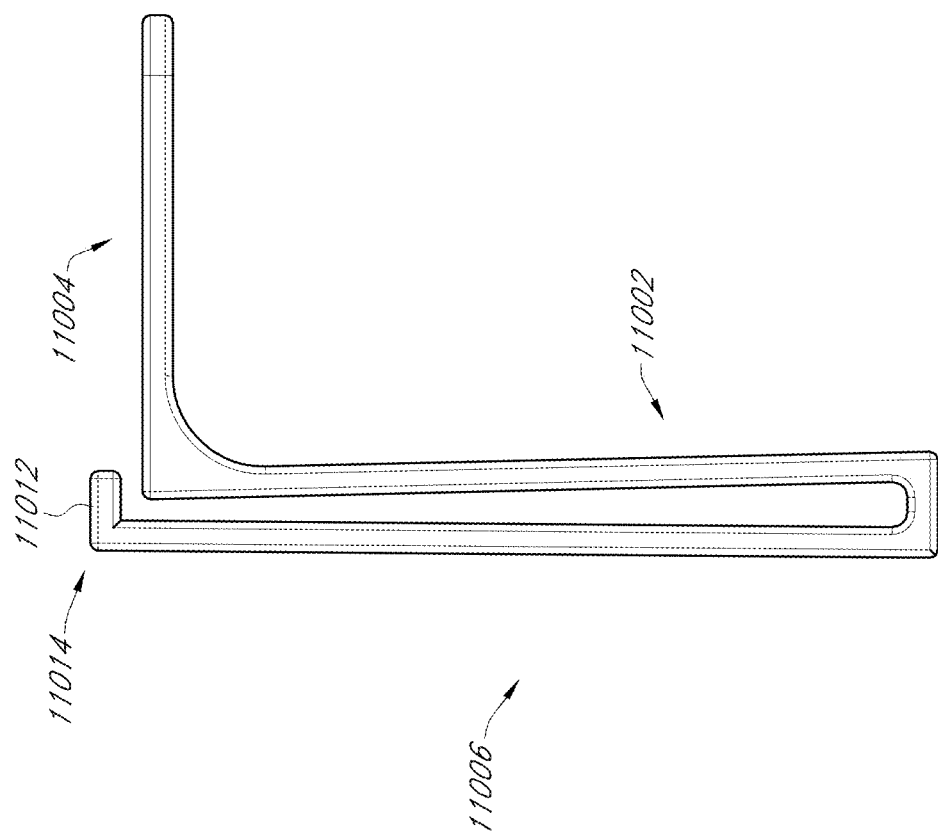
Figure 57D:
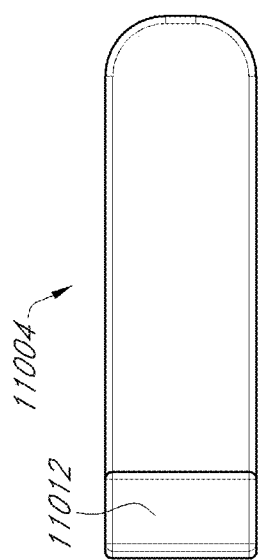
Figure 57E:
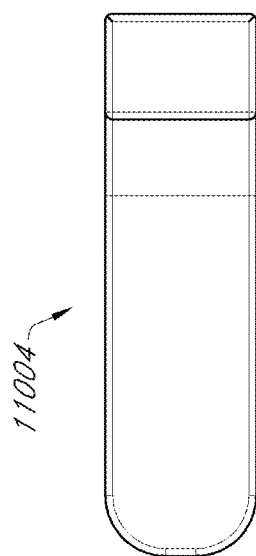
Figure 57F:
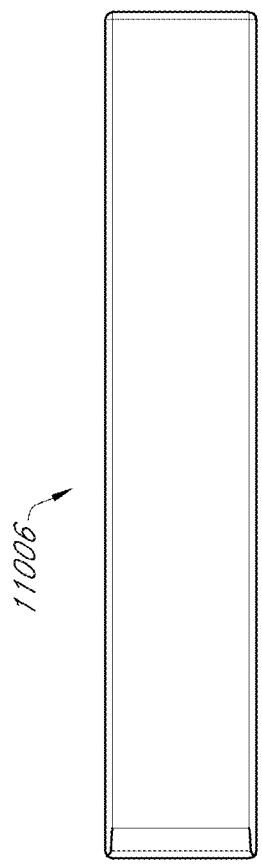
Figure 57G:
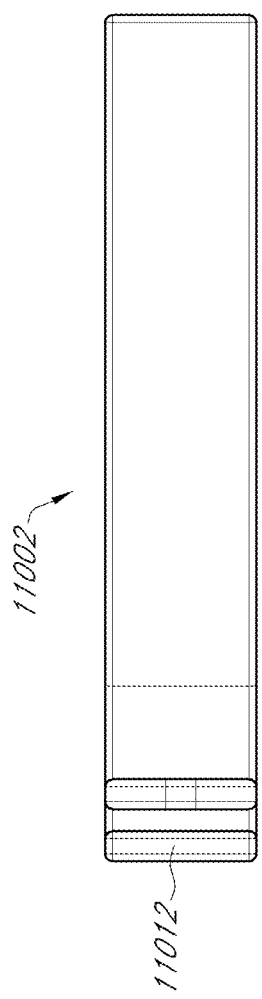
Figure 57H:
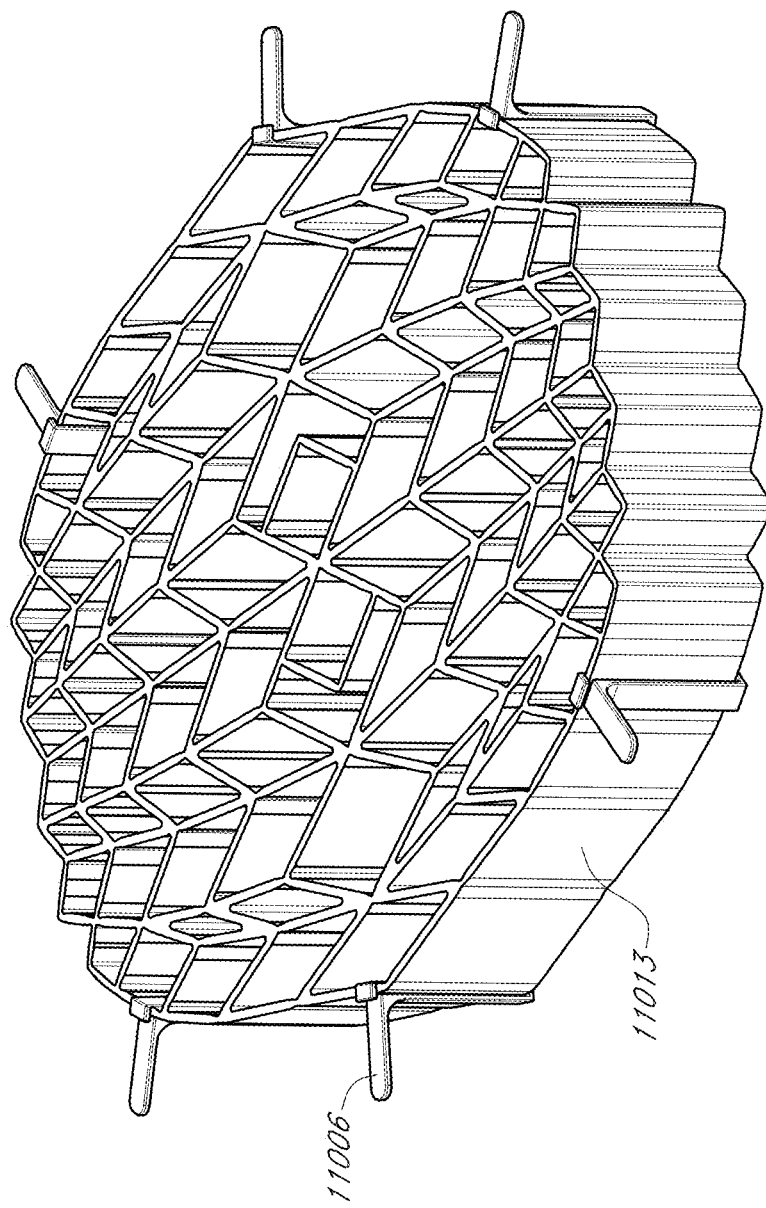
Figure 57I:
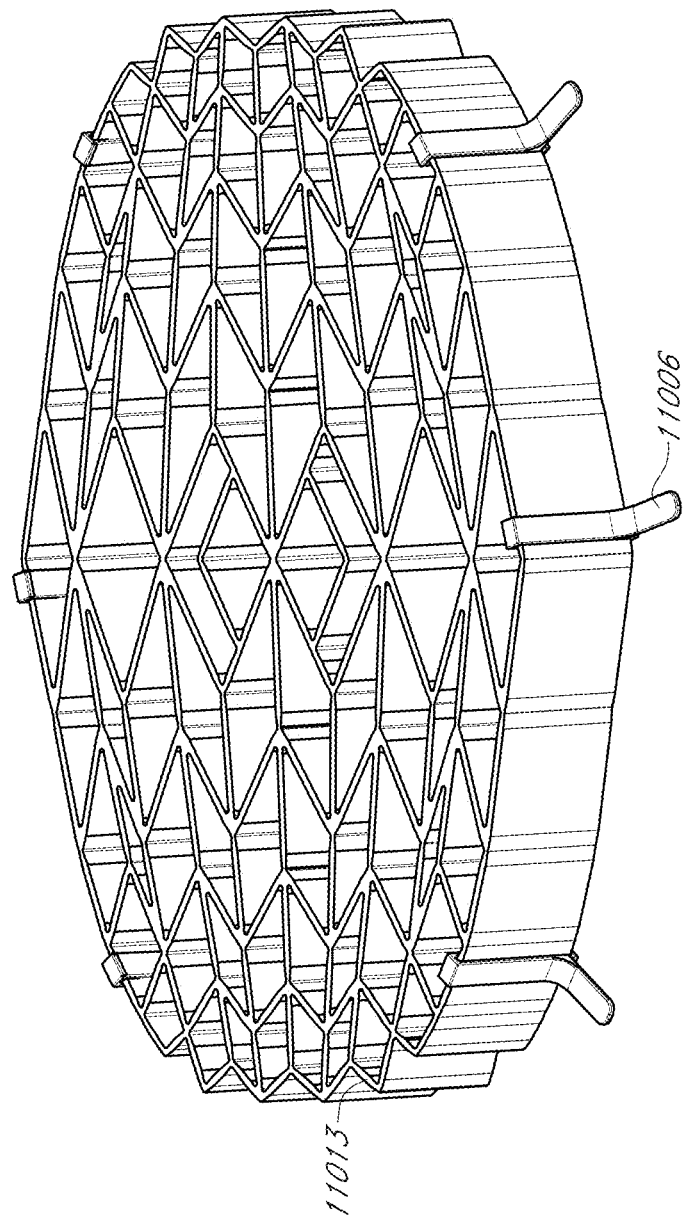
Figure 57J:
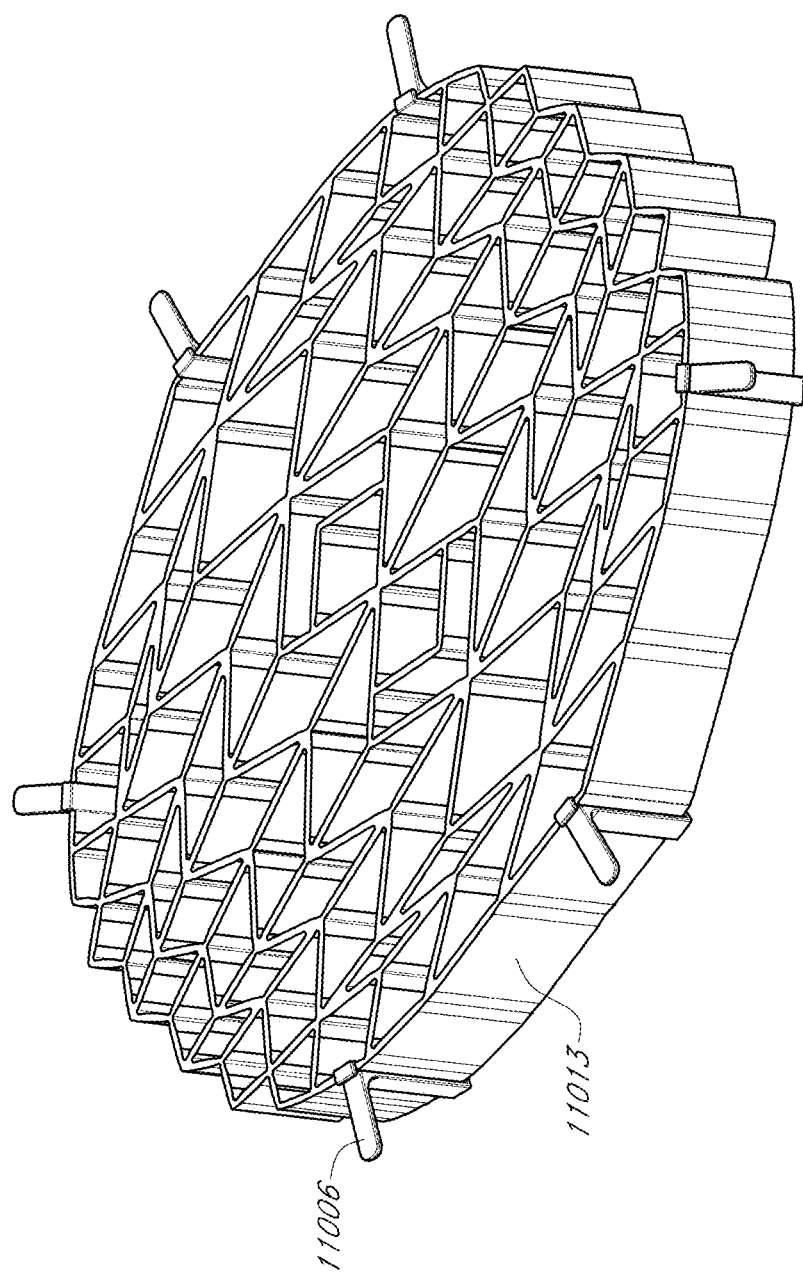

FIGS. 57A-J illustrate an embodiment of stabilizing clip 11006, similar to the stabilizing clip of FIG. 52C. As with the other stabilizing clip embodiments illustrated in FIG. 52C, stabilizing clip 11006 may comprise an attachment portion 11002 that loops over the top of a wall of a stabilizing structure and a securing portion 11004 that extends below a layer of tissue to maintain the stabilizing structure in place. The stabilizing clip 11006, as illustrated in FIGS. 21A-J, may include a foot 11012 to latch to the bottom of the stabilizing structure 11013. The foot 11012 may be provided at the end 11014 of the loop of the attachment portion 11002 that loops over the top of a wall of the stabilizing structure 11004. The foot 11012 can provide strengthening in the corner of the stabilizing clip 11006. The stabilizing clip 11006 with the foot 11012 improves the stability and strength of the stabilizing clip 11006. FIGS. 57H-57J are pictures of the stabilizing clip 10006 attached to the stabilizing structure 10013. The stabilizing clip 11006 can include a foot and grippers as illustrated in some embodiments in FIGS. 55A-G.

Figure 58A:
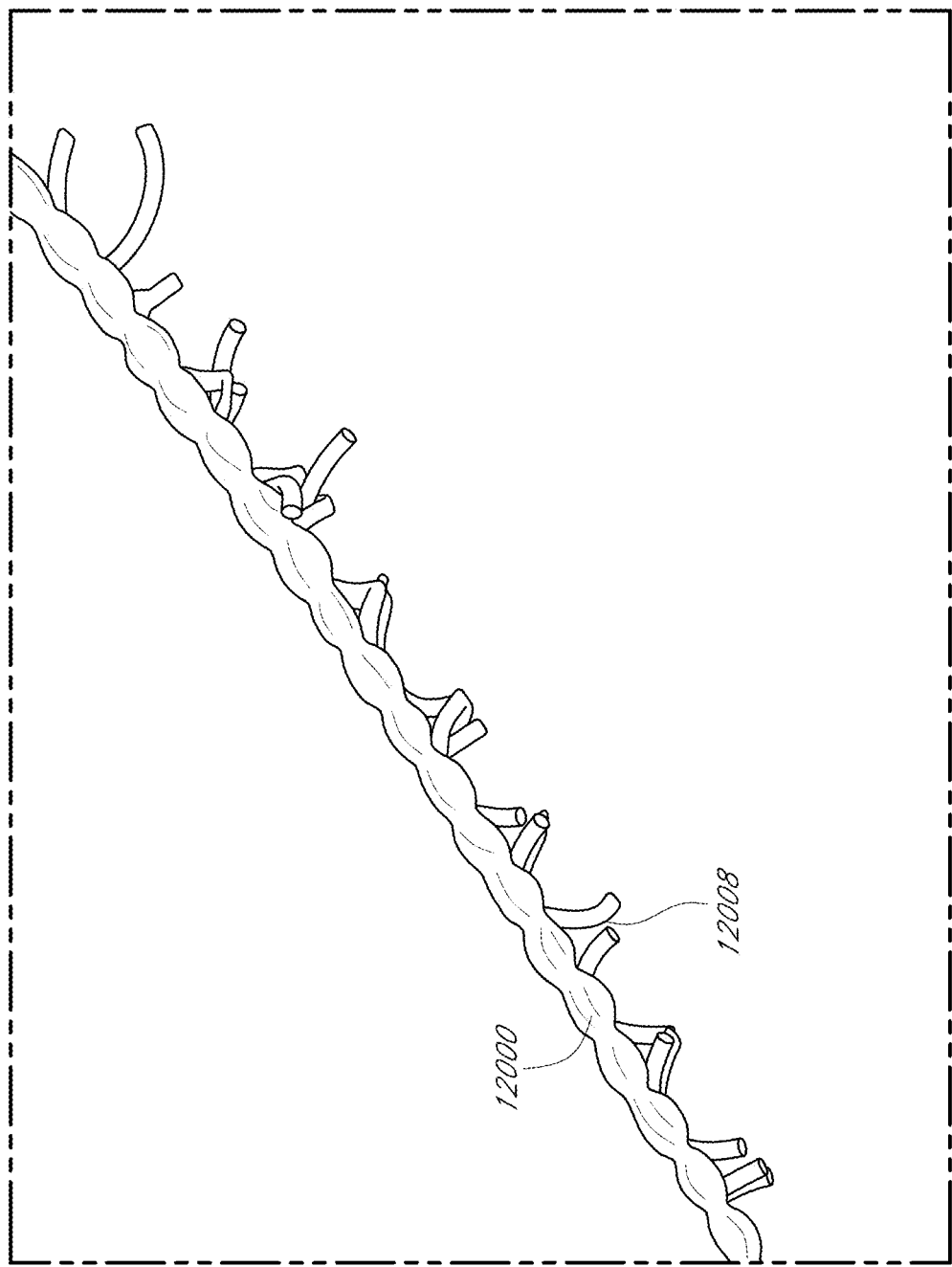
FIGS. 58A-B illustrate embodiments of a stabilizing device for attachment to a stabilizing structure.
Figure 58B:
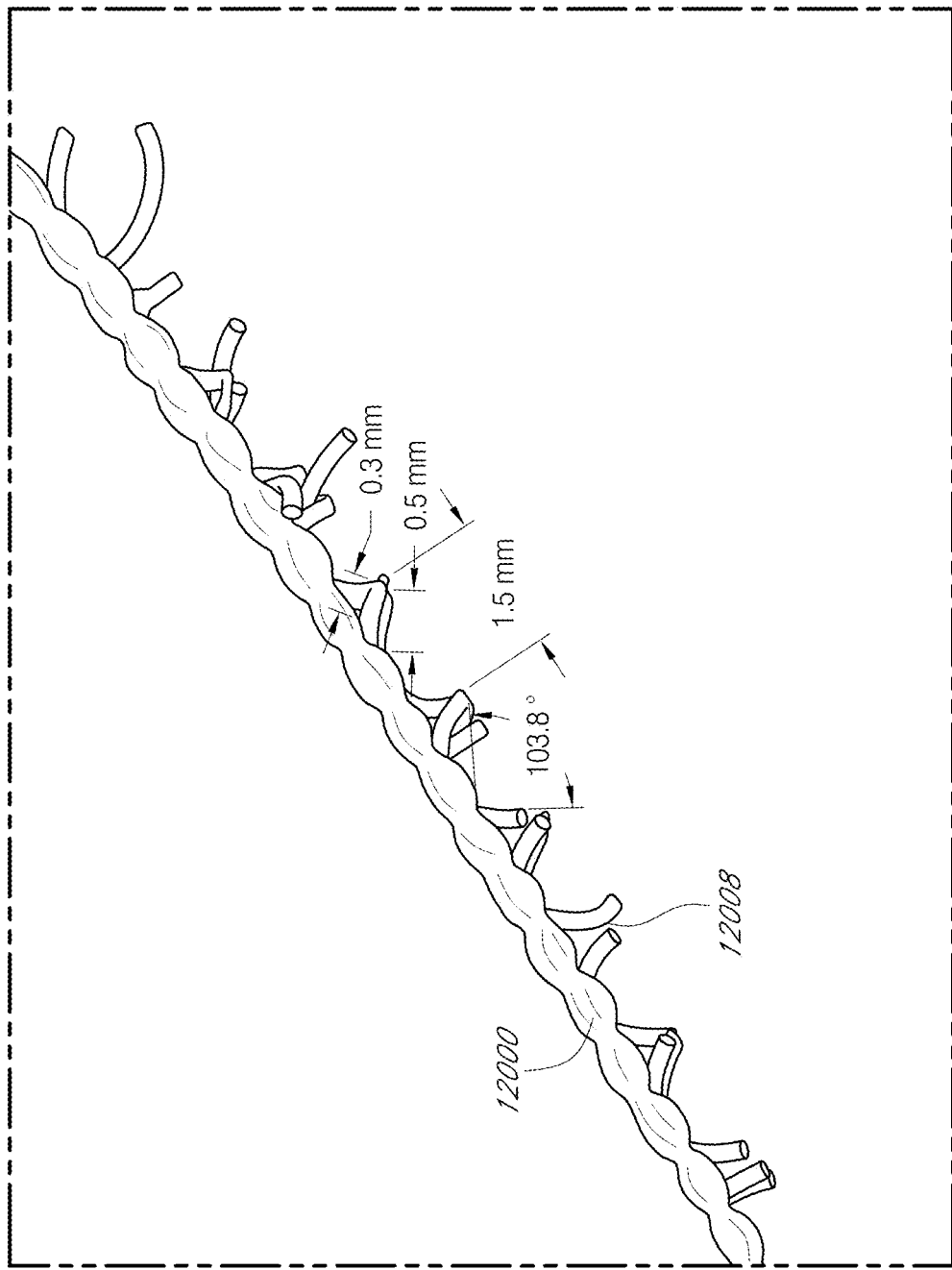

FIGS. 58A-B are pictures of embodiments of a stabilizing device. The stabilizing device 12000 can include grippers 12008 on an outside surface of the stabilizing device. The grippers can be similar to the tissue anchors described with reference to FIGS. 5A-D. Examples of such grippers may be available from Alfatex. In one embodiment, an anchoring layer may be provided comprising a 3D fabric material or portion thereof. For example, a 3D fabric may comprise a woven fabric layer provided along a first plane and a plurality of monofilaments extending perpendicularly from or at an angle relative to the woven fabric layer. The woven fabric layer may be configured to be attached to directly or indirectly to the outside of a stabilizing structure as described elsewhere in this specification and in the applications incorporated by reference. Monofilaments may have a mushroom-shaped head or other shapes configured to engage tissue surrounding the stabilizing structure. The head of the monofilaments may be similar to a peened rivet with a flatted head and extended edges that engage the surrounding tissues. If the monofilaments protrude at an angle then the material creates more grip in one direction of shear than another. This directionality means the anchoring layer and monofilaments can be positioned on a stabilizing structure so that the shear acts to stop the device being forced up or out of the wound by the viscera but can be easily released by pushing it down.

As described above, a stabilizing structure such as those described herein this section or elsewhere in the specification may be securing within a wound through the use of any stabilizing clip described herein this section or elsewhere in the specification. The following steps need not be completed in any particularly order, but are provided in the following order as an example. As depicted above in relation to FIG. 10A, the stabilizing structure may first be sized for a particular wound by trimming or removing portions of the stabilizing structure. Upon sizing the stabilizing structure to a particular wound shape, stabilizing clips may then be attached to the stabilizing structure. Then, the stabilizing structure is partially closed so as to facilitate placing the stabilizing structure into an abdominal wound and securing the stabilizing clips such that the clips extend under the fascia layer. Since the fascia is a relative strong tissue, by securing the stabilizing clips underneath the fascia, the stabilizing structure cannot be pushed up in a direction out of the wound by the underlying viscera. As described above, any number of stabilizing clips may be used and they may extend above and/or below various layers of tissue.

Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensible. Moreover, while illustrative embodiments have been described herein, the scope of any and all embodiments having equivalent elements, modifications, omissions, combinations (e.g., of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A porous wound dressing for use in negative-pressure therapy of wounds, comprising:
   an outer edge which defines an oval outer shape of the wound dressing, the wound dressing comprising a major axis and a minor axis;
   a plurality of arc-shaped pre-cut lines, the pre-cut lines configured to serve for cutting the wound dressing to size in order to adapt the wound dressing to the size of a wound;
   wherein each of the pre-cut lines extends asymmetrically with respect to the major axis and/or to the minor axis and encloses, together with a portion of the outer edge, a segment of the wound dressing that is designed for separation from the wound dressing and for subsequent use in the negative-pressure therapy of wounds,
   wherein individual segments are arranged asymmetrically with respect to the major axis and/or to the minor axis and comprise an oval outer shape which corresponds to the oval outer shape of the wound dressing, such that an observer is able to readily recognize the oval outer shape of the wound dressing in the oval outer shape of the segment, and
   wherein individual arc-shaped pre-cut lines are arranged at regular intervals from one another and individual arc-shaped pre-cut lines extend at least approximately parallel to one another, individual arc-shaped pre-cut lines extending from a first position on the outer edge of the wound dressing to a second position on the outer edge of the wound dressing, such that an oval-shaped division of the wound dressing into the segments is obtained.

2. The porous wound dressing of claim 1, wherein the porous wound dressing comprises foam.

3. The porous wound dressing of claim 1, wherein individual pre-cut lines comprise markings to facilitate removal of individual segments.

4. The porous wound dressing of claim 1, wherein individual pre-cut lines comprise scoring to facilitate removal of individual segments.

5. The porous wound dressing of claim 1, wherein individual pre-cut lines comprise partial cuts through a thickness of the porous wound dressing.

6. The porous wound dressing of claim 1, wherein individual pre-cut lines comprises full cuts through the thickness of the porous wound dressing.

7. The porous wound dressing of claim 1, wherein the porous wound dressing further comprises tissue anchors.

8. The porous wound dressing of claim 7, wherein the tissue anchors are configured to be exposed once a segment is removed.

9. The porous wound dressing of claim 8, wherein the porous wound dressing comprises six pre-cut lines.

10. The porous wound dressing of claim 1, wherein the porous wound dressing comprises three or more pre-cut lines.

11. The porous wound dressing of claim 1, wherein the individual pre-cut lines extend asymmetrically with respect to both the major axis and the minor axis.

12. A wound cover kit for use in negative-pressure therapy of wounds, comprising:
    a wound contact layer configured to be placed directly against a wound;
    a wound cover configured to be cover and seal the wound; and
    a wound dressing comprising:
    an outer edge which defines an oval outer shape of the wound dressing, the wound dressing comprising a major axis and a minor axis,
    a plurality of arc-shaped pre-cut lines, the pre-cut lines configured to serve for cutting the wound dressing to size in order to adapt the wound dressing to the size of a wound,
    wherein each of the pre-cut lines extends asymmetrically with respect to the major axis and/or to the minor axis and encloses, together with a portion of the outer edge, a segment of the wound dressing that is designed for separation from the wound dressing and for subsequent use in the negative-pressure therapy of wounds,
    wherein individual segments are arranged asymmetrically with respect to the major axis and/or to the minor axis and comprise an oval outer shape which corresponds to the oval outer shape of the wound dressing, such that an observer is able to readily recognize the oval outer shape of the wound dressing in the oval outer shape of the segment, and wherein individual arc-shaped pre-cut lines are arranged at regular intervals from one another and individual arc-shaped pre-cut lines extend at least approximately parallel to one another, individual arc-shaped pre-cut lines extending from a first position on the outer edge of the wound dressing to a second position on and to a further portion of the outer edge of the wound dressing, such that an oval-shaped division of the wound dressing into the segments is obtained.

13. The wound cover kit of claim 12, wherein the wound dressing is porous.

14. The wound cover kit of claim 13, wherein the wound dressing comprises foam.

15. The wound cover kit of claim 12, wherein individual pre-cut lines comprise markings to facilitate removal of individual segments.

16. The wound cover kit of claim 12, wherein individual pre-cut lines comprise scoring to facilitate removal of individual segments.

17. The wound cover kit of claim 12, wherein individual pre-cut lines comprise partial cuts through a thickness of the porous wound dressing.

18. The wound cover kit of claim 12, wherein individual pre-cut lines comprises full cuts through the thickness of the porous wound dressing.

19. The wound cover kit of claim 12, wherein the wound dressing further comprises tissue anchors.

20. The wound cover kit of claim 19, wherein the tissue anchors are configured to be exposed once a segment is removed.

* * * * *

UNITED STATES PATENT AND TRADEMARK OFFICE
CERTIFICATE OF CORRECTION

| | |
|---|---|
| PATENT NO. | : 12,239,509 B2 |
| APPLICATION NO. | : 18/130317 |
| DATED | : March 4, 2025 |
| INVENTOR(S) | : Philip David Canner et al. |

It is certified that error appears in the above-identified patent and that said Letters Patent is hereby corrected as shown below:

In the Specification

In Column 30, Line 6, delete "be tom at" and insert --be torn at--.

In Column 30, Line 9, delete "be tom at" and insert --be torn at--.

In Column 54, Line 9, delete "broken, tom, cut)" and insert --broken, torn, cut)--.

In the Claims

In Column 73, Claim 12, Lines 9-10 (Approx.), delete "on and to a further portion of the" and insert --on the--.

Signed and Sealed this
Sixth Day of May, 2025

Coke Morgan Stewart
*Acting Director of the United States Patent and Trademark Office*